US012774276B2

(12) United States Patent
DeChristopher et al.

(10) Patent No.: US 12,774,276 B2
(45) Date of Patent: Oct. 27, 2026

(54) MALT1 MODULATORS AND USES THEREOF

(71) Applicant: Rarefied Biosciences, Inc., Santa Monica, CA (US)

(72) Inventors: Brian Addison DeChristopher, Cambridge, MA (US); Guillaume Barbe, Cambridge, MA (US)

(73) Assignee: Rarefield Biosciences, Inc., Santa Monica, CA (US)

( * ) Notice: Subject to any disclaimer, the term of this patent is extended or adjusted under 35 U.S.C. 154(b) by 230 days.

(21) Appl. No.: 18/850,955

(22) PCT Filed: Mar. 30, 2023

(86) PCT No.: PCT/US2023/016941
§ 371 (c)(1),
(2) Date: Sep. 25, 2024

(87) PCT Pub. No.: WO2023/192506
PCT Pub. Date: Oct. 5, 2023

(65) Prior Publication Data

US 2025/0326738 A1 Oct. 23, 2025

Related U.S. Application Data

(60) Provisional application No. 63/325,852, filed on Mar. 31, 2022.

(51) Int. Cl.

| | |
|---|---|
| ***C07D 401/14*** | (2006.01) |
| ***A61K 31/4155*** | (2006.01) |
| ***A61K 31/4439*** | (2006.01) |
| ***A61K 31/454*** | (2006.01) |
| ***A61K 31/4545*** | (2006.01) |
| ***A61K 31/4709*** | (2006.01) |
| ***A61K 31/497*** | (2006.01) |
| ***A61K 31/501*** | (2006.01) |
| ***A61K 31/506*** | (2006.01) |
| ***C07D 231/38*** | (2006.01) |
| ***C07D 401/04*** | (2006.01) |
| ***C07D 401/12*** | (2006.01) |
| ***C07D 403/04*** | (2006.01) |
| ***C07D 403/12*** | (2006.01) |
| ***C07D 409/12*** | (2006.01) |
| ***C07D 409/14*** | (2006.01) |

(52) U.S. Cl.
CPC ........ *C07D 401/14* (2013.01); *A61K 31/4155* (2013.01); *A61K 31/4439* (2013.01); *A61K 31/454* (2013.01); *A61K 31/4545* (2013.01); *A61K 31/4709* (2013.01); *A61K 31/497* (2013.01); *A61K 31/501* (2013.01); *A61K 31/506* (2013.01); *C07D 231/38* (2013.01); *C07D 401/04* (2013.01); *C07D 401/12* (2013.01); *C07D 403/04* (2013.01); *C07D 403/12* (2013.01); *C07D 409/12* (2013.01); *C07D 409/14* (2013.01)

(58) Field of Classification Search
CPC .................................................... C07D 401/14
See application file for complete search history.

(56) References Cited

U.S. PATENT DOCUMENTS

| | | | |
|---|---|---|---|
| 5,593,996 | A | 1/1997 | Pees et al. |
| 9,504,692 | B2 | 11/2016 | Krappmann et al. |
| 2007/0275961 | A1 | 11/2007 | Bower et al. |
| 2009/0105242 | A1 | 4/2009 | Edwards et al. |
| 2015/0297570 | A1 | 10/2015 | Melnick et al. |
| 2019/0381019 | A1 | 12/2019 | Lu |
| 2020/0289514 | A1 | 9/2020 | Kammertoens et al. |

FOREIGN PATENT DOCUMENTS

| | | |
|---|---|---|
| WO | WO 2017/000277 | 1/2017 |
| WO | WO 2018/020474 | 2/2018 |
| WO | WO 2021/138298 | 7/2021 |
| WO | WO 2021/207343 | 10/2021 |

OTHER PUBLICATIONS

Biswas Pharmacological Inhibition of MALT1 Ameliorates Autoimmune Pathogenesis and Can Be Uncoupled From Effects on Regulatory T-Cells. Front Immunol. May 9, 2022;13:87532.*
Biswas et al, Pharmacological inhibition of MALT1 ameilorates autoimmune pathogenesis and can be uncoupled . . ., 2022, Front. Immunol. vol. 13, pp. 1-13.
Ferch et al, Inhibition of MALT1 protease activity is selectively toxic for activated B cell-like diffuse large B cell lymphoma cells, 2009, J. Exp Med vol. 206, pp. 2313-2320.
Oukoloff et al, 1,2,4-triazol[1,5-a]pyrimidines in drug design, 2019, Eur. J. Medicinal Chem vol. 165, pp. 332-346.

* cited by examiner

*Primary Examiner* — Nizal S Chandrakumar
(74) *Attorney, Agent, or Firm* — HelixIP LLP

(57) ABSTRACT

Provided herein are compounds, compositions, and methods useful for modulating MALT1 and for treating related diseases, disorders, and conditions.

15 Claims, No Drawings

MALT1 MODULATORS AND USES THEREOF

CROSS REFERENCE OF RELATED APPLICATIONS

This application is a 371 of PCT/US2023/016941, having an international filing date of Mar. 30, 2023, which claims the benefit of U.S. Provisional Patent Application No. 63/325,852 filed Mar. 31, 2022, the entire disclosure of each of which is hereby incorporated by reference in its entirety for all purposes.

BACKGROUND

Mucosa associated lymphoid tissue lymphoma translocation protein 1 (MALT1) is an intracellular signaling protein, known from innate (e.g., natural killer cells NK, dendritic cells DC, and mast cells) and adaptive immune cells (e.g., T cells and B cells). MALT1 plays an essential role in influencing immune responses. For example, in T cell receptor signaling, MALT1 mediates nuclear factor κB (NFKB) signaling, leading to T cell activation and proliferation. Accordingly, MALT1 is of interest in the mechanism of autoimmune and inflammatory pathologies. In addition, constitutive (dysregulated) MALT1 activity is associated with cancers such as MALT lymphoma and activated B cell-like diffuse large B Cell lymphoma (ABC-DLBCL). Modulators of MALT1 activity may be useful as potential therapeutics.

SUMMARY

Provided herein are compounds designed to act as MALT1 modulators. In some embodiments, such compounds are envisioned to be useful as therapeutic agents for treating autoimmune and inflammatory diseases, disorders, or conditions or cancers.

In one aspect, provided herein are compounds represented by Formula (I):

(I)

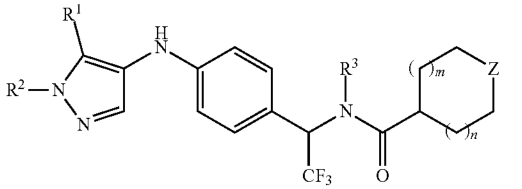

or a stereoisomer and/or a pharmaceutically acceptable salt thereof, wherein:

$R^1$ is selected from the group consisting of $C_{1-6}$alkyl, $C_{1-3}$haloalkyl, $C_{3-6}$cycloalkyl, and aryl, wherein $R^1$ may be optionally substituted on one or more available carbons by one, two, three, or more substituents each independently selected from $R^{1a}$;

$R^2$ is selected from the group consisting of $C_{1-6}$alkyl, $C_{3-6}$cycloalkyl, aryl, and 5-10 membered heteroaryl, wherein $R^2$ may be optionally substituted on one or more available carbons by one, two, three, or more substituents each independently selected from $R^2$, $R^3$ is hydrogen or $C_{1-3}$alkyl;

$R^{1a}$ is independently, for each occurrence, hydroxyl or —O—$C_{1-3}$alkyl;

$R^{2a}$ is independently, for each occurrence, selected from the group consisting of hydroxyl, cyano, $C_{1-6}$alkyl, and —O—$C_{1-3}$alkyl;

Z is —C(H)($R^A$)—, —$SO_2$—, or —$NR^A$—;

$R^A$ is —C(O)$C_{1-6}$alkyl, —C(O)OH, or 5-6 membered heteroaryl;

m is 0 or 1; and n is 0 or 1.

In another aspect, provided herein are compounds represented by Formula (Ia)

(Ia)

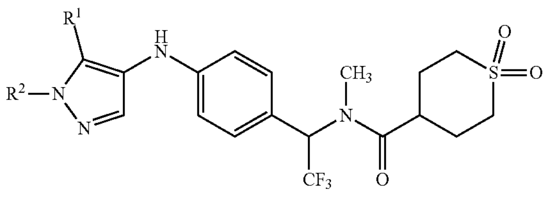

or a stereoisomer and/or a pharmaceutically acceptable salt thereof, wherein:

$R^1$ is selected from $C_{1-6}$alkyl, $C_{1-3}$haloalkyl, or aryl, wherein the $C_{1-6}$alkyl may be optionally substituted on one or more available carbons by one, two, three, or more substituents each independently selected from $R^{1a}$;

$R^2$ is selected from the group consisting of $C_{1-6}$alkyl, $C_{3-6}$cycloalkyl, aryl, and 5-10 membered heteroaryl, wherein $R^2$ may be optionally substituted on one or more available carbons by one, two, three, or more substituents each independently selected from $R^{2a}$;

$R^{1a}$ is independently, for each occurrence, hydroxyl or —O—$C_{1-3}$alkyl; and $R^{2a}$ is independently, for each occurrence, selected from the group consisting of hydroxyl, cyano, $C_{1-6}$alkyl, and —O—$C_{1-3}$alkyl.

In another aspect, provided herein are compounds represented by Formula (Ib)

(Ib)

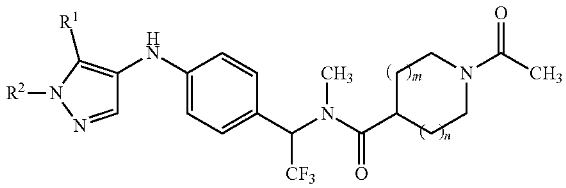

or a stereoisomer and/or a pharmaceutically acceptable salt thereof, wherein:

$R^1$ is $C_{1-6}$alkyl, $C_{1-3}$haloalkyl, or $C_{3-6}$cycloalkyl, wherein the $C_{1-6}$alkyl may be optionally substituted with —O—$C_{1-3}$alkyl;

$R^2$ is aryl or 5-6 membered heteroaryl, wherein the aryl may be optionally substituted with cyano;

m is 0 or 1; and n is 0 or 1.

In another aspect, provided herein are compounds represented by Formula (Ic)

(Ic)

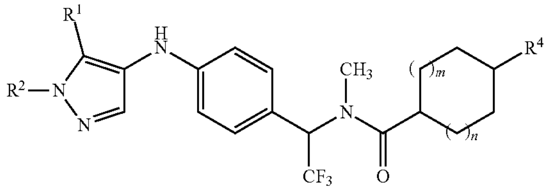

or a stereoisomer and/or a pharmaceutically acceptable salt thereof, wherein:

$R^1$ is $C_{1-6}$alkyl or $C_{1-3}$haloalkyl, wherein the $C_{1-6}$alkyl may be optionally substituted with —O—$C_{1-3}$alkyl;

$R^2$ is aryl or 5-6 membered heteroaryl, wherein the aryl may be optionally substituted with cyano;

$R^4$ is —C(O)OH or 5-6 membered heteroaryl;

m is 0 or 1; and n is 0 or 1.

In some embodiments, a compound provided herein is selected from a compound set forth in Table 1, or a pharmaceutically acceptable salt thereof.

In another aspect, provided herein is a pharmaceutical composition comprising a compound disclosed herein and a pharmaceutically acceptable carrier.

In another aspect, provided herein is a method of treating a cancer in a subject in need thereof, the method comprising administering to the subject a therapeutically effective amount of a compound or a stereoisomer and/or a pharmaceutical composition disclosed herein.

In another aspect, provided herein is a method of treating an autoimmune or inflammatory disorder or disease in a subject in need thereof, the method comprising administering to the subject a therapeutically effective amount of a compound or a pharmaceutical composition disclosed herein.

DETAILED DESCRIPTION

As generally described herein, the present invention provides compounds designed, for example, to act as MALT1 modulators. In certain embodiments, such compounds are envisioned to be useful as therapeutic agents for treating autoimmune and inflammatory diseases, disorders, or conditions or cancers.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

It is to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," "alkynylene," "cycloalkylene," "heterocyclylene," "heteroarylene," and "phenylene" refer to a divalent radical of an alkyl, alkenyl, alkynyl, cycloalkyl, heterocyclyl (e.g., saturated and partially saturated), heteroaryl, and phenyl group respectively.

When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, and indenyl.

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. For bicyclic heteroaryl groups wherein one ring does not contain a heteroatom (e.g., indolyl, quinolinyl, carbazolyl, and the like), the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

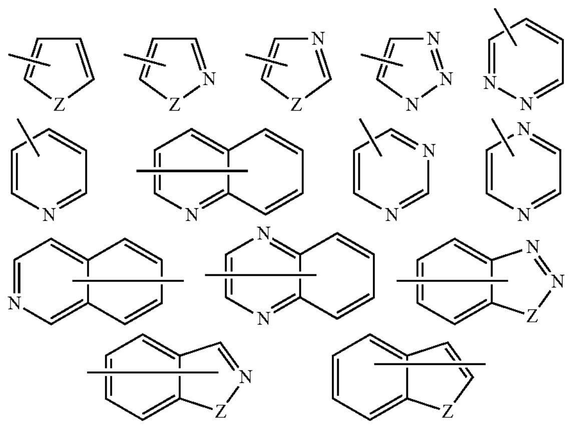

wherein each Z is selected from carbonyl, N, $NR^{65}$, O, and S; and $R^{65}$ is independently hydrogen, $C_{1-8}$ alkyl, $C_{3-10}$ carbocyclyl, 4-10 membered heterocyclyl, $C_6$-$C_{10}$ aryl, and 5-10 membered heteroaryl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes.

As used herein, "$C_{3-6}$ monocyclic cycloalkyl" or "monocyclic $C_{3-6}$ cycloalkyl" refers to a 3- to 7-membered monocyclic hydrocarbon ring system that is saturated. 3- to 7-membered monocyclic cycloalkyl groups include, without limitation, cyclopropyl, cyclobutyl, cyclopentyl, and cyclohexyl. Where specified as being optionally substituted or substituted, substituents on a cycloalkyl (e.g., in the case of an optionally substituted cycloalkyl) may be present on any substitutable position and, include, e.g., the position at which the cycloalkyl group is attached.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms "heterocycle," "heterocyclyl," "heterocyclyl ring," "heterocyclic group," "heterocyclic moiety," and "heterocyclic radical," may be used interchangeably.

In some embodiments, a heterocyclyl group is a 4-7 membered non-aromatic ring system having ring carbon atoms and 1-4 ring heteroatoms, wherein each heteroatom is independently selected from nitrogen, oxygen, and sulfur ("4-7 membered heterocyclyl"). In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Examples of saturated or partially unsaturated heterocyclic radicals include, without limitation, tetrahydrofuranyl, tetrahydrothienyl, tetrahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. Where specified as being optionally substituted or substituted, substituents on a heterocyclyl (e.g., in the case of an optionally substituted heterocyclyl) may be present on any substitutable position and, include, e.g., the position at which the heterocyclyl group is attached.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g., heteroaryl; and the like having from 1 to 5, and particularly from 1 to 3 heteroatoms.

As used herein, "cyano" refers to —CN.

The terms "halo" and "halogen" as used herein refer to an atom selected from fluorine (fluoro, —F), chlorine (chloro, —Cl), bromine (bromo, —Br), and iodine (iodo, —I). In certain embodiments, the halo group is either fluoro or chloro.

The term "alkoxy," as used herein, refers to an alkyl group which is attached to another moiety via an oxygen atom (—O(alkyl)). Non-limiting examples include e.g., methoxy, ethoxy, propoxy, and butoxy.

"Haloalkoxy" is a haloalkyl group which is attached to another moiety via an oxygen atom such as, e.g., but are not limited to —$OCHF_2$ or —$OCF_3$.

The term "haloalkyl" includes mono, poly, and perhaloalkyl groups substituted with one or more halogen atoms where the halogens are independently selected from fluorine, chlorine, bromine, and iodine. For the group $C_{1-4}$haloalkyl-O—$C_{1-4}$alkyl, the point of attachment occurs on the alkyl moiety which is halogenated.

As used herein, "oxo" refers to —C═O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)$N(R^{cc})_2$, —$SO_2N(R^{cc})$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═$O)_2R^{aa}$, —P(═O)($R^{aa}$), —P(═$O)_2N(R^{cc})_2$, —P(═O)($NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Compounds

In one aspect, provided herein are compounds represented by Formula (I):

(I)

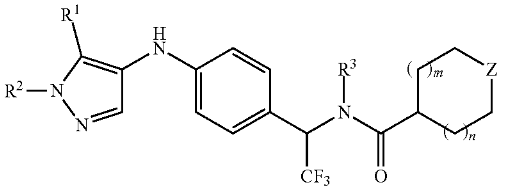

or a stereoisomer and/or a pharmaceutically acceptable salt thereof, wherein:

$R^1$ is selected from the group consisting of $C_{1-6}$alkyl, $C_{1-3}$haloalkyl, $C_{3-6}$cycloalkyl, and aryl, wherein $R^1$ may be optionally substituted on one or more available carbons by one, two, three, or more substituents each independently selected from $R^{1a}$;

$R^2$ is selected from the group consisting of $C_{1-6}$alkyl, $C_{3-6}$cycloalkyl, aryl, and 5-10 membered heteroaryl, wherein $R^2$ may be optionally substituted on one or more available carbons by one, two, three, or more substituents each independently selected from $R^{2a}$;

$R^3$ is hydrogen or $C_{1-3}$alkyl;

$R^{1a}$ is independently, for each occurrence, hydroxyl or —O—$C_{1-3}$alkyl;

$R^{2a}$ is independently, for each occurrence, selected from the group consisting of hydroxyl, cyano, $C_{1-6}$alkyl, and —O—$C_{1-3}$alkyl;

Z is —C(H)($R^A$)—, —$SO_2$—, or —$NR^A$—;

$R^A$ is —C(O)$C_{1-6}$alkyl, —C(O)OH, or 5-6 membered heteroaryl;

m is 0 or 1; and n is 0 or 1.

In some embodiments, the compound is represented by Formula (I'):

(I')

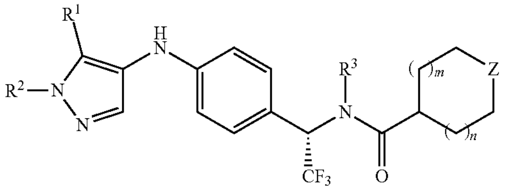

or a stereoisomer and/or a pharmaceutically acceptable salt thereof, wherein:

$R^1$ is selected from the group consisting of $C_{1-6}$alkyl, $C_{1-3}$haloalkyl, $C_{3-6}$cycloalkyl, and aryl, wherein $R^1$ may be optionally substituted on one or more available carbons by one, two, three, or more substituents each independently selected from $R^{1a}$;

$R^2$ is selected from the group consisting of $C_{1-6}$alkyl, $C_{3-6}$cycloalkyl, aryl, and 5-10 membered heteroaryl, wherein $R^2$ may be optionally substituted on one or more available carbons by one, two, three, or more substituents each independently selected from $R^2$, $R^3$ is hydrogen or $C_{1-3}$alkyl;

$R^{1a}$ is independently, for each occurrence, hydroxyl or —O—$C_{1-3}$alkyl;

$R^{2a}$ is independently, for each occurrence, selected from the group consisting of hydroxyl, cyano, $C_{1-6}$alkyl, and —O—$C_{1-3}$alkyl;

Z is —C(H)($R^A$)—, —$SO_2$—, or —$NR^A$—.

$R^A$ is —C(O)$C_{1-6}$alkyl, —C(O)OH, or 5-6 membered heteroaryl;

m is 0 or 1; and n is 0 or 1.

In some embodiments, $R^1$ is selected from the group consisting of $C_{1-6}$alkyl, $C_{1-3}$haloalkyl, $C_{3-6}$cycloalkyl, and aryl, wherein the $C_{1-6}$alkyl may be optionally substituted with hydroxyl or —O—$C_{1-3}$alkyl.

In some embodiments, $R^1$ is selected from the group consisting of $C_{1-6}$alkyl, $C_{1-3}$haloalkyl, $C_{3-6}$cycloalkyl, and aryl, wherein the $C_{1-6}$alkyl may be optionally substituted with hydroxyl or —O—$CH_3$.

In some embodiments, $R^1$ is selected from the group consisting of —$CH(CH_3)_2$, $CF_3$, cyclopropyl, phenyl,

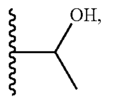

and

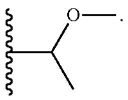

In some embodiments, $R^2$ is selected from the group consisting of $C_{1-6}$alkyl, $C_{3-6}$cycloalkyl, aryl, and 5-10 membered heteroaryl, wherein the $C_{1-6}$alkyl and aryl may be optionally substituted with hydroxyl, cyano, $C_{1-6}$alkyl, or —O—$C_{1-3}$alkyl.

In some embodiments, $R^2$ is selected from the group consisting of $C_{1-6}$alkyl, $C_{3-6}$cycloalkyl, aryl, and 5-10 membered heteroaryl, wherein the $C_{1-6}$alkyl and aryl may be optionally substituted with hydroxyl, cyano, $CH_3$, or —O—$CH_3$.

In some embodiments, $R^2$ is selected from the group consisting of $CH_3$, cyclopropyl, —$C(H)(CH_3)_2$, —$CH_2C(CH_3)_3$, phenyl,

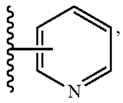, 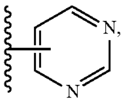 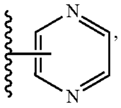, 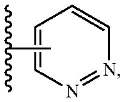 and 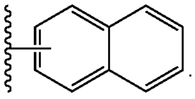.

In some embodiments, $R^2$ is selected from the group consisting of $CH_3$, cyclopropyl, —$C(H)(CH_3)_2$, —$CH_2C(CH_3)_3$, phenyl,

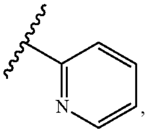, 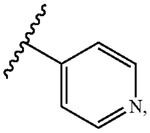 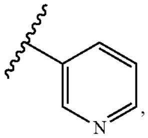, 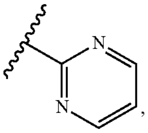, 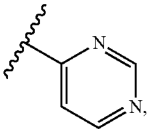 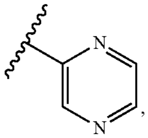, 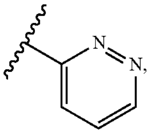 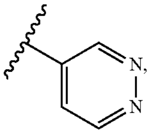 and 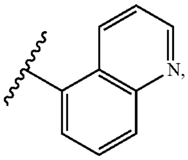

In some embodiments, $R^2$ is $C_{1-6}$alkyl or aryl, wherein the $C_{1-6}$alkyl and aryl is substituted with hydroxyl, cyano, $CH_3$, or —O—$CH_3$.

In some embodiments, $R^2$ is $C_{1-6}$alkyl or phenyl, wherein the $C_{1-6}$alkyl or phenyl is substituted with hydroxyl, cyano, $CH_3$, or —O—$CH_3$.

In some embodiments, $R^2$ is selected from the group consisting of

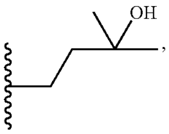, 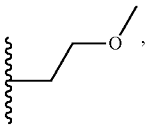, 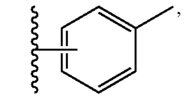, and 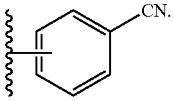

In some embodiments, $R^2$ is selected from the group consisting of

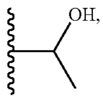 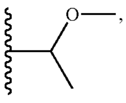,

-continued

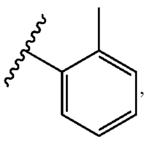, 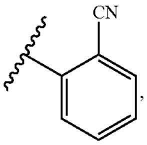, and 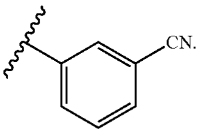

In some embodiments, $R^2$ is selected from the group consisting of $CH_3$, cyclopropyl, —$C(H)(CH_3)_2$, —$CH_2C(CH_3)_3$, phenyl,

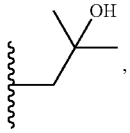, 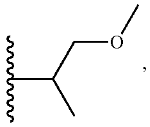, 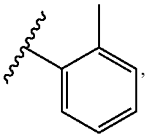, 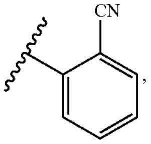, 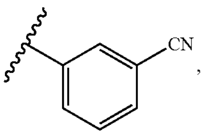, 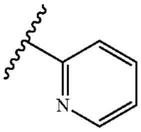, 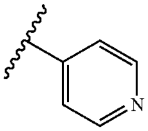, 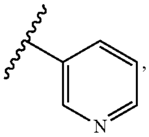, 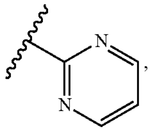, 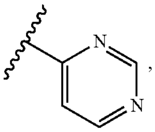, 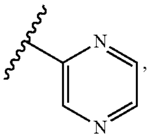, 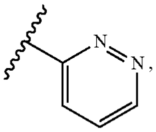 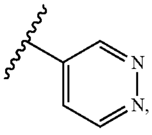 and 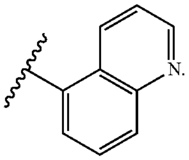

In some embodiments, $R^3$ is hydrogen or $CH_3$. In some embodiments, $R^3$ is $CH_3$.

In some embodiments, Z is —$SO_2$—.

In some embodiments, m is 1 and n is 1.

In some embodiments, Z is —$NR^A$—.

In some embodiments, m is 0 and n is 0. In some embodiments, m is 1 and n is 1.

In some embodiments, $R^A$ is —$C(O)C_{1-6}$alkyl. In some embodiments, $R^A$ is —$C(O)CH_3$.

In some embodiments, Z is —$C(H)(R^A)$—.

In some embodiments, m is 0 and n is 0.

In some embodiments, $R^A$ is —C(O)OH.

In some embodiments, m is 1 and n is 1.

In some embodiments, $R^A$ is —C(O)OH or 5-6 membered heteroaryl. In some embodiments, $R^A$ is —C(O)OH or

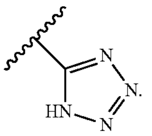 [SMILES: *c1nnn[nH]1]

In another aspect, provided herein are compounds represented by Formula (Ia):

(Ia)

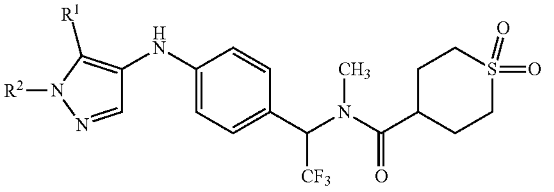

or a stereoisomer and/or a pharmaceutically acceptable salt thereof, wherein:

$R^1$ is selected from $C_{1-6}$alkyl, $C_{1-3}$haloalkyl, or aryl, wherein the $C_{1-6}$alkyl may be optionally substituted on one or more available carbons by one, two, three, or more substituents each independently selected from $R^{1a}$;

$R^2$ is selected from the group consisting of $C_{1-6}$alkyl, $C_{3-6}$cycloalkyl, aryl, and 5-10 membered heteroaryl, wherein $R^2$ may be optionally substituted on one or more available carbons by one, two, three, or more substituents each independently selected from $R^{2a}$;

$R^{1a}$ is independently, for each occurrence, hydroxyl or —O—$C_{1-3}$alkyl; and $R^{2a}$ is independently, for each occurrence, selected from the group consisting of hydroxyl, cyano, $C_{1-6}$alkyl, and —O—$C_{1-3}$alkyl.

In some embodiments, the compound is represented by Formula (Ia'):

(Ia')

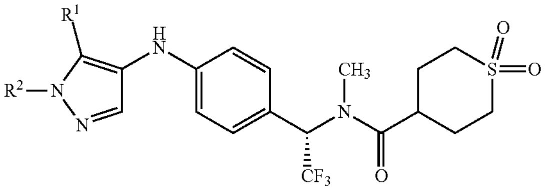

or a stereoisomer and/or a pharmaceutically acceptable salt thereof, wherein:

$R^1$ is selected from $C_{1-6}$alkyl, $C_{1-3}$haloalkyl, or aryl, wherein the $C_{1-6}$alkyl may be optionally substituted on one or more available carbons by one, two, three, or more substituents each independently selected from $R^{1a}$;

$R^2$ is selected from the group consisting of $C_{1-6}$alkyl, $C_{3-6}$cycloalkyl, aryl, and 5-10 membered heteroaryl, wherein $R^2$ may be optionally substituted on one or more available carbons by one, two, three, or more substituents each independently selected from $R^2$;

$R^{1a}$ is independently, for each occurrence, hydroxyl or —O—$C_{1-3}$alkyl; and $R^{2a}$ is independently, for each occurrence, selected from the group consisting of hydroxyl, cyano, $C_{1-6}$alkyl, and —O—$C_{1-3}$alkyl.

In some embodiments, $R^1$ is $C_{1-6}$alkyl, $C_{1-3}$haloalkyl, or aryl, wherein the $C_{1-6}$alkyl may be optionally substituted with hydroxyl or —O—$C_{1-3}$alkyl.

In some embodiments, $R^1$ is $C_{1-6}$alkyl, $C_{1-3}$haloalkyl, or aryl, wherein the $C_{1-6}$alkyl may be optionally substituted with hydroxyl or —O—$CH_3$.

In some embodiments, $R^1$ is selected from the group consisting of —$CH(CH_3)_2$, $CF_3$, phenyl,

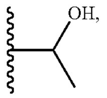 and 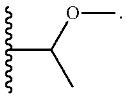

In some embodiments, $R^2$ is selected from the group consisting of $C_{1-6}$alkyl, $C_{3-6}$cycloalkyl, aryl, and 5-10 membered heteroaryl, wherein the $C_{1-6}$alkyl and aryl may be optionally substituted with hydroxyl, cyano, $C_{1-6}$alkyl, or —O—$C_{1-3}$alkyl.

In some embodiments, $R^2$ is selected from the group consisting of $C_{1-6}$alkyl, $C_{3-6}$cycloalkyl, aryl, and 5-10 membered heteroaryl, wherein the $C_{1-6}$alkyl and aryl may be optionally substituted with hydroxyl, cyano, $CH_3$, or —O—$CH_3$.

In some embodiments, $R^2$ is selected from the group consisting of $CH_3$, cyclopropyl, —$C(H)(CH_3)_2$, —$CH_2C(CH_3)_3$, phenyl,

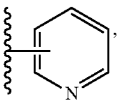, 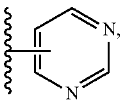, 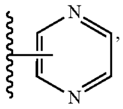, 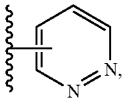, and 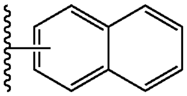.

In some embodiments, $R^2$ is selected from the group consisting of $CH_3$, cyclopropyl, —$C(H)(CH_3)_2$, —$CH_2C(CH_3)_3$, phenyl,

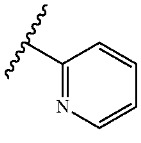, 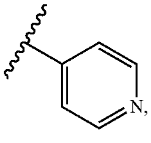, 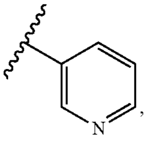, 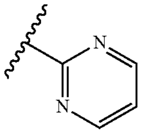, 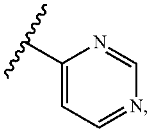, 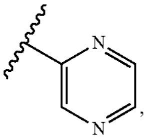, 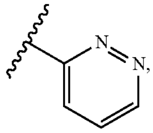, 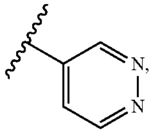, and -continued

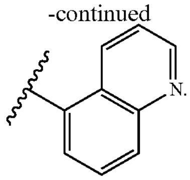

In some embodiments, $R^2$ is $C_{1-6}$alkyl or aryl, wherein the $C_{1-6}$alkyl and aryl is substituted with hydroxyl, cyano, $CH_3$, or —O—$CH_3$.

In some embodiments, $R^2$ is $C_{1-6}$alkyl or phenyl, wherein the $C_{1-6}$alkyl or phenyl is substituted with hydroxyl, cyano, $CH_3$, or —O—$CH_3$.

In some embodiments, $R^2$ is selected from the group consisting of

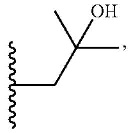,
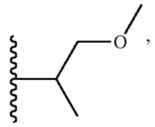,
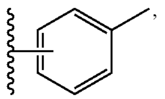, and 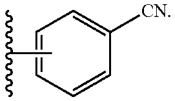

In some embodiments, $R^2$ is selected from the group consisting of

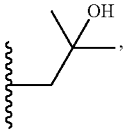,
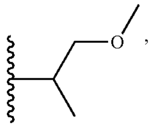,
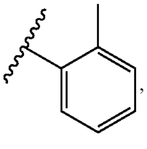,
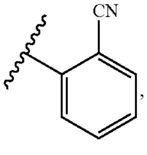, and
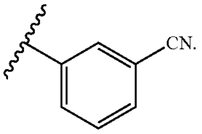

In some embodiments, $R^2$ is selected from the group consisting of $CH_3$, cyclopropyl, —C(H)($CH_3$)$_2$, —$CH_2$C($CH_3$)$_3$, phenyl

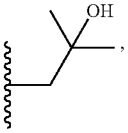,
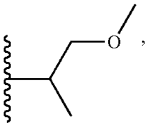,
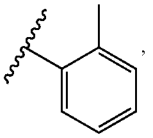,
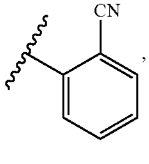,
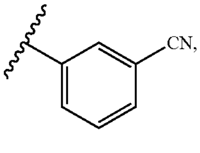,
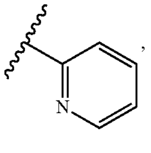,

-continued

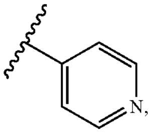,
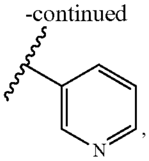,
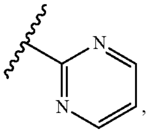,
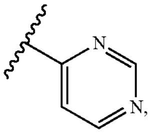,
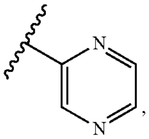,
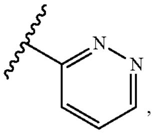,
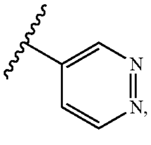, and
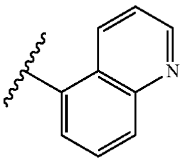.

In another aspect, provided herein are compounds represented by Formula (Ib):

(Ib)

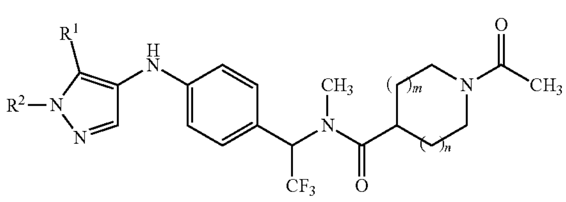

or a stereoisomer and/or a pharmaceutically acceptable salt thereof, wherein:

$R^1$ is $C_{1-6}$alkyl, $C_{1-3}$haloalkyl, or $C_{3-6}$cycloalkyl, wherein the $C_{1-6}$alkyl may be optionally substituted with —O—$C_{1-3}$alkyl;

$R^2$ is aryl or 5-6 membered heteroaryl, wherein the aryl may be optionally substituted with cyano;

m is 0 or 1; and n is 0 or 1.

In some embodiments, the compound is represented by Formula (Ib'):

(Ib')

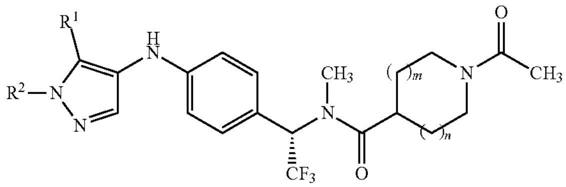

or a stereoisomer and/or a pharmaceutically acceptable salt thereof, wherein:

$R^1$ is $C_{1-6}$alkyl, $C_{1-3}$haloalkyl, or $C_{3-6}$cycloalkyl, wherein the $C_{1-6}$alkyl may be optionally substituted with —O—$C_{1-3}$alkyl;

$R^2$ is aryl or 5-6 membered heteroaryl, wherein the aryl may be optionally substituted with cyano;

m is 0 or 1; and n is 0 or 1.

In some embodiments, $R^1$ is $C_{1-6}$alkyl, $C_{1-3}$haloalkyl, or $C_{3-6}$cycloalkyl, wherein the $C_{1-6}$alkyl may be optionally substituted with —O—$CH_3$.

In some embodiments, $R^1$ is selected from the group consisting of —$CH(CH_3)_2$, $CF_3$, cyclopropyl, and

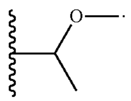 [SMILES: *C(C)OC]

In some embodiments, $R^2$ is phenyl or

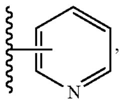

wherein the phenyl is optionally substituted with cyano.

In some embodiments, $R^2$ is selected from the group consisting of phenyl,

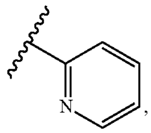
,
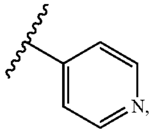
and
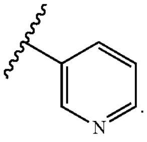

In some embodiments, $R^2$ is

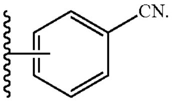

In some embodiments, $R^2$ is

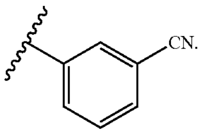 [SMILES: *c1cccc(C#N)c1]

In some embodiments, $R^2$ is selected from the group consisting of phenyl,

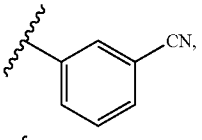
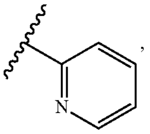
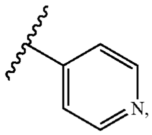
and
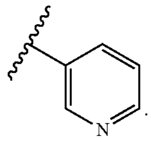

In some embodiments, m is 0 and n is 0. In some embodiments, m is 1 and n is 1.

In another aspect, provided herein are compounds represented by Formula (Ic):

(Ic)

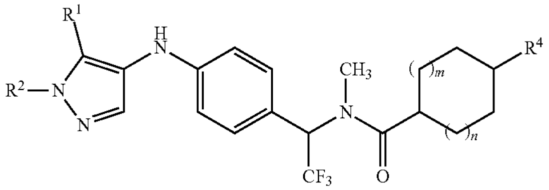

or a stereoisomer and/or a pharmaceutically acceptable salt thereof, wherein:

$R^1$ is $C_{1-6}$alkyl or $C_{1-3}$haloalkyl, wherein the $C_{1-6}$alkyl may be optionally substituted with —O—$C_{1-3}$alkyl;

$R^2$ is aryl or 5-6 membered heteroaryl, wherein the aryl may be optionally substituted with cyano;

$R^4$ is —C(O)OH or 5-6 membered heteroaryl;

m is 0 or 1; and n is 0 or 1.

In some embodiments, the compound is represented by formula (Ic'):

(Ic')

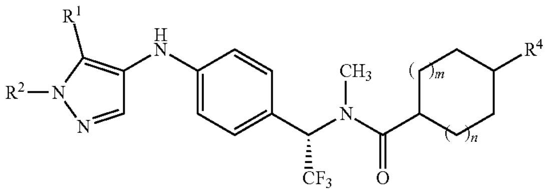

or a stereoisomer and/or a pharmaceutically acceptable salt thereof, wherein:

$R^1$ is $C_{1-6}$alkyl or $C_{1-3}$haloalkyl, wherein the $C_{1-6}$alkyl may be optionally substituted with —O—$C_{1-3}$alkyl;

$R^2$ is aryl or 5-6 membered heteroaryl, wherein the aryl may be optionally substituted with cyano;

$R^4$ is —C(O)OH or 5-6 membered heteroaryl;

m is 0 or 1; and n is 0 or 1.

In some embodiments, $R^1$ is $C_{1-6}$alkyl or $C_{1-3}$haloalkyl, wherein the $C_{1-6}$alkyl may be optionally substituted with —O—$CH_3$.

In some embodiments, $R^1$ is $CF_3$ or

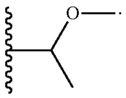

In some embodiments, $R^2$ is phenyl,

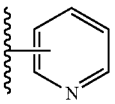
or
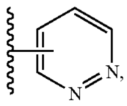

wherein the phenyl is optionally substituted with cyano.

In some embodiments, $R^2$ is selected from the group consisting of phenyl,

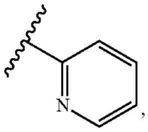, 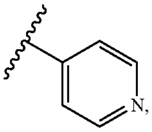 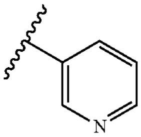, and 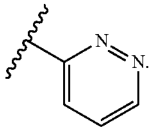

In some embodiments, $R^2$ is

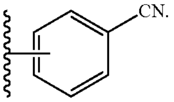

In some embodiments, $R^2$ is

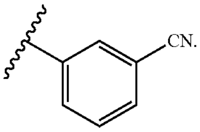 [SMILES: *c1cccc(C#N)c1]

In some embodiments, $R^2$ is selected from the group consisting of phenyl,

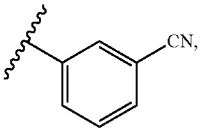 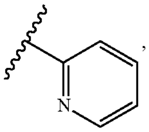, 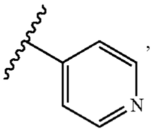,

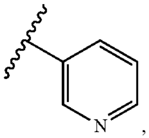, and 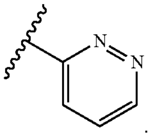.

In some embodiments, m is 0 and n is 0.

In some embodiments, $R^4$ is —C(O)OH.

In some embodiments, the compound is selected from any compound set forth in Table 1, or a pharmaceutically acceptable salt thereof.

TABLE 1

List of compounds.

| Cmpd No. | Structure |
|---|---|
| 1.1 | 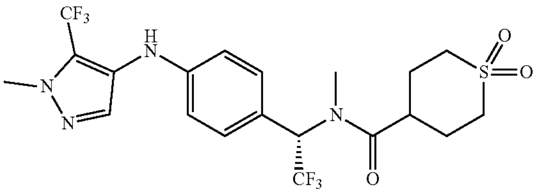 |
| 1.2 | 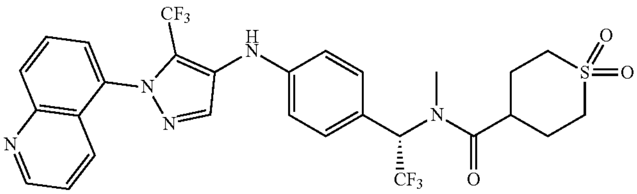 |
| 1.3 | 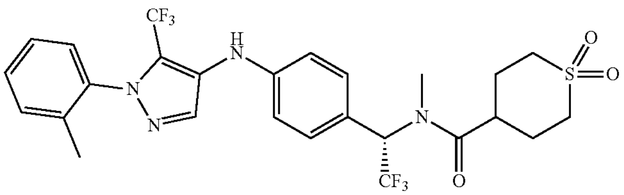 |

TABLE 1-continued
List of compounds.
| Cmpd No. | Structure |
|---|---|
| 1.4 | 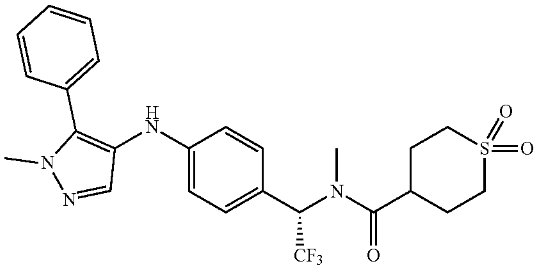 |
| 1.5 | 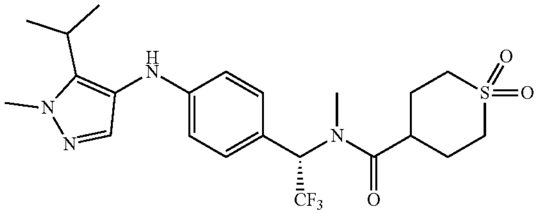 |
| 1.6 | 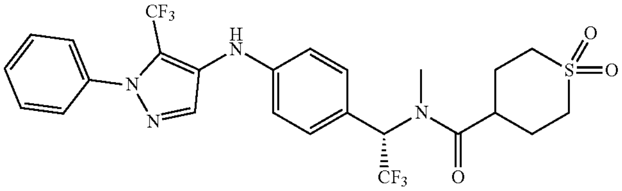 |
| 1.7 | 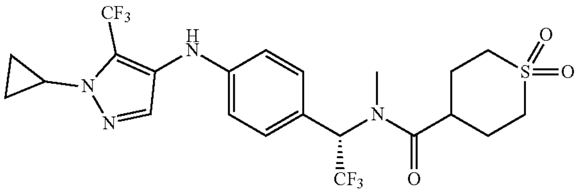 |
| 1.8 | 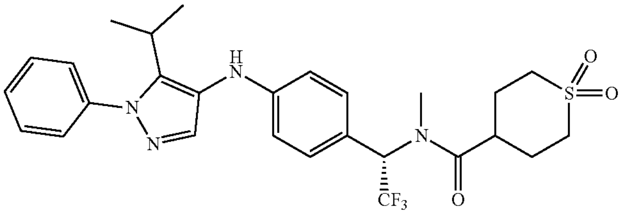 |
| 1.9 | 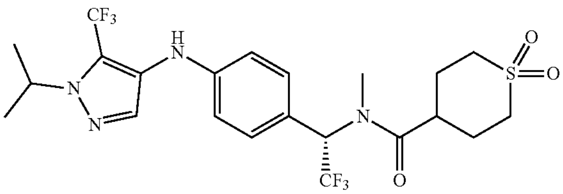 |
| 1.10 | 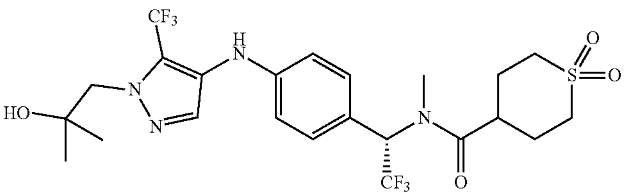 |

TABLE 1-continued
List of compounds.
| Cmpd No. | Structure |
|---|---|
| 1.11 | 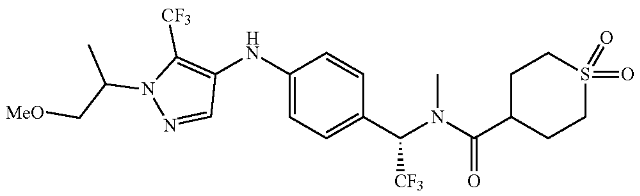 |
| 1.12 | 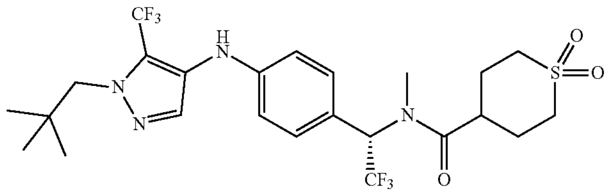 |
| 1.13 | 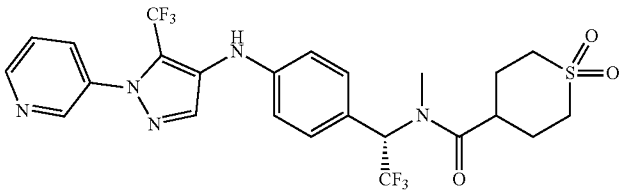 |
| 1.14 | 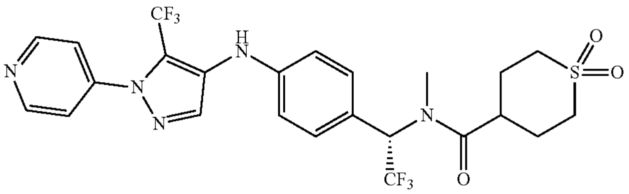 |
| 1.15 | 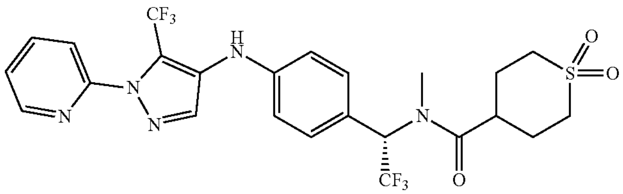 |
| 1.16 | 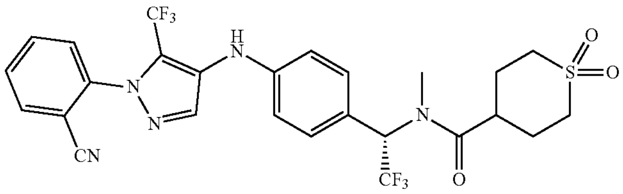 |
| 1.17 | 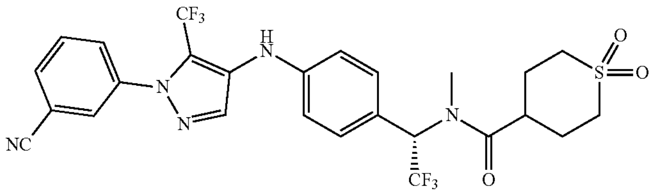 |

TABLE 1-continued
| List of compounds. | |
|---|---|
| Cmpd No. | Structure |
| 1.18 | 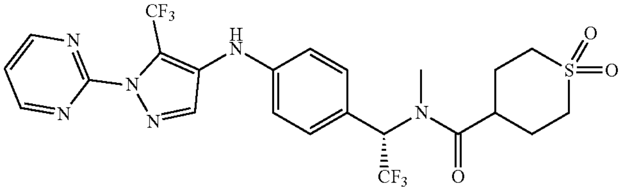 |
| 1.19 | 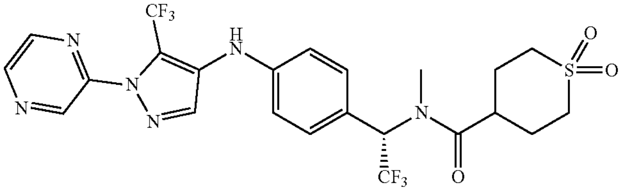 |
| 1.20 | 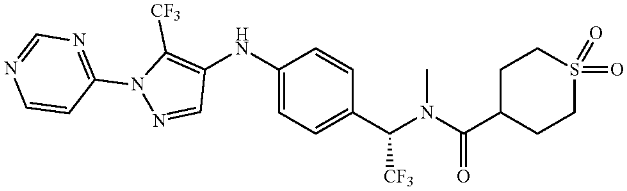 |
| 1.21 | 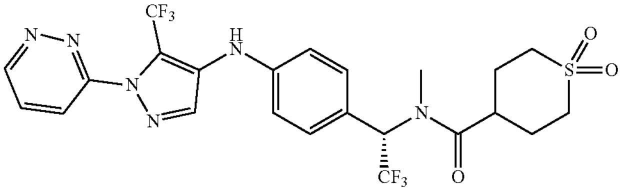 |
| 1.22 | 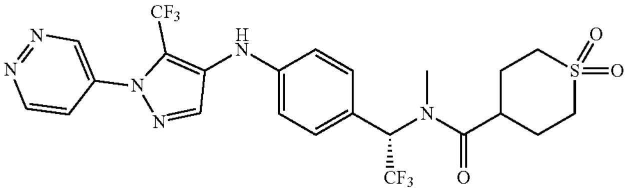 |
| 1.23 | 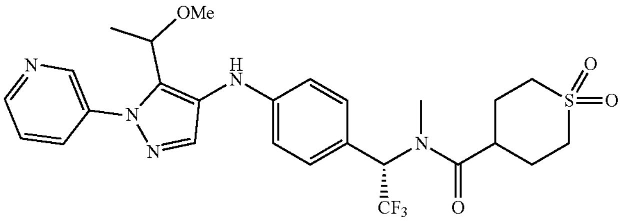 |
| 1.24 | 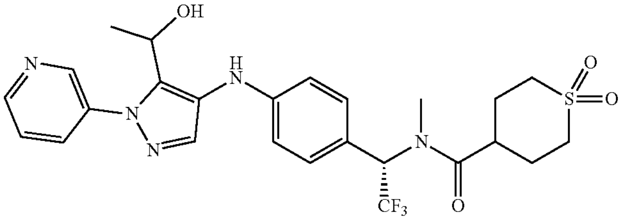 |

TABLE 1-continued
| List of compounds. | |
|---|---|
| Cmpd No. | Structure |
| 1.25 | 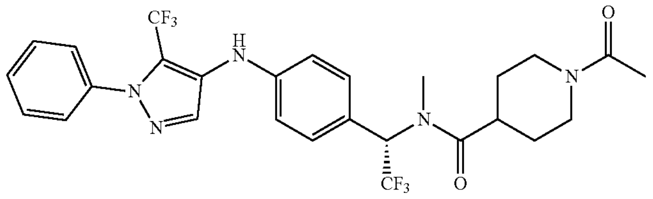 |
| 1.26 | 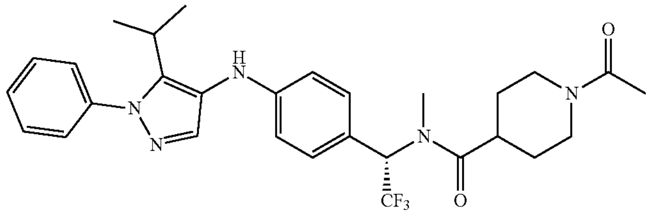 |
| 1.27 | 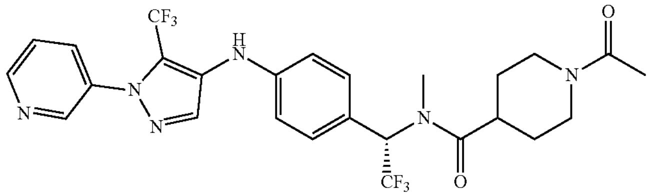 |
| 1.28 | 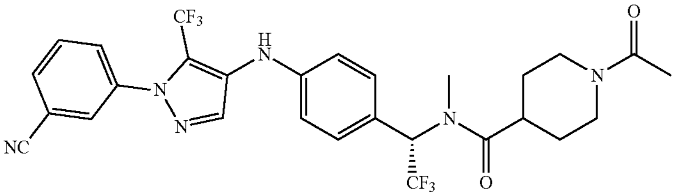 |
| 1.29 | 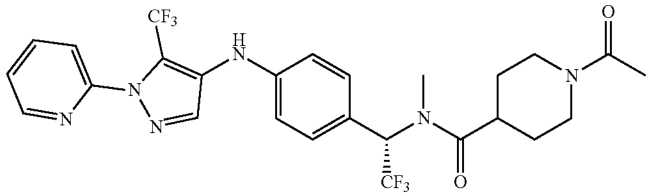 |
| 1.30 | 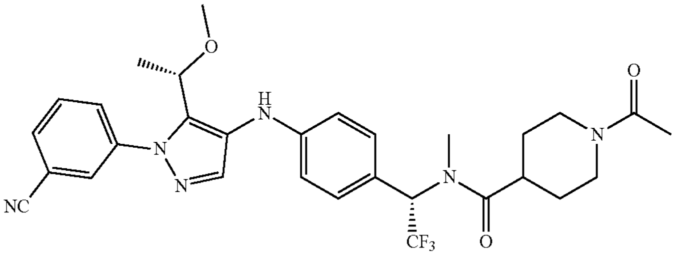 |

TABLE 1-continued
List of compounds.
| Cmpd No. | Structure |
|---|---|
| 1.31 | 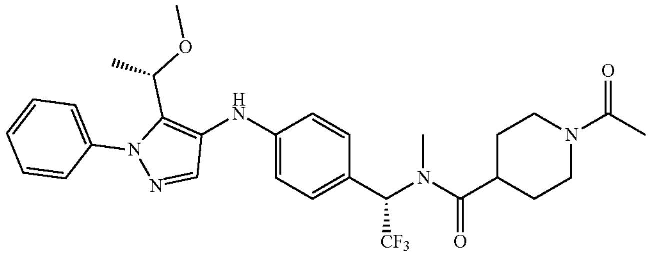 |
| 1.32 | 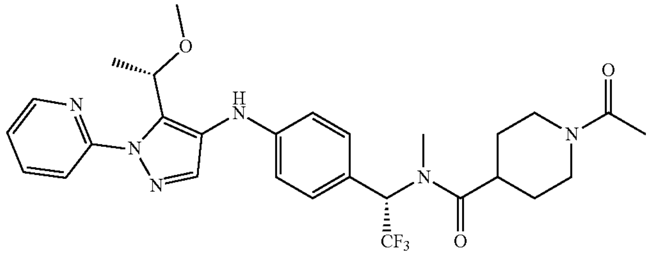 |
| 1.33 | 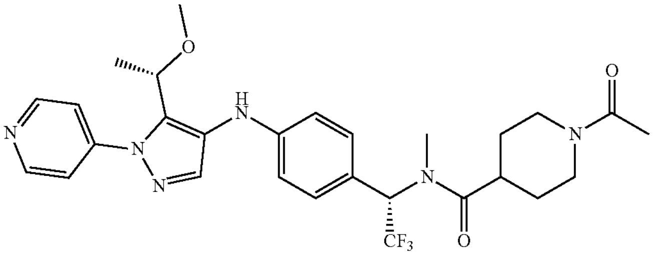 |
| 1.34 | 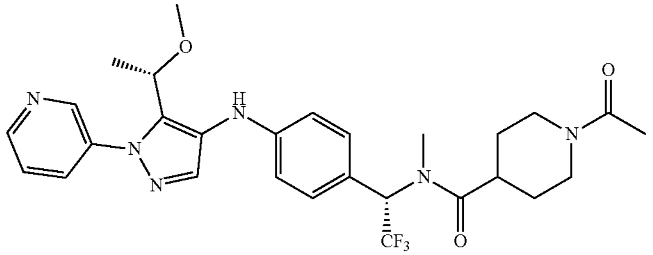 |
| 1.35 | 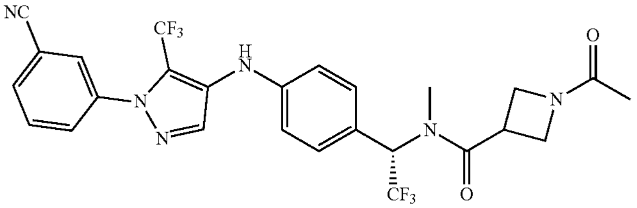 |
| 1.36 | 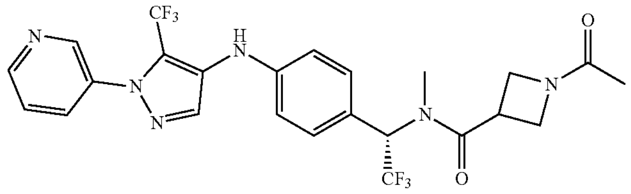 |

TABLE 1-continued
List of compounds.
| Cmpd No. | Structure |
|---|---|
| 1.37 | 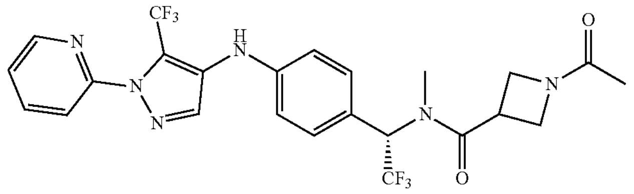 |
| 1.38 | 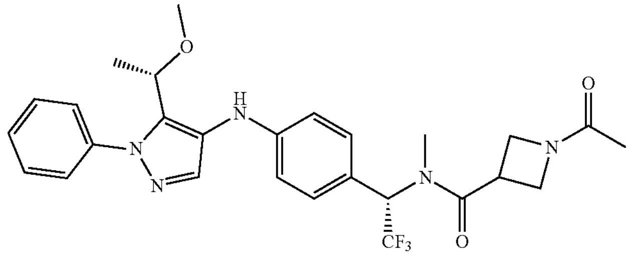 |
| 1.39 | 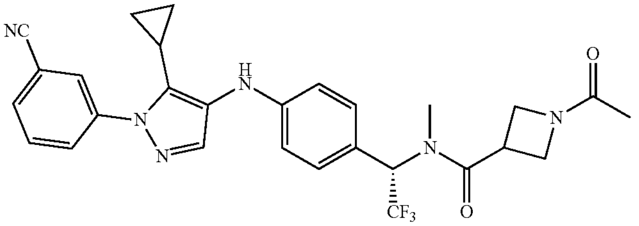 |
| 1.40 | 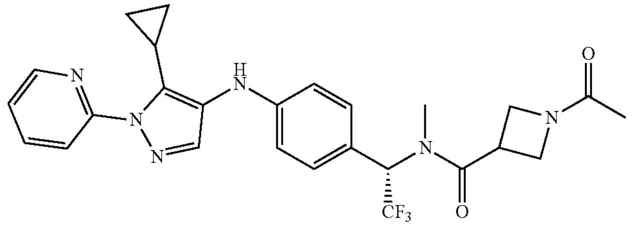 |
| 1.41 | 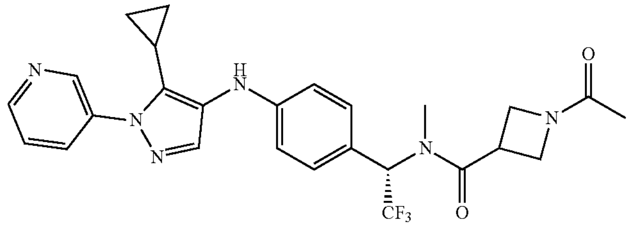 |
| 2.1 | 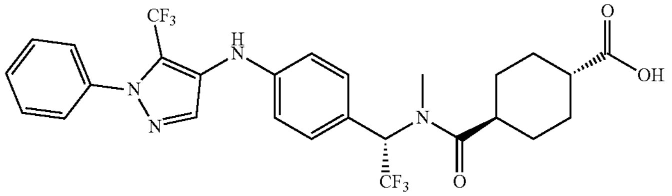 |

TABLE 1-continued
List of compounds.
| Cmpd No. | Structure |
|---|---|
| 2.2 | 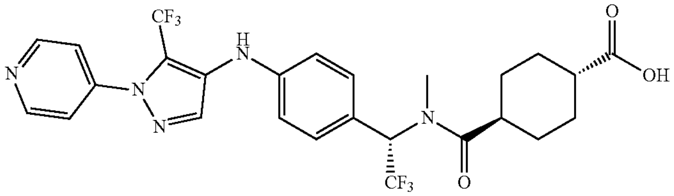 |
| 2.3 | HCl 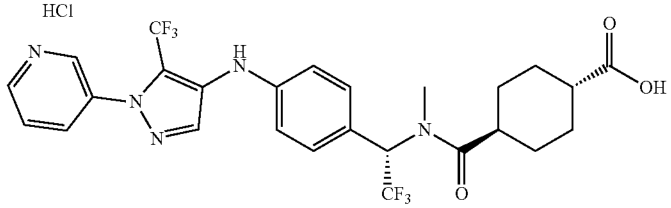 |
| 2.4 | 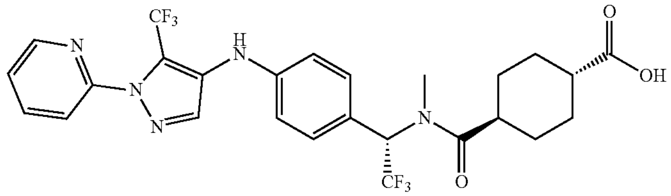 |
| 2.5 | 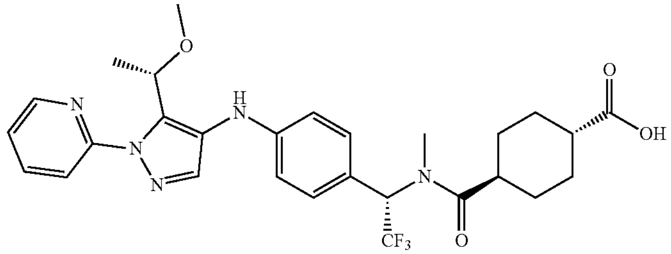 |
| 2.6 | 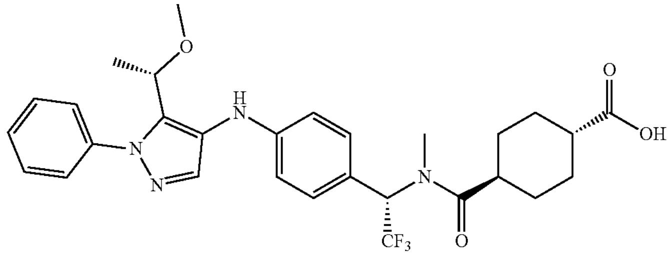 |
| 2.7 | 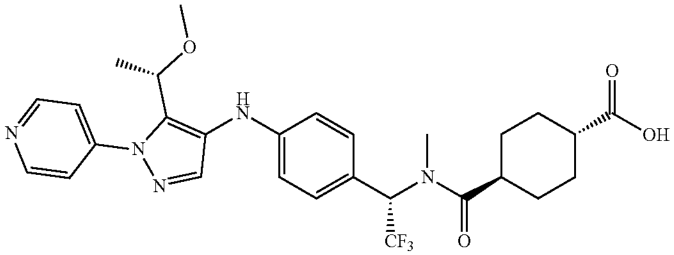 |

TABLE 1-continued
List of compounds.
| Cmpd No. | Structure |
| --- | --- |
| 2.8 | 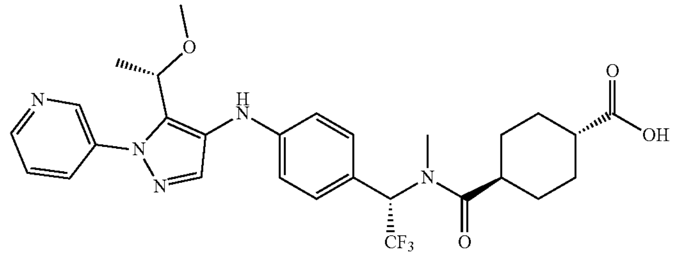 |
| 2.9 | 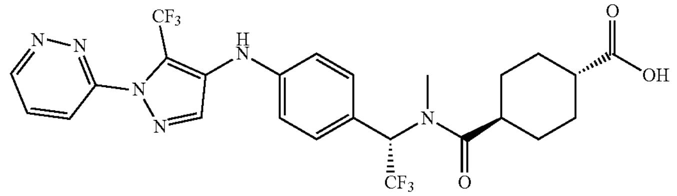 |
| 2.10 | 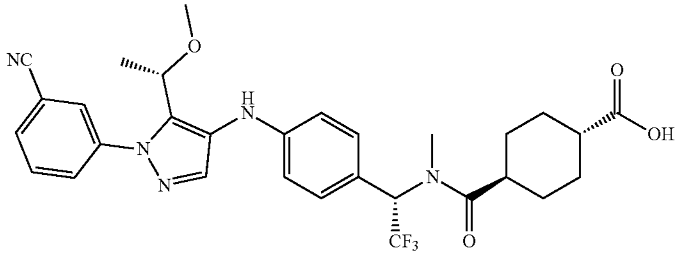 |
| 2.11 | 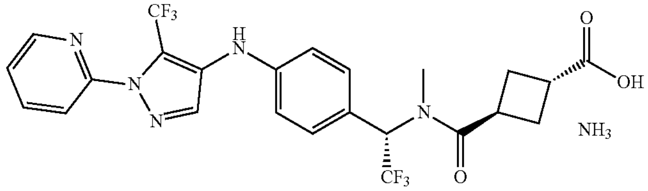 |
| 2.12 | 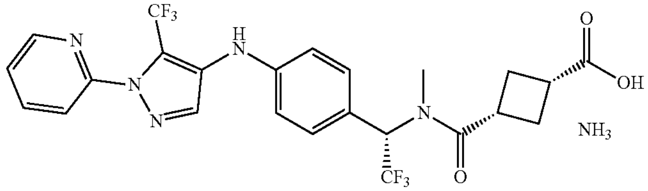 |
| 2.13 | 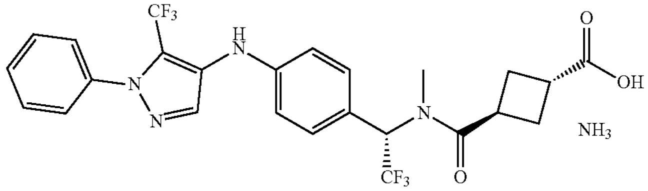 |
| 2.14 | 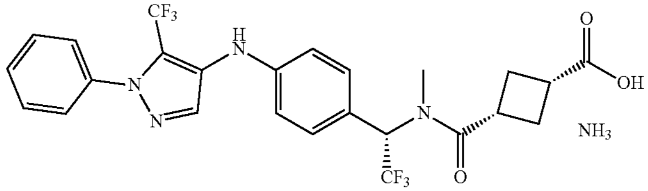 |

TABLE 1-continued

| List of compounds. | |
|---|---|
| Cmpd No. | Structure |
| 3.1 | 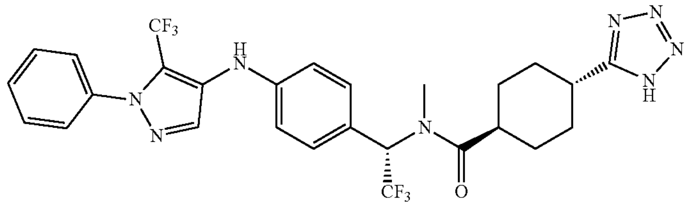 |

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches").

Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprises a disclosed compound, or a stereoisomer and/or pharmaceutically acceptable salt thereof, and a pharmaceutically acceptable carrier.

Methods of Use

Compounds and compositions described herein are generally useful for modulating MALT1 and are useful for treating diseases or disorders, in particular those susceptible to modulation of proteolytic and/or autoproteolytic activity of MALT1. In some embodiments, the compounds and compositions described herein are useful for inhibiting MALT1. In some embodiments, it is contemplated that the compounds and compositions of the present invention may be useful in the treatment of a disease, a disorder, or a condition characterized by dysregulated NF-kB activation, for example, autoimmune or immunological and inflammatory disorders, allergic disorders, respiratory disorders and oncological disorders.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein, e.g., a compound of Formula I, Ia, Ib, or Ic.

In some embodiments, the autoimmune and inflammatory disorders are selected from arthritis, ankylosing spondylitis, inflammatory bowel disease, ulcerative colitis, gastritis, pancreatitis, Crohn's disease, celiac disease, multiple sclerosis, systemic lupus erythematosus, lupus nephritis, rheumatoid arthritis, rheumatic fever, gout, organ or transplant rejection, acute or chronic graft-versus-host disease, chronic allograft rejection, Behcet's disease, uveitis, psoriasis, psoriatic arthritis, BENTA disease, polymyositis, dermatitis, atopic dermatitis, dermatomyositis, acne vulgaris, myasthenia gravis, hidradenitis suppurativa, Grave's disease, Hashimoto thyroiditis, Sjogren's syndrome, and blistering disorders (e.g., pemphigus vulgaris), antibody-mediated vasculitis syndromes, including ANCA-associated vasculitides, Henoch-Schonlein Purpura, and immune-complex vasculitides (either primary or secondary to infection or cancers).

In some embodiments, the autoimmune or inflammatory disorder or disease is selected from the group consisting of acute graft-versus-host disease, chronic graft-versus-host disease, lupus, scleroderma, psoriatic arthritis, primary sclerosing cholangitis, rheumatoid arthritis, and an inflammatory bowel disease.

In some embodiments, the oncological disorders are selected from carcinoma, sarcoma, lymphoma, leukemia and germ cell tumors, adenocarcinoma, bladder cancer, clear cell carcinoma, skin cancer, brain cancer, cervical cancer, colon cancer, colorectal cancer, endometrial cancer, brain tumors, breast cancer, gastric cancer, germ cell tumors, glioblastoma, hepatic adenomas, Hodgkin's lymphoma, liver cancer, kidney cancer, lung cancer, pancreatic cancer, head/neck/throat cancer, ovarian cancer, dermal tumors, prostate cancer, renal cell carcinoma, stomach cancer, hematologic cancer, medulloblastoma, non-Hodgkin's lymphoma, diffuse large B-cell lymphoma (DLBCL), activated B cell-like diffuse large B Cell lymphoma (ABC-DLBCL), mantle cell lymphoma, marginal zone lymphoma, T cell lymphomas, in particular Sezary syndrome, Mycosis fungoides, cutaneous T-cell lymphoma, T-cell acute lymphoblastic leukemia, melanoma, mucosa-associated lymphoid tissue (MALT)

lymphoma, multiple myeloma, plasma cell neoplasm, lentigo maligna melanomas, acral lentiginous melanoma, squamous cell carcinoma, chronic myelogenous leukemia, myeloid leukemia, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, uveal melanoma, precursor T-cell, leukemia/lymphoma, acute myeloid leukemia, chronic myeloid leukemia, acute lymphocytic leukemia, follicular lymphoma, chronic lymphocytic leukemia/lymphoma, Burkitt's lymphoma, mycosis fungoides, peripheral T-cell lymphoma, nodular sclerosis form of Hodgkin lymphoma, mixed-cellularity subtype of Hodgkin lymphoma, non-small-cell lung cancer, large-cell carcinoma, and small-cell lung carcinoma.

In some embodiments, the oncological disorder is a cancer in the form of a tumor or a blood born cancer. In some embodiments, the tumor is a solid tumor. In some embodiments, the tumor is malignant and/or metastatic. In some embodiments, the tumor is selected from an adenoma, an adenocarcinoma, a blastoma (e.g., hepatoblastoma, glioblastoma, neuroblastoma and retinoblastoma), a carcinoma (e.g., colorectal carcinoma or hepatocellular carcinoma, pancreatic, prostate, gastric, esophageal, cervical, and head and neck carcinomas, and adenocarcinoma), a desmoid tumor, a desmoplastic small round cell tumor, an endocrine tumor, a germ cell tumor, a lymphoma, a leukemia, a sarcoma (e.g., Ewing sarcoma, osteosarcoma, rhabdomyosarcoma, or any other soft tissue sarcoma), a Wilms tumor, a lung tumor, a colon tumor, a lymph tumor, a breast tumor or a melanoma.

In some embodiments, the allergic disorder is selected from contact dermatitis, celiac disease, asthma, hypersensitivity to house dust mites, pollen and related allergens, and berylliosis.

In some embodiments, the respiratory disorder is selected from asthma, bronchitis, chronic obstructive pulmonary disease (COPD), cystic fibrosis, pulmonary edema, pulmonary embolism, pneumonia, pulmonary sarcoidosis, silicosis, pulmonary fibrosis, respiratory failure, acute respiratory distress syndrome, primary pulmonary hypertension and emphysema.

In some embodiments, the compounds and compositions of the present invention may be useful in the treatment of rheumatoid arthritis, systemic lupus erythematosus, vasculitic conditions, allergic diseases, asthma, chronic obstructive pulmonary disease (COPD), acute or chronic transplant rejection, graft versus host disease, cancers of hematopoietic origin or solid tumors, chronic myelogenous leukemia, myeloid leukemia, non-Hodgkin lymphoma or other B cell lymphomas.

Combination Therapy

A compound of composition described herein may be administered in combination with another agent or therapy. A subject to be administered a compound disclosed herein may have a disease, disorder, or condition, or a symptom thereof, that would benefit from treatment with another agent or therapy.

In some embodiments, the compound of composition described herein may be administered either simultaneously with, or before or after, one or more other therapeutic agent. In some embodiments, the compound of composition described herein may be administered separately, by the same or different route of administration, or together in the same pharmaceutical composition as the other agents.

In some embodiments, the compound described herein may be administered as the sole active ingredient or in conjunction with, e.g., as an adjuvant to, other drugs e.g., immunosuppressive or immunomodulating agents or other anti-inflammatory agents, e.g., for the treatment or prevention of alio- or xenograft acute or chronic rejection or inflammatory or autoimmune disorders, or a chemotherapeutic agent, e.g., a malignant cell anti-proliferative agent. For example, the compounds of the invention may be used in combination with a calcineurin inhibitor, e.g., cyclosporin A or FK 506; a mTOR inhibitor, e.g., rapamycin, 40-0-(2-hydroxyethyl)-rapamycin, biolimus-7 or biolimus-9; an ascomycin having immunosuppressive properties, e.g., ABT-281, ASM981; corticosteroids; cyclophosphamide; azathioprene; methotrexate; leflunomide; mizoribine; mycophenolic acid or salt; mycophenolate mofetil; or IL-1 beta inhibitor.

In some embodiments, the compound described herein is combined with a co-agent which is a PI3K inhibitor.

In some embodiments, the compound described herein is combined with co-agent that influence BTK (Bruton's tyrosine kinase).

For the treatment of oncological diseases, the compound described herein may be used in combination with B-cell modulating agents, e.g., Rituximab, Ofatumumab, BTK or SYK inhibitors, inhibitors of PKC, PI3K, PDK, PIM, JAK and mTOR and BH3 mimetics.

EXAMPLES

The representative examples that follow are intended to help illustrate the invention, and are not intended to, nor should they be construed to, limit the scope of the invention.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

LIST OF ABBREVIATIONS

EtOAc, EA ethyl acetate
THF tetrahydrofuran

PE petroleum ether
MeOH methanol
EtOH ethanol
DMF NN-dimethylformamide
FA formic acid
DCM dichloromethane
MeCN, ACN, $CH_3CN$ acetonitrile
xantphos 4,5-Bis(diphenylphosphino)-9,9-dimethylxanthene
h, hr, hrs hour(s)
Calcd calculated
UV ultraviolet
rt room temperature
DIEA, DIPEA N,N-Diisopropylethylamine
$Pd_2(dba)_3$ tris(dibenzylideneacetone)dipalladium(0)
$Et_3N$, TEA triethylamine
$Cs_2CO_3$ cesium carbonate
INT intermediate
t-BuOH tert-butyl alcohol
Boc tert-butyloxycarbonyl
$LiOH{\cdot}H_2O$ lithium hydroxide monohydrate
$NH_4Cl$ ammonium chloride
DPPA diphenylphosphoryl azide
NaOH sodium hydroxide
$(COCl)_2$ oxalyl chloride
$NaN_3$ sodium azide
CDI 1,1'-Carbonyldiimidazole
BnOH benzyl alcohol
Cbz benzyloxycarbonyl
$SnCl_2$ stannous chloride
HCl hydrochloric acid
$NaNO_2$ sodium nitrite
KOH potassium hydroxide
$BH_3{\cdot}DMS$ borane dimethyl sulfide complex
$H_2O_2$ hydrogen peroxide
$RuCl_3$ ruthenium trichloride
NaIO4 sodium periodate
NaH sodium hydride
$KNO_3$ potassium nitrate
$H_2SO_4$ sulfuric acid
Pd/C palladium on carbon
DMF-DMA, N,N-Dimethylformamide dimethyl acetal $(CH_3)_2NCH(OCH_3)_2$
$CF_3CH_2OH$ 2,2,2-Trifluoroethanol
$N_2H_4$ hydrazine
$CH_3(NH)NH_2$ methylhydrazine
MeI methyl iodide
LiHMDS lithium bis(trimethylsilyl)amide
$(n\text{-}Bu)_4NOAc$ tetrabutylammonium acetate
$TMSCF_3$ trimethyl(trifluoromethyl)silane
AcOH acetic acid
$PtO_2$ platinum oxide
$NaBH_3CN$ sodium cyanoborohydride
CuCN cuprous cyanide
$MgCl_2$ magnesium chloride
$K_2CO_3$ potassium carbonate
CuI cuprous iodide
$CH_2I_2$ diiodomethane
$Pd(PPh_3)_2CO_2$ bis(triphenylphosphine)palladium(II) dichloride
$NaBH_4$ sodium borohydride Example 1. Preparation of the Compounds Methods for preparing compounds described herein are illustrated in the following synthetic schemes. These schemes are given for the purpose of illustrating the invention and should not be regarded in any manner as limiting the scope or the spirit of the invention. Starting materials shown in the schemes may be obtained from commercial sources or can be prepared from commercially available sources based on procedures described in the literature.

1. Compounds Prepared Using Scheme 1

Scheme 1

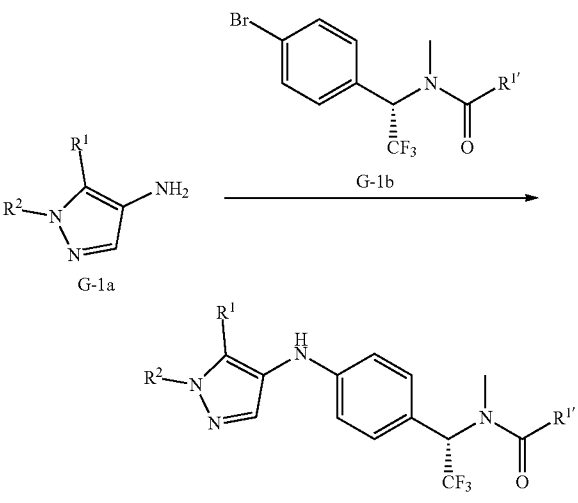
G-1b
G-1a

Compound of Formula (A)

G-1a is reacted with $R^{1'}$-containing carboxamide G-1b to provide a compound of Formula (A).

Exemplary procedure of compounds prepared using scheme 1:

Synthesis of (S)—N-methyl-N-(2,2,2-trifluoro-1-(4-((1-methyl-5-(trifluoromethyl)-1H-pyrazol-4-yl)amino)phenyl)ethyl)tetrahydro-2H-thiopyran-4-carboxamide 1,1-dioxide (Compound 1.1)

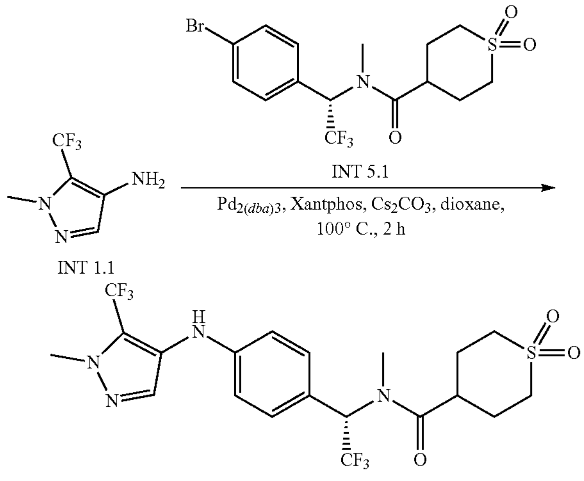

INT 5.1
INT 1.1

Compound 1.1

To a mixture of 1-methyl-5-(trifluoromethyl)-1H-pyrazol-4-amine [free base of INT 1.1] (50 mg, 302 μmol) and (S)—N-(1-(4-bromophenyl)-2,2,2-trifluoroethyl)-N-methyltetrahydro-2H-thiopyran-4-carboxamide 1,1-dioxide [INT 5.1] (155 mg, 362 μmol) in dioxane (2 mL) was added $Pd_2(dba)_3$ (27.6 mg, 30.2 μmol), xantphos (34.9 mg, 60.4 μmol) and $Cs_2CO_3$ (295 mg, 906 μmol). The mixture was stirred at 100° C. for 2 hr under $N_2$ atmosphere, after which it was quenched with water (30 mL) and extracted with EtOAc (3×20 mL). The combined organic layers were dried over anhydrous $Na_2SO_4$ and concentrated under reduced pressure to give the crude product, which was purified by prep-HPLC (column: YMC-Actus Triart C18 150*30 mm*5 μm, condition: 42%-62% $CH_3CN$ in water (0.05% ammonia hydroxide v/v)-ACN, flow rate: 35 mL/min) to give (S)—N-methyl-N-(2,2,2-trifluoro-1-(4-((1-methyl-5-(trifluoromethyl)-1H-pyrazol-4-yl)amino)phenyl)ethyl)tetrahydro-2H-thiopyran-4-carboxamide 1,1-dioxide [Compound 1.1] (20.6 mg, 40.1 μmol, 13.3% yield) as a white dry powder. m/z: [M+H]+ Calcd for C20H23F6N4O3S 513.1. Found 513.2. $^1$H NMR (400 MHz, $CD_3OD$) δ=7.55 (s, 1H), 7.19 (d, J=8.4 Hz, 2H), 6.82 (d, J=8.4 Hz, 2H), 6.57-5.95 (m, 1H), 4.00 (s, 3H), 3.30-3.09 (m, 5H), 2.98 (s, 3H), 2.39-2.10 (m, 4H).

2. Compounds Prepared Using Scheme 2

Scheme 2

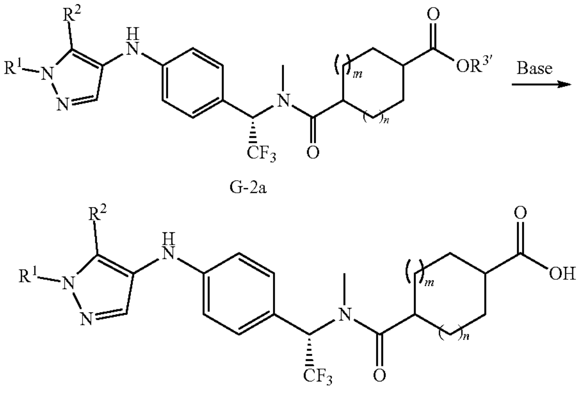

G-2a

Compound of Formula (B)

Starting material G-2a is treated with base ($LiOH \cdot H_2O$ or NaOH) to provide a compound of Formula (B). $R^2$ is phenyl, pyridyl, or pyridazine; $R^1$ is $CF_3$ or (S)-methoxyethane; and m and n are each independently 0 or 1. $R^{3'}$ is methyl or benzyl.

Exemplary procedures of compounds prepared using scheme 2:

Synthesis of (1S,4r)-4-(methyl((S)-2,2,2-trifluoro-1-(4-((1-phenyl-5-(trifluoromethyl)-1H-pyrazol-4-yl)amino)phenyl)ethyl)carbamoyl)cyclohexane-1-carboxylic Acid (Compound 2.1)

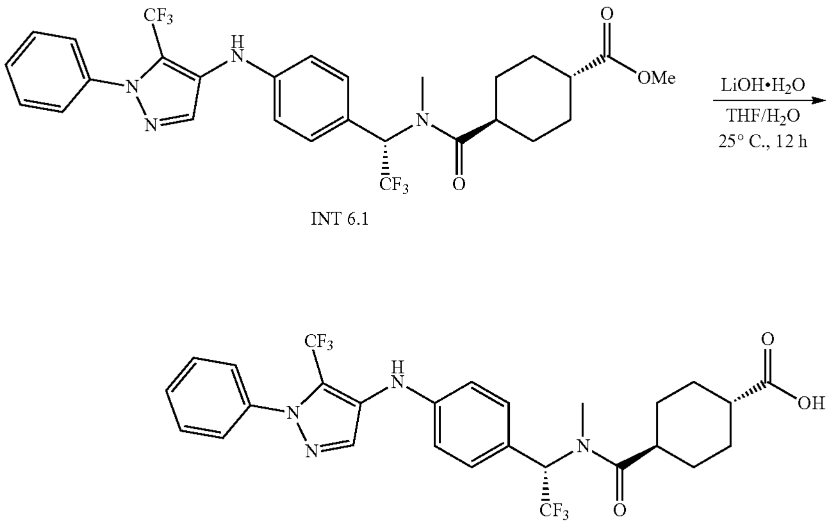

INT 6.1

Compound 2.1

To a mixture of methyl (1r,4r)-4-{methyl[(1S)-2,2,2-trifluoro-1-(4-{[1-phenyl-5-(trifluoromethyl)-1H-pyrazol-4-yl]amino}phenyl)ethyl]carbamoyl}cyclohexane-1-carboxylate [INT 6.1] (280 mg, 480 μmol) in THF (3 mL) and $H_2O$ (1 mL) was added $LiOH \cdot H_2O$ (60.4 mg, 1.44 mmol) and the mixture was stirred at 25° C. for 12 hr. The mixture was concentrated under reduced pressure to afford the crude product, which was purified by Prep-HPLC (column: YMC Actus Triart C18 150*30 mm*5 μm, table: 50-70% B (A=water(0.225% formic acid)-ACN), B=acetonitrile), flowrate: 35 mL/min, UV Detector 220 nm) to afford (1S,4r)-4-(methyl((S)-2,2,2-trifluoro-1-(4-((1-phenyl-5-(trifluoromethyl)-1H-pyrazol-4-yl)amino)phenyl)ethyl)carbamoyl)cyclohexane-1-carboxylic acid [Compound 2.1] (30.5 mg, 53.6 μmol, 11.2% yield) as a white dry powder. m/z: [M+H]+ Calcd for C27H27F6N4O3, 569.2. Found 569.1. $^1$H NMR (400 MHz, $CDCl_3$) δ=7.80 (s, 1H), 7.54-7.44 (m, 5H), 7.26-7.24 (m, 2H), 6.94 (d, J=8.8 Hz, 2H), 6.60 (q, J=9.2 Hz, 1H), 5.51 (s, 1H), 2.90 (s, 3H), 2.62-2.53 (m, 1H), 2.42 (tt, J=3.6, 12.0 Hz, 1H), 2.15 (br t, J=8.8 Hz, 2H), 2.01-1.82 (m, 2H), 1.67 (q, J=12.8 Hz, 2H), 1.56-1.42 (m, 2H).

Synthesis of (1r,3r)-3-{methyl[(1S)-2,2,2-trifluoro-1-(4-{[1-(pyridin-2-yl)-5-(trifluoromethyl)-1H-pyrazol-4-yl]amino}phenyl)ethyl]carbamoyl}cyclobutane-1-carboxylic Acid Amine (Compound 2.11) and (1s,3s)-3-{methyl[(1S)-2,2,2-trifluoro-1-(4-{[1-(pyridin-2-yl)-5-(trifluoromethyl)-1H-pyrazol-4-yl]amino}phenyl)ethyl]carbamoyl}cyclobutane-1-carboxylic Acid Amine (Compound 2.12)

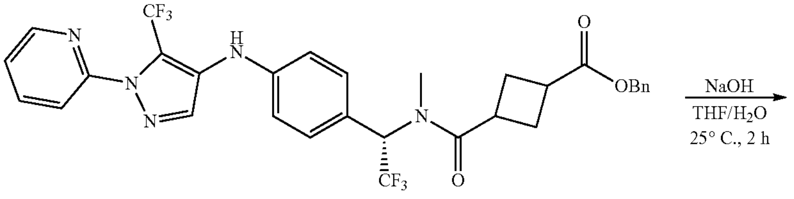

INT 6.12

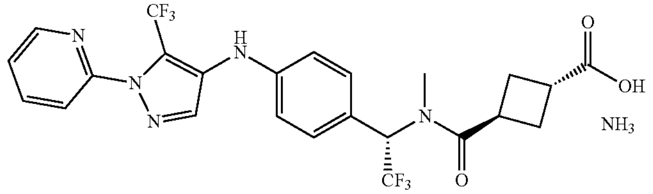

Compound 2.11

+

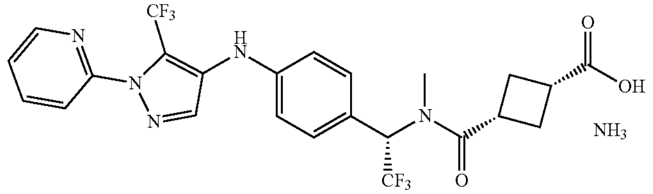

Compound 2.12

A mixture of benzyl 3-{methyl[(1S)-2,2,2-trifluoro-1-(4-{[1-(pyridin-2-yl)-5-(trifluoromethyl)-1H-pyrazol-4-yl]amino}phenyl)ethyl]carbamoyl}cyclobutane-1-carboxylate [INT 6.12] (390 mg, 617 μmol) and sodium hydroxide (98.3 mg, 2.46 mmol) in THF (5 mL) and water (5 mL) was stirred at 25° C. for 2 h. The reaction mixture was combined with another of the same type. The mixture was diluted with water (10 mL), adjusted with 1 N HCl to pH=4, and extracted with EtOAc (50 mL×2). The combined organic phase was concentrated under reduced pressure to give the crude product, which was purified by Prep-HPLC (column: YMC-Triart Prep C18 150*40 mm*7 μm, table: 9-49% B (A=water (0.1% $NH_3·H_2O$ and 10 mM $NH_4HCO_3$), B=acetonitrile), flow rate: 60 mL/min, UV Detector 220 nm) to give 120 mg of an off-white solid. The material was purified by SFC (column: DAICEL CHIRALPAK AS (250 mm*30 mm, 10 μm, table: 25% B (A=$CO_2$ (0.1% $NH_3·H_2O$ EtOH), B=EtOH), flow rate: 60 mL/min, UV Detector 220 nm) to give (1r,3r)-3-(methyl[(1S)-2,2,2-trifluoro-1-(4-{[1-(pyridin-2-yl)-5-(trifluoromethyl)-1H-pyrazol-4-yl]amino)phenyl)ethyl]carbamoyl}cyclobutane-1-carboxylic acid amine [Compound 2.11] (41.0 mg, 73.4 μmol, 11.9% yield) and (1s,3s)-3-{methyl[(1S)-2,2,2-trifluoro-1-(4-{[1-(pyridin-2-yl)-5-(trifluoromethyl)-1H-pyrazol-4-yl]amino}phenyl)ethyl]carbamoyl}cyclobutane-1-carboxylic acid amine [Compound 2.12](55.1 mg, 98.6 μmol, 16.0% yield) as white solids.

Compound 2.11: m/z: [M+H]+ Calcd for C24H22F6N5O3, 542.2. Found 542.2. $^1$H NMR (400 MHz, $CDCl_3$) δ=8.58-8.48 (m, 1H), 7.89 (dt, J=2.0, 8.0 Hz, 1H), 7.84 (s, 1H), 7.75 (d, J=8.8 Hz, 1H), 7.34 (dd, J=4.0, 6.8 Hz, 1H), 7.31-7.27 (m, 2H), 6.97 (d, J=8.4 Hz, 2H), 6.57 (q, J=8.4 Hz, 1H), 5.67 (s, 1H), 3.51 (br t, J=8.3 Hz, 1H), 3.23 (td, J=4.4, 9.5 Hz, 1H), 2.78 (s, 3H), 2.74-2.65 (m, 2H), 2.64-2.49 (m, 2H).

Compound 2.12: m/z: [M+H]+ Calcd for C24H22F6N5O3, 542.2. Found 542.2. $^1$H NMR (400 MHz, $CDCl_3$) δ=8.58-8.49 (m, 1H), 7.88 (dt, J=1.6, 8.0 Hz, 1H), 7.85 (s, 1H), 7.75 (d, J=8.8 Hz, 1H), 7.34 (dd, J=4.8, 7.2 Hz, 1H), 7.31-7.27 (m, 2H), 6.97 (d, J=8.4 Hz, 2H), 6.55 (q, J=8.8 Hz, 1H), 5.68 (s, 1H), 3.29 (quin, J=8.8 Hz, 1H), 3.17 (quin, J=8.8 Hz, 1H), 2.80 (s, 3H), 2.75-2.62 (m, 2H), 2.61-2.46 (m, 2H).

3. Compounds Prepared Using Scheme 3

Scheme 3

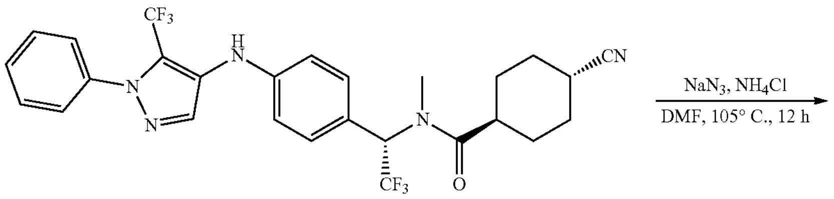

INT 6.11

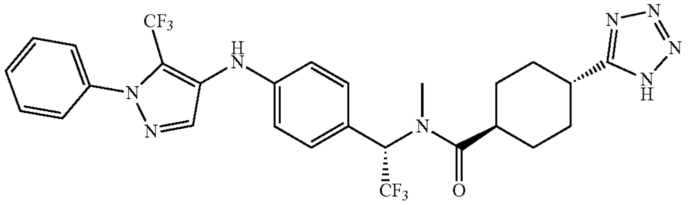

Compound 3.1

Synthesis of (1r,4S)—N—((S)-1-(4-((4-cyclopropyl-1,5-naphthyridin-3-yl)amino)phenyl)-2,2,2-trifluoroethyl)-N-methyl-4-(1H-tetrazol-5-yl)cyclohexane-1-carboxamide (Compound 3.1)

To a solution of (1r,4r)-4-cyano-N-methyl-N-[(1S)-2,2,2-trifluoro-1-(4-{[1-phenyl-5-(trifluoromethyl)-1H-pyrazol-4-yl]amino}phenyl)ethyl]cyclohexane-1-carboxamide [INT 6.11] (100 mg, 181 μmol) and ammonium chloride (14.4 mg, 271 μmol) in DMF (5 mL) was added azidosodium (40 mg, 615 μmol). The reaction mixture was stirred at 105° C. for 12 h under nitrogen. $H_2O$ (10 mL) was added and the mixture was extracted with EtOAc (20 mL×2). The combined organic layers were washed with brine (20 mL×2), dried over anhydrous $Na_2SO_4$ and concentrated under reduced pressure to give crude (1r,4S)—N—((S)-1-(4-((4-cyclopropyl-1,5-naphthyridin-3-yl)amino)phenyl)-2,2,2-trifluoroethyl)-N-methyl-4-(1H-tetrazol-5-yl)cyclohexane-1-carboxamide [Compound 3.1] (100 mg, 168 μmol, 93.4% yield). The material was purified by prep-HPLC (column: YMC-Triart Prep C18 150*40 mm*7 μm, table: 16-56% B (A=water (ammonia hydroxide), B=acetonitrile), flowrate: 60 mL/min, UV Detector 220 nm) to give (1r,4S)—N—((S)-1-(4-((4-cyclopropyl-1,5-naphthyridin-3-yl)amino)phenyl)-2,2,2-trifluoroethyl)-N-methyl-4-(1H-tetrazol-5-yl)cyclohexane-1-carboxamide [Compound 3.1](3.90 mg, 6.58 μmol, 3.9% yield) as an off-white solid. m/z: [M+H]+ Calcd for C27H27F6N8O 593.2. Found 593.2. $^1$H NMR (400 MHz, $CDCl_3$) δ=7.81 (s, 1H), 7.49 (br s, 5H), 7.27 (s, 2H), 6.96 (d, J=8.8 Hz, 2H), 6.67-6.51 (m, 1H), 5.60 (s, 1H), 3.22-3.15 (m, 1H), 3.03-2.85 (m, 3H), 2.79 (br s, 1H), 2.28 (br s, 2H), 2.13-1.95 (m, 2H), 1.82 (br s, 4H).

Synthesis of Exemplary Intermediates

The following exemplary intermediates were synthesized and used for the synthesis of one or more exemplified compounds of the present disclosure.

Synthesis of 1-methyl-5-(trifluoromethyl)-1H-pyrazol-4-amine Hydrochloride [Intermediate 1.1]

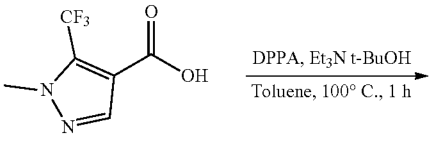

INT 1-a

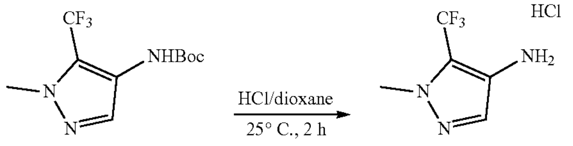

INT 1-b INT 1-1

Synthesis of tert-butyl N-[1-methyl-5-(trifluoromethyl)-1H-pyrazol-4-yl]carbamate [INT 1-b]

To a solution of 1-methyl-5-(trifluoromethyl)-1H-pyrazole-4-carboxylic acid [INT 1-a] (500 mg, 2.57 mmol), 2-methylpropan-2-ol (285 mg, 3.85 mmol), and triethylamine (780 mg, 7.71 mmol) in toluene (5 mL) was added DPPA (1.05 g, 3.85 mmol). The reaction mixture was stirred at 100° C. for 1 h under $N_2$. The reaction was concentrated under reduced pressure to give the crude product, which was purified by flash chromatography on silica gel (EtOAC/PE=0/1 to 1/1) to give tert-butyl N-[1-methyl-5-(trifluoromethyl)-1H-pyrazol-4-yl]carbamate [INT 1-b] (540 mg, 2.03 mmol, 79% yield) as a white solid. m/z: [M+H]+ Calcd for C10H15F3N3O2 266.1. Found 266.1.

1-methyl-5-(trifluoromethyl)-1H-pyrazol-4-amine Hydrochloride [INT 1.1]

A solution of tert-butyl N-[1-methyl-5-(trifluoromethyl)-1H-pyrazol-4-yl]carbamate [INT 1-b] (540 mg, 2.03 mmol) in 4 M HCl/dioxane (10 mL) was stirred at 25° C. for 2 h.

The reaction was concentrated under reduced pressure to give 1-methyl-5-(trifluoromethyl)-1H-pyrazol-4-amine hydrochloride [INT 1.1] (350 mg, 1.73 mmol, 86% yield) as a brown solid. m/z: [M+H]+ Calcd for C5H7F3N3, 166.1. Found 166.1.

Synthesis of 1-(quinolin-5-yl)-5-(trifluoromethyl)-1H-pyrazol-4-amine [Intermediate 1.2]

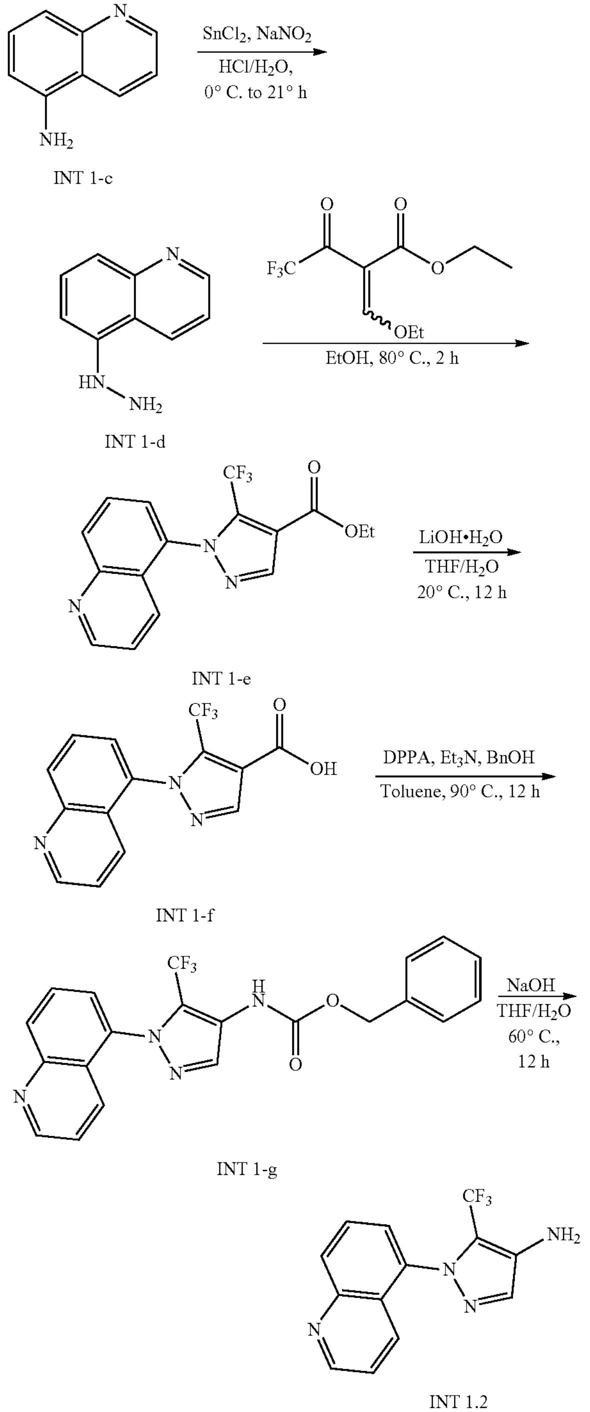

Synthesis of 5-hydrazinylquinoline [INT 1-d]

To a solution of quinolin-5-amine [INT 1-c] (1 g, 6.93 mmol) in HCl (6 mL) was added a solution of $NaNO_2$ (525 mg, 7.62 mmol) in $H_2O$ (1.5 mL) dropwise at 0° C. The mixture was stirred at 0° C. for 30 min and allowed to warm to 21° C. over 30 min until an orange solution was formed. The mixture was cooled to 0° C. and a solution of Tin(II) chloride (3.11 g, 13.8 mmol) dissolved in HCl (3 mL) was added dropwise. A yellow precipitate formed immediately upon addition of the tin salt. The mixture was stirred at 0° C. for 30 minutes and was then allowed to warm to 21° C. with vigorous stirring for 12 hours. The reaction mixture was filtered. The filter cake was washed with cold EtOH (10 mL×3) and dried under reduced pressure to give crude 5-hydrazinylquinoline [INT 1-d] (1.10 g, 6.90 mmol) as a yellow solid. $^1$H NMR (400 MHz, DMSO-d6) δ=10.05 (br s, 1H), 9.28-9.18 (m, 2H), 8.05-7.96 (m, 2H), 7.92 (d, J=8.4 Hz, 1H), 7.29 (d, J=7.6 Hz, 1H).

Synthesis of ethyl 1-(quinolin-5-yl)-5-(trifluoromethyl)-1H-pyrazole-4-carboxylate [INT 1-e]

To a solution of ethyl 2-(ethoxymethylene)-4,4,4-trifluoro-3-oxobutanoate (668 mg, 2.78 mmol) in EtOH (5 mL), 5-hydrazinylquinoline [INT 1-d] (367 mg, 2.31 mmol) was added. The mixture was stirred at 80° C. for 2 hours. The reaction mixture was concentrated under reduced pressure to give the crude product, which was purified by flash chromatography on silica gel ($CH_2Cl_2$/MeOH=100/0 to 95/5) to give ethyl 1-(quinolin-5-yl)-5-(trifluoromethyl)-1H-pyrazole-4-carboxylate [INT 1-e] (185 mg, 551 μmol, 23.9% yield) as a brown semisolid. m/z: [M+H]+ Calcd for C16H13F3N3O2, 336.1. Found 336.2.

Synthesis of 1-(quinolin-5-yl)-5-(trifluoromethyl)-1H-pyrazole-4-carboxylic Acid [INT 1-f]

To a solution of ethyl 1-(quinolin-5-yl)-5-(trifluoromethyl)-1H-pyrazole-4-carboxylate [INT 1-e] (419 mg, 1.24 mmol) in $H_2O$ (0.5 mL) and THF (3 mL) was added lithium hydroxide monohydrate (104 mg, 2.48 mmol). The mixture was stirred at 21° C. for 2 h, after which it was concentrated under reduced pressure to give a brown solid. Then $H_2O$ (3 mL) was added and the pH of the reaction mixture was adjusted to 5 with 1 M HCl. The mixture was extracted with EtOAc (10 mL×3). The combined organic layers were washed with brine (2×30 mL), dried over anhydrous $Na_2SO_4$ and concentrated under reduced pressure to give the crude 1-(quinolin-5-yl)-5-(trifluoromethyl)-1H-pyrazole-4-carboxylic acid [INT 1-f] (120 mg, 390 μmol, 31.5% yield) as a brown solid. m/z: [M+H]+ Calcd for C14H9F3N3O2, 308.1. Found 308.0.

Synthesis of benzyl (1-(quinolin-5-yl)-5-(trifluoromethyl)-1H-pyrazol-4-yl)carbamate [INT 1-g]

A solution of 1-(quinolin-5-yl)-5-(trifluoromethyl)-1H-pyrazole-4-carboxylic acid [INT 1-f] (180 mg, 585 μmol), benzyl alcohol (75.9 mg, 702 mol), $Et_3N$ (59.1 mg, 585 μmol) and DPPA (241 mg, 877 μmol) in toluene (2 mL) was stirred at 90° C. for 12 h. The reaction mixture was concentrated under reduced pressure to give the crude product, which was purified by flash chromatography on silica gel (EtOAc/Petroleum ether=0/1 to 1/3) to give benzyl (1-(quinolin-5-yl)-5-(trifluoromethyl)-1H-pyrazol-4-yl)carbamate [INT 1-g] (100 mg, 242 μmol, 41.4% yield) as a yellow solid. m/z: [M+H]+ Calcd for C21H16F3N4O2, 413.1. Found 413.1.

Synthesis of 1-(quinolin-5-yl)-5-trifluoromethyl)-1H-pyrazol-4-amine [INT 1.2]

To a solution of benzyl (1-(quinolin-5-yl)-5-(trifluoromethyl)-1H-pyrazol-4-yl)carbamate [INT 1-g] (100 mg, 242 μmol) in THF (2 mL) was added NaOH (96.8 mg, 2.42 mmol) and $H_2O$ (2 mL). The resulting mixture was stirred at 60° C. for 12 h. Water (10 mL) was added and the mixture was extracted with EtOAc (15 mL×2). The combined organic layers were washed with brine (20 mL), dried over $Na_2SO_4$ and concentrated under reduced pressure to give the crude product, which was purified by flash chromatography on silica gel (EtOAc/hexane=0/1 to 1/1) to give 1-(quinolin-5-yl)-5-(trifluoromethyl)-1H-pyrazol-4-amine [INT 1.2] (45.0 mg, 161 μmol, 66.8% yield) as a white solid. m/z: [M+H]+ Calcd for C13H10F3N4 279.1. Found 279.1.

Synthesis of 1-(o-tolyl)-5-(trifluoromethyl)-1H-pyrazol-4-amine [Intermediate 1.3]

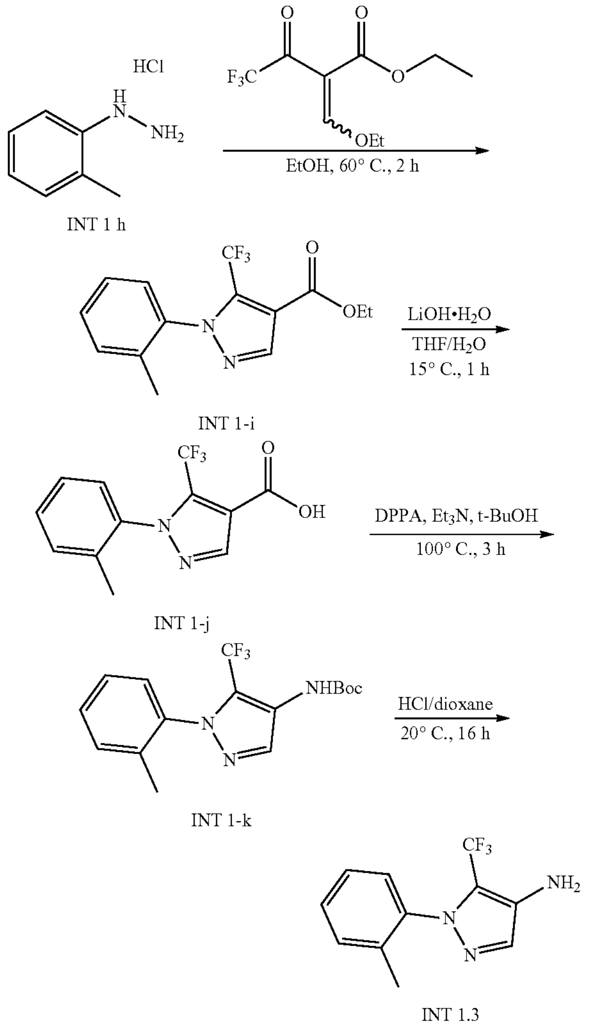

INT 1 h

INT 1-i

INT 1-j

INT 1-k

INT 1.3

Synthesis of ethyl 1-(o-tolyl)-5-(trifluoromethyl)-1H-pyrazole-4-carboxylate [INT 1-i]

To a solution of ethyl 2-(ethoxymethylene)-4,4,4-trifluoro-3-oxobutanoate (3 g, 12.4 mmol) in EtOH (30 mL) was added (2-methylphenyl)hydrazine hydrochloride [INT 1-h] (1.96 g, 12.4 mmol) at 25° C. and the reaction mixture was stirred at 60° C. for 2 h. The reaction mixture was concentrated under reduced pressure to give the crude product, which was purified by flash chromatography on silica gel (PE/EA=1/0 to 3/1) to give ethyl 1-(o-tolyl)-5-(trifluoromethyl)-1H-pyrazole-4-carboxylate [INT 1-i] (3.10 g, 10.3 mmol, 84.0% yield) as a yellow oil. m/z: [M+H]+ Calcd for C14H14F3N2O2, 299.1. Found 298.9.

Synthesis of 1-(o-tolyl)-5-(trifluoromethyl)-1H-pyrazole-4-carboxylic acid [INT 1-i]

To a mixture of ethyl 1-(o-tolyl)-5-(trifluoromethyl)-1H-pyrazole-4-carboxylate [INT 1-i] (3.1 g, 10.3 mmol) in $H_2O$ (10 mL) and THF (20 mL) was added lithium hydroxide monohydrate (1.07 g, 25.7 mmol). The reaction mixture was stirred at 15° C. for 1 hour. The reaction mixture was concentrated under reduced pressure. The mixture was then acidified with 1 M HCl to pH=4 and concentrated under reduced pressure to provide crude 1-(o-tolyl)-5-(trifluoromethyl)-1H-pyrazole-4-carboxylic acid [INT 1-j] (2.6 g, 9.62 mmol, 93.5% yield). m/z: [M+H]+ Calcd for C12H10F3N2O2, 271.1. Found 270.8.

Synthesis of tert-butyl (1-(o-tolyl)-5-(trifluoromethyl)-1H-pyrazol-4-yl)carbamate [INT 1-k]

To a mixture of 1-(o-tolyl)-5-(trifluoromethyl)-1H-pyrazole-4-carboxylic acid [INT 1-j] (2 g, 7.40 mmol) in t-BuOH (20 mL) was added DPPA (3.05 g, 11.1 mmol) and triethylamine (1.49 g, 14.8 mmol). The reaction mixture was stirred at 100° C. under nitrogen for 3 hours. The reaction mixture was concentrated under reduced pressure to give a solid, which was purified by flash chromatography on silica gel (EtOAc/PE=0/1 to 1/3) to give tert-butyl (1-(o-tolyl)-5-(trifluoromethyl)-1H-pyrazol-4-yl)carbamate [INT 1-k] (400 mg, 1.17 mmol, 15.8% yield) as a white solid. m/z: [M+H]+ Calcd for C16H19F3N3O2, 342.1. Found 342.0.

Synthesis of 1-(o-tolyl)-5-(trifluoromethyl)-1H-pyrazol-4-amine [INT 1.3]

A mixture of tert-butyl (1-(o-tolyl)-5-(trifluoromethyl)-1H-pyrazol-4-yl)carbamate [INT 1-k] (220 mg, 644 μmol) in 4 M HCl/dioxane (6 mL) was stirred at 20° C. for 16 h. The reaction mixture was concentrated under reduced pressure to give crude 1-(o-tolyl)-5-(trifluoromethyl)-1H-pyrazol-4-amine [INT 1.3] (100 mg, 414 μmol, 70.9% yield). m/z: [M+H]+ Calcd for C11H11F3N3, 242.1. Found 241.9.

Synthesis of 1-methyl-5-phenyl-1H-pyrazol-4-amine [Intermediate 1.4]

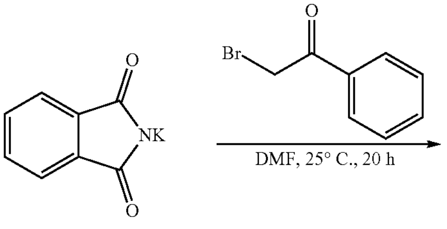

INT 1-l

-continued

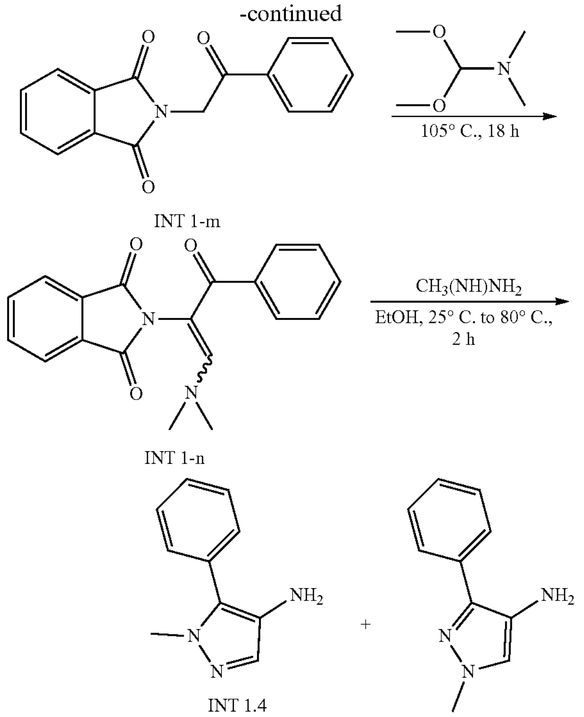

INT 1-m

INT 1-n

INT 1.4

Synthesis of 2-(2-oxo-2-phenylethyl)isoindoline-1,3-dione [INT 1-m]

To a solution of potassium 1,3-dioxo-2,3-dihydro-1H-isoindol-2-ide [INT 1-4] (3 g, 16.1 mmol) in DMF (10 mL) was added 2-bromo-1-phenylethan-1-one (3.20 g, 16.1 mmol). The reaction mixture was stirred at 25° C. for 20 h. Water (20 mL) was added, and the mixture was extracted with DCM (30 mLx2). The combined organic layers were washed with brine (40 mLx2), dried over anhydrous $Na_2SO_4$ and concentrated under reduced pressure to give the crude product, which was purified by flash chromatography on silica gel (EtOAc/PE=0/1 to 5/1) to give 2-(2-oxo-2-phenylethyl)isoindoline-1,3-dione [INT 1-m] (4.16 g, 15.6 mmol, 97.4% yield) as a white solid. m/z: [M+H]+ Calcd for C16H12NO3 266.1. Found 266.1. $^1$H NMR (400 MHz, $CDCl_3$) δ=8.05-8.00 (m, 2H), 7.96-7.86 (m, 2H), 7.79-7.74 (m, 2H), 7.67-7.62 (m, 1H), 7.56-7.50 (m, 2H), 5.15 (s, 2H).

Synthesis of 2-[1-(dimethylamino)-3-oxo-3-phenylprop-1-en-2-yl]-2,3-dihydro-1H-isoindole-1,3-dione [INT 1-n]

A suspension of 2-(2-oxo-2-phenylethyl)-2,3-dihydro-1H-isoindole-1,3-dione [INT 1-m] (1.0 g, 3.76 mmol) in (dimethoxymethyl)dimethylamine (3 mL, 15.0 mmol) was heated at 105° C. for 18 hr and concentrated under reduced pressure. The resulting amber oil was crystallized from isopropanol (10 mL) and washed with isopropanol (2x5 mL) to give 2-[1-(dimethylamino)-3-oxo-3-phenylprop-1-en-2-yl]-2,3-dihydro-1H-isoindole-1,3-dione [INT 1-n](930 mg, 2.90 mmol, 77.5% yield) as a yellow solid. m/z: [M+H]+ Calcd for C19H17N2O3 321.1. Found 321.1. $^1$H NMR (400 MHz, $CDCl_3$) δ=7.94-7.89 (m, 2H), 7.78-7.73 (m, 2H), 7.59 (d, J=6.8 Hz, 2H), 7.45 (s, 1H), 7.43-7.35 (m, 3H), 2.99 (s, 6H).

Synthesis of 1-methyl-5-phenyl-1H-pyrazol-4-amine [INT 1.4]

To a solution of 2-[1-(dimethylamino)-3-oxo-3-phenylprop-1-en-2-yl]-2,3-dihydro-1H-isoindole-1,3-dione [INT 1-n] (930 mg, 2.90 mmol) in EtOH (6 mL) was added methylhydrazine (723 mg, 15.7 mmol). The reaction was stirred at 25° C. for 1 h under $N_2$. The reaction was then heated to 80° C. for 1 h. The reaction was cooled to 25° C. and concentrated under reduced pressure to give the crude product, which was purified by flash chromatography on silica gel (EtOAc/PE=0/1 to 1/1) to give a mixture of 1-methyl-5-phenyl-1H-pyrazol-4-amine [INT 1.4](152 mg, 877 μmol, 30.2% yield) and 1-methyl-3-phenyl-1H-pyrazol-4-amine (190 mg, 1.09 mmol, 37.8% yield) as a brown solid. The mixture was purified Prep-HPLC (column: Phenomenex Gemini C18 250*50 mm*10 μm, table: 1-41% B (A=water (0.05% $NH_3H_2O$+10 mM $NH_4HCO_3$), B=acetonitrile), flow rate: 25 mL/min, UV Detector 220 nm) to afford 1-methyl-5-phenyl-1H-pyrazol-4-amine [INT 1.4] (40.0 mg, 230 μmol) as a white solid. m/z: [M+H]+ Calcd for C10H12N3, 174.1. Found 174.1.

Synthesis of 5-isopropyl-1-methyl-1H-pyrazol-4-amine [Intermediate 1.5]

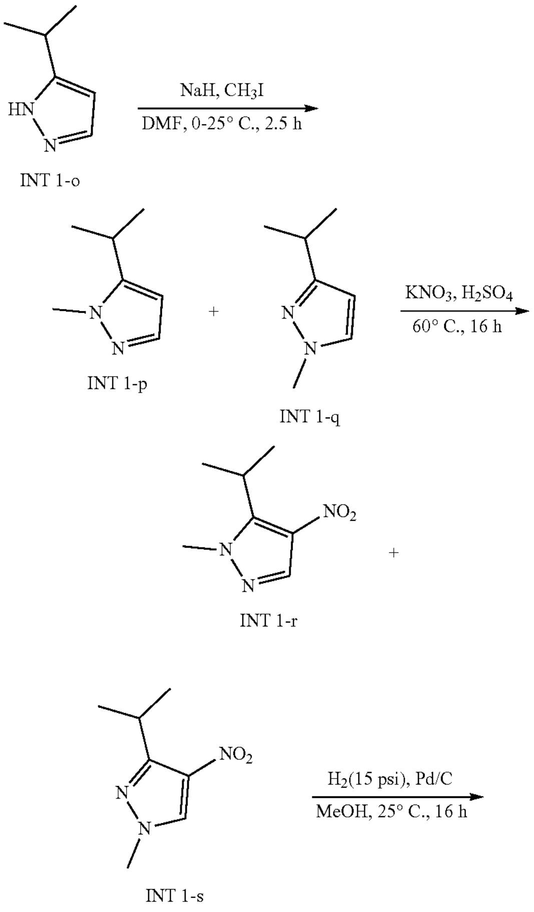

INT 1-o

INT 1-p

INT 1-q

INT 1-r

INT 1-s

-continued

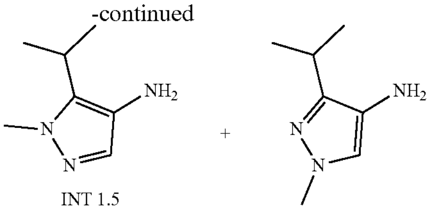

INT 1.5

Synthesis of 1-methyl-5-(propan-2-yl)-1H-pyrazole [INT 1-p] and 1-methyl-3-(propan-2-yl)-1H-pyrazole [INT 1-q]

To a solution of 5-(propan-2-yl)-1H-pyrazole [INT 1-o] (3 g, 27.2 mmol) in DMF (20 mL) was added sodium hydride (1.63 g, 40.8 mmol) at 0° C. and the reaction mixture was stirred at 0° C. for 0.5 h under nitrogen. Iodomethane (11.5 g, 81.6 mmol) was then added and the reaction was allowed to warm to 25° C. over 2 h. The reaction was quenched by adding $NH_4Cl$ (aq) (30 mL) and was extracted with EtOAc (3x20 mL). The combined organic layers were washed with brine (2x50 mL), dried over anhydrous $Na_2SO_4$ and concentrated under reduced pressure to give the crude product, which was purified by flash chromatography on silica gel (PE/EtOAc=1/0 to 1/2) to give a mixture of 1-methyl-5-(propan-2-yl)-1H-pyrazole [INT 1-p]1-methyl-3-(propan-2-yl)-1H-pyrazole [INT 1-q] (1.30 g, 5.23 mmol, 19.2% yield) as a colorless oil. m/z: [M+H]+ Calcd for C7H13N2, 125.1. Found 125.3.

Synthesis of 1-methyl-4-nitro-5-(propan-2-yl)-1H-pyrazole [INT 1-r] and 1-methyl-4-nitro-3-(propan-2-yl)-1H-pyrazole [INT 1-s]

To a mixture of 1-methyl-5-(propan-2-yl)-1H-pyrazole [INT 1-p] and 1-methyl-3-(propan-2-yl)-1H-pyrazole [INT 1-q] in $H_2SO_4$ (1 mL) was added $KNO_3$ (203 mg, 2.01 mmol) and the reaction mixture was stirred at 60° C. for 16 h under nitrogen. The reaction was quenched by adding 1 N NaOH (aq) (10 mL) and was extracted with EtOAc (3x10 mL). The combined organic layers were washed with brine (2x10 mL), dried over anhydrous $Na_2SO_4$ and concentrated under reduced pressure to give 1-methyl-4-nitro-5-(propan-2-yl)-1H-pyrazole [INT 1-r] and 1-methyl-4-nitro-3-(propan-2-yl)-1H-pyrazole [INT 1-s] (100 mg, 295 μmol, 73.5% yield) as a yellow solid. m/z: [M+H]+ Calcd for C7H12N3O2, 170.1. Found 170.1.

Synthesis of 1-methyl-5-(propan-2-yl)-1H-pyrazol-4-amine [INT 1.5]

To a solution of 1-methyl-4-nitro-5-(propan-2-yl)-1H-pyrazole [INT 1-r] and 1-methyl-4-nitro-3-(propan-2-yl)-1H-pyrazole [INT 1-s] (1 g, 2.95 mmol) in MeOH (10 mL) was added Pd/C (313 mg, 295 μmol) and the suspension was degassed under vacuum and purged with $H_2$ several times. The mixture was stirred under $H_2$ (15 psi) at 25° C. for 16 hours. The reaction mixture was filtered and the filtrate was concentrated under reduced pressure to give 1-methyl-5-(propan-2-yl)-1H-pyrazol-4-amine [INT 1.5] and 1-methyl-3-(propan-2-yl)-1H-pyrazol-4-amine. The mixture was purified by SFC (column: REGIS(S,S)WHELK-O1 (250 mm*25 mm, 10 μm), condition: 15%-15% 0.1% $NH_3H_2O$ ETOH, flowrate: 60 mL/min) to give 1-methyl-5-(propan-2-yl)-1H-pyrazol-4-amine [INT 1.5] (100 mg, 718 μmol) as a blue oil (m/z: [M+H]+ Calcd for C7H14N3, 140.1. Found 140.3) and 1-methyl-3-(propan-2-yl)-1H-pyrazol-4-amine (200 mg, 1.43 mmol) as a blue oil ([M+H]+ Calcd for C7H14N3, 140.1. Found 140.3).

Synthesis of 1-phenyl-5-(trifluoromethyl)-1H-pyrazol-4-amine Hydrochloride [Intermediate 1.6]

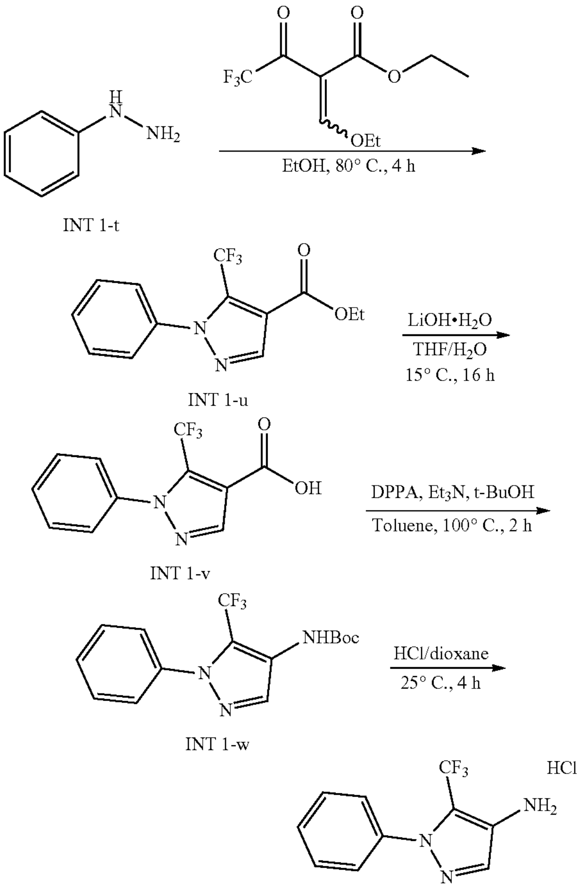

INT 1-t

INT 1-u

INT 1-v

INT 1-w

INT 1.6

Synthesis of ethyl 1-phenyl-5-(trifluoromethyl)-1H-pyrazole-4-carboxylate [INT 1-u]

A mixture of ethyl 2-(ethoxymethylene)-4,4,4-trifluoro-3-oxobutanoate (3 g, 12.4 mmol) and phenylhydrazine [INT 1-t] (1.47 g, 13.6 mmol) in EtOH (35 mL) was stirred at 80° C. for 4 hr. The mixture was concentrated under reduced pressure to afford the crude product, which was purified by flash chromatography on silica gel (EtOAc/Petroleum ether=1/1 to 1/0) to give ethyl 1-phenyl-5-(trifluoromethyl)-1H-pyrazole-4-carboxylate [INT 1-u] (2.44 g, 8.58 mmol, 69.3% yield) as a yellow oil. m/z: [M+H]+ Calcd for C13H12F3N2O2, 285.1. Found 285.1. $^1H$ NMR (400 MHz, $CDCl_3$) δ=8.13 (s, 1H), 7.56-7.49 (m, 3H), 7.47-7.41 (m, 2H), 4.44-4.35 (m, 2H), 1.40 (t, J=7.2 Hz, 3H)

Synthesis of 1-phenyl-5-(trifluoromethyl)-1H-pyrazole-4-carboxylic Acid [INT 1-v]

To a mixture of ethyl 1-phenyl-5-(trifluoromethyl)-1H-pyrazole-4-carboxylate [INT 1-u] (2.34 g, 8.23 mmol) in THF (15 mL) and $H_2O$ (5 mL) was added $LiOH{\cdot}H_2O$ (1.03 g, 24.6 mmol) and the mixture was stirred at 15° C. for 16 hr. The mixture was concentrated under reduced pressure to afford the crude product. $H_2O$ (30 mL) and EtOAc (30 mL) were added and the precipitate was collected by filtration. The aqueous phase was washed with EtOAc (30 mL×2), acidified with 1 M HCl to pH=3 and extracted with EtOAc (30 mL×2). The combined organic layers were dried over $Na_2SO_4$ and filtered. The filtrate was concentrated to give a yellow solid, which was combined with the precipitate to give 1-phenyl-5-(trifluoromethyl)-1H-pyrazole-4-carboxylic acid [INT 1-v] (1.88 g, 7.33 mmol, 89.5% yield) as a yellow solid. m/z: [M+H]+ Calcd for C11H8F3N2O2, 257.0. Found 256.9. $^1H$ NMR (400 MHz, $CDCl_3$) δ=8.22 (s, 1H), 7.59-7.50 (m, 3H), 7.49-7.43 (m, 2H).

Synthesis of tert-butyl (1-phenyl-5-(trifluoromethyl)-1H-pyrazol-4-yl)carbamate [INT 1-w]

A mixture of 1-phenyl-5-(trifluoromethyl)-1H-pyrazole-4-carboxylic acid [INT 1-v](400 mg, 1.56 mmol), 2-methylpropan-2-ol (1.73 g, 23.4 mmol), diphenylphosphoryl azide (569 mg, 2.34 mmol) and triethylamine (473 mg, 4.68 mmol) in toluene (4 mL) was stirred at 100° C. for 2 hr. $NaHCO_3$ (30 mL) was added and the mixture was extracted with EtOAc (30 mL×2). The combined organic layers were washed with brine (30 mL×2), dried over anhydrous $Na_2SO_4$, filtered and concentrated under reduced pressure to give the crude product, which was purified by flash chromatography on silica gel (EtOAc/Petroleum ether=1/20 to 1/0) to give tert-butyl (1-phenyl-5-(trifluoromethyl)-1H-pyrazol-4-yl)carbamate [INT 1-w] (335 mg, 1.02 mmol, 65.6% yield) as a yellow oil. m/z: [M+H]+ Calcd for C15H17F3N3O2, 328.1. Found 328.2. $^1H$ NMR ($CDCl_3$) δ=8.27 (br s, 1H), 7.52-7.46 (m, 3H), 7.46-7.39 (m, 2H), 6.54 (br s, 1H), 1.56-1.54 (m, 9H).

Synthesis of 1-phenyl-5-(trifluoromethyl)-1H-pyrazol-4-amine Hydrochloride [INT 1.6]

A mixture of tert-butyl N-[1-phenyl-5-(trifluoromethyl)-1H-pyrazol-4-yl]carbamate [INT 1-w] (235 mg, 717 μmol) in 4 M HCl/dioxane (10 mL, 40.0 mmol) was stirred at 25° C. for 4 hr. The mixture was concentrated under reduced pressure to afford 1-phenyl-5-(trifluoromethyl)-1H-pyrazol-4-amine hydrochloride [INT 1.6] (160 mg, 606 μmol, 84.6% yield) as a yellow solid. m/z: [M+H]+ Calcd for C10H9F3N3, 228.1. Found 228.0.

Synthesis of 1-cyclopropyl-5-(trifluoromethyl)-1H-pyrazol-4-amine Hydrochloride [Intermediate 1.7]

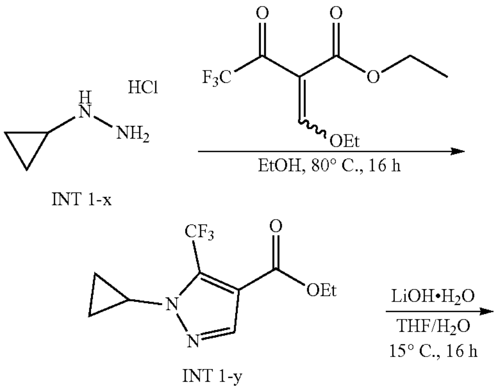

INT 1-x

INT 1-y

-continued

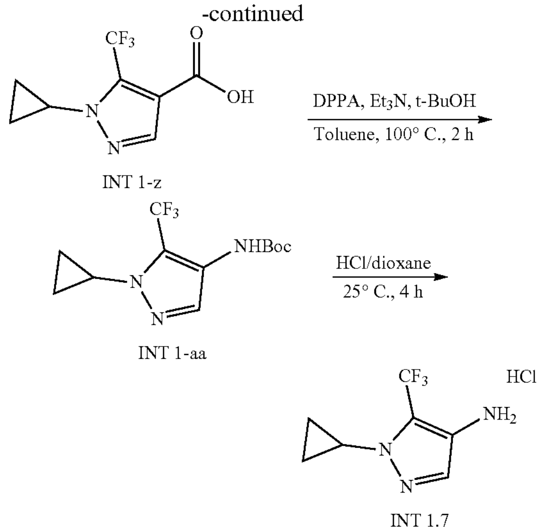

INT 1-z

INT 1-aa

INT 1.7

Synthesis of ethyl 1-cyclopropyl-5-(trifluoromethyl)-1H-pyrazole-4-carboxylate [INT 1-y]

A mixture of ethyl 2-(ethoxymethylene)-4,4,4-trifluoro-3-oxobutanoate (5 g, 20.8 mmol) and cyclopropylhydrazine hydrochloride [INT 1-x] (2.47 g, 22.8 mmol) in EtOH (50 mL) was stirred at 80° C. for 16 hr. The mixture was concentrated under reduced pressure to afford the crude product, which was purified by flash chromatography on silica gel (EtOAc/Petroleum ether=1/10 to 1/0) to give ethyl 1-cyclopropyl-5-(trifluoromethyl)-1H-pyrazole-4-carboxylate [INT 1-y] (608 mg, 2.44 mmol, 11.7% yield) as a yellow oil. m/z: [M+H]+ Calcd for C10H12F3N2O2, 249.1. Found 249.1. $^1H$ NMR (400 MHz, $CDCl_3$) δ=7.85 (s, 1H), 4.36-4.30 (m, 2H), 3.73 (dtt, J=1.2, 3.6, 7.2 Hz, 1H), 1.39-1.34 (m, 3H), 1.33-1.29 (m, 2H), 1.17-1.10 (m, 2H).

Synthesis of 1-cyclopropyl-5-(trifluoromethyl)-1H-pyrazole-4-carboxylic Acid [INT 1-z]

To a mixture of ethyl 1-cyclopropyl-5-(trifluoromethyl)-1H-pyrazole-4-carboxylate [INT 1-y] (608 mg, 2.44 mmol) in THF (3 mL) and $H_2O$ (1 mL) was added $LiOH{\cdot}H_2O$ (307 mg, 7.32 mmol) and the mixture was stirred at 15° C. for 16 hr. The mixture was concentrated under reduced pressure to afford the crude product. 1N HCl was added to adjust the pH to 3-4 and the mixture was extracted with EtOAc (50 mL×2). The combined organic layers were dried over anhydrous $Na_2SO_4$, filtered and concentrated under reduced pressure to give 1-cyclopropyl-5-(trifluoromethyl)-1H-pyrazole-4-carboxylic acid [INT 1-z] (436 mg, 1.98 mmol, 81.1% yield) as a yellow solid. m/z: [M+H]+ Calcd for C8H8F3N2O2, 221.0. Found 221.0. $^1H$ NMR (400 MHz, $CDCl_3$) δ=7.95 (s, 1H), 2.17-2.11 (m, 1H), 1.38-1.32 (m, 2H), 1.20-1.14 (m, 2H).

Synthesis of tert-butyl N-[1-cyclopropyl-5-(trifluoromethyl)-1H-pyrazol-4-yl]carbamate [INT 1-aa]

A mixture of 1-cyclopropyl-5-(trifluoromethyl)-1H-pyrazole-4-carboxylic acid [INT 1-z] (336 mg, 1.52 mmol), 2-methylpropan-2-ol (1.69 g, 22.8 mmol), diphenylphosphoryl azide (554 mg, 2.28 mmol), and triethylamine (461 mg, 4.56 mmol) in toluene (4 mL) was stirred at 100° C. for 2 hr. $NaHCO_3$ (30 mL) was added and the mixture was extracted with EtOAc (30 mL×2). The combined organic layers were washed with brine (30 mL×2), dried over anhydrous $Na_2SO_4$, filtered and concentrated under reduced pressure to give the crude product, which was purified by flash chromatography on silica gel (EtOAc/Petroleum ether=1/10 to 1/0) to give tert-butyl N-[1-cyclopropyl-5-(trifluoromethyl)-1H-pyrazol-4-yl]carbamate [INT 1-aa] (287 mg, 985 μmol, 64.9% yield) as a colorless oil. m/z: [M+H]+ Calcd for C12H17F3N3O2, 292.1. Found 292.1. $^1H$ NMR (400 MHz, $CDCl_3$) δ=7.94 (br s, 1H), 7.43-7.36 (m, 1H), 3.55 (tt, J=3.6, 7.2 Hz, 1H), 1.51 (s, 9H), 1.30-1.23 (m, 2H), 1.09-1.02 (m, 2H).

Synthesis of 1-cyclopropyl-5-(trifluoromethyl)-1H-pyrazol-4-amine Hydrochloride [INT 1.7]

A mixture of tert-butyl N-[1-cyclopropyl-5-(trifluoromethyl)-1H-pyrazol-4-yl]carbamate [INT 1-aa] (187 mg, 642 μmol) in 4 M HCl/dioxane (10 mL, 40.0 mmol) was stirred at 25° C. for 4 hr. The mixture was concentrated under reduced pressure to afford 1-cyclopropyl-5-(trifluoromethyl)-1H-pyrazol-4-amine hydrochloride [INT 1.7] (100 mg, 439 μmol, 68.4% yield) as a brown solid. m/z: [M+H]+ Calcd for C7H9F3N3, 192.1. Found 192.0.

Synthesis of 1-phenyl-5-(propan-2-yl)-1H-pyrazol-4-amine Hydrochloride [Intermediate 1.8]

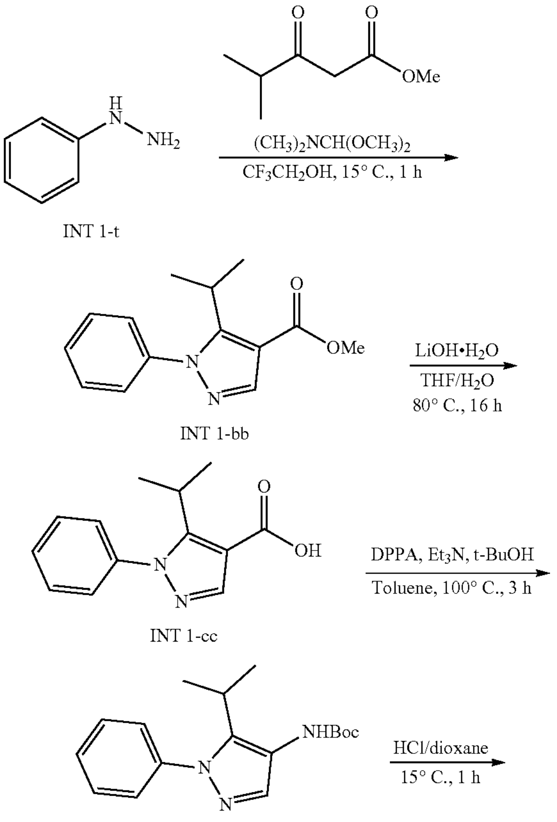

INT 1-t
INT 1-bb
INT 1-cc
INT 1-dd

-continued

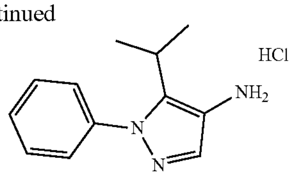
INT 1.8

Synthesis of methyl 1-phenyl-5-(propan-2-yl)-1H-pyrazole-4-carboxylate [INT 1-bb]

To a mixture of methyl 4-methyl-3-oxopentanoate (1 g, 6.93 mmol) and (dimethoxymethyl)dimethylamine (990 mg, 8.31 mmol) in 2,2,2-trifluoroethanol (5 mL) was added phenylhydrazine [INT 1-t] (898 mg, 8.31 mmol) in 2,2,2-trifluoroethanol (5 mL). The reaction mixture was stirred at 15° C. for 1 hour. The reaction was quenched with water (20 mL) and extracted with EtOAc (10 mL×3). The combined organic layers were dried over anhydrous sodium sulfate and filtered. The filtrate was concentrated to give the crude product, which was purified by flash chromatography on silica gel (0-6% EtOAc in petroleum ether) to give methyl 1-phenyl-5-(propan-2-yl)-1H-pyrazole-4-carboxylate [INT 1-bb] (620 mg, 2.53 mmol, 36.6% yield) as an orange solid. m/z: [M+H]+ Calcd for C14H17N2O2, 245.1. Found 245.0. $^1H$ NMR (400 MHz, $CDCl_3$) δ=8.03 (s, 1H), 7.55-7.48 (m, 3H), 7.40-7.34 (m, 2H), 3.87 (s, 3H), 3.34-3.21 (m, 1H), 1.36 (d, J=7.2 Hz, 6H).

Synthesis of 1-phenyl-5-(propan-2-yl)-1H-pyrazole-4-carboxylic Acid [INT 1-cc]

To a mixture of methyl 1-phenyl-5-(propan-2-yl)-1H-pyrazole-4-carboxylate [INT 1-bb] (620 mg, 2.53 mmol) in THF (6 mL) and $H_2O$ (2 mL) was added lithium hydroxide monohydrate (318 mg, 7.58 mmol). The reaction mixture was stirred at 80° C. for 16 hours. The reaction mixture was concentrated, diluted with water (20 mL) and washed with EtOAc (10 mL×2). The aqueous phase was acidified with 1 M HCl to pH=3 and extracted with EtOAc (10 mL×2). The combined organic layers were dried over anhydrous sodium sulfate and filtered. The filtrate was concentrated to give 1-phenyl-5-(propan-2-yl)-1H-pyrazole-4-carboxylic acid [INT 1-cc] (460 mg, 1.99 mmol, 79.0%) as a yellow solid. $^1H$ NMR (400 MHz, $CDCl_3$) δ=8.13 (s, 1H), 7.57-7.48 (m, 3H), 7.43-7.36 (m, 2H), 3.37-3.24 (m, 1H), 1.39 (d, J=6.8 Hz, 6H).

Synthesis of tert-butyl N-[1-phenyl-5-(propan-2-yl)-1H-pyrazol-4-yl]carbamate [INT 1-dd]

To a mixture of 1-phenyl-5-(propan-2-yl)-1H-pyrazole-4-carboxylic acid [INT 1-cc](410 mg, 1.78 mmol), 2-methyl-propan-2-ol (1.97 g, 26.7 mmol) and triethylamine (540 mg, 5.34 mmol) in toluene (5 mL) was added diphenylphosphoryl azide (734 mg, 2.67 mmol). The reaction mixture was stirred at 100° C. under nitrogen for 3 hours. The reaction mixture was diluted with EtOAc (20 mL) and washed with saturated $NaHCO_3$ (20 mL) and brine (20 mL). The organic layer was dried over anhydrous $Na_2SO_4$ and filtered. The filtrate was concentrated to give the crude product, which was purified by flash chromatography on silica gel (0-20% EtOAc in petroleum ether) to give tert-butyl N-[1-phenyl-5-(propan-2-yl)-1H-pyrazol-4-yl]carbamate [INT 1-dd]

(270 mg, 895 μmol, 50.3% yield) as a colorless oil. m/z: [M+H]+ Calcd for C17H24N3O2, 302.2. Found 302.1. $^1$H NMR (400 MHz, $CDCl_3$) δ=7.82 (br s, 1H), 7.55-7.44 (m, 3H), 7.41-7.36 (m, 2H), 5.81 (br s, 1H), 3.07 (spt, J=7.2 Hz, 1H), 1.53 (s, 9H), 1.29 (d, J=7.2 Hz, 6H).

Synthesis of 1-phenyl-5-(propan-2-yl)-1H-pyrazol-4-amine Hydrochloride [INT 1.8]

A mixture of tert-butyl N-[1-phenyl-5-(propan-2-yl)-1H-pyrazol-4-yl]carbamate [INT 1-dd] (270 mg, 895 μmol) in 4 M HCl/dioxane (5 mL, 20 mmol) was stirred at 15° C. for 1 hour. The reaction mixture was concentrated to give 1-phenyl-5-(propan-2-yl)-1H-pyrazol-4-amine hydrochloride [INT 1.8] (210 mg, 883 μmol, 99.0% yield) as a yellow solid. $^1$H NMR (400 MHz, MeOD) δ=7.71 (s, 1H), 7.63-7.55 (m, 3H), 7.46-7.39 (m, 2H), 3.23-3.09 (m, 1H), 1.27 (d, J=7.2 Hz, 6H).

Synthesis of 1-(propan-2-yl)-5-(trifluoromethyl)-1H-pyrazol-4-amine Hydrochloride [Intermediate 1.9]

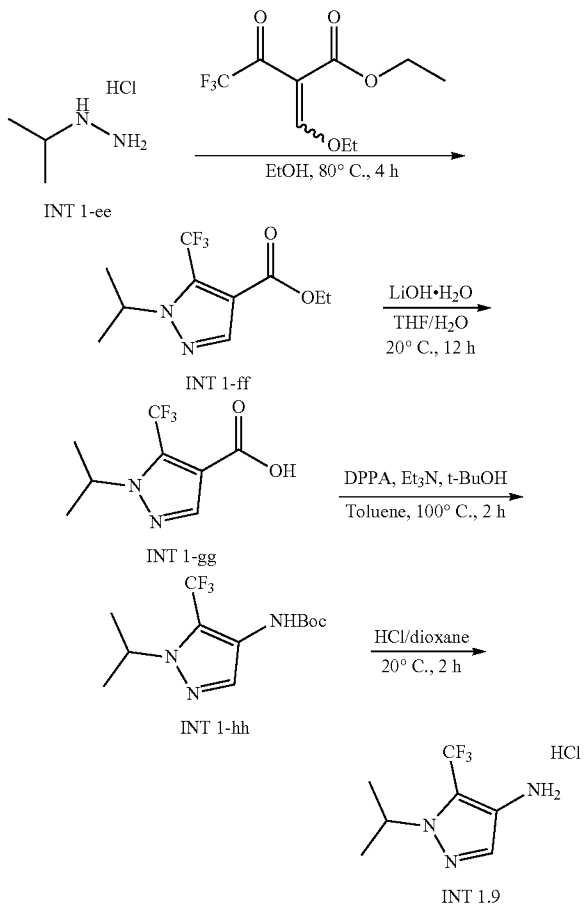

Synthesis of ethyl 1-(propan-2-yl)-5-(trifluoromethyl)-1H-pyrazole-4-carboxylate [INT 1-ff]

A mixture of ethyl 2-(ethoxymethylene)-4,4,4-trifluoro-3-oxobutanoate (2 g, 8.32 mmol) and (propan-2-yl)hydrazine hydrochloride [INT 1-ee] (920 mg, 8.32 mmol) in EtOH (20 mL) was stirred at 80° C. for 16 hr. The mixture was concentrated under reduced pressure to afford the crude product, which was purified by flash chromatography on silica gel (EtOAc/Petroleum ether=0/1 to 1/10) to give ethyl 1-(propan-2-yl)-5-(trifluoromethyl)-1H-pyrazole-4-carboxylate [INT 1-f] (1.40 g, 5.59 mmol, 67.3% yield) as a colorless oil. m/z: [M+H]+ Calcd for C10H14F3N2O2, 251.1. Found 251.1. $^1$H NMR (400 MHz, DMSO-d6) δ=8.08 (s, 1H), 4.80 (spt, J=6.4 Hz, 1H), 4.25 (q, J=7.2 Hz, 2H), 1.45 (d, J=6.4 Hz, 6H), 1.26 (t, J=7.2 Hz, 3H).

Synthesis of 1-(propan-2-yl)-5-(trifluoromethyl)-1H-pyrazole-4-carboxylic Acid [INT 1-gg]

To a solution of ethyl 1-(propan-2-yl)-5-(trifluoromethyl)-1H-pyrazole-4-carboxylate [INT 1-ff] (900 mg, 3.59 mmol) in THF (9 mL) and $H_2O$ (3 mL) was added lithium hydroxide monohydrate (448 mg, 10.7 mmol). The reaction mixture was stirred at 20° C. for 12 hr, after which it was concentrated under reduced pressure. The crude product was quenched with water (20 mL) and washed with EtOAc (30 mL×2). The aqueous phase was then acidified with 1 M HCl to pH=4 and extracted with EtOAc (20 mL×2). The combined organic layers were washed with brine (50 mL×2), dried over anhydrous $Na_2SO_4$, filtered, and concentrated under reduced pressure to give 1-(propan-2-yl)-5-(trifluoromethyl)-1H-pyrazole-4-carboxylic acid [INT 1-gg](250 mg, 1.12 mmol, 31.3% yield) as a colorless oil. m/z: [M+H]+ Calcd for C8H10F3N2O2 223.1. Found 223.0.

Synthesis of tert-butyl N-[1-(propan-2-yl)-5-(trifluoromethyl)-1H-pyrazol-4-yl]carbamate [INT 1-hh]

A mixture of 1-(propan-2-yl)-5-(trifluoromethyl)-1H-pyrazole-4-carboxylic acid [INT 1-gg] (250 mg, 1.12 mmol), 2-methylpropan-2-ol (1.24 g, 16.8 mmol), diphenylphosphoryl azide (408 mg, 1.68 mmol) and triethylamine (340 mg, 3.36 mmol) in toluene (4 mL) was stirred at 100° C. for 2 hr. The reaction mixture was concentrated under reduced pressure to give the crude product, which was purified by flash chromatography on silica gel (EtOAc/Petroleum ether=0/1 to 1/20) to give tert-butyl N-[1-(propan-2-yl)-5-(trifluoromethyl)-1H-pyrazol-4-yl]carbamate [INT 1-hh] (150 mg, 511 μmol, 45.7% yield) as a yellow oil. m/z: [M+H]+ Calcd for C12H19F3N3O2, 294.1. Found 294.1.

Synthesis of 1-(propan-2-yl)-5-(trifluoromethyl)-1H-pyrazol-4-amine Hydrochloride [INT 1.9]

A solution of tert-butyl N-[1-(propan-2-yl)-5-(trifluoromethyl)-1H-pyrazol-4-yl]carbamate [INT 1-hh] (150 mg, 511 μmol) in 4 M HCl in dioxane (3 mL) was stirred at 20° C. for 2 hr. The reaction mixture was concentrated under reduced pressure to give 1-(propan-2-yl)-5-(trifluoromethyl)-1H-pyrazol-4-amine hydrochloride [INT 1.9] (110 mg, 479 μmol, 94.0% yield). m/z: [M+H]+ Calcd for C7H11F3N3, 194.1. Found 193.9.

Synthesis of 1-[4-amino-5-(trifluoromethyl)-1H-pyrazol-1-yl]-2-methylpropan-2-ol Hydrochloride [Intermediate 1.10]

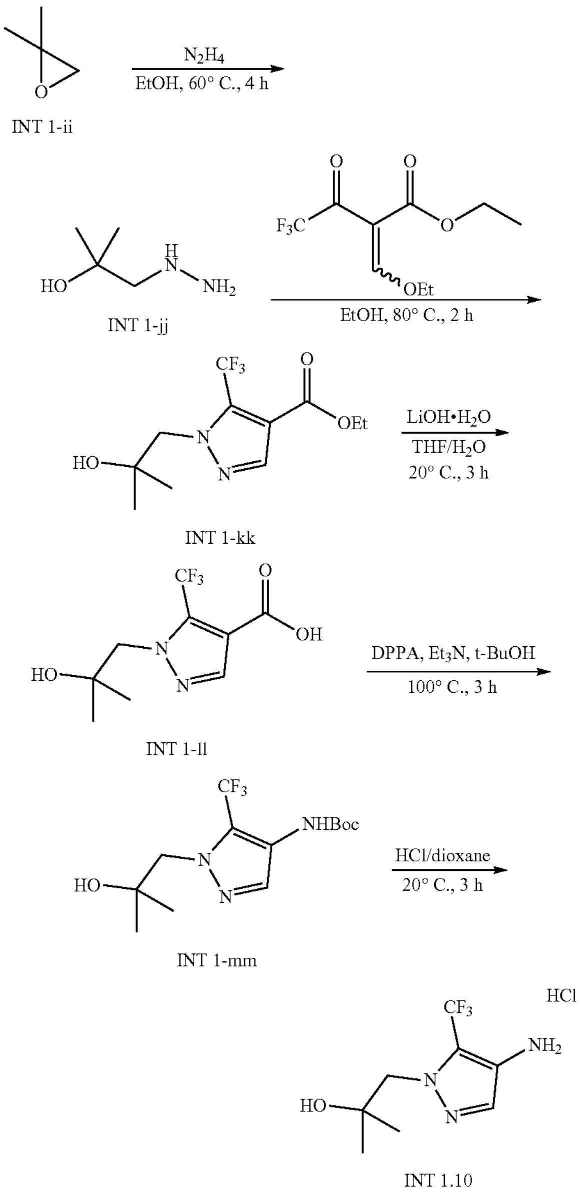

INT 1-ii

INT 1-jj

INT 1-kk

INT 1-ll

INT 1-mm

INT 1.10

Synthesis of 1-hydrazinyl-2-methylpropan-2-ol [INT 1-ii]

To a suspension of 2,2-dimethyloxirane [INT 1-i] (1.0 g, 13.8 mmol) in EtOH (5 mL) was added hydrazine (884 mg, 27.6 mmol). The reaction mixture was stirred at 60° C. for 4 h, after which it was concentrated under reduced pressure to give 1-hydrazinyl-2-methylpropan-2-ol [INT 1-jj] (1.24 g, 11.9 mmol, 86.7% yield) as a colorless oil. $^1$H NMR (400 MHz, $CDCl_3$) δ=3.52 (s, 4H), 2.71 (s, 2H), 1.21-1.18 (m, 6H).

Synthesis of ethyl 1-(2-hydroxy-2-methylpropyl)-5-(trifluoromethyl)-1H-pyrazole-4-carboxylate [INT 1-kk]

To a solution of ethyl 2-(ethoxymethylene)-4,4,4-trifluoro-3-oxobutanoate (2.0 g, 8.32 mmol) in EtOH (8 mL) was added 1-hydrazinyl-2-methylpropan-2-ol [INT 1-jj] (1.03 g, 9.98 mmol). The reaction was stirred at 80° C. for 2 h. The reaction mixture was concentrated under reduced pressure to give the crude product, which was purified by flash chromatography on silica gel (EtOAc/PE=0/1 to 1/3) to give ethyl 1-(2-hydroxy-2-methylpropyl)-5-(trifluoromethyl)-1H-pyrazole-4-carboxylate [INT 1-kk] (1 g, 3.56 mmol, 42.9% yield) as a yellow oil. m/z: [M+H]+ Calcd for C11H16F3N2O3, 281.1. Found 280.9. $^1$H NMR (400 MHz, $CDCl_3$) δ=8.01 (s, 1H), 4.40-4.30 (m, 4H), 3.85 (s, 1H), 1.37 (t, J=7.2 Hz, 3H), 1.19 (s, 6H).

Synthesis of 1-(2-hydroxy-2-methylpropyl)-5-(trifluoromethyl)-1H-pyrazole-4-carboxylic Acid [INT 1-ll]

To a solution of ethyl 1-(2-hydroxy-2-methylpropyl)-5-(trifluoromethyl)-1H-pyrazole-4-carboxylate [INT 1-kk] (1.0 g, 3.56 mmol) in THF (5 mL) was added lithium hydroxide monohydrate (298 mg, 7.12 mmol) in $H_2O$ (5 mL). The reaction was stirred at 20° C. for 3 h. The reaction mixture was poured into water (10 mL), acidified with 1 N HCl to pH=5-6 and extracted with EtOAc (20 mL×2). The combined organic layers were washed with brine (20 mL×2), dried over anhydrous $Na_2SO_4$ and concentrated under reduced pressure to give 1-(2-hydroxy-2-methylpropyl)-5-(trifluoromethyl)-1H-pyrazole-4-carboxylic acid [INT 1-H] (710 mg, 2.81 mmol, 79.1% yield) as a yellow solid. m/z: [M+H]+ Calcd for C9H12F3N2O3, 253.1. Found 252.9.

Synthesis of tert-butyl N-[1-(2-hydroxy-2-methylpropyl)-5-(trifluoromethyl)-1H-pyrazol-4-yl]carbamate [INT 1-mm]

A mixture of 1-(2-hydroxy-2-methylpropyl)-5-(trifluoromethyl)-1H-pyrazole-4-carboxylic acid [INT 1-ll] (710 mg, 2.81 mmol), diphenylphosphoryl azide (1.54 g, 5.62 mmol) and triethylamine (1.41 g, 14.0 mmol) in t-BuOH (8 mL) was stirred at 100° C. for 3 h under $N_2$. The reaction mixture was concentrated under reduced pressure to give the crude product, which was purified by flash chromatography on silica gel (EtOAc/PE=0/1 to 1/3) to give tert-butyl N-[1-(2-hydroxy-2-methylpropyl)-5-(trifluoromethyl)-1H-pyrazol-4-yl]carbamate [INT 1-mm] (600 mg, 1.85 mmol, 66.0% yield) as a yellow oil. m/z: [M+H]+ Calcd for C13H21F3N3O3 324.1. Found 323.9. $^1$H NMR (400 MHz, $CDCl_3$) δ=8.11 (s, 1H), 6.47 (s, 1H), 4.42 (s, 1H), 4.08 (s, 2H), 1.52 (s, 9H), 1.17 (s, 6H).

Synthesis of 1-[4-amino-5-(trifluoromethyl)-1H-pyrazol-1-yl]-2-methylpropan-2-ol Hydrochloride [INT 1.10]

A solution of tert-butyl N-[1-(2-hydroxy-2-methylpropyl)-5-(trifluoromethyl)-1H-pyrazol-4-yl]carbamate [INT 1-mm] (600 mg, 1.85 mmol) in HCl/Dioxane (5 mL) was stirred at 20° C. for 3 h. The reaction mixture was concentrated under reduced pressure to give 1-[4-amino-5-(trifluoromethyl)-1H-pyrazol-1-yl]-2-methylpropan-2-ol hydrochloride [INT 1.10] (480 mg, 1.84 mmol) as a yellow oil. m/z: [M+H]+ Calcd for C8H13F3N3O, 224.1. Found 223.9.

Synthesis of 1-(1-methoxypropan-2-yl)-5-(trifluoromethyl)-1H-pyrazol-4-amine Hydrochloride [Intermediate 1.11]

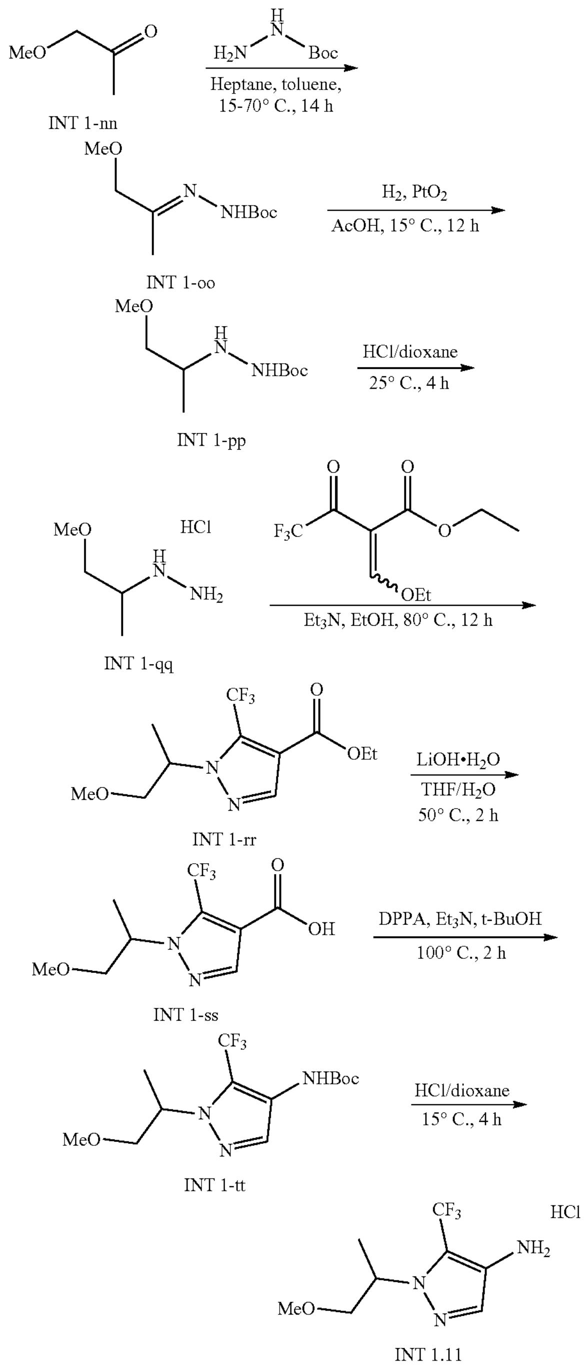

Synthesis of N'-[(2Z)-1-methoxypropan-2-ylidene](tert-butoxy)carbohydrazide [INT 1-oo]

To a mixture of 1-methoxypropan-2-one [INT 1-nn] (10 g, 113 mmol) in heptane (400 mL) at 50° C. was added (tert-butoxy)carbohydrazide (19.2 g, 146 mmol) in toluene (30 ml). The mixture was stirred at 70° C. for 2 hr. The mixture was then stirred at 15° C. for 12 hr. The precipitate formed was collected, washed with heptane and dried to give N'-[(2Z)-1-methoxypropan-2-ylidene](tert-butoxy)carbohydrazide [INT 1-oo] (19.6 g, 96.9 mmol, 85.9% yield) as a white solid. $^1$H NMR (400 MHz, $CDCl_3$) δ=7.59 (br d, J=6.8 Hz, 1H), 4.02 (d, J=2.4 Hz, 2H), 3.32-3.28 (m, 3H), 1.84 (s, 3H), 1.50 (d, J=2.4 Hz, 9H).

Synthesis of N'-(1-methoxypropan-2-yl)(tert-butoxy)carbohydrazide [INT 1-pp]

A mixture of N'-[(2Z)-1-methoxypropan-2-ylidene](tert-butoxy)carbohydrazide [INT 1-oo] (5 g, 24.7 mmol) and $PtO_2$ (0.05 g, 220 μmol) in AcOH (50 ml) under $H_2$ (15 psi) was stirred at 15° C. for 12 h. After filtering the mixture through celite a solution of $NaHCO_3$ was added to adjust the pH to 8-9. The mixture was extracted with EtOAc (100 mL×2). The combined organic layers were dried over $Na_2SO_4$, filtered and concentrated under reduced pressure to give the crude product, which was purified by flash chromatography on silica gel ($CH_2Cl_2$/MeOH=1/20 to 1/0) to give N'-(1-methoxypropan-2-yl)(tert-butoxy)carbohydrazide [INT 1-pp] (3.25 g, 15.9 mmol, 64.4% yield) as a yellow oil. m/z: [M−56+H]+ Calcd for C9H21N2O3, 149.0. Found 148.9. $^1$H NMR (400 MHz, $CDCl_3$) δ=6.45-5.99 (m, 1H), 4.25 (br s, 1H), 3.34 (s, 3H), 3.31 (t, J=4.4 Hz, 1H), 3.27-3.17 (m, 2H), 1.44 (s, 9H), 0.99 (br s, 3H).

Synthesis of (1-methoxypropan-2-yl)hydrazine Hydrochloride [INT 1-qq]

A mixture of N'-(1-methoxypropan-2-yl)(tert-butoxy)carbohydrazide [INT 1-pp] (3.25 g, 15.9 mmol) in 4 M HCl/dioxane (30 mL, 120 mmol) was stirred at 25° C. for 4 hr. The mixture was concentrated under reduced pressure to afford (1-methoxypropan-2-yl)hydrazine hydrochloride [INT 1-qq] (2.00 g, 14.2 mmol, 89.6% yield) as a yellow oil. m/z: [M+H]+ Calcd for C4H13N2O, 105.1. Found 104.8.

Synthesis of ethyl 1-(1-methoxypropan-2-yl)-5-(trifluoromethyl)-1H-pyrazole-4-carboxylate [INT 1-rr]

A mixture of ethyl 2-(ethoxymethylene)-4,4,4-trifluoro-3-oxobutanoate (2 g, 8.32 mmol), (1-methoxypropan-2-yl) hydrazine hydrochloride [INT 1-qq] (1.28 g, 9.10 mmol), and triethylamine (841 mg, 8.32 mmol) in EtOH (20 mL) was stirred at 80° C. for 12 hr. The mixture was concentrated under reduced pressure to afford the crude product, which was purified by flash chromatography on silica gel (EtOAc/Petroleum ether=1/10 to 1/0) to give ethyl 1-(1-methoxypropan-2-yl)-5-(trifluoromethyl)-1H-pyrazole-4-carboxylate [INT 1-rr] (990 mg, 3.55 mmol, 42.8% yield) as a yellow oil. m/z: [M+H]+ Calcd for C11H16F3N2O3, 281.1. Found 281.1. $^1$H NMR (400 MHz, DMSO-d6) δ=8.11 (s, 1H), 4.88-4.77 (m, 1H), 4.25 (q, J=6.8 Hz, 2H), 3.74-3.66 (m, 1H), 3.62-3.55 (m, 1H), 3.19-3.12 (m, 3H), 1.40 (d, J=6.8 Hz, 3H), 1.27 (t, J=7.2 Hz, 3H).

Synthesis of 1-(1-methoxypropan-2-yl)-5-(trifluoromethyl)-1H-pyrazole-4-carboxylic Acid [INT 1-ss]

To a mixture of ethyl 1-(1-methoxypropan-2-yl)-5-(trifluoromethyl)-1H-pyrazole-4-carboxylate [INT 1-rr] (890 mg, 3.17 mmol) in THF (6 mL) and $H_2O$ (2 mL) was added $LiOH{\cdot}H_2O$ (1.06 g, 25.3 mmol) and the mixture was stirred at 50° C. for 2 hr. The mixture was concentrated under reduced pressure to afford the crude product. 1N HCl was added to adjust the pH to 3-4 and the mixture was extracted with EtOAc (50 mL×2). The combined organic layers were dried over anhydrous $Na_2SO_4$, filtered and concentrated under reduced pressure to give 1-(1-methoxypropan-2-yl)-5-(trifluoromethyl)-1H-pyrazole-4-carboxylic acid [INT 1-ss] (395 mg, 1.56 mmol, 49.4% yield) as a yellow oil. m/z: [M+H]+ Calcd for C9H12F3N2O3, 253.1. Found 253.0. $^1H$ NMR (400 MHz, $CDCl_3$) δ=8.07 (s, 1H), 4.88 (qd, J=6.8, 13.2 Hz, 1H), 3.85 (t, J=9.2 Hz, 1H), 3.63 (dd, J=5.2, 10.0 Hz, 1H), 3.30 (s, 3H), 1.52 (d, J=6.8 Hz, 3H).

Synthesis of tert-butyl N-[1-(1-methoxypropan-2-yl)-5-(trifluoromethyl)-H-pyrazol-4-yl]carbamate [INT 1-tt]

A mixture of 1-(1-methoxypropan-2-yl)-5-(trifluoromethyl)-1H-pyrazole-4-carboxylic acid [INT 1-ss] (295 mg, 1.16 mmol), 2-methylpropan-2-ol (1.28 g, 17.4 mmol), diphenylphosphoryl azide (423 mg, 1.74 mmol) and triethylamine (352 mg, 3.48 mmol) in toluene (3 mL) was stirred at 100° C. for 2 hr. $NaHCO_3$ (30 mL) was added and the mixture was extracted with EtOAc (30 mL×2). The combined organic layers were washed with brine (30 mL×2), dried over anhydrous $Na_2SO_4$, filtered and concentrated under reduced pressure to give the crude product, which was purified by flash chromatography on silica gel (EtOAc/Petroleum ether=1/10 to 1/0) to give tert-butyl N-[1-(1-methoxypropan-2-yl)-5-(trifluoromethyl)-1H-pyrazol-4-yl] carbamate [INT 1-tt] (208 mg, 643 μmol, 55.4% yield) as a yellow oil. m/z: [M+H]+ Calcd for C13H21F3N3O3 324.1. Found 324.1. $^1H$ NMR (400 MHz, $CDCl_3$) δ=8.07 (br s, 1H), 6.44 (br s, 1H), 4.55 (sxt, J=6.8 Hz, 1H), 3.84 (dd, J=7.6, 9.6 Hz, 1H), 3.60 (dd, J=5.6, 10.0 Hz, 1H), 3.30 (s, 3H), 1.51 (s, 9H), 1.45 (d, J=6.8 Hz, 3H).

1-(1-methoxypropan-2-yl)-5-(trifluoromethyl)-1H-pyrazol-4-amine Hydrochloride [INT 1.11]

A mixture of tert-butyl N-[1-(1-methoxypropan-2-yl)-5-(trifluoromethyl)-1H-pyrazol-4-yl]carbamate [INT 1-tt] (158 mg, 488 μmol) in 4 M HCl/dioxane (15 mL, 60.0 mmol) was stirred at 15° C. for 4 hr. The mixture was concentrated under reduced pressure to afford 1-(1-methoxypropan-2-yl)-5-(trifluoromethyl)-1H-pyrazol-4-amine hydrochloride [INT 1.11] (150 mg, 577 μmol) as a yellow oil. m/z: [M+H]+ Calcd for C8H13F3N3O 224.1. Found 223.9.

Synthesis of 1-neopentyl-5-(trifluoromethyl)-1H-pyrazol-4-amine [Intermediate 1.12]

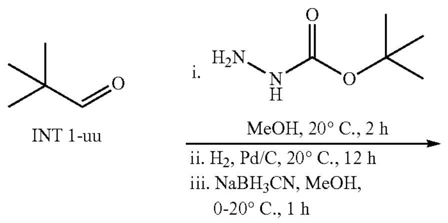

-continued

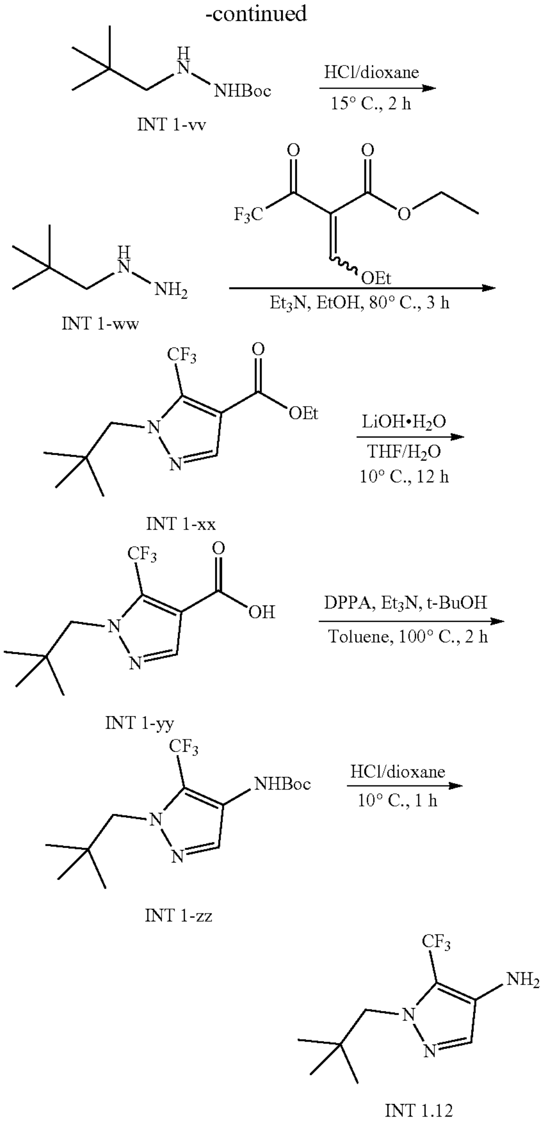

Synthesis of N'-(2,2-dimethylpropyl)(tertbutoxy) carbohydrazide [INT 1-vv]

A mixture of 2,2-dimethylpropanal [INT 1-uu] (5 g, 58.0 mmol) and (tert-butoxy)carbohydrazide (7.66 g, 58.0 mmol) in MeOH (80 mL) was stirred at 20° C. for 2 hours. Then 10% Pd/C (1 g) was added. The flask was evacuated and backfilled with $N_2$ three times, then evacuated and backfilled with $H_2$ three more times. The reaction mixture was stirred at 20° C. under $H_2$ (15 psi) for 12 h. The reaction was filtered and the filter cake was washed with MeOH (20 mL×3). The filtrate was cooled to 0° C., then sodium cyanoborohydride (3.64 g, 58.0 mmol) was added. The mixture was stirred at 20° C. for 1 hour. The reaction was quenched by adding water (80 mL). The mixture was concentrated under reduced pressure to remove MeOH. The residue was diluted with water (100 mL) and was extracted with EtOAc (2×150 mL). The combined organic layers were washed with brine (2×80 mL), dried over anhydrous $Na_2SO_4$ and concentrated under reduced pressure to give N'-(2,2-dimethylpropyl)(tertbutoxy)carbohydrazide [INT 1-vv] (11.0 g, 54.3 mmol, 94% yield) as a gray solid. m/z: [M–t-Bu+H]+ Calcd for C6H15N2O2, 147.2. Found 147.1. $^1$H NMR (400 MHz, $CDCl_3$) δ=2.59 (s, 2H), 1.39 (s, 9H), 0.88 (s, 9H).

Synthesis of (2,2-dimethylpropyl)hydrazine [INT 1-ww]

N'-(2,2-dimethylpropyl)(tert-butoxy)carbohydrazide [INT 1-vv] (6 g, 29.6 mmol) was added to HCl/dioxane (40 mL) at 15° C. and the mixture was stirred for 2 h. The mixture was concentrated under reduced pressure to give (2,2-dimethylpropyl)hydrazine [INT 1-ww] (3.02 g, 29.5 mmol). $^1$H NMR (400 MHz, DMSO-d6) δ=2.67 (s, 2H), 0.91 (s, 9H).

Synthesis of ethyl 1-(2,2-dimethylpropyl)-5-(trifluoromethyl)-1H-pyrazole-4-carboxylate [INT 1-xx]

To a solution of ethyl 2-(ethoxymethylene)-4,4,4-trifluoro-3-oxobutanoate (8.50 g, 35.4 mmol) in EtOH (100 mL) at 10° C. was added (2,2-dimethylpropyl)hydrazine [INT 1-ww] (3.02 g, 29.5 mmol) and $Et_3N$ (5.97 g, 59.0 mmol). The mixture was stirred at 80° C. for 3 h. The reaction was concentrated under reduced pressure, quenched by adding water (50 mL) and was extracted with EtOAc (50 mL×3). The combined organic layers were washed with brine (50 mL×2), dried over anhydrous $Na_2SO_4$ and concentrated under reduced pressure to give the crude product, which was purified by flash chromatography on silica gel (PE/EtOAc=1/0 to 20/1) to give ethyl 1-(2,2-dimethylpropyl)-5-(trifluoromethyl)-1H-pyrazole-4-carboxylate [INT 1-xx](1.81 g, 6.50 mmol, 22.0% yield) as a colorless oil. m/z: [M+H]+ Calcd for C12H18F3N2O2 279.1. Found 278.9. (400 MHz, $CDCl_3$) δ=7.97 (s, 1H), 4.34 (q, J=8.0 Hz, 2H), 4.19 (s, 2H), 1.37 (t, J=8.0 Hz, 3H), 0.99 (s, 9H).

1-(2,2-dimethylpropyl)-5-(trifluoromethyl)-1H-pyrazole-4-carboxylic Acid [INT 1-yy]

To a solution of ethyl 1-(2,2-dimethylpropyl)-5-(trifluoromethyl)-1H-pyrazole-4-carboxylate [INT 1-xx] (1.81 g, 6.50 mmol) in THF (10 mL) and $H_2O$ (3 mL) at 10° C. was added lithium hydroxide monohydrate (1.36 g, 32.5 mmol), then the mixture was stirred for 12 h. The aqueous phase was acidified with 1 M HCl to pH=4 and extracted with EtOAc (30 mL×2). The combined organic layers were concentrated under reduced pressure to give to give 1-(2,2-dimethylpropyl)-5-(trifluoromethyl)-1H-pyrazole-4-carboxylic acid [INT 1-yy] (1.16 g, 4.63 mmol, 71.6% yield) as a white solid. $^1$H NMR (400 MHz, DMSO) δ=8.04 (s, 1H), 4.16 (s, 2H), 0.91 (s, 9H).

Synthesis of tert-butyl N-[1-(2,2-dimethylpropyl)-5-(trifluoromethyl)-1H-pyrazol-4-yl]carbamate [INT 1-zz]

A mixture of 1-(2,2-dimethylpropyl)-5-(trifluoromethyl)-1H-pyrazole-4-carboxylic acid [INT 1-yy] (1.06 g, 4.23 mmol), 2-methylpropan-2-ol (4.69 g, 63.4 mmol), diphenylphosphoryl azide (1.54 g, 6.34 mmol) and triethylamine (2.13 g, 21.1 mmol) in toluene (10 mL) was stirred at 100° C. for 2 hr. The mixture was worked up with material from two of the same reactions. Water (40 mL) was added and the mixture was extracted with EtOAc (40 mL×2). The combined organic layers were washed with brine (40 mL×2), dried over anhydrous $Na_2SO_4$, filtered and concentrated under reduced pressure to give the crude product, which was purified by flash chromatography on silica gel (Petroleum ether/EtOAc=1/10 to 20/1) to give tert-butyl N-[1-(2,2-dimethylpropyl)-5-(trifluoromethyl)-1H-pyrazol-4-yl]carbamate [INT 1-zz] (1.27 g, 3.95 mmol) as a white solid. $^1$H NMR (400 MHz, $CDCl_3$) δ=8.02 (s, 1H), 6.43 (s, 1H), 3.94 (s, 2H), 1.52 (s, 9H), 0.99 (s, 9H).

1-neopentyl-5-(trifluoromethyl)-1H-pyrazol-4-amine [INT 1.12]

A solution of tert-butyl N-[1-(2,2-dimethylpropyl)-5-(trifluoromethyl)-1H-pyrazol-4-yl]carbamate [INT 1-zz] (500 mg, 1.55 mmol) in HCl/dioxane (10 mL) was stirred at 10° C. for 1 h. TLC showed complete consumption of the starting material and formation of a new spot. The mixture was concentrated under reduced pressure to give 1-neopentyl-5-(trifluoromethyl)-1H-pyrazol-4-amine [INT 1.12] (342 mg, 1.54 mmol).

Synthesis of 1-(pyridin-3-yl)-5-(trifluoromethyl)-1H-pyrazol-4-amine Hydrochloride [Intermediate 1.13]

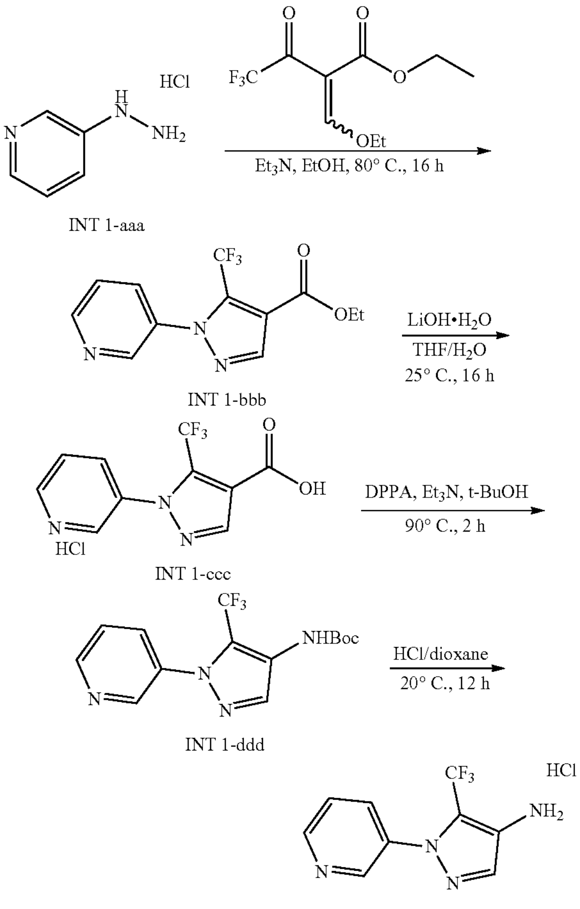

INT 1-aaa

INT 1-bbb

INT 1-ccc

INT 1-ddd

INT 1.13

Synthesis of ethyl 1-(pyridin-3-yl)-5-(trifluoromethyl)-1H-pyrazole-4-carboxylate [INT 1-bbb]

A solution consisting of ethyl 2-(ethoxymethylidene)-4,4-trifluoro-3-oxobutanoate (9.39 g, 39.1 mmol), 3-hydrazinylpyridine hydrochloride [INT 1-aaa] (5.7 g, 39.1 mmol), $Et_3N$ (7.91 g, 78.2 mmol) and EtOH (50 mL) was stirred at 80° C. for 16 h. The mixture was concentrated under reduced pressure to afford the crude product, which was purified by flash column chromatography (petroleum ether:ethyl acetate=100:0 to 80:20) to give ethyl 1-(pyridin-3-yl)-5-(trifluoromethyl)-1H-pyrazole-4-carboxylate [INT 1-bbb] (3.45 g, 12.0 mmol, 31.0% yield). m/z: [M+H]+ Calcd for C12H11F3N3O2, 286.1. Found 285.9. $^1$H NMR (400 MHz, $CDCl_3$) δ=8.78 (dd, J=1.2, 4.8 Hz, 1H), 8.74 (d, J=2.4 Hz, 1H), 8.18 (s, 1H), 7.84-7.76 (m, 1H), 7.50 (dd, J=4.8, 8.0 Hz, 1H), 4.40 (q, J=7.2 Hz, 2H), 1.41 (t, J=7.2 Hz, 3H).

1-(pyridin-3-yl)-5-(trifluoromethyl)-1H-pyrazole-4-carboxylic Acid Hydrochloride [INT 1-ccc]

To a solution of ethyl 1-(pyridin-3-yl)-5-(trifluoromethyl)-1H-pyrazole-4-carboxylate [INT 1-bbb] (3.45 g, 12.0 mmol) in THF (1 mL) was added lithium hydroxide monohydrate (12.0 mL, 24.0 mmol). The mixture was stirred at 25° C. for 16 h. The resulting solution was concentrated to dryness under reduced pressure to afford the crude product, which was poured into water (20 mL) and acidified with 1 M HCl to pH=5. The resulting solution was filtered and the filter cake was washed water (20 mL) and then dried under reduced pressure to afford 1-(pyridin-3-yl)-5-(trifluoromethyl)-1H-pyrazole-4-carboxylic acid hydrochloride [INT 1-ccc] (2.30 g, 7.83 mmol, 65.3% yield) as a white solid. m/z: [M+H]+ Calcd for C10H7F3N3O2 258.0. Found 257.9.

Synthesis of tert-butyl N-[1-(pyridin-3-yl)-5-(trifluoromethyl)-1H-pyrazol-4-yl]carbamate [INT 1-ddd]

A solution of 1-(pyridin-3-yl)-5-(trifluoromethyl)-1H-pyrazole-4-carboxylic acid hydrochloride [INT 1-ccc] (500 mg, 1.70 mmol), triethylamine (472 μL, 3.40 mmol) and diphenylphosphoryl azide (701 mg, 2.55 mmol) in tert-butanol (2 mL, 21.1 mmol) was stirred at 90° C. for 2 h under $N_2$. The reaction was quenched by adding water (15 mL) and was extracted with EtOAc (2×15 mL). The combined organic layers were washed with brine (2×30 mL), dried over anhydrous $Na_2SO_4$ and concentrated under reduced pressure to give the crude product, which was purified by flash chromatography on silica gel (EtOAc/Petroleum ether=0/1 to 1/4) to give tert-butyl N-[1-(pyridin-3-yl)-5-(trifluoromethyl)-1H-pyrazol-4-yl]carbamate [INT 1-ddd] (443 mg, 1.34 mmol, 79.3% yield) as a white solid. m/z: [M+H]+ Calcd for C14H16F3N4O2, 329.1. Found 328.9. $^1$H NMR (400 MHz, $CDCl_3$) δ=8.80-8.69 (m, 2H), 8.35 (br s, 1H), 7.81 (br d, J=8.0 Hz, 1H), 7.47 (dd, J=4.8, 8.0 Hz, 1H), 6.60 (br s, 1H), 1.56 (s, 9H).

1-(pyridin-3-yl)-5-(trifluoromethyl)-1H-pyrazol-4-amine Hydrochloride [INT 1.13]

A solution of tert-butyl N-[1-(pyridin-3-yl)-5-(trifluoromethyl)-1H-pyrazol-4-yl]carbamate [INT 1-ddd] (443 mg, 1.34 mmol) in HCl (4 M in dioxane, 5 mL, 20.0 mmol) was stirred at 20° C. for 12 h. The reaction mixture was concentrated under reduced pressure to give 1-(pyridin-3-yl)-5-(trifluoromethyl)-1H-pyrazol-4-amine hydrochloride [INT 1.13] (343 mg, 1.29 mmol, 96.8% yield) as a yellow solid. m/z: [M+H]+ Calcd for C9H8F3N4 229.1. Found 228.9. $^1$H NMR (400 MHz, DMSO-d6) δ=8.81 (d, J=2.4 Hz, 1H), 8.79 (dd, J=1.2, 4.8 Hz, 1H), 8.12 (br d, J=8.4 Hz, 1H), 7.83 (s, 1H), 7.75 (dd, J=4.8, 8.4 Hz, 1H).

Synthesis of 1-(pyridin-4-yl)-5-(trifluoromethyl)-1H-pyrazol-4-amine [Intermediate 1.14]

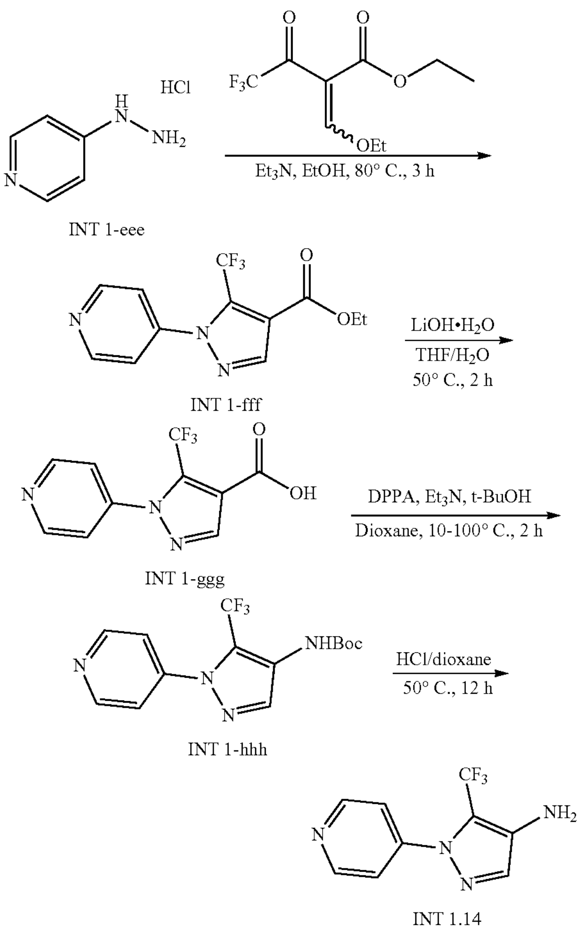

Synthesis of ethyl 1-(pyridin-4-yl)-5-(trifluoromethyl)-1H-pyrazole-4-carboxylate [INT 1-ff]

To a solution of ethyl 2-(ethoxymethylidene)-4,4,4-trifluoro-3-oxobutanoate (7.20 g, 30.0 mmol) in EtOH (50 mL) at 10° C. was added 4-hydrazinylpyridine hydrochloride [INT 1-eee] (4.37 g, 30.0 mmol) and $Et_3N$ (3.03 g, 30.0 mmol), then the mixture was stirred at 80° C. for 3 h. The reaction was concentrated under reduced pressure, quenched by adding water (50 mL) and was extracted with EtOAc (50 mL×3). The combined organic layers were washed with brine (50 mL×2), dried over anhydrous $Na_2SO_4$ and concentrated under reduced pressure to give the crude product, which was purified by flash chromatography on silica gel (PE/EtOAc=1/0 to 3/1) to give ethyl 1-(pyridin-4-yl)-5-(trifluoromethyl)-1H-pyrazole-4-carboxylate [INT 1-fff] (3.00 g, 10.5 mmol, 35.0% yield) as a yellow solid. m/z: [M+H]+ Calcd for C12H11F3N3O2, 286.0. Found 285.9.

Synthesis of 1-(pyridin-4-yl)-5-(trifluoromethyl)-1H-pyrazole-4-carboxylic Acid [INT 1-ggg]

To a solution of ethyl 1-(pyridin-4-yl)-5-(trifluoromethyl)-1H-pyrazole-4-carboxylate [INT 1-fff] (2.5 g, 8.76 mmol) in THF (15 mL) and $H_2O$ (3 mL) at 10° C. was added lithium hydroxide monohydrate (1.83 g, 43.8 mmol), then the mixture was stirred at 50° C. for 2 h. The aqueous phase was acidified with 1 M HCl to pH=4 and extracted with EtOAc (30 mL×2). The combined organic layers were concentrated under reduced pressure to give 1-(pyridin-4-yl)-5-(trifluoromethyl)-1H-pyrazole-4-carboxylic acid [INT 1-ggg] (1.45 g, 5.63 mmol, 64.4% yield) as a white solid. m/z: [M+H]+ Calcd for C10H7F3N3O2, 258.0. Found 257.8.

Synthesis of tert-butyl N-[1-(pyridin-4-yl)-5-(trifluoromethyl)-1H-pyrazol-4-yl]carbamate [INT 1-hhh]

To a mixture of 1-(pyridin-4-yl)-5-(trifluoromethyl)-1H-pyrazole-4-carboxylic acid [INT 1-ggg] (1 g, 3.88 mmol) in t-BuOH (3 mL) and dioxane (5 mL) was added triethylamine (1.96 g, 19.4 mmol) and diphenylphosphoryl azide (1.88 g, 7.76 mmol) at 10° C., then the mixture was stirred at 100° C. for 2 hr. Water (30 mL) was added and the mixture was extracted with EtOAc (30 mL×2). The combined organic layers were washed with brine (30 mL×2), dried over anhydrous $Na_2SO_4$, filtered and concentrated under reduced pressure to give the crude product, which was purified by flash chromatography on silica gel (Petroleum ether/EtOAc=1/10 to 3/1) to give tert-butyl N-[1-(pyridin-4-yl)-5-(trifluoromethyl)-1H-pyrazol-4-yl]carbamate [INT 1-hhh] (360 mg, 1.09 mmol, 28.3% yield) as a white solid. $^1$H NMR (400 MHz, DMSO) δ=8.78 (d, J=4.0 Hz, 2H), 8.58 (s, 1H), 8.00 (s, 1H), 7.56 (d, J=4.0 Hz, 2H), 1.46 (s, 9H).

Synthesis of 1-(pyridin-4-yl)-5-(trifluoromethyl)-1H-pyrazol-4-amine [INT 1.14]

A solution of tert-butyl N-[1-(pyridin-4-yl)-5-(trifluoromethyl)-1H-pyrazol-4-yl]carbamate [INT 1-hhh] (360 mg, 1.09 mmol) in HCl/dioxane (10 mL) was stirred at 50° C. for 12 h. The mixture was concentrated under reduced pressure to give 1-(pyridin-4-yl)-5-(trifluoromethyl)-1H-pyrazol-4-amine [INT 1.14] (248 mg, 1.08 mmol). m/z: [M+H]+ Calcd for C9H8F3N4 229.1. Found 229.1.

Synthesis of 1-(pyridin-2-yl)-5-(trifluoromethyl)-1H-pyrazol-4-amine [Intermediate 1.15]

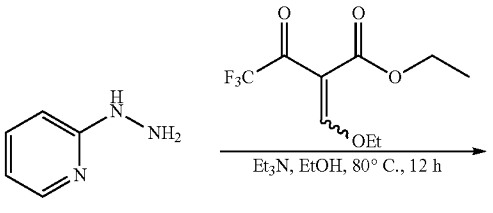

INT 1-iii

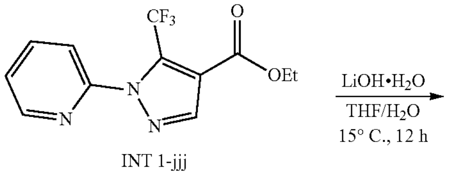

INT 1-jjj

-continued

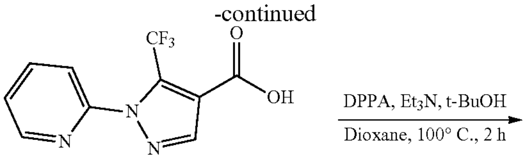

INT 1-kkk

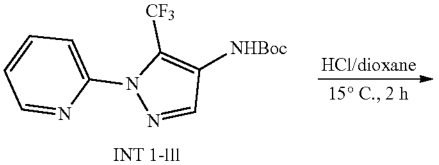

INT 1-lll

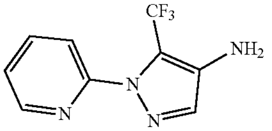

INT 1.15

Synthesis of ethyl 1-(pyridin-2-yl)-5-(trifluoromethyl)-1H-pyrazole-4-carboxylate [INT 1-iii]

To a solution of ethyl 2-(ethoxymethylidene)-4,4,4-trifluoro-3-oxobutanoate (5 g, 20.8 mmol) and 2-hydrazinylpyridine [INT 1-iii] (2.26 g, 20.8 mmol) in EtOH (30 mL) was added triethylamine (2.10 g, 20.8 mmol). The mixture was stirred at 80° C. for 12 hr. The reaction mixture was concentrated under reduced pressure to give the crude product, which was purified by flash chromatography on silica gel (EtOAc/PE=0/1 to 10/1) to give ethyl 1-(pyridin-2-yl)-5-(trifluoromethyl)-1H-pyrazole-4-carboxylate [INT 1-jjj] (5.00 g, 17.5 mmol, 84.3% yield) as yellow oil. m/z: [M+H]+ Calcd for C12H11F3N3O2, 286.1. Found 285.9. $^1$H NMR (400 MHz, DMSO-d6) δ=8.64-8.59 (m, 1H), 8.34 (s, 1H), 8.19-8.12 (m, 1H), 7.80 (dd, J=0.8, 8.0 Hz, 1H), 7.68-7.63 (m, 1H), 4.33 (q, J=7.2 Hz, 2H), 1.31 (t, J=7.2 Hz, 3H).

Synthesis of 1-(pyridin-2-yl)-5-(trifluoromethyl)-1H-pyrazole-4-carboxylic Acid [INT 1-kkk]

To a mixture of ethyl 1-(pyridin-2-yl)-5-(trifluoromethyl)-1H-pyrazole-4-carboxylate [INT 1-jjj] (1 g, 3.50 mmol) in THF (6 mL) and $H_2O$ (2 mL) was added lithium hydroxide monohydrate (440 mg, 10.5 mmol). The reaction mixture was stirred at 15° C. for 12 hours. The reaction mixture was concentrated under reduced pressure. The residue was acidified with 1 M HCl to pH=4. The reaction mixture was quenched by the addition of $H_2O$ (20 mL) and extracted with EtOAc (20 mL×2). The combined organic layers were washed with brine (20 mL), dried over $Na_2SO_4$, filtered and concentrated under reduced pressure to give 1-(pyridin-2-yl)-5-(trifluoromethyl)-1H-pyrazole-4-carboxylic acid [INT 1-kkk] (800 mg, 3.11 mmol, 88.8% yield) as a yellow solid. $^1$H NMR (400 MHz, DMSO-d6) δ=13.43 (br s, 1H), 8.60 (td, J=0.8, 4.8 Hz, 1H), 8.28 (s, 1H), 8.14 (dt, J=2.0, 7.6 Hz, 1H), 7.79 (d, J=8.0 Hz, 1H), 7.64 (ddd, J=0.8, 4.8, 7.6 Hz, 1H).

Synthesis of tert-butyl N-[1-(pyridin-2-yl)-5-(trifluoromethyl 1H-pyrazol-4-yl]carbamate [INT 1-lll]

A mixture of 1-(pyridin-2-yl)-5-(trifluoromethyl)-1H-pyrazole-4-carboxylic acid [INT 1-kkk] (400 mg, 1.55 mmol), triethylamine (784 mg, 7.75 mmol), and diphenylphosphoryl azide (564 mg, 2.32 mmol) in t-BuOH (3 mL) and dioxane (3 mL) was stirred at 100° C. for 2 hr. The reaction mixture was concentrated under reduced pressure to give the crude product, which was purified by flash chromatography on silica gel (Petroleum ether/EtOAc=1/0 to 1/1) to give tert-butyl N-[1-(pyridin-2-yl)-5-(trifluoromethyl)-1H-pyrazol-4-yl]carbamate [INT 1-lll] (470 mg, 1.43 mmol, 92.5% yield) as a white solid. m/z: [M+H]+ Calcd for C14H16F3N4O2, 329.1. Found 328.9. $^1$H NMR (400 MHz, DMSO-d6) δ=9.14 (br s, 1H), 8.56-8.51 (m, 1H), 8.06 (dt, J=1.8, 7.6 Hz, 1H), 7.95 (s, 1H), 7.77 (d, J=8.0 Hz, 1H), 7.55-7.46 (m, 1H), 1.46 (s, 9H).

Synthesis of 1-(pyridin-2-yl)-5-(trifluoromethyl)-1H-pyrazol-4-amine [INT 1.15]

To a solution of tert-butyl N-[1-(pyridin-2-yl)-5-(trifluoromethyl)-1H-pyrazol-4-yl]carbamate [INT 1-lll] (470 mg, 1.43 mmol) in 4 M HCl/dioxane (4 mL) was stirred at 15° C. for 2 h. The reaction mixture was concentrated under reduced pressure to give 1-(pyridin-2-yl)-5-(trifluoromethyl)-1H-pyrazol-4-amine [INT 1.15] (260 mg, 1.13 mmol, 79.7% yield) as a white solid. m/z: [M+H]+ Calcd for C9H8F3N4 229.1. Found 228.9. $^1$H NMR (400 MHz, DMSO-d6) δ=8.48 (dd, J=1.2, 4.8 Hz, 1H), 8.01 (dt, J=1.6, 7.6 Hz, 1H), 7.76-7.72 (m, 2H), 7.65 (br s, 2H), 7.43 (dd, J=4.8, 6.8 Hz, 1H).

Synthesis of 2-[4-amino-5-(trifluoromethyl)-1H-pyrazol-1-yl]benzonitrile [Intermediate 1.16]

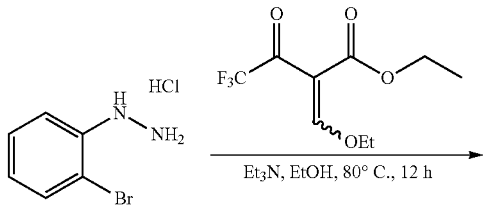

INT 1-mmm

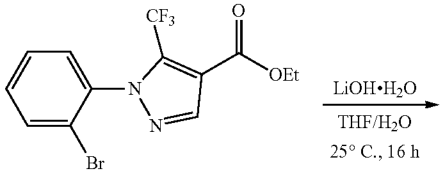

INT 1-nnn

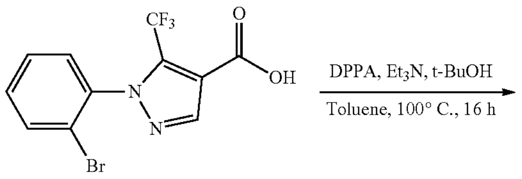

INT 1-ooo

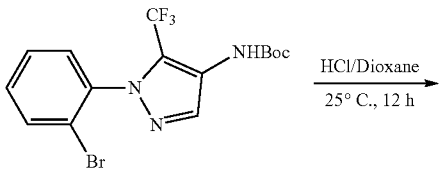

INT 1-ppp

-continued

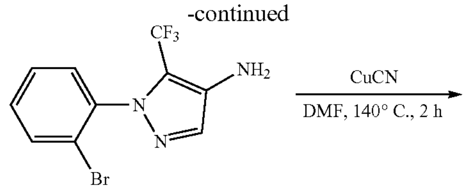

INT 1-qqq

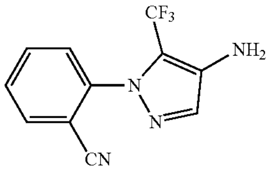

INT 1.16

Synthesis of ethyl 1-(2-bromophenyl)-5-(trifluoromethyl)-1H-pyrazole-4-carboxylate [INT 1-nnn]

To a solution of (2-bromophenyl)hydrazine hydrochloride [INT 1-mmm] (5 g, 22.3 mmol) and ethyl 2-(ethoxymethylidene)-4,4,4-trifluoro-3-oxobutanoate (4.44 g, 18.5 mmol) in EtOH (6 mL) was added triethylamine (2.81 g, 27.8 mmol). The mixture was stirred at 80° C. for 12 hr. The reaction was quenched by adding water (50 mL) and was extracted with EtOAc (3×50 mL). The combined organic layers were washed with brine (2×50 mL), dried over anhydrous $Na_2SO_4$ and concentrated under reduced pressure to give the crude product, which was purified by flash chromatography on silica gel (PE/EtOAc=1/0 to 1/10) to give ethyl 1-(2-bromophenyl)-5-(trifluoromethyl)-1H-pyrazole-4-carboxylate [INT 1-nnn] (3.00 g, 8.26 mmol, 44.7% yield) as a red oil. m/z: [M+H]+ Calcd for C13H11BrF3N2O2, 363.0. Found 362.9.

Synthesis of 1-(2-bromophenyl)-5-(trifluoromethyl)-1H-pyrazole-4-carboxylic Acid [INT 1-ooo]

To a solution of ethyl 1-(2-bromophenyl)-5-(trifluoromethyl)-1H-pyrazole-4-carboxylate [INT 1-nnn] (2 g, 3.30 mmol) in THF (3 mL) and $H_2O$ (1 mL) was added lithium hydroxide monohydrate (276 mg, 6.60 mmol). The mixture was stirred at 25° C. for 16 hr. The reaction was quenched by adding 1 N HCl (10 mL) and $H_2O$ (20 mL) and was extracted with EtOAc (3×20 mL). The combined organic layers were washed with brine (2×50 mL), dried over anhydrous $Na_2SO_4$ and concentrated under reduced pressure to give 1-(2-bromophenyl)-5-(trifluoromethyl)-1H-pyrazole-4-carboxylic acid [INT 1-ooo] (800 mg, 2.38 mmol, 72.7% yield) as a red solid. $^1$H NMR (400 MHz, DMSO-d6) δ=13.43 (br s, 1H), 8.31 (s, 1H), 7.88 (dd, J=1.6, 7.6 Hz, 1H), 7.74 (dd, J=2.0, 7.6 Hz, 1H), 7.59 (dquin, J=1.6, 7.6 Hz, 2H).

Synthesis of tert-butyl N-[1-(2-bromophenyl)-5-(trifluoromethyl)-1H-pyrazol-4-yl]carbamate [INT 1-ppp]

To a solution of 1-(2-bromophenyl)-5-(trifluoromethyl)-1H-pyrazole-4-carboxylic acid [INT 1-ooo] (1.2 g, 3.58 mmol) in toluene (1 mL) was added diphenylphosphoryl azide (1.47 g, 5.37 mmol), triethylamine (1.08 g, 10.7 mmol) and 2-methyl-2-propanol (2.65 g, 35.8 mmol). The reaction mixture was stirred at 100° C. for 16 h under $N_2$. The reaction was diluted with water (50 mL) and was extracted with EtOAc (100 mL×2). The combined organic layers were washed with brine (50 mL×2), dried over anhydrous $Na_2SO_4$ and concentrated under reduced pressure to give the crude product, which was purified by flash chromatography on silica gel (EtOAc/PE=0/1 to 1/5) to give tert-butyl N-[1-(2-bromophenyl)-5-(trifluoromethyl)-1H-pyrazol-4-yl]carbamate [INT 1-ppp] (400 mg, 984 μmol, 27.5% yield) as a yellow oil. m/z: [M+H]+ Calcd for C15H16BrF3N3O2, 406.0. Found 406.1. $^1$H NMR (400 MHz, DMSO-d6) δ=9.04 (br s, 1H), 7.92 (br s, 1H), 7.88-7.85 (m, 1H), 7.65-7.52 (m, 3H), 1.46 (s, 9H).

Synthesis of 1-(2-bromophenyl)-5-(trifluoromethyl)-1H-pyrazol-4-amine [INT 1-qqq]

A mixture of tert-butyl N-[1-(2-bromophenyl)-5-(trifluoromethyl)-1H-pyrazol-4-yl]carbamate [INT 1-ppp] (400 mg, 1.13 mmol) in HCl/dioxane (4 mL) was stirred at 25° C. for 12 h under $N_2$. The reaction was quenched by adding saturated $NaHCO_3$ (aq) (50 mL) and was extracted with EtOAc (3×50 mL). The combined organic layers were washed with brine (2×50 mL), dried over anhydrous $Na_2SO_4$ and concentrated under reduced pressure to give 1-(2-bromophenyl)-5-(trifluoromethyl)-1H-pyrazol-4-amine [INT 1-qqq] (290 mg, 947 μmol, 96.6% yield) as a yellow oil. m/z: [M+H]+ Calcd for C10H8BrF3N3, 306.0. Found 305.8. $^1$H NMR (400 MHz, DMSO-d6) δ=7.81 (d, J=7.6 Hz, 1H), 7.56-7.35 (m, 4H), 4.81 (s, 2H).

Synthesis of 2-[4-amino-5-(trifluoromethyl)-1H-pyrazol-1-yl]benzonitrile [INT 1.16]

A mixture of 1-(2-bromophenyl)-5-(trifluoromethyl)-1H-pyrazol-4-amine [INT 1-qqq](240 mg, 784 μmol) and copper cyanide (351 mg, 3.92 mmol) in DMF (3 mL) was stirred at 140° C. for 2 h under $N_2$. The reaction was combined with another of the same and was quenched by adding $NH_3 \cdot H_2O$ (5 mL) and $H_2O$ (20 mL), then the mixture was extracted with EtOAc (3×20 mL). The combined organic layers were washed with brine (3×20 mL), dried over anhydrous $Na_2SO_4$ and concentrated under reduced pressure to give the crude product, which was purified by flash chromatography on silica gel (Petroleum ether/EtOAc=1/0 to 1/1) to give 2-[4-amino-5-(trifluoromethyl)-1H-pyrazol-1-yl]benzonitrile [INT 1.16] (160 mg, 634 μmol, 81.2% yield) as a yellow oil. m/z: [M+H]+ Calcd for C11H8F3N4 253.1. Found 252.9. $^1$H NMR (400 MHz, DMSO-d6) δ=8.06 (d, J=7.6 Hz, 1H), 7.91-7.84 (m, 1H), 7.77-7.70 (m, 1H), 7.65 (d, J=8.0 Hz, 1H), 7.47 (s, 1H), 5.01 (s, 2H).

Synthesis of 3-[4-amino-5-(trifluoromethyl)-1H-pyrazol-1-yl]benzonitrile Hydrochloride [Intermediate 1.17]

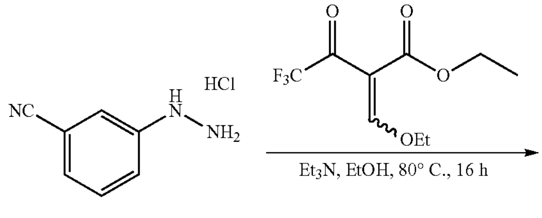

INT 1-rrr

-continued

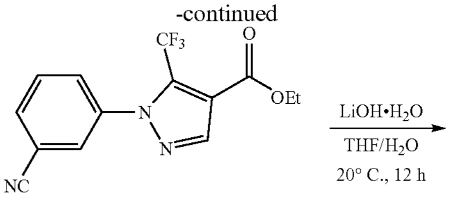

INT 1-sss

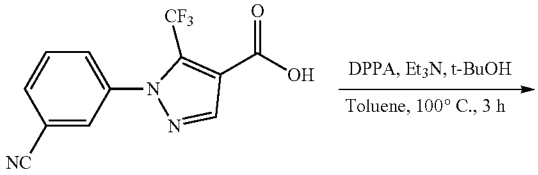

INT 1-ttt

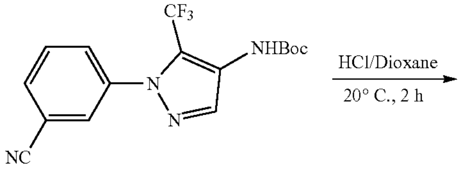

INT 1-uuu

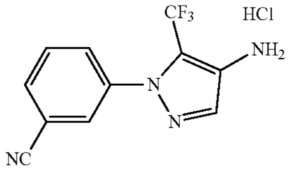

INT 1.17

Synthesis of ethyl 1(3-cyanophenyl-5-(trifluoromethyl)-1H-pyrazole-4-carboxylate [INT 1-sss]

To a solution of ethyl 2-(ethoxymethylidene)-4,4,4-trifluoro-3-oxobutanoate (3.0 g, 12.4 mmol) in EtOH (5 mL) was added 3-hydrazinylbenzonitrile hydrochloride [INT1-rrr] (2.10 g, 12.4 mmol) and triethylamine (1.37 g, 13.6 mmol). The reaction was stirred at 20° C. for 16 h. The reaction mixture was concentrated under reduced pressure to give the crude product, which was purified by flash chromatography on silica gel (EtOAc/PE=0/1 to 1/5) to give ethyl 1-(3-cyanophenyl)-5-(trifluoromethyl)-1H-pyrazole-4-carboxylate [INT 1-sss] (350 mg, 1.13 mmol, 9.1% yield) as a red solid. m/z: [M+H]+ Calcd for C14H11F3N3O2, 310.1. Found 310.0. $^1$H NMR (400 MHz, $CDCl_3$) δ=8.17 (s, 1H), 7.87-7.81 (m, 1H), 7.79 (s, 1H), 7.75-7.62 (m, 2H), 4.41 (q, J=7.2 Hz, 2H), 1.41 (t, J=7.2 Hz, 3H).

Synthesis of 1-(3-cyanophenyl)-5-(trifluoromethyl)-1H-pyrazole-4-carboxylic Acid [INT 1-ttt]

To a solution of ethyl 1-(3-cyanophenyl)-5-(trifluoromethyl)-1H-pyrazole-4-carboxylate [INT 1-sss] (2.35 g, 5.30 mmol) in THF (15 mL) was added lithium hydroxide monohydrate (444 mg, 10.6 mmol) in $H_2O$ (5 mL). The reaction was stirred at 20° C. for 12 h. The reaction mixture was poured into 10 mL of water, acidified with 1 N HCl to pH=3-4 and extracted with EtOAc (20 mL×2). The combined organic layers were washed with brine (30 mL×2), dried over anhydrous $Na_2SO_4$ and concentrated under reduced pressure to give the crude product, which was purified by flash chromatography on silica gel (MeOH/DCM=0/1 to 1/20) to give 1-(3-cyanophenyl)-5-(trifluoromethyl)-1H-pyrazole-4-carboxylic acid [INT 1-ttt] (1.50 g, 5.33 mmol, 100% yield) as a brown solid. $^1$H NMR (400 MHz, DMSO-d6) δ=13.41 (br s, 1H), 8.29 (s, 1H), 8.20 (t, J=1.6 Hz, 1H), 8.12-8.07 (m, 1H), 7.94 (br d, J=8.8 Hz, 1H), 7.83-7.78 (m, 1H).

Synthesis of tert-butyl N-[1-(3-cyanophenyl)-5-(trifluoromethyl)-1H-pyrazol-4-yl]carbamate [INT 1-uuu]

A solution of 1-(3-cyanophenyl)-5-(trifluoromethyl)-1H-pyrazole-4-carboxylic acid [INT 1-tt] (1.45 g, 5.15 mmol), triethylamine (781 mg, 7.72 mmol) and diphenylphosphoryl azide (2.83 g, 10.3 mmol) in t-BuOH (6 mL) was stirred at 100° C. for 3 h under $N_2$. The reaction mixture was concentrated under reduced pressure to give the crude product, which was purified by flash chromatography on silica gel (EtOAc/PE=0/1 to 1/5) to give tert-butyl N-[1-(3-cyanophenyl)-5-(trifluoromethyl)-1H-pyrazol-4-yl]carbamate [INT 1-uuu] (1 g, 2.83 mmol, 55.2% yield) as a white solid. m/z: [M+H]+ Calcd for C16H16F3N4O2, 353.1. Found 353.1. $^1$H NMR (400 MHz, $CDCl_3$) δ=8.32 (br s, 1H), 7.79-7.73 (m, 2H), 7.71 (br d, J=8.0 Hz, 1H), 7.65-7.59 (m, 1H), 6.55 (br s, 1H), 1.55 (s, 9H).

Synthesis of 3-[4-amino-5-(trifluoromethyl)-1H-pyrazol-1-yl]benzonitrile Hydrochloride [INT 1.17]

A solution of tert-butyl N-[1-(3-cyanophenyl)-5-(trifluoromethyl)-1H-pyrazol-4-yl]carbamate [INT 1-uuu] (100 mg, 283 μmol) in HCl/Dioxane (1.5 mL) was stirred at 20° C. for 2 h. The reaction was concentrated under reduced pressure to give 3-[4-amino-5-(trifluoromethyl)-1H-pyrazol-1-yl]benzonitrile hydrochloride [INT 1.17] (82.0 mg, 284 μmol, 100% yield) as an off-white solid. m/z: [M+H]+ Calcd for C11H8F3N4 253.1. Found 253.0. $^1$H NMR (400 MHz, DMSO-d6) δ=8.04-7.94 (m, 2H), 7.85-7.71 (m, 2H), 7.61 (s, 1H).

Synthesis of 1-(pyrimidin-2-yl)-5-(trifluoromethyl)-1H-pyrazol-4-amine [Intermediate 1.18]

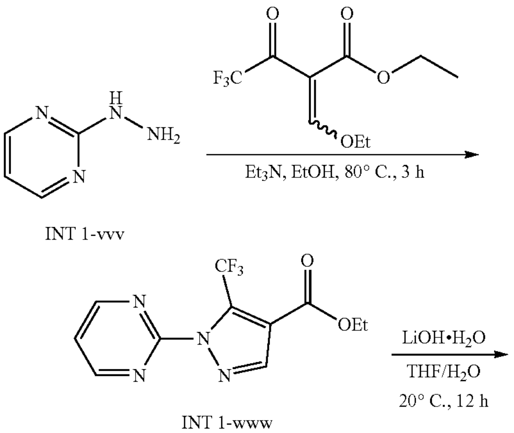

INT 1-vvv

INT 1-www

-continued

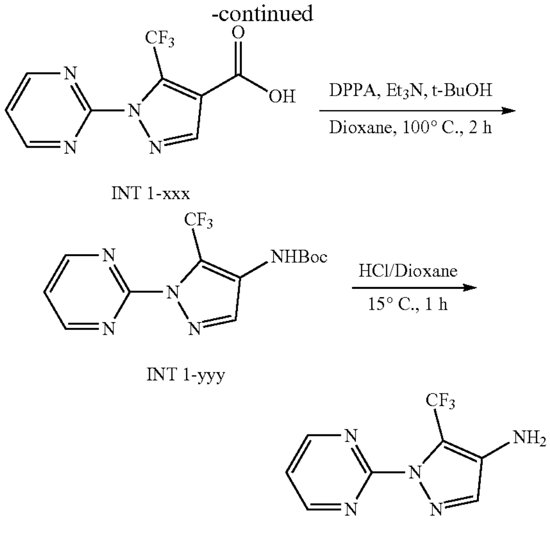

INT 1-xxx

INT 1-yyy

INT 1.18

Synthesis of ethyl 1-(pyrimidin-2-yl)-5-(trifluoromethyl)-1H-pyrazole-4-carboxylate [INT 1-www]

To a solution of ethyl 2-(ethoxymethylidene)-4,4,4-trifluoro-3-oxobutanoate (5.45 g, 22.7 mmol) in EtOH (10 mL) at 10° C. was added 2-hydrazinylpyrimidine [INT 1-vvv] (2.5 g, 22.7 mmol) and $Et_3N$ (2.29 g, 22.7 mmol). The mixture was stirred at 80° C. for 3 h. The reaction was concentrated under reduced pressure, quenched by adding water (100 mL) and was extracted with EtOAc (80 mL×3). The combined organic layers were washed with brine (80 mL×2), dried over anhydrous $Na_2SO_4$ and concentrated under reduced pressure to give the crude product, which was purified by flash chromatography on silica gel (PE/EtOAc=1/0 to 5/1) to give ethyl 1-(pyrimidin-2-yl)-5-(trifluoromethyl)-1H-pyrazole-4-carboxylate [INT 1-www] (4.72 g, 16.5 mmol, 72.7% yield) as a yellow oil. $^1$H NMR (400 MHz, DMSO) δ=9.08 (d, J=4.0 Hz, 2H), 8.38 (s, 1H), 7.83 (t, J=4.0 Hz, 1H), 4.33 (q, J=8.0 Hz, 2H), 1.31 (t, J=8.0 Hz, 3H).

Synthesis of 1-(pyrimidin-2-yl)-5-(trifluoromethyl)-1H-pyrazole-4-carboxylic Acid [INT 1-xxx]

To a solution of ethyl 1-(pyrimidin-2-yl)-5-(trifluoromethyl)-1H-pyrazole-4-carboxylate [INT 1-www] (4 g, 13.9 mmol) in THF (6 mL) and $H_2O$ (2 mL) at 10° C. was added lithium hydroxide monohydrate (2.91 g, 69.5 mmol). The mixture was then stirred at 50° C. for 2 h. The mixture was worked up with another of the same reaction. The mixture was acidified with 1 M HCl to pH=5 and extracted with EtOAc (60 mL×2). The combined organic layers were washed with brine (40 mL×2), dried over anhydrous $Na_2SO_4$ and concentrated under reduced pressure to afford 1-(pyrimidin-2-yl)-5-(trifluoromethyl)-1H-pyrazole-4-carboxylic acid [INT 1-xxx] (3.80 g, 14.7 mmol) as a pale yellow solid. $^1$H NMR (400 MHz, DMSO) δ=9.07 (d, J=4.0 Hz, 2H), 8.30 (s, 1H), 7.82 (t, J=6.0 Hz, 1H)

Synthesis of tert-butyl N-[1-(pyrimidin-2-yl)-5-(trifluoromethyl)-1H-pyrazol-4-yl]carbamate [INT 1-yyy]

To a mixture of 1-(pyrimidin-2-yl)-5-(trifluoromethyl)-1H-pyrazole-4-carboxylic acid [INT 1-xxx] (500 mg, 1.93 mmol) in t-BuOH (2 mL) and dioxane (6 mL) was added triethylamine (781 mg, 7.72 mmol) and diphenylphosphoryl azide (1.40 g, 5.79 mmol) at 10° C. The mixture was then stirred at 100° C. for 2 hr. Water (30 mL) was added and the mixture was extracted with EtOAc (30 mL×2). The combined organic layers were washed with brine (30 mL×2), dried over anhydrous $Na_2SO_4$, filtered and concentrated under reduced pressure to give the crude product, which was purified by flash chromatography on silica gel (Petroleum ether/EtOAc=1/0 to 3/1) to give tert-butyl N-[1-(pyrimidin-2-yl)-5-(trifluoromethyl)-1H-pyrazol-4-yl]carbamate [INT 1-yyy] (340 mg, 1.03 mmol, 53.5% yield) as a white solid. $^1H$ NMR (400 MHz, DMSO) δ=9.23 (s, 1H), 8.98 (d, J=4.0 Hz, 2H), 7.99 (s, 1H), 7.65 (t, J=4.0 Hz, 1H), 1.47 (s, 9H).

Synthesis of 1-(pyrimidin-2-yl)-5-(trifluoromethyl)-1H-pyrazol-4-amine [INT 1.18]

A solution of tert-butyl N-[1-(pyrimidin-2-yl)-5-(trifluoromethyl)-1H-pyrazol-4-yl]carbamate [INT 1-yyy] (340 mg, 1.03 mmol) in HCl/dioxane (10 mL) was stirred at 15° C. for 1 h. The mixture was concentrated under reduced pressure to give 1-(pyrimidin-2-yl)-5-(trifluoromethyl)-1H-pyrazol-4-amine [INT 1.18] (236 mg, 1.02 mmol, 100% yield) as a brown solid. $^1H$ NMR (400 MHz, DMSO) δ=8.86 (d, J=4.0 Hz, 2H), 7.56 (s, 1H), 7.49 (t, J=4.0 Hz, 1H).

Synthesis of 1-(pyrazin-2-yl)-5-(trifluoromethyl)-1H-pyrazol-4-amine Hydrochloride [Intermediate 1.19]

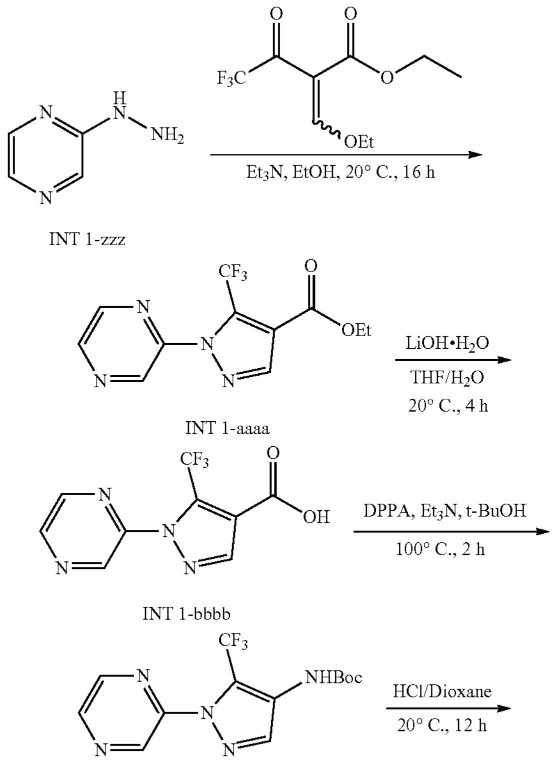

INT 1-zzz

INT 1-aaaa

INT 1-bbbb

INT 1-cccc

-continued

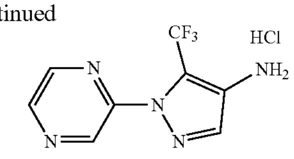

INT 1.19

Synthesis of ethyl 1-(pyrazin-2-yl)-5-(trifluoromethyl)-1H-pyrazole-4-carboxylate [INT 1-aaaa]

To a solution of 2-hydrazinylpyrazine [INT 1-zzz] (2.0 g, 18.1 mmol) in EtOH (15 mL) was added ethyl 2-(ethoxymethylidene)-4,4,4-trifluoro-3-oxobutanoate (4.34 g, 18.1 mmol) and triethylamine (2.01 g, 19.9 mmol). The reaction was stirred at 20° C. for 16 h. The reaction mixture was concentrated under reduced pressure to give the crude product, which was purified by flash chromatography on silica gel (EtOAc/PE=0/1 to 1/5) to give ethyl 1-(pyrazin-2-yl)-5-(trifluoromethyl)-1H-pyrazole-4-carboxylate [INT 1-aaaa] (3.00 g, 10.4 mmol, 57.9% yield) as an oil. m/z: [M+H]+ Calcd for C11H10F3N4O2, 287.1. Found 287.1. $^1H$ NMR (400 MHz, $CDCl_3$) δ=9.01 (d, J=1.2 Hz, 1H), 8.73 (d, J=2.8 Hz, 1H), 8.59-8.54 (m, 1H), 8.18 (s, 1H), 4.40 (q, J=6.8 Hz, 2H), 1.40 (t, J=7.2 Hz, 3H).

Synthesis of 1-(pyrazin-2-yl)-5-(trifluoromethyl-1H-pyrazole-4-carboxylic Acid [INT 1-bbbb]

To a solution of ethyl 1-(pyrazin-2-yl)-5-(trifluoromethyl)-1H-pyrazole-4-carboxylate [INT 1-aaaa] (2.8 g, 9.78 mmol) in THF (12 mL) was added lithium hydroxide monohydrate (818 mg, 19.5 mmol) in $H_2O$ (4 mL). The reaction was stirred at 20° C. for 4 h. The reaction mixture was poured into 20 mL of water, acidified with 1 N HCl to pH=3-4 and extracted with EtOAc (30 mL×2). The combined organic layers were washed with brine (30 mL×2), dried over anhydrous $Na_2SO_4$ and concentrated under reduced pressure to give 1-(pyrazin-2-yl)-5-(trifluoromethyl)-1H-pyrazole-4-carboxylic acid [INT 1-bbbb] (2.25 g, 8.71 mmol, 89.2% yield) as a white solid. $^1H$ NMR (400 MHz, $CDCl_3$) δ=13.57 (br s, 1H), 9.14 (s, 1H), 8.92 (d, J=2.4 Hz, 1H), 8.75 (d, J=1.2 Hz, 1H), 8.37 (s, 1H).

Synthesis of tert-butyl N-[1-(pyrazin-2-yl)-5-(trifluoromethyl)-1H-pyrazol-4-yl]carbamate [INT 1-cccc]

A solution of 1-(pyrazin-2-yl)-5-(trifluoromethyl)-1H-pyrazole-4-carboxylic acid [INT 1-bbbb] (2.25 g, 8.71 mmol), triethylamine (1.31 g, 13.0 mmol) and diphenylphosphoryl azide (4.78 g, 17.4 mmol) in t-BuOH (20 mL) was stirred at 100° C. for 2 h under $N_2$. The reaction mixture was concentrated under reduced pressure to give the crude product, which was purified by flash chromatography on silica gel (EtOAc/PE=0/1 to 1/5) to give tert-butyl N-[1-(pyrazin-2-yl)-5-(trifluoromethyl)-1H-pyrazol-4-yl]carbamate [INT 1-cccc] (2.33 g, 7.07 mmol, 81.4% yield) as a white solid. m/z: [M+H]+ Calcd for C13H15F3N5O2 330.1. Found 330.0. $^1H$ NMR (400 MHz, $CDCl_3$) δ=9.15 (d, J=0.8 Hz, 1H), 8.56 (d, J=2.4 Hz, 1H), 8.51-8.36 (m, 2H), 6.76 (br s, 1H), 1.54 (s, 9H).

Synthesis of 1-(pyrazin-2-yl)-5-(trifluoromethyl)-1H-pyrazol-4-amine Hydrochloride [INT 1.19]

A mixture of tert-butyl N-[1-(pyrazin-2-yl)-5-(trifluoromethyl)-1H-pyrazol-4-yl]carbamate [INT 1-cccc] (100 mg, 303 μmol) in HCl/Dioxane (5 mL) was stirred at 20° C. for 12 h. The reaction mixture was concentrated under reduced pressure to give 1-(pyrazin-2-yl)-5-(trifluoromethyl)-1H-pyrazol-4-amine hydrochloride [INT 1.19] (81.0 mg, 304 μmol) as a brown solid. m/z: [M+H]+ Calcd for C8H7F3N5 230.1. Found 229.9. $^1$H NMR (400 MHz, DMSO-d6) δ=9.04 (d, J=1.6 Hz, 1H), 8.59 (d, J=2.4 Hz, 1H), 8.53-8.49 (m, 1H), 7.64 (s, 1H).

Synthesis of 1-(pyrimidin-4-yl)-5-(trifluoromethyl)-1H-pyrazol-4-amine Hydrochloride [Intermediate 1.20]

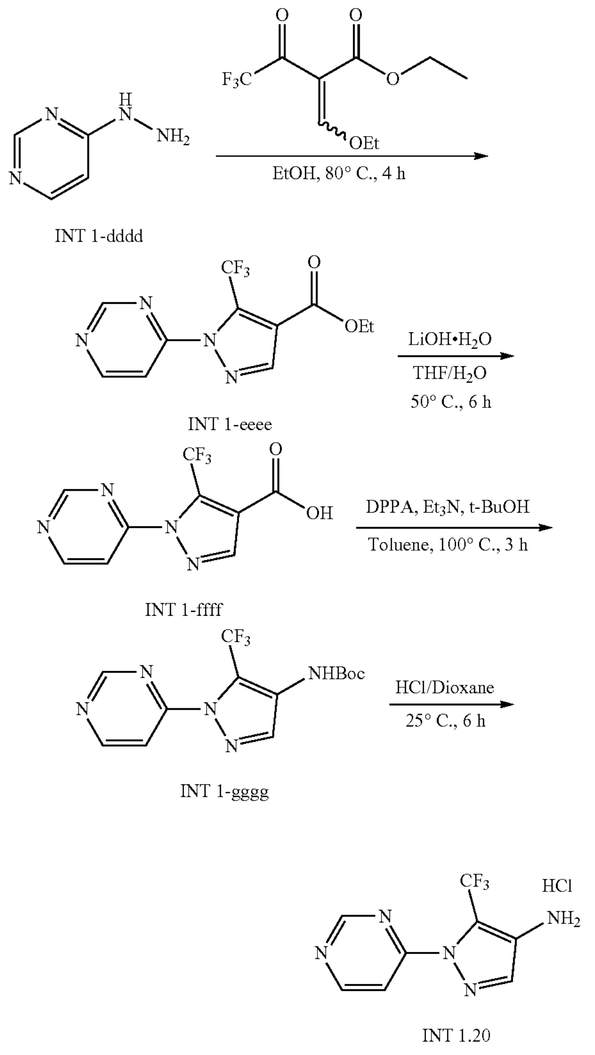

Synthesis of ethyl 1-(pyrimidin-4-yl)-5-(trifluoromethyl)-1H-pyrazole-4-carboxylate [INT 1-eee]

A mixture of ethyl 2-(ethoxymethylidene)-4,4,4-trifluoro-3-oxobutanoate (5 g, 20.8 mmol) and 4-hydrazinylpyrimidine [INT 1-dddd] (2.74 g, 24.9 mmol) in EtOH (50 mL) was stirred at 80° C. for 4 hr. The mixture was concentrated under reduced pressure to afford the crude product, which was purified by flash chromatography on silica gel (0-15% EtOAc in Petroleum ether) to give ethyl 1-(pyrimidin-4-yl)-5-(trifluoromethyl)-1H-pyrazole-4-carboxylate [INT 1-eeee] (3.90 g, 13.6 mmol, 65.5% yield) as a white solid. m/z: [M+H]+ Calcd for C11H10F3N4O2, 287.1. Found 287.0. $^1$H NMR (400 MHz, $CDCl_3$) δ=9.21 (s, 1H), 8.96 (dd, J=2.0, 5.6 Hz, 1H), 8.14 (s, 1H), 7.80 (td, J=1.2, 5.6 Hz, 1H), 4.40 (tq, J=1.6, 7.2 Hz, 2H), 1.44-1.36 (m, 3H).

Synthesis of 1-(pyrimidin-4-yl)-5-trifluoromethyl)-1H-pyrazole-4-carboxylic Acid [INT 1-ffff]

To a mixture of ethyl 1-(pyrimidin-4-yl)-5-(trifluoromethyl)-1H-pyrazole-4-carboxylate [INT 1-eeee] (2.9 g, 10.1 mmol) in THF (15 mL) and $H_2O$ (5 mL) was added LiOH·$H_2O$ (1.27 g, 30.3 mmol) and the mixture was stirred at 50° C. for 6 hr. The mixture was concentrated under reduced pressure to afford the crude product. $H_2O$ (200 mL) and EtOAc (200 mL) were added and the precipitate was collected by filtration. The aqueous phase was washed with EtOAc (200 mL×2), acidified with 1 M HCl to pH=3 and extracted with EtOAc (200 mL×2). The combined organic layers were dried over $Na_2SO_4$ and filtered. The filtrate was concentrated to give a yellow solid, which was combined with the precipitate to give 1-(pyrimidin-4-yl)-5-(trifluoromethyl)-1H-pyrazole-4-carboxylic acid [INT 1-ffff] (2.10 g, 8.13 mmol, 80.7% yield) as a white solid. $^1$H NMR (400 MHz, $CDCl_3$) δ=9.23 (s, 1H), 8.99 (d, J=5.6 Hz, 1H), 8.22 (s, 1H), 7.81 (d, J=4.4 Hz, 1H).

Synthesis of tert-butyl N-[1-(pyrimidin-4-yl)-5-(trifluoromethyl)-1H-pyrazol-4-yl]carbamate [INT 1-gggg]

A mixture of 1-(pyrimidin-4-yl)-5-(trifluoromethyl)-1H-pyrazole-4-carboxylic acid [INT 1-ffff] (1.6 g, 6.19 mmol), 2-methylpropan-2-ol (6.87 g, 92.8 mmol), diphenylphosphoryl azide (2.25 g, 9.28 mmol) and triethylamine (1.87 g, 18.5 mmol) in toluene (20 mL) was stirred at 100° C. for 3 hr. $NaHCO_3$ (100 mL) was added and the mixture was extracted with EtOAc (100 mL×2). The combined organic layers were washed with brine (100 mL×2), dried over anhydrous $Na_2SO_4$, filtered and concentrated under reduced pressure to give the crude product, which was purified by flash chromatography on silica gel (0-10% EtOAc in Petroleum ether) to give tert-butyl N-[1-(pyrimidin-4-yl)-5-(trifluoromethyl)-1H-pyrazol-4-yl]carbamate [INT 1-gggg] (1.80 g, 5.46 mmol, 88.6% yield) as a white solid. m/z: [M+H]+ Calcd for C13H15F3N5O2 330.1. Found: 330.1. $^1$H NMR (400 MHz, $CDCl_3$) δ=9.06 (s, 1H), 8.79 (d, J=5.6 Hz, 1H), 8.49 (br s, 1H), 7.88 (d, J=5.6 Hz, 1H), 6.82 (br s, 1H), 1.54 (s, 9H).

Synthesis of 1-(pyrimidin-4-yl)-5-(trifluoromethyl)-1H-pyrazol-4-amine Hydrochloride [INT 1.20]

A mixture of tert-butyl N-[1-(pyrimidin-4-yl)-5-(trifluoromethyl)-1H-pyrazol-4-yl]carbamate [INT 1-gggg] (150 mg, 455 μmol) in 4 M HCl/dioxane (10 mL, 40.0 mmol) was stirred at 25° C. for 6 hr. The mixture was concentrated under reduced pressure to afford 1-(pyrimidin-4-yl)-5-(trifluoromethyl)-1H-pyrazol-4-amine hydrochloride [INT 1.20] (120 mg, 451 μmol) as a brown solid. m/z: [M+H]+ Calcd for C8H7F3N5 230.1. Found 230.0.

Synthesis of 1-(pyridazin-3-yl)-5-(trifluoromethyl)-1H-pyrazol-4-amine Hydrochloride [Intermediate 1.21]

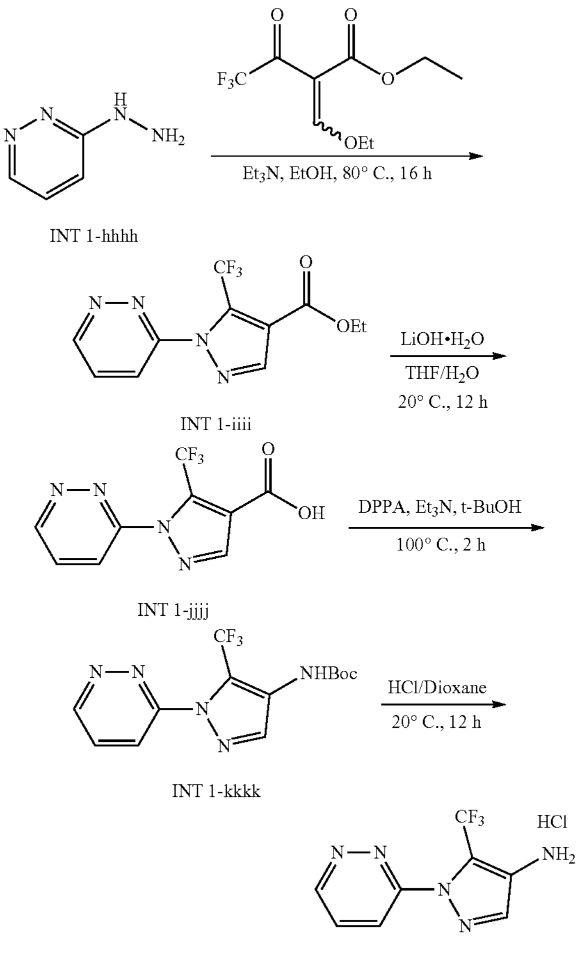

INT 1-hhhh

INT 1-iiii

INT 1-jjjj

INT 1-kkkk

INT 1.21

Synthesis of ethyl 1-(pyridazin-3-yl)-5-(trifluoromethyl)-1H-pyrazole-4-carboxylate [INT 1-iiii]

A solution consisting of 3-hydrazinylpyridazine [INT 1-hhhh] (800 mg, 7.26 mmol), $Et_3N$ (1.46 g, 14.5 mmol), ethyl 2-(ethoxymethylidene)-4,4,4-trifluoro-3-oxobutanoate (1.74 g, 7.26 mmol) and EtOH (50 mL) was stirred at 80° C. for 16 h. The mixture was concentrated under reduced pressure to afford a brown oil, which was purified by flash column chromatography (petroleum ether:ethyl acetate=0:1 to 85:15) to give ethyl 1-(pyridazin-3-yl)-5-(trifluoromethyl)-1H-pyrazole-4-carboxylate [INT 1-iiii] (1 g, 3.49 mmol, 48.3% yield) as a white solid. m/z: [M+H]+ Calcd for C11H10F3N4O2, 287.1. Found 286.9. $^1$H NMR (400 MHz, $CDCl_3$) δ=9.36 (dd, J=1.2, 4.8 Hz, 1H), 8.23 (s, 1H), 7.95 (dd, J=1.6, 8.8 Hz, 1H), 7.80 (dd, J=4.8, 8.8 Hz, 1H), 4.46-4.41 (m, 2H), 1.45-1.41 (m, 3H).

Synthesis of 1-(pyridazin-3-yl)-5-(trifluoromethyl)-1H-pyrazole-4-carboxylic Acid [INT 1-jjjj]

A mixture of ethyl 1-(pyridazin-3-yl)-5-(trifluoromethyl)-1H-pyrazole-4-carboxylate [INT 1-iiii] (800 mg, 2.79 mmol) in THF (9 mL) and $H_2O$ (3 mL) was stirred at 20° C. for 12 h. The reaction was concentrated under reduced pressure to give a residue, which was purified by Prep-HPLC (column: Boston Prime C18 150*30 mm*5 μm, table: 2-42% B (A=water (0.05% HCl), B=acetonitrile), flow rate: 30 mL/min, UV Detector 220 nm) to afford 1-(pyridazin-3-yl)-5-(trifluoromethyl)-1H-pyrazole-4-carboxylic acid [INT 1-jjjj] (240 mg, 929 μmol, 33.3% yield) as a yellow solid. m/z: [M+H]+ Calcd for C9H6F3N4O2, 259.0. Found 258.9. $^1$H NMR (400 MHz, DMSO-d6) δ=9.46 (dd, J=1.2, 4.8 Hz, 1H), 8.41 (s, 1H), 8.21 (dd, J=1.2, 8.8 Hz, 1H), 8.10 (dd, J=4.8, 8.8 Hz, 1H).

Synthesis of tert-butyl N-[1-(pyridazin-3-yl)-5-(trifluoromethyl)-1H-pyrazol-4-yl]carbamate [INT 1-kkkk]

To a solution of 1-(pyridazin-3-yl)-5-(trifluoromethyl)-1H-pyrazole-4-carboxylic acid [INT 1-jjjj] (200 mg, 774 μmol) in t-BuOH (3 mL) was added diphenylphosphoryl azide (319 mg, 1.16 mmol) and $Et_3N$ (234 mg, 2.32 mmol). The reaction mixture was stirred at 100° C. for 2 h under $N_2$, after which it was quenched by adding water (15 mL) and was extracted with EtOAc (2×10 mL). The combined organic layers were washed with brine (2×20 mL), dried over anhydrous $Na_2SO_4$ and concentrated under reduced pressure to give the crude product, which was purified by flash chromatography on silica gel (EtOAc/Petroleum ether=0/1 to 1/4) to give tert-butyl N-[1-(pyridazin-3-yl)-5-(trifluoromethyl)-1H-pyrazol-4-yl]carbamate [INT 1-kkkk] (142 mg, 431 μmol, 55.9% yield) as a colorless oil. m/z: [M+H]+ Calcd for C13H15F3N5O2 330.1. Found 330.0. $^1$H NMR (400 MHz, $CDCl_3$) δ=9.20 (d, J=4.4 Hz, 1H), 8.51 (br s, 1H), 8.07 (br d, J=8.8 Hz, 1H), 7.68 (dd, J=4.8, 8.8 Hz, 1H), 6.79 (br s, 1H), 1.57 (s, 9H).

Synthesis of 1-(pyridazin-3-yl)-5-(trifluoromethyl)-1H-pyrazol-4-amine Hydrochloride [INT 1.21]

Tert-butyl N-[1-(pyridazin-3-yl)-5-(trifluoromethyl)-1H-pyrazol-4-yl]carbamate [INT 1-kkkk] (142 mg, 431 μmol) in HCl (4 M in dioxane, 5 mL, 20.0 mmol) was stirred at 20° C. for 12 h. The mixture was concentrated under reduced pressure to give 1-(pyridazin-3-yl)-5-(trifluoromethyl)-1H-pyrazol-4-amine hydrochloride [INT 1.21] (114 mg, 429 μmol) as a yellow solid. m/z: [M+H]+ Calcd for C8H7F3N5 230.1. Found 230.0.

Synthesis of 1-(pyridazin-4-yl)-5-(trifluoromethyl)-1H-pyrazol-4-amine Hydrochloride [Intermediate 1.22]

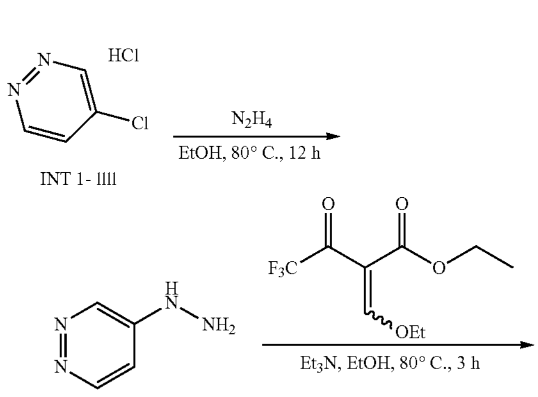

INT 1- llll

INT 1-mmmm

-continued

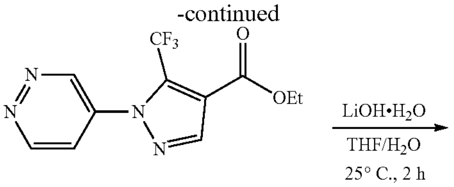

INT 1-nnnn

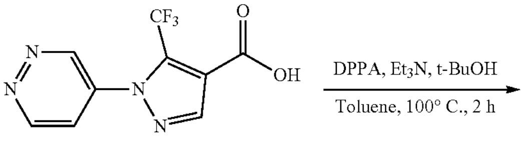

INT 1-oooo

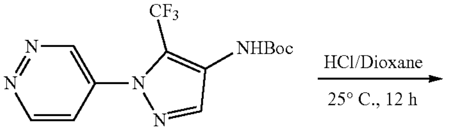

INT 1-pppp

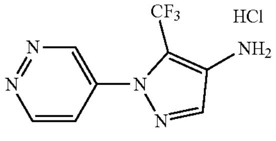

INT 1.22

Synthesis of 4-hydrazinylpyridazine [INT 1-mmmm]

To a mixture of 4-chloropyridazine hydrochloride [INT 1-llll] (900 mg, 5.96 mmol) in EtOH (10 mL) was added $NH_2NH_2 \cdot H_2O$ (3.50 g, 59.6 mmol). The reaction mixture was stirred at 80° C. for 12 hours. The reaction mixture was concentrated to give 4-hydrazinylpyridazine [INT 1-mmmm] (656 mg, 5.95 mmol) as a brown oil. $^1H$ NMR (400 MHz, DMSO-d6) δ=8.59 (d, J=2.4 Hz, 1H), 8.47 (dd, J=0.8, 6.0 Hz, 1H), 6.73 (dd, J=2.8, 6.0 Hz, 1H).

Synthesis of ethyl 1-(pyridazin-4-yl)-5-(trifluoromethyl)-1H-pyrazole-4-carboxylate [INT 1-nnnn]

To a mixture of 4-hydrazinylpyridazine [INT 1-mmmm] (656 mg, 5.95 mmol) and ethyl 2-(ethoxymethylidene)-4,4,4-trifluoro-3-oxobutanoate (7.13 g, 29.7 mmol) in EtOH (10 mL) was added triethylamine (6.02 g, 59.5 mmol). The reaction mixture was stirred at 80° C. for 3 hours. The reaction mixture was concentrated, diluted with water (100 mL) and extracted with EtOAc (50 mL×3). The combined organic layers were washed with brine (100 mL), dried over anhydrous sodium sulfate and filtered. The filtrate was concentrated to give the crude product, which was purified by flash chromatography on silica gel (20-25% EtOAc in petroleum ether) to give ethyl 1-(pyridazin-4-yl)-5-(trifluoromethyl)-1H-pyrazole-4-carboxylate [INT 1-nnnn] (1 g, 3.49 mmol, 58.8% yield) as brown oil. m/z: [M+H]+ Calcd for C11H10F3N4O2, 287.1. Found 287.0. $^1H$ NMR (400 MHz, $CDCl_3$) δ=9.55-9.42 (m, 2H), 8.25 (s, 1H), 7.71 (br s, 1H), 4.42 (q, J=7.2 Hz, 2H), 1.41 (t, J=7.2 Hz, 3H).

Synthesis of 1-(pyridazin-4-yl)-5-(trifluoromethyl)-1H-pyrazole-4-carboxylic Acid [INT 1-oooo]

To a mixture of ethyl 1-(pyridazin-4-yl)-5-(trifluoromethyl)-1H-pyrazole-4-carboxylate [INT 1-nnnn] (950 mg, 3.31 mmol) in THF (10 mL) and $H_2O$ (3 mL) was added lithium hydroxide monohydrate (416 mg, 9.93 mmol). The reaction mixture was stirred at 25° C. for 2 hours. The reaction mixture was concentrated, diluted with water (50 mL) and washed with EtOAc (50 mL×2). The aqueous phase was acidified with 1 M HCl to pH=3 and extracted with EtOAc (50 mL×3). The combined organic layers were dried over anhydrous sodium sulfate and filtered. The filtrate was concentrated to give 1-(pyridazin-4-yl)-5-(trifluoromethyl)-1H-pyrazole-4-carboxylic acid [INT 1-oooo] (530 mg, 2.05 mmol, 62.0% yield) as a yellow solid. m/z: [M+H]+ Calcd for C9H6F3N4O2, 259.0. Found 258.9. $^1H$ NMR (400 MHz, DMSO-d6) δ=9.58 (d, J=2.4 Hz, 1H), 9.56 (dd, J=1.2, 5.6 Hz, 1H), 8.42 (s, 1H), 8.06 (dd, J=2.4, 5.6 Hz, 1H).

Synthesis of tert-butyl N-[1-(pyridazin-4-yl)-5-(trifluoromethyl)-1H-pyrazol-4-yl]carbamate [INT 1-pppp]

To a mixture of 1-(pyridazin-4-yl)-5-(trifluoromethyl)-1H-pyrazole-4-carboxylic acid [INT 1-oooo] (500 mg, 1.93 mmol) and 2-methylpropan-2-ol (2.14 g, 28.9 mmol) in toluene (5 mL) were added diphenylphosphoryl azide (795 mg, 2.89 mmol) and triethylamine (585 mg, 5.79 mmol). The reaction mixture was stirred at 100° C. under nitrogen for 2 hours. The mixture was concentrated under reduced pressure to give the crude product, which was purified by flash chromatography on silica gel (EtOAc/PE=0/1 to 1/3) to give tert-butyl N-[1-(pyridazin-4-yl)-5-(trifluoromethyl)-1H-pyrazol-4-yl]carbamate [INT 1-pppp] (250 mg, 759 μmol, 39.3% yield) as a white solid. m/z: [M+H]+ Calcd for C13H15F3N5O2, 330.1. Found 330.1. $^1H$ NMR (400 MHz, $CDCl_3$) δ=9.51 (d, J=2.4 Hz, 1H), 9.32 (dd, J=0.8, 5.6 Hz, 1H), 8.48 (br s, 1H), 7.66-7.59 (m, 1H), 6.69 (br s, 1H), 1.58-1.51 (m, 9H).

Synthesis of 1-(pyridazin-4-yl)-5-(trifluoromethyl)-1H-pyrazol-4-amine Hydrochloride [INT 1.22]

A solution of tert-butyl N-[1-(pyridazin-4-yl)-5-(trifluoromethyl)-1H-pyrazol-4-yl]carbamate [INT 1-pppp] (230 mg, 698 μmol) in HCl/Dioxane (5 mL) was stirred at 25° C. for 12 h. The reaction mixture was concentrated under reduced pressure to give 1-(pyridazin-4-yl)-5-(trifluoromethyl)-1H-pyrazol-4-amine hydrochloride [INT 1.22] (185 mg, 696 μmol) as a white solid. $^1H$ NMR (400 MHz, DMSO-d6) δ=9.47 (d, J=2.4 Hz, 1H), 9.35 (dd, J=0.8, 6.0 Hz, 1H), 7.76-7.71 (m, 1H), 7.68 (s, 1H).

Synthesis of 5-(1-methoxyethyl)-1-(pyridin-3-yl)-1H-pyrazol-4-amine [Intermediate 1.23]

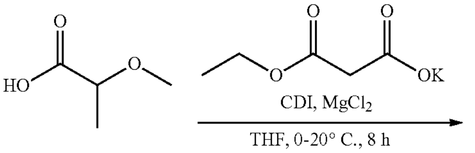

INT 1-qqqq

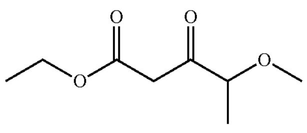

INT 1-rrrr

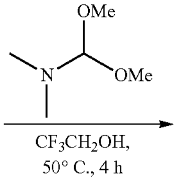

-continued

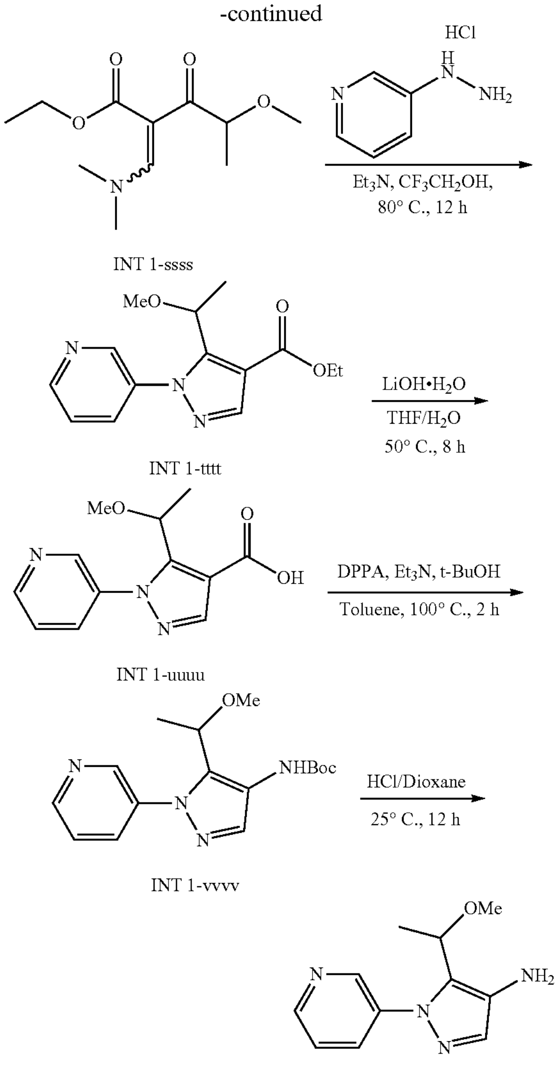

INT 1-ssss

INT 1-tttt

INT 1-uuuu

INT 1-vvvv

INT 1.23

Synthesis of ethyl 4-methoxy-3-oxopentanoate [INT 1-rrrr]

To a solution of 2-methoxypropanoic acid [INT 1-qqqq] (5 g, 48.0 mmol) in THF (50 mL) was added CDI (9.32 g, 57.5 mmol) at 0° C., and the mixture was stirred at 20° C. for 2 hours. Magnesium chloride (4.57 g, 48.0 mmol) and ethyl potassium malonate (12.2 g, 72.0 mmol) were added to the reaction solution, and the mixture was stirred at 20° C. for 6 hours. 1 N HCl (200 mL) was then added and the mixture was extracted with EtOAc (2x200 mL). The combined organic layers were washed with brine (2x200 mL), dried over anhydrous $Na_2SO_4$ and concentrated under reduced pressure to give the crude product ethyl 4-methoxy-3-oxopentanoate [INT 1-rrrr] (6.15 g, 35.3 mmol, 73.5% yield) as a yellow oil. $^1H$ NMR (400 MHz, $CDCl_3$) δ=4.24-4.10 (m, 2H), 3.79 (q, J=6.8 Hz, 1H), 3.60-3.47 (m, 2H), 3.40-3.29 (m, 3H), 1.37-1.17 (m, 6H).

Synthesis of ethyl 2-((dimethylamino)methylene)-4-methoxy-3-oxopentanoate [INT 1-ssss]

A mixture of ethyl 4-methoxy-3-oxopentanoate [INT 1-rrrr] (6.15 g, 35.3 mmol) and (dimethoxymethyl)dimethylamine (8.41 g, 70.6 mmol) in 2,2,2-trifluoroethanol (60 mL) was stirred at 50° C. for 4 hrs. The mixture was concentrated under reduced pressure to afford the crude product ethyl 2-((dimethylamino)methylene)-4-methoxy-3-oxopentanoate [INT 1-ssss].

Synthesis of ethyl 5-(1-methoxyethyl)-1-(pyridin-3-yl)-1H-pyrazole-4-carboxylate [INT 1-tttt]

To a mixture of ethyl 2-((dimethylamino)methylene)-4-methoxy-3-oxopentanoate [INT 1-ssss] (5.38 g, 23.4 mmol) and triethylamine (11.8 g, 117 mmol) in 2,2,2-trifluoroethanol (50 mL) was added 3-hydrazinylpyridine hydrochloride (11.9 g, 81.9 mmol). The reaction mixture was stirred at 80° C. for 12 hours. The mixture was concentrated under reduced pressure to afford the crude product. Brine (200 mL) was added and the mixture was extracted with EtOAc (200 mLx2). The combined organic layers were washed with brine (200 mLx2), dried over anhydrous $Na_2SO_4$, filtered and concentrated under reduced pressure to give the crude product, which was purified by flash chromatography on silica gel (0-40% EtOAc in Petroleum ether) to give ethyl 5-(1-methoxyethyl)-1-(pyridin-3-yl)-1H-pyrazole-4-carboxylate [INT 1-tttt](4.40 g, 15.9 mmol, 68.3% yield) as a yellow oil. m/z: [M+H]+ Calcd for C14H18N3O3, 276.1. Found 276.1. $^1H$ NMR (400 MHz, $CDCl_3$) δ=8.80 (d, J=2.4 Hz, 1H), 8.70 (d, J=4.4 Hz, 1H), 8.08 (s, 1H), 7.91-7.87 (m, 1H), 7.43 (dd, J=4.8, 8.4 Hz, 1H), 5.44 (q, J=6.8 Hz, 1H), 4.39-4.31 (m, 2H), 3.27-3.21 (m, 3H), 1.39 (t, J=7.2 Hz, 3H), 1.34 (d, J=6.8 Hz, 3H).

Synthesis of 5-(1-methoxyethyl)-1-(pyridin-3-yl)-1H-pyrazole-4-carboxylic Acid [INT 1-uuuu]

To a mixture of ethyl 5-(1-methoxyethyl)-1-(pyridin-3-yl)-1H-pyrazole-4-carboxylate [INT 1-tttt] (4.4 g, 15.9 mmol) in THF (30 mL) and $H_2O$ (10 mL) was added $LiOH{\cdot}H_2O$ (2.00 g, 47.7 mmol) and the mixture was stirred at 50° C. for 8 hr. The mixture was concentrated under reduced pressure to afford the crude product. $H_2O$ (200 mL) and EtOAc (200 mL) was added and the precipitate was collected by filtration. The aqueous phase was washed with EtOAc (100 mLx2), acidified with 1 M HCl to pH=3 and extracted with EtOAc (100 mLx2). The combined organic layers were dried over $Na_2SO_4$ and filtered. The filtrate was concentrated and combined with the precipitate to give 5-(1-methoxyethyl)-1-(pyridin-3-yl)-1H-pyrazole-4-carboxylic acid [INT 1-uuuu] (2.80 g, 11.3 mmol, 71.2% yield) as a white solid. m/z: [M+H]+ Calcd for C12H14N3O3, 248.1. Found 248.1. $^1H$ NMR (400 MHz, DMSO-d6) δ=8.80-8.66 (m, 2H), 8.06 (s, 1H), 8.02-7.96 (m, 1H), 7.59 (dd, J=4.8, 8.0 Hz, 1H), 5.30 (q, J=6.8 Hz, 1H), 3.08 (s, 3H), 1.28 (d, J=6.8 Hz, 3H).

Synthesis of tert-butyl N-[5-(1-methoxyethyl)-1-(pyridin-3-yl)-1H-pyrazol-4-yl]carbamate [INT 1-vvvv]

A mixture of 5-(1-methoxyethyl)-1-(pyridin-3-yl)-1H-pyrazole-4-carboxylic acid [INT 1-uuuu] (2.8 g, 11.3 mmol), 2-methylpropan-2-ol (12.5 g, 169 mmol), diphenylphosphoryl azide (4.11 g, 16.9 mmol) and triethylamine (3.43 g, 33.9 mmol) in toluene (20 mL) was stirred at 100° C. for 2 hr. Saturated aq. $NaHCO_3$ solution (200 mL) was added and the mixture was extracted with EtOAc (100 mLx2). The combined organic layers were washed with brine (100 mLx2), dried over anhydrous $Na_2SO_4$, filtered and concentrated under reduced pressure to give the crude product, which was purified by flash chromatography on silica gel (0-10% EtOAc in Petroleum ether) to give tert-butyl N-[5-(1-methoxyethyl)-1-(pyridin-3-yl)-1H-pyrazol-4-yl]carbamate [INT 1-vvvv] (2.50 g, 7.85 mmol, 69.6% yield) as a white solid. m/z: [M+H]+ Calcd for C16H23N4O3, 319.2. Found 319.2. $^{1}$H NMR (400 MHz, $CDCl_3$) δ=8.66 (br s, 2H), 8.20 (br s, 1H), 7.82-7.74 (m, 1H), 7.45 (dd, J=5.2, 8.0 Hz, 1H), 6.88 (br s, 1H), 4.48 (q, J=6.8 Hz, 1H), 3.28 (s, 3H), 1.54 (s, 9H), 1.50 (d, J=6.8 Hz, 3H).

Synthesis of 5-(1-methoxyethyl)-1-(pyridin-3-yl)-1H-pyrazol-4-amine [INT 1.23]

A mixture of tert-butyl N-[5-(1-methoxyethyl)-1-(pyridin-3-yl)-1H-pyrazol-4-yl]carbamate [INT 1-vvvv] (500 mg, 1.57 mmol) in 4 M HCl/dioxane (10 mL, 40.0 mmol) was stirred at 25° C. for 12 hr. The mixture was concentrated under reduced pressure to afford a yellow solid, which was purified by Prep-HPLC (column: Boston Prime C18 150*30 mm*5 μm, table: 0-30% B (A=water (ammonia hydroxide v/v)-ACN), B=acetonitrile), flowrate: 20 mL/min, UV Detector 220 nm) to afford 5-(1-methoxyethyl)-1-(pyridin-3-yl)-1H-pyrazol-4-amine [INT 1.23] (185 mg, 847 μmol, 53.9% yield) as a white solid. [M+H]+ Calcd for C11H15N4O, 219.1. Found: 219.0. $^{1}$H NMR (400 MHz, $CDCl_3$) δ=8.68 (d, J=2.3 Hz, 1H), 8.63 (d, J=4.8 Hz, 1H), 7.78 (dd, J=1.5, 8.0 Hz, 1H), 7.47-7.42 (m, 1H), 7.42-7.39 (m, 1H), 4.49 (q, J=6.5 Hz, 1H), 3.27 (d, J=1.3 Hz, 3H), 3.13-2.80 (m, 2H), 1.53 (d, J=6.5 Hz, 3H).

Synthesis of 1-[4-amino-1-(pyridin-3-yl)-1H-pyrazol-5-yl]ethan-1-ol[ Intermediate 1.24]

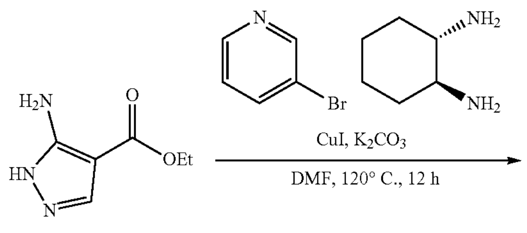

INT 1-wwww

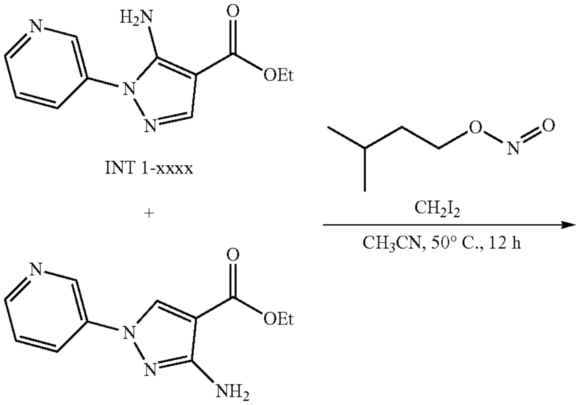

INT 1-xxxx

+

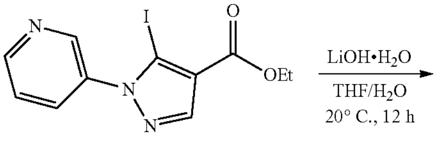

INT 1-yyyy

-continued

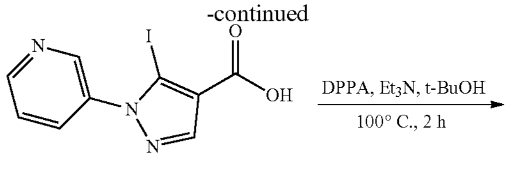

INT 1-zzzz

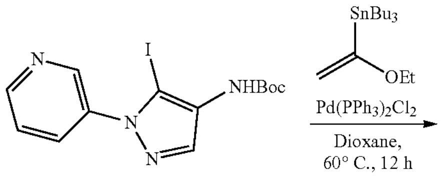

INT 1-aaaaa

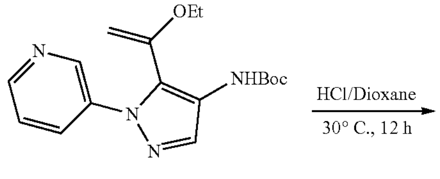

INT 1-bbbbb

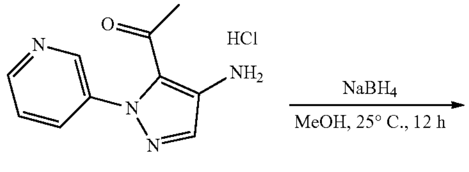

INT 1-ccccc

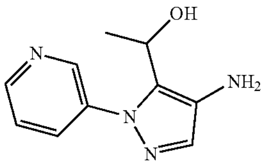

INT 1.24

Synthesis of ethyl 5-amino-1-(pyridin-3-yl)-1H-pyrazole-4-carboxylate [INT 1-xxxx]

A suspension of ethyl 5-amino-1H-pyrazole-4-carboxylate [INT 1-wwww] (18.5 g, 119 mmol), 3-bromopyridine (15.6 g, 99.1 mmol), CuI (942 mg, 4.95 mmol), $K_2CO_3$ (27.3 g, 198 mmol) and trans-1,2-diaminocyclohexane (1.13 g, 9.91 mmol) in DMF (100 mL) was stirred at 120° C. for 12 h under $N_2$. The reaction mixture was filtered. The filtrate was diluted with water (30 mL) and was extracted with EtOAc (2×20 mL). The combined organic layers were washed with brine (2×50 mL), dried over anhydrous $Na_2SO_4$ and concentrated under reduced pressure to give the crude product, which was purified by flash chromatography on silica gel (EtOAc/Petroleum ether=1/4 to 1/1) to give a mixture of ethyl 5-amino-1-(pyridin-3-yl)-1H-pyrazole-4-carboxylate [INT 1-xxxx] (10.1 g, 43.4 mmol, 43.9% yield) and ethyl 3-amino-1-(pyridin-3-yl)-1H-pyrazole-4-carboxylate (5.20 g, 22.3 mmol, 22.6% yield) as a yellow oil. m/z: [M+H]+ Calcd for C11H13N4O2, 233.1. Found 233.2.

Synthesis of ethyl 5-iodo-1-(pyridin-3-yl)-1H-pyrazole-4-carboxylate [INT 1-yyyy]

Ethyl 5-amino-1-(pyridin-3-yl)-1H-pyrazole-4-carboxylate [INT 1-xxx] (6.78 g, 29.2 mmol) was suspended in acetonitrile (100 mL) at ambient temperature. Diiodomethane (46.8 g, 175 mmol) was added followed by isopentyl nitrite (10.2 g, 87.6 mmol). The reaction was heated at 50° C. for 12 hours, after which it was combined with another of the same type and partitioned between water (500 mL) and ethyl acetate (300 mL). The aqueous layer was extracted with ethyl acetate (300 mL×2). The combined organic layers were dried over anhydrous sodium sulfate. After removal of solvents under reduced pressure, the crude material was purified using silica gel column chromatography (10-25% ethyl acetate in Petroleum ether). Compound ethyl 5-iodo-1-(pyridin-3-yl)-1H-pyrazole-4-carboxylate [INT 1-yyyy] (2.25 g, 6.55 mmol) was obtained as a yellow solid. m/z: [M+H]+ Calcd for C11H11IN3O2, 344.0. Found 343.9. $^{1}$H NMR (400 MHz, $CDCl_3$) δ=8.76 (d, J=2.4 Hz, 1H), 8.68 (d, J=4.8 Hz, 1H), 8.14 (s, 1H), 7.86-7.78 (m, 1H), 7.43 (dd, J=4.8, 8.0 Hz, 1H), 4.35-4.29 (m, 2H), 1.33 (t, J=7.2 Hz, 3H).

Synthesis of 5-iodo-1-(pyridin-3-yl)-1H-pyrazole-4-carboxylic Acid [INT 1-zzzz]

A solution of ethyl 5-iodo-1-(pyridin-3-yl)-1H-pyrazole-4-carboxylate [INT 1-yyyy](156 mg, 454 μmol) and lithium hydroxide monohydrate (28.5 mg, 681 μmol) in a mixture of THF (3 mL) and $H_2O$ (1 mL) was stirred at 20° C. for 12 h. The mixture was adjusted to pH=4 by 1 N HCl. The resulting suspension was filtered and washed with water (5 mL×2). The filter cake was dried to obtained 5-iodo-1-(pyridin-3-yl)-1H-pyrazole-4-carboxylic acid [INT 1-zzzz](56.0 mg, 177 μmol, 39.1% yield) as a yellow solid. m/z: [M+H]+ Calcd for C9H7IN3O2 316.0. Found 315.9. $^{1}$H NMR (400 MHz, DMSO-d6) δ=12.81 (br s, 1H), 8.83-8.70 (m, 2H), 8.20 (s, 11H), 8.11-8.01 (m, 1H), 7.66 (dd, J=4.8, 8.0 Hz, 1H).

Synthesis of tert-butyl N-[5-iodo-1-(pyridin-3-yl)-1H-pyrazol-4-yl]carbamate [INT 1-aaaaa]

To a solution of 5-iodo-1-(pyridin-3-yl)-1H-pyrazole-4-carboxylic acid [INT 1-zzzz](2.2 g, 6.98 mmol) in t-BuOH (20 mL) were added diphenylphosphoryl azide (2.86 g, 10.4 mmol) and $Et_3N$ (2.11 g, 20.9 mmol). The reaction mixture was stirred at 100° C. for 2 h under $N_2$. The reaction was quenched by adding water (100 mL) and was extracted with EtOAc (2×30 mL). The combined organic layers were washed with brine (2×50 mL), dried over anhydrous $Na_2SO_4$ and concentrated under reduced pressure to give the crude product, which was purified by flash chromatography on silica gel (EtOAc/Petroleum ether=0/1 to 1/1) to give tert-butyl N-[5-iodo-1-(pyridin-3-yl)-1H-pyrazol-4-yl]carbamate [INT 1-aaaaa] (1.80 g, 4.66 mmol, 66.9% yield) as a white solid. m/z: [M+H]+ Calcd for C13H16IN4O2, 387.0. Found 387.0. $^{1}$H NMR (400 MHz, $CDCl_3$) δ=8.89 (d, J=1.6 Hz, 1H), 8.68 (br d, J=4.4 Hz, 1H), 8.20 (br s, 1H), 7.96 (br d, J=8.0 Hz, 1H), 7.49 (dd, J=4.8, 8.0 Hz, 1H), 6.15 (br s, 1H), 1.56 (s, 9H).

Synthesis of tert-butyl N-[5-(1-ethoxyethenyl)-1-(pyridin-3-yl)-1H-pyrazol-4-yl]carbamate [INT 1-bbbbb]

A mixture of tert-butyl N-[5-iodo-1-(pyridin-3-yl)-1H-pyrazol-4-yl]carbamate [INT 1-aaaaa] (500 mg, 1.29 mmol), $Pd(PPh_3)_2Cl_2$ (90.5 mg, 129 μmol), tributyl(1-ethoxyethenyl)stannane (1 g, 2.76 mmol) and dioxane (10 mL) under N2 was stirred at 60° C. for 12 h. The mixture was quenched with sat. KF solution (100 mL) and stirred at 25° C. for 1 h. The aqueous layer was extracted with ethyl acetate (20 mL×3). The combined organic layers were dried over sodium sulfate, filtered and concentrated. The residue was purified by flash column chromatography on silica gel (30% ethyl acetate in PE) to give tert-butyl N-[5-(1-ethoxyethenyl)-1-(pyridin-3-yl)-1H-pyrazol-4-yl]carbamate [INT 1-bbbbb] (400 mg, 1.21 mmol, 93.8% yield) as a brown gum. m/z: [M+H]+ Calcd for C17H23N4O3, 331.2. Found 331.1. $^{1}$H NMR (400 MHz, DMSO-d6) δ=8.64 (d, J=2.4 Hz, 1H), 8.57 (dd, J=1.3, 4.7 Hz, 1H), 8.49 (br s, 1H), 7.88-7.84 (m, 1H), 7.81 (br s, 1H), 7.54 (dd, J=4.8, 8.2 Hz, 1H), 4.66 (d, J=2.6 Hz, 1H), 4.62 (d, J=2.6 Hz, 1H), 3.68 (q, J=7.1 Hz, 2H), 1.45 (s, 9H), 0.86 (t, J=7.0 Hz, 3H).

Synthesis of 1-[4-amino-1-(pyridin-3-yl)-1H-pyrazol-5-yl]ethan-1-one Hydrochloride [INT 1-ccccc]

Tert-butyl N-[5-(1-ethoxyethenyl)-1-(pyridin-3-yl)-1H-pyrazol-4-yl]carbamate [INT 1-bbbbb] (400 mg, 1.21 mmol) was dissolved in 1 M HCl (10 mL) and the mixture was stirred at 25° C. for 3 h. The mixture was adjusted to pH 8 with aqueous sat. $NaHCO_3$ and extracted with ethyl acetate (20 mL×2). The combined organic layers were dried over $Na_2SO_4$, filtered and concentrated. The residue was diluted with 4 N HCl in dioxane (5 mL) and stirred at 30° C. for 12 h. The mixture was concentrated to give 1-[4-amino-1-(pyridin-3-yl)-1H-pyrazol-5-yl]ethan-1-one hydrochloride [INT 1-ccccc] (280 mg, 1.17 mmol, 97.2% yield) as a brown solid. m/z: [M+H]+ Calcd for C10H11N4O, 203.1. Found 203.0.

Synthesis of 1-[4-amino-1-(pyridin-3-yl)-1H-pyrazol-5-yl]ethan-1-ol [INT 1.24]

A solution of 1-[4-amino-1-(pyridin-3-yl)-1H-pyrazol-5-yl]ethan-1-one [free base of INT 1-ccccc] (180 mg, 0.8901 mmol) in methanol (5 mL) was cooled to 0° C. Sodium borohydride (101 mg, 2.67 mmol) was added and the reaction mixture was stirred at 0-25° C. for 12 h. MeOH was removed and the residue was diluted with water (10 mL). The reaction mixture's pH was adjusted to 8-9 with aqueous sat. $NaHCO_3$ and the resulting mixture was extracted with ethyl acetate (15 mL×3). The combined organic layers were dried over $Na_2SO_4$, filtered and concentrated to give crude 1-[4-amino-1-(pyridin-3-yl)-1H-pyrazol-5-yl]ethan-1-ol [INT 1.24] (180 mg, 0.8813 mmol, 99.4% yield) as brown gum. m/z: [M+H]+ Calcd for C10H13N4O, 205.1. Found 204.8. $^{1}$H NMR (400 MHz, DMSO-d6) δ=8.78 (d, J=2.4 Hz, 1H), 8.61 (dd, J=1.3, 4.7 Hz, 1H), 8.01-7.97 (m, 1H), 7.58 (dd, J=4.7, 7.8 Hz, 1H), 7.30 (s, 1H), 5.47 (br s, 1H), 4.94-4.80 (m, 1H), 4.45-4.02 (m, 2H), 1.41 (d, J=6.8 Hz, 3H).

Synthesis of (S)-3-(4-amino-5-(1-methoxyethyl)-1H-pyrazol-1-yl)benzonitrile [Intermediate 1.25]

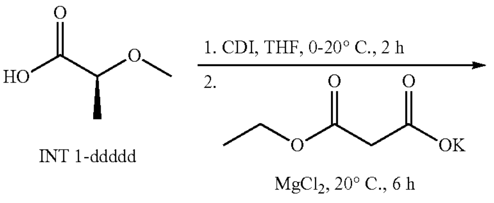

INT 1-ddddd

-continued

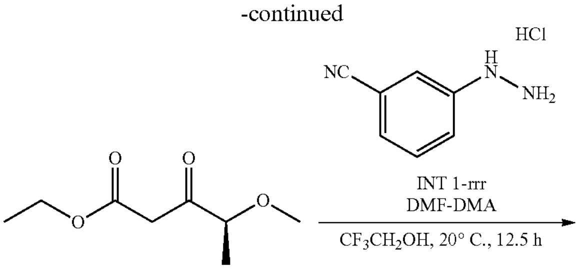

INT 1-eeeee

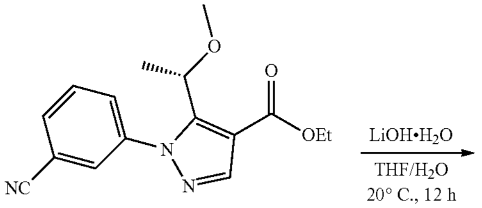

INT 1-fffff

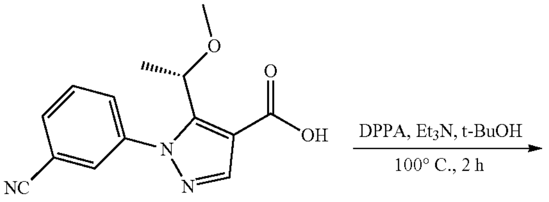

INT 1-ggggg

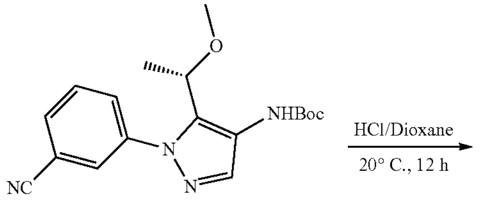

INT 1-hhhhh

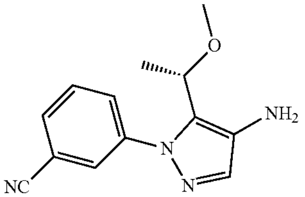

INT 1.25

Synthesis of ethyl (4S)-4-methoxy-3-oxopentanoate [INT 1-eeee]

To a solution of (2S)-2-methoxypropanoic acid [INT 1-ddddd] (5 g, 48.0 mmol) in THF (50 mL) was added 1,1'-carbonyldiimidazole (9.32 g, 57.5 mmol) at 0° C., and the mixture was stirred at 20° C. for 2 hours. Magnesium chloride (4.57 g, 48.0 mmol) and 1-ethyl 3-potassium propanedioate (12.2 g, 72.0 mmol) were added to the reaction solution, and the mixture was stirred at 20° C. for 6 hours. The reaction was quenched by adding aqueous 1 N HCl (200 mL) and was extracted with EtOAc (3×200 mL). The combined organic layers were washed with brine (2×100 mL), dried over anhydrous $Na_2SO_4$ and concentrated under reduced pressure to give ethyl (4S)-4-methoxy-3-oxopentanoate [INT 1-eeeee] (8.00 g, 45.9 mmol, 95.6% yield) as a yellow oil. $^1$H NMR (400 MHz, $CDCl_3$) δ=4.24-4.06 (m, 2H), 3.86-3.70 (m, 1H), 3.62-3.47 (m, 2H), 3.39-3.32 (m, 3H), 1.32-1.23 (m, 6H).

Synthesis of ethyl 1-(3-cyanophenyl)-5-[(1S)-1-methoxyethyl]-1H-pyrazole-4-carboxylate [INT 1-fffff]

To a mixture of ethyl (4S)-4-methoxy-3-oxopentanoate [INT 1-eeeee] (1.5 g, 8.61 mmol) in 2,2,2-trifluoroethanol (15 mL) was added N,N-dimethylformamide dimethyl acetal (1.22 g, 10.3 mmol). The mixture was stirred at 20° C. for 30 min. 3-hydrazinylbenzonitrile hydrochloride [INT 1-rrr] (1.74 g, 10.3 mmol) was added and the mixture was stirred at 20° C. for 12 h. The mixture was concentrated to give the crude product, which was purified by flash chromatography on silica gel (EtOAc/PE=0/1 to 1/3) to give ethyl 1-(3-cyanophenyl)-5-[(1S)-1-methoxyethyl]-1H-pyrazole-4-carboxylate [INT 1-fffff] (1.95 g, 6.51 mmol, 75.8% yield) as an orange solid. m/z: [M+H]+ Calcd for C16H18N3O3, 300.1. Found 300.0. $^1$H NMR (400 MHz, $CDCl_3$) δ=8.06 (s, 1H), 7.90 (t, J=1.6 Hz, 1H), 7.87-7.82 (m, 1H), 7.74 (td, J=1.6, 8.0 Hz, 1H), 7.62-7.57 (m, 1H), 5.47 (q, J=6.8 Hz, 1H), 4.40-4.29 (m, 2H), 3.27 (s, 3H), 1.39 (t, J=7.2 Hz, 3H), 1.33-1.30 (m, 3H).

Synthesis of 1-(3-cyanophenyl)-5-[(1S)-1-methoxyethyl]-1H-pyrazole-4-carboxylic Acid [INT 1-ggggg]

To a solution of ethyl 1-(3-cyanophenyl)-5-[(1S)-1-methoxyethyl]-1H-pyrazole-4-carboxylate [INT 1-fffff] (1.8 g, 6.01 mmol) in THF (15 mL) was added lithium hydroxide monohydrate (302 mg, 7.21 mmol) in $H_2O$ (5 mL). The reaction was stirred at 20° C. for 12 h. The reaction mixture was poured into 10 mL of water, acidified with 1 N HCl to pH=5-6 and extracted with EtOAc (30 mL×2). The combined organic layers were washed with brine (30 mL×2), dried over anhydrous $Na_2SO_4$ and concentrated under reduced pressure to give the crude product, which was purified by flash chromatography on silica gel (MeOH/DCM=0/1 to 1/20) to give 1-(3-cyanophenyl)-5-[(1S)-1-methoxyethyl]-1H-pyrazole-4-carboxylic acid [INT 1-ggggg] (1.20 g, 4.42 mmol, 73.6% yield) as a yellow solid. $^1$H NMR (400 MHz, DMSO-d6) δ=12.76 (br s, 1H), 8.07-8.03 (m, 2H), 8.00 (d, J=8.0 Hz, 1H), 7.90-7.86 (m, 1H), 7.77-7.71 (m, 1H), 5.29 (q, J=6.8 Hz, 1H), 3.08 (s, 3H), 1.28 (d, J=6.8 Hz, 3H).

Synthesis of tert-butyl N-[1-(3-cyanophenyl)-5-[(1S)-1-methoxyethyl]-1H-pyrazol-4-yl]carbamate [INT 1-hhhhh]

A solution of 1-(3-cyanophenyl)-5-[(1S)-1-methoxyethyl]-1H-pyrazole-4-carboxylic acid [INT 1-ggggg] (1.2 g, 4.42 mmol), triethylamine (670 mg, 6.63 mmol) and diphenylphosphoryl azide (2.43 g, 8.84 mmol) in t-BuOH (15 mL) was stirred at 100° C. for 2 h under $N_2$. The reaction mixture was concentrated under reduced pressure to give the crude product, which was purified by flash chromatography on silica gel (EtOAc/PE=0/1 to 1/3) to give tert-butyl N-[1-(3-cyanophenyl)-5-[(1S)-1-methoxyethyl]-1H-pyrazol-4-yl]carbamate [INT 1-hhhhh] (1 g, 2.92 mmol, 66.2% yield) as a yellow oil. m/z: [M+H]+ Calcd for C18H23N4O3 343.2. Found 343.2. $^1$H NMR (400 MHz, $CDCl_3$) δ=8.18 (br s, 1H), 7.73-7.67 (m, 2H), 7.67-7.57 (m, 2H), 6.86 (br s, 1H), 4.49 (q, J=6.8 Hz, 1H), 3.28 (s, 3H), 1.54 (s, 9H), 1.50 (d, J=6.8 Hz, 3H).

Synthesis of (S)-3-(4-amino-5-(1-methoxyethyl)-1H-pyrazol-1-yl)benzonitrile [INT 1.25]

A mixture of tert-butyl N-[1-(3-cyanophenyl)-5-[(1S)-1-methoxyethyl]-1H-pyrazol-4-yl]carbamate [INT 1-hhhhh] (500 mg, 1.46 mmol) in 4 M HCl/Dioxane (8 mL) was stirred at 20° C. for 12 h. The reaction mixture was poured into 10 mL of water, basified with $NH_3 \cdot H_2O$ to pH=9-10 and extracted with EtOAc (30 mL×2). The combined organic layers were washed with brine (30 mL×2), dried over anhydrous $Na_2SO_4$ and concentrated under reduced pressure to give the crude product, which was purified by flash chromatography on silica gel (EtOAc/PE=0/1 to 1/3) to give (S)-3-(4-amino-5-(1-methoxyethyl)-1H-pyrazol-1-yl)benzonitrile [INT 1.25](100 mg, 412 μmol, 28.3% yield) as a yellow solid. m/z: [M−OCH3]+ Calcd for C12H11N4 211.1. Found 210.9. $^1$H NMR (400 MHz, $CDCl_3$) δ=7.76-7.73 (m, 1H), 7.69-7.64 (m, 2H), 7.62-7.55 (m, 1H), 7.39 (s, 1H), 4.50 (q, J=6.8 Hz, 1H), 3.28 (s, 3H), 1.53 (d, J=6.4 Hz, 3H).

Synthesis of 5-[(1S)-1-methoxyethyl]-1-phenyl-1H-pyrazol-4-amine Hydrochloride [Intermediate 1.26]

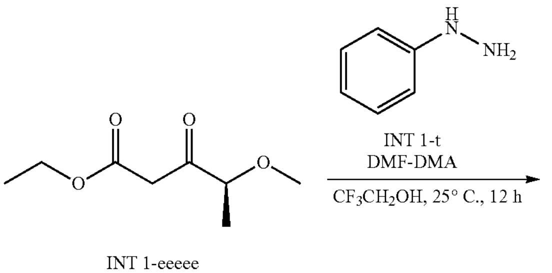

INT 1-eeeee

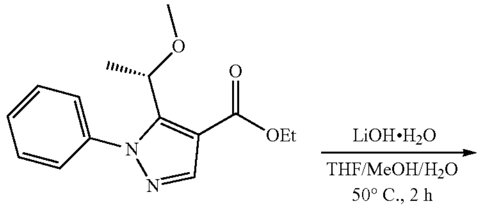

INT 1-iiiii

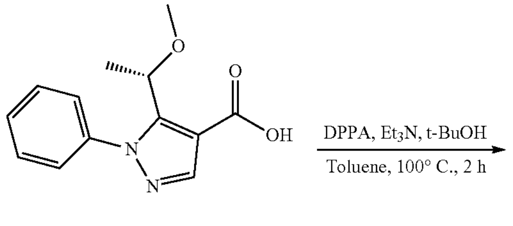

INT 1-jjjjj

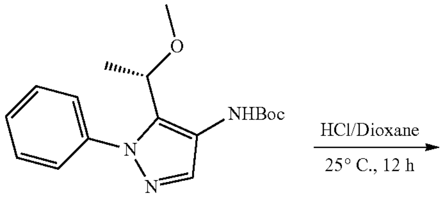

INT 1-kkkkk

-continued

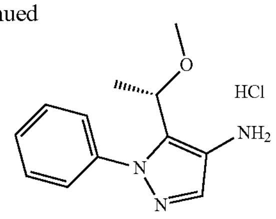

INT 1.26

Synthesis of ethyl 5-[(1S)-1-methoxyethyl]-1-phenyl-1H-pyrazole-4-carboxylate [INT 1-iiiii]

To a mixture of phenylhydrazine [INT 1-t] (1.5 g, 13.8 mmol) and N,N-dimethylformamide dimethyl acetal (1.96 g, 16.5 mmol) in 2,2,2-trifluoroethanol (20 mL) was added ethyl (4S)-4-methoxy-3-oxopentanoate [INT 1-eeeee] (2.87 g, 16.5 mmol) in 2,2,2-trifluoroethanol (10 mL). The reaction mixture was stirred at 25° C. for 12 hours. The reaction was quenched with water (100 mL) and extracted with EtOAc (100 mL×3). The combined organic layers were dried over anhydrous sodium sulfate and filtered. The filtrate was concentrated to give the crude product, which was purified by flash chromatography on silica gel (0-15% EtOAc in petroleum ether) to give ethyl 5-[(1 S)-1-methoxyethyl]-1-phenyl-1H-pyrazole-4-carboxylate [INT 1-iiiii] (2.00 g, 7.29 mmol, 52.9% yield) as a brown oil. m/z: [M+H]+ Calcd for C15H19N2O3, 275.1. Found 275.1. $^1$H NMR (400 MHz, $CDCl_3$) δ=8.05 (s, 1H), 7.53-7.43 (m, 5H), 5.34 (q, J=6.8 Hz, 1H), 4.40-4.29 (m, 2H), 3.25 (s, 3H), 1.39 (t, J=7.2 Hz, 3H), 1.35 (d, J=6.8 Hz, 3H).

Synthesis of 5-[(1S)-1-methoxyethyl]-1-phenyl-1H-pyrazole-4-carboxylic acid [INT 1-jjjjj]

To a mixture of ethyl 5-[(1S)-l-methoxyethyl]-1-phenyl-1H-pyrazole-4-carboxylate [INT 1-iiiii] (1.8 g, 6.56 mmol) in THF (5 mL), MeOH (5 mL) and $H_2O$ (5 mL) was added lithium hydroxide monohydrate (822 mg, 19.6 mmol). The reaction mixture was stirred at 50° C. for 2 hours, after which it was concentrated, diluted with water (50 mL) and washed with EtOAc (100 mL×2). The aqueous phase was acidified with aqueous 1 M HCl to pH=3 and extracted with EtOAc (100 mL×2). The combined organic layers were dried over anhydrous sodium sulfate and filtered. The filtrate was concentrated to give 5-[(1S)-1-methoxyethyl]-1-phenyl-1H-pyrazole-4-carboxylic acid [INT 1-jjjjj] (950 mg, 3.85 mmol, 59.0% yield) as an orange solid. [M+H]+ Calcd for C13H15N2O3, 247.1. Found: 247.2. $^1$H NMR (400 MHz, $CDCl_3$) δ=8.18 (d, J=1.2 Hz, 1H), 7.51 (br d, J=2.0 Hz, 3H), 7.48-7.42 (m, 2H), 5.13-5.00 (m, 1H), 3.32 (d, J=3.6 Hz, 3H), 1.46 (t, J=5.6 Hz, 3H).

Synthesis of tert-butyl N-{5-[(1S)-1-methoxyethyl]-1-phenyl-1H-pyrazol-4-yl}carbamate [INT 1-kkkkk]

To a mixture of 5-[(1S)-1-methoxyethyl]-1-phenyl-1H-pyrazole-4-carboxylic acid [INT 1-jjjjj] (850 mg, 3.45 mmol), 2-methylpropan-2-ol (3.83 g, 51.7 mmol) and triethylamine (1.04 g, 10.3 mmol) in toluene (10 mL) was added diphenylphosphoryl azide (1.42 g, 5.17 mmol). The reaction mixture was stirred at 100° C. under nitrogen for 2 hours. The reaction mixture was diluted with EtOAc (100 mL×3) and washed with aqueous saturated $NaHCO_3$ (100 mL) and brine (100 mL). The organic layer was dried over anhydrous sodium sulfate and filtered. The filtrate was concentrated to give the crude product, which was purified by flash chromatography on silica gel (0-13% EtOAc in petroleum ether) to give tert-butyl N-{5-[(1S)-1-methoxyethyl]-1-phenyl-1H-pyrazol-4-yl}carbamate [INT 1-kkkkk] (770 mg, 2.42 mmol, 70.6% yield) as a yellow solid. m/z: [M+H]+ Calcd for C17H24N3O3, 318.2. Found 318.1. $^{1}H$ NMR (400 MHz, $CDCl_3$) δ=8.15 (br s, 1H), 7.52-7.33 (m, 5H), 6.90 (br s, 1H), 4.48 (q, J=6.4 Hz, 1H), 3.27 (s, 3H), 1.54 (br s, 9H), 1.48 (d, J=6.4 Hz, 3H).

Synthesis of 5-[(1S)-1-methoxyethyl]-1-phenyl-1H-pyrazol-4-amine Hydrochloride [INT 1.26]

A mixture of tert-butyl N-{5-[(1S)-1-methoxyethyl]-1-phenyl-1H-pyrazol-4-yl}carbamate [INT 1-kkkkk] (150 mg, 472 μmol) in 4 M HCl/dioxane (10 mL, 40.0 mmol) was stirred at 25° C. for 12 hr. The mixture was concentrated under reduced pressure to afford 5-[(1S)-1-methoxyethyl]-1-phenyl-1H-pyrazol-4-amine hydrochloride [INT 1.26] (119 mg, 469 μmol) as a brown oil. m/z: [M+H]+ Calcd for C12H16N3O, 218.1. Found 217.9.

Synthesis of 5-[(1S)-1-methoxyethyl]-1-(pyridin-2-yl)-1H-pyrazol-4-amine Hydrochloride [Intermediate 1.27]

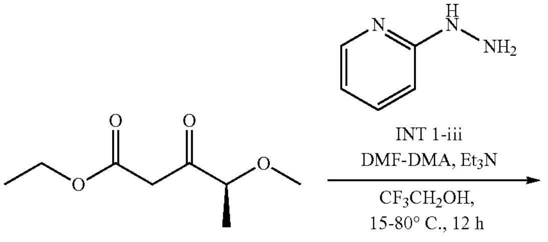

INT 1-eeeee

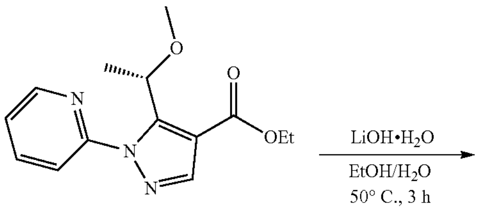

INT 1-lllll

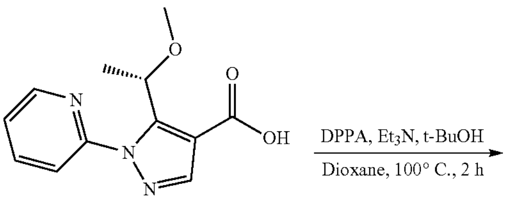

INT 1-mmmmm

-continued

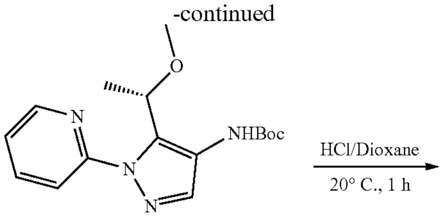

INT 1-nnnnn

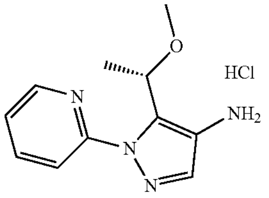

INT 1.27

Synthesis of ethyl 5-[(1S)-1-methoxyethyl]-1-(pyridin-2-yl)-H-pyrazole-4-carboxylate [INT 1-lllll]

To a mixture of ethyl (4S)-4-methoxy-3-oxopentanoate [INT 1-eeeee] (3 g, 17.2 mmol) and triethylamine (2.08 g, 20.6 mmol) in 2,2,2-trifluoroethanol (50 mL) was added N,N-dimethylformamide dimethyl acetal (10.2 g, 85.9 mmol) and 2-hydrazinylpyridine [INT 1-iii](2.24 g, 20.6 mmol) at 15° C. The reaction mixture was stirred at 80° C. for 12 hours. The mixture was concentrated, and the resulting residue was quenched with water (60 mL) and extracted with EtOAc (50 mL×3). The combined organic layers were dried over anhydrous sodium sulfate and filtered. The filtrate was concentrated to give the crude product, which was purified by flash chromatography on silica gel (PE/EtOAc=1/0 to 5/1) to give ethyl 5-[(1S)-1-methoxyethyl]-1-(pyridin-2-yl)-1H-pyrazole-4-carboxylate [INT 1-lllll] (1.30 g, 4.72 mmol, 27.4% yield) as a yellow oil. $^{1}H$ NMR (400 MHz, DMSO) δ=8.59-8.53 (m, 1H), 8.10-8.01 (m, 2H), 7.67-7.61 (m, 1H), 7.58-7.52 (m, 1H), 5.19 (q, J=8.0 Hz, 1H), 4.26 (q, J=8.0 Hz, 2H), 2.91 (s, 3H), 1.61 (d, J=8.0 Hz, 3H), 1.30 (t, J=8.0 Hz, 3H).

Synthesis of 5-[(1S)-1-methoxyethyl]-1-(pyridin-2-yl)-1H-pyrazole-4-carboxylic Acid [INT 1-mmmmm]

A solution of ethyl 5-[(1S)-1-methoxyethyl]-1-(pyridin-2-yl)-1H-pyrazole-4-carboxylate [INT 1-lllll] (1.3 g, 4.72 mmol) and lithium hydroxide monohydrate (990 mg, 23.6 mmol) in EtOH (10 mL) and $H_2O$ (3 mL) was stirred at 50° C. for 3 h. The reaction was acidified with aqueous 1 M HCl to pH=4 and extracted with EtOAc (25 mL×2). The combined organic layers were concentrated under reduced pressure to give to 5-[(1S)-1-methoxyethyl]-1-(pyridin-2-yl)-1H-pyrazole-4-carboxylic acid [INT 1-mmmmm] (946 mg, 3.82 mmol, 81.5% yield) as a pale yellow solid. $^{1}H$ NMR (400 MHz, DMSO) δ=8.59-8.50 (m, 1H), 8.10-7.96 (m, 2H), 7.65-7.58 (m, 1H), 7.57-7.51 (m, 1H), 5.22 (q, J=8.0 Hz, 1H), 2.90 (s, 3H), 1.59 (d, J=8.0 Hz, 3H).

Synthesis of tert-butyl N-{5-[(1S)-1-methoxyethyl]-1-(pyridin-2-yl)-1H-pyrazol-4-yl}carbamate [INT 1-nnnnn]

To a mixture of 5-[(1S)-1-methoxyethyl]-1-(pyridin-2-yl)-1H-pyrazole-4-carboxylic acid [INT 1-mmmmm] (946 mg, 3.82 mmol) in t-BuOH (3 mL) and dioxane (9 mL) was added triethylamine (1.92 g, 19.0 mmol) and diphenylphosphoryl azide (2.77 g, 11.4 mmol) at 10° C. The mixture was then stirred at 100° C. for 2 hr. Water (30 mL) was added and the mixture was extracted with EtOAc (30 mL×2). The combined organic layers were washed with brine (30 mL×2), dried over anhydrous $Na_2SO_4$, filtered and concentrated under reduced pressure to give the crude product, which was purified by flash chromatography on silica gel (Petroleum ether/EtOAc=1/0 to 17/3) to give tert-butyl N-{5-[(1S)-1-methoxyethyl]-1-(pyridin-2-yl)-1H-pyrazol-4-yl}carbamate [INT 1-nnnnn] (265 mg, 832 μmol, 21.9% yield) as a white solid. m/z: [M+H]+ Calcd for C16H23N4O3, 319.2. Found 319.3. $^1$H NMR (400 MHz, DMSO) δ=8.49-8.45 (m, 1H), 7.99-7.81 (m, 4H), 7.40-7.35 (m, 1H), 5.35 (q, J=8.0 Hz, 1H), 3.15 (s, 3H), 1.52 (d, J=8.0 Hz, 3H), 1.46 (s, 9H).

Synthesis of 5-[(1S)-1-methoxyethyl]-1-(pyridin-2-yl)-1H-pyrazol-4-amine Hydrochloride [INT 1.27]

A solution of tert-butyl N-{5-[(1S)-1-methoxyethyl]-1-(pyridin-2-yl)-1H-pyrazol-4-yl}carbamate [INT 1-nnnnn] (265 mg, 832 μmol) in HCl/dioxane (10 mL) was stirred at 20° C. for 1 h. The mixture was concentrated under reduced pressure to give 5-[(1S)-1-methoxyethyl]-1-(pyridin-2-yl)-1H-pyrazol-4-amine hydrochloride [INT 1.27] (211 mg, 828 μmol) as a black solid. $^1$H NMR (400 MHz, $CDCl_3$) δ=8.41-8.32 (m, 1H), 7.86 (d, J=8.0 Hz, 1H), 7.80-7.71 (m, 1H), 7.35 (s, 1H), 7.15-7.08 (m, 1H), 5.62 (q, J=8.0 Hz, 1H), 3.35 (s, 3H), 1.62 (s, 3H).

Synthesis of 5-[(1S)-1-methoxyethyl]-1-(pyridin-4-yl)-1H-pyrazol-4-amine [Intermediate 1.28]

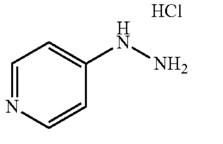

INT 1-eee

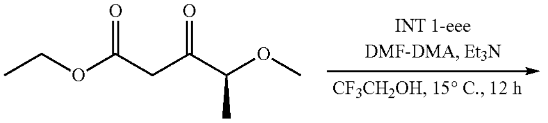

INT 1-eeeee

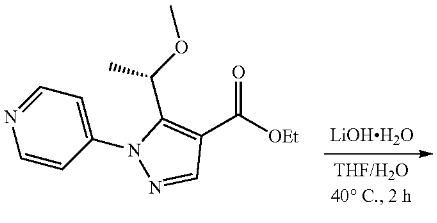

INT 1-ooooo

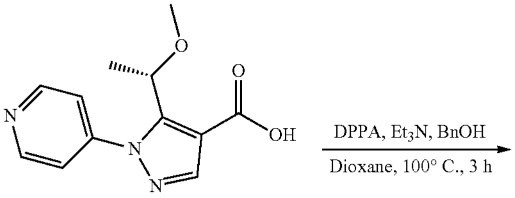

INT 1-ppppp

-continued

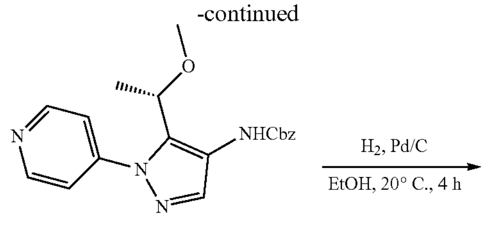

INT 1-qqqqq

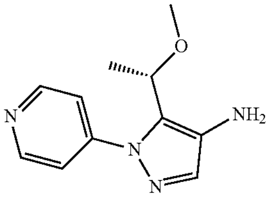

INT 1.28

Synthesis of ethyl 5-[(1S)-1-methoxyethyl]-1-(pyridin-4-yl)-1H-pyrazole-4-carboxylate [INT 1-ooooo]

To a mixture of ethyl (4S)-4-methoxy-3-oxopentanoate [INT 1-eeeee] (1.7 g, 9.75 mmol) and N,N-dimethylformamide dimethyl acetal (1.39 g, 11.7 mmol) in 2,2,2-trifluoroethanol (30 mL) were added 4-hydrazinylpyridine hydrochloride [INT 1-eee] (1.70 g, 11.7 mmol) and triethylamine (1.18 g, 11.7 mmol). The reaction mixture was stirred at 15° C. for 12 hrs. The mixture was concentrated to give the crude product. The mixture was worked up with another of the same type. The residue was quenched with water (30 mL) and extracted with EtOAc (30 mL×3). The combined organic layers were dried over anhydrous sodium sulfate and filtered. The filtrate was concentrated to give the crude product, which was purified by flash chromatography on silica gel (PE/EtOAc=1/0 to 5/1) to give ethyl 5-[(1S)-1-methoxyethyl]-1-(pyridin-4-yl)-1H-pyrazole-4-carboxylate [INT 1-ooooo] (1.80 g, 6.53 mmol, 67.1% yield) as a yellow oil. $^1$H NMR (400 MHz, DMSO) δ=8.80-8.71 (m, 2H), 8.14 (s, 1H), 7.67-7.64 (m, 2H), 5.29 (q, J=8.0 Hz, 1H), 4.28 (q, J=8.0 Hz, 2H), 3.10 (s, 3H), 1.36 (d, J=8.0 Hz, 3H), 1.31 (t, J=8.0 Hz, 3H).

Synthesis of 5-[(1S)-1-methoxyethyl]-1-(pyridin-4-yl)-1H-pyrazole-4-carboxylic Acid [INT 1-ppppp]

To a solution of ethyl 5-[(1S)-1-methoxyethyl]-1-(pyridin-4-yl)-1H-pyrazole-4-carboxylate [INT 1-ooooo] (1.76 g, 6.39 mmol) in THF (20 mL) and $H_2O$ (4 mL) at 10° C. was added lithium hydroxide monohydrate (1.33 g, 31.9 mmol). The mixture was stirred at 40° C. for 2 h. The mixture was acidified with aqueous 1 M HCl to pH=5 and extracted with EtOAc (60 mL×2). The combined organic layers were washed with brine (30 mL×2), dried over anhydrous $Na_2SO_4$ and concentrated under reduced pressure to afford 5-[(1S)-1-methoxyethyl]-1-(pyridin-4-yl)-1H-pyrazole-4-carboxylic acid [INT 1-ppppp] (1.57 g, 6.34 mmol) as a pale yellow solid. $^1$H NMR (400 MHz, DMSO) δ=8.66 (d, J=4.0 Hz, 2H), 7.89 (s, 1H), 7.74 (d, J=4.0 Hz, 2H), 6.04 (q, J=4.0 Hz, 1H), 3.19 (s, 3H), 1.21 (d, J=8.0 Hz, 3H).

Synthesis of benzyl N-{5-[(1S)-1-methoxyethyl]-1-(pyridin-4-yl)-1H-pyrazol-4-yl}carbamate [INT 1-qqqqq]

To a mixture of 5-[(1S)-1-methoxyethyl]-1-(pyridin-4-yl)-1H-pyrazole-4-carboxylic acid [INT 1-ppppp] (1.25 g, 5.05 mmol) in BnOH (3 mL) and dioxane (12 mL) was added diphenylphosphoryl azide (3.67 g, 15.1 mmol) and triethylamine (2.55 g, 25.2 mmol) at 20° C. The mixture was then stirred at 100° C. for 3 h under $N_2$. The reaction was quenched by adding water (40 mL) and was extracted with EtOAc (30 mL×2). The combined organic layers were washed with brine (40 mL×2), dried over anhydrous $Na_2SO_4$ and concentrated under reduced pressure to give the crude product, which was purified by flash chromatography on silica gel (PE/EtOAc=1/0 to 5/1) to give benzyl N-{5-[(1S)-1-methoxyethyl]-1-(pyridin-4-yl)-1H-pyrazol-4-yl}carbamate [INT 1-qqqqq] (390 mg, 1.10 mmol, 22.0% yield) as a pale yellow oil. m/z: [M+H]+ Calcd for C19H21N4O3, 353.2. Found 353.2.

Synthesis of 5-[(1S)-1-methoxyethyl]-1-(pyridin-4-yl)-1H-pyrazol-4-amine [INT 1.28]

To a mixture of 10% Pd/C (40 mg) in EtOH (40 mL) at 20° C. was added benzyl N-{5-[(1S)-1-methoxyethyl]-1-(pyridin-4-yl)-1H-pyrazol-4-yl}carbamate [INT 1-qqqqq] (390 mg, 1.10 mmol). The mixture was then stirred for 4 h under $H_2$ (15 psi). The mixture was filtered and the filtrate was concentrated under reduced pressure to give 5-[(1S)-1-methoxyethyl]-1-(pyridin-4-yl)-1H-pyrazol-4-amine [INT 1.28] (200 mg, 916 μmol, 83.3% yield) as a white solid. $^1H$ NMR (400 MHz, DMSO) δ=8.60 (d, J=8.0 Hz, 2H), 7.60 (d, J=8.0 Hz, 2H), 7.36 (s, 1H), 4.71 (q, J=8.0 Hz, 1H), 4.24 (s, 2H), 3.18 (s, 3H), 1.37 (d, J=8.0 Hz, 3H).

Synthesis of 5-[(1S)-1-methoxyethyl]-1-(pyridin-3-yl)-1H-pyrazol-4-amine Hydrochloride [Intermediate 1.29]

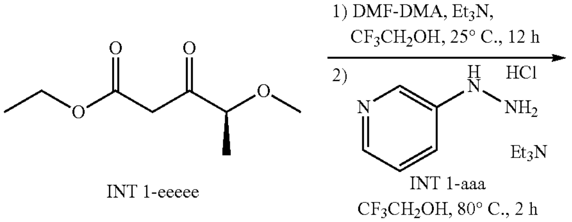

INT 1-eeeee

INT 1-aaa
CF3CH2OH, 80° C., 2 h

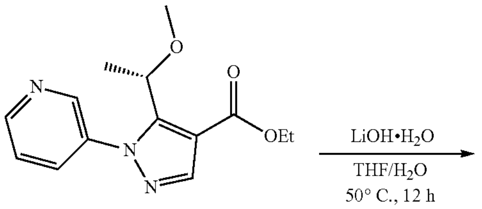

INT 1-rrrrr

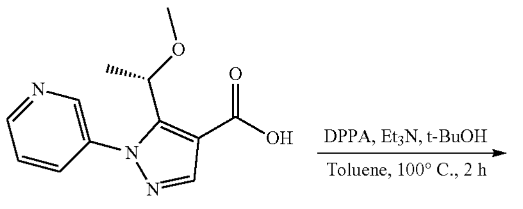

INT 1-sssss

-continued

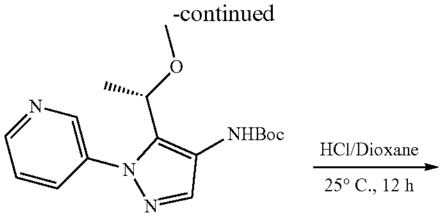

INT 1-ttttt

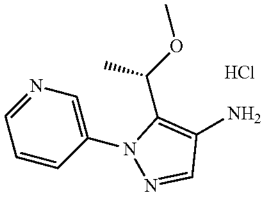

INT 1.29

Synthesis of ethyl 5-[(1S)-1-methoxyethyl]-1-(pyridin-3-yl)-1H-pyrazole-4-carboxylate [INT 1-rrrrr]

A mixture of ethyl (4S)-4-methoxy-3-oxopentanoate [INT 1-eeeee] (3 g, 17.2 mmol) and N,N-dimethylformamide dimethyl acetal (3.07 g, 25.8 mmol) in 2,2,2-trifluoroethanol (20 mL) was stirred at 25° C. for 12 hours. The mixture was concentrated under reduced pressure to afford the crude ethyl (2Z,4S)-2-[(dimethylamino)methylidene]-4-methoxy-3-oxopentanoate, which was used directly in the next step.

To a mixture of ethyl (2Z,4S)-2-[(dimethylamino)methylidene]-4-methoxy-3-oxopentanoate (3.94 g, 17.1 mmol) and triethylamine (8.65 g, 85.5 mmol) in 2,2,2-trifluoroethanol (20 mL) was added 3-hydrazinylpyridine hydrochloride [INT 1-aaa] (7.46 g, 51.3 mmol). The reaction mixture was stirred at 80° C. for 2 hours. The mixture was concentrated under reduced pressure to afford the crude product. Brine (200 mL) was added and the mixture was extracted with EtOAc (200 mL×2). The combined organic layers were washed with brine (200 mL×2), dried over anhydrous $Na_2SO_4$, filtered and concentrated under reduced pressure to give the crude product, which was purified by flash chromatography on silica gel (0-40% EtOAc in Petroleum ether) to give ethyl 5-[(1S)-1-methoxyethyl]-1-(pyridin-3-yl)-1H-pyrazole-4-carboxylate [INT 1-rrrrr] (2.20 g, 7.99 mmol, 46.8% yield) as a yellow oil. m/z: [M+H]+ Calcd for C14H18N3O3, 276.1. Found 276.1. $^1H$ NMR (400 MHz, $CDCl_3$) δ=8.80 (br s, 1H), 8.70 (br d, J=3.6 Hz, 1H), 8.11-8.05 (m, 1H), 7.94-7.86 (m, 1H), 7.44 (dd, J=4.8, 8.0 Hz, 1H), 5.49-5.39 (m, 1H), 4.42-4.29 (m, 2H), 3.30-3.20 (m, 3H), 1.42-1.36 (m, 3H), 1.36-1.31 (m, 3H).

Synthesis of 5-[(1S)-1-methoxyethyl]-1-(pyridin-3-yl)-1H-pyrazole-4-carboxylic Acid [INT 1-sssss]

To a mixture of ethyl 5-[(1S)-1-methoxyethyl]-1-(pyridin-3-yl)-1H-pyrazole-4-carboxylate [INT 1-rrrrr] (2.2 g, 7.99 mmol) in THF (15 mL) and $H_2O$ (5 mL) was added lithium hydroxide monohydrate (1 g, 23.9 mmol). The reaction mixture was stirred at 50° C. for 12 hours, after which it was concentrated, diluted with water (100 mL) and washed with EtOAc (200 mL×2). The aqueous phase was acidified with aqueous 1 M HCl to pH=3 and extracted with EtOAc (200 mL×2). The combined organic layers were dried over anhydrous sodium sulfate and filtered. The filtrate was concentrated to give 5-[(1S)-1-methoxyethyl]-1-(pyridin-3-yl)-1H-pyrazole-4-carboxylic acid [INT 1-sssss] (1.30 g, 5.25 mmol, 65.9% yield) as a white solid. [M+H]+ Calcd for C12H14N3O3, 248.1. Found 248.2. $^1$H NMR (400 MHz, $CDCl_3$) δ=8.83 (d, J=1.6 Hz, 1H), 8.76 (br d, J=4.0 Hz, 1H), 8.20 (s, 1H), 7.94 (td, J=1.6, 8.0 Hz, 1H), 7.51 (dd, J=4.8, 8.0 Hz, 1H), 5.30 (q, J=6.8 Hz, 1H), 3.30 (s, 3H), 1.43 (d, J=6.8 Hz, 3H).

Synthesis of tert-butyl N-{5-[(1S)-1-methoxyethyl]-1-(pyridin-3-yl)-1H-pyrazol-4-yl}carbamate [INT 1-ttttt]

To a mixture of 5-[(1S)-1-methoxyethyl]-1-(pyridin-3-yl)-1H-pyrazole-4-carboxylic acid [INT 1-sssss] (1.2 g, 4.85 mmol), 2-methylpropan-2-ol (5.38 g, 72.7 mmol) and diphenylphosphoryl azide (2.00 g, 7.27 mmol) in toluene (10 mL) was added triethylamine (1.46 g, 14.5 mmol). The reaction mixture was stirred at 100° C. under nitrogen for 2 hours. The reaction mixture was diluted with EtOAc (100 mL×3) and washed with saturated $NaHCO_3$ (100 mL) and brine (100 mL). The organic layer was dried over anhydrous sodium sulfate and filtered. The filtrate was concentrated to give the crude product, which was purified by flash chromatography on silica gel (0-40% EtOAc in petroleum ether) to give tert-butyl N-{5-[(1S)-1-methoxyethyl]-1-(pyridin-3-yl)-1H-pyrazol-4-yl}carbamate [INT 1-ttttt] (490 mg, 1.53 mmol, 31.8% yield) as a white solid. m/z: [M+H]+ Calcd for C16H23N4O3, 319.2. Found 319.1. $^1$H NMR (400 MHz, $CDCl_3$) δ=8.76-8.65 (m, 2H), 8.21 (br s, 1H), 7.99-7.78 (m, 1H), 7.59-7.43 (m, 1H), 6.86 (br d, J=12.8 Hz, 1H), 4.56-4.45 (m, 1H), 3.29 (d, J=6.8 Hz, 3H), 1.55 (s, 9H), 1.52-1.48 (m, 3H).

Synthesis of 5-[(1S)-1-methoxyethyl]-1-(pyridin-3-yl)-H-pyrazol-4-amine Hydrochloride [INT 1.29]

A mixture of tert-butyl N-{5-[(1S)-1-methoxyethyl]-1-(pyridin-3-yl)-1H-pyrazol-4-yl}carbamate [INT 1-ttttt] (490 mg, 1.53 mmol) in 4 M HCl/dioxane (10 mL, 40.0 mmol) was stirred at 25° C. for 12 hr. The mixture was concentrated under reduced pressure to afford 5-[(1S)-1-methoxyethyl]-1-(pyridin-3-yl)-1H-pyrazol-4-amine hydrochloride [INT 1.29] (389 mg, 1.52 mmol) as a yellow solid. m/z: [M+H]+ Calcd for C11H15N4O, 219.1. Found: 219.1.

Synthesis of 3-(4-amino-5-cyclopropyl-1H-pyrazol-1-yl)benzonitrile Hydrochloride [Intermediate 1.30]

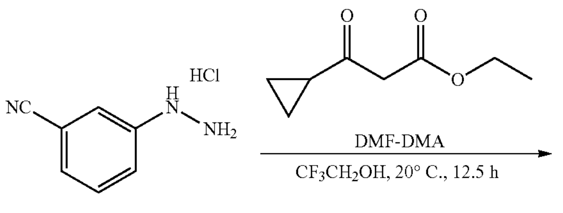

INT 1-rrr

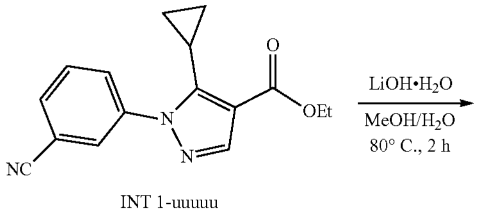

INT 1-uuuuu

-continued

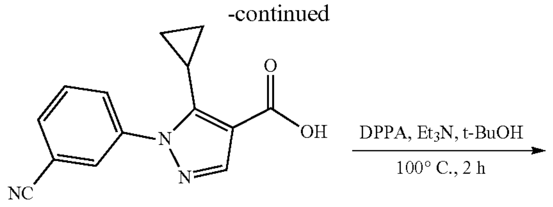

INT 1-vvvvv

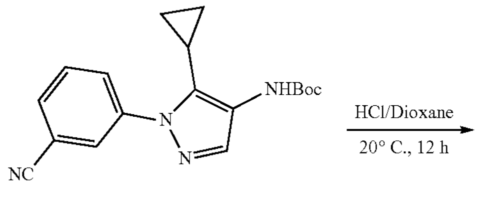

INT 1-wwwww

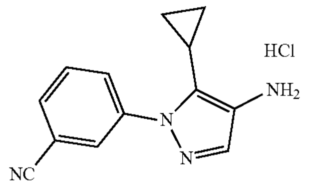

INT 1.30

Synthesis of ethyl 1-(3-cyanophenyl)-5-cyclopropyl-1H-pyrazole-4-carboxylate [INT 1-uuuuu]

To a mixture of ethyl 3-cyclopropyl-3-oxopropanoate (2.0 g, 12.8 mmol) in 2,2,2-trifluoroethanol (15 mL) was added N,N-dimethylformamide dimethyl acetal (1.82 g, 15.3 mmol). The mixture was stirred at 20° C. for 30 min. 3-hydrazinylbenzonitrile hydrochloride [INT 1-rrr] (2.59 g, 15.3 mmol) was added and the mixture was stirred at 20° C. for 12 h. The mixture was concentrated to give the crude product. The residue was quenched with water (40 mL) and extracted with EtOAc (30 mL×3). The combined organic layers were washed with brine (40 mL×2), dried over anhydrous $Na_2SO_4$ and concentrated under reduced pressure to give the crude product, which was purified by flash chromatography on silica gel (EtOAc/PE=0/1 to 1/5) to give ethyl 1-(3-cyanophenyl)-5-cyclopropyl-1H-pyrazole-4-carboxylate [INT 1-uuuuu] (2.00 g, 7.10 mmol, 55.5% yield) as an orange solid. m/z: [M+H]+ Calcd for C16H16N3O2, 282.1. Found 282.0. $^1$H NMR (400 MHz, $CDCl_3$) δ=8.04 (s, 1H), 7.90 (s, 1H), 7.85 (d, J=8.0 Hz, 1H), 7.75-7.70 (m, 1H), 7.67-7.59 (m, 1H), 4.34 (q, J=7.2 Hz, 2H), 1.66 (br s, 1H), 1.39 (t, J=7.2 Hz, 3H), 1.05-0.98 (m, 2H), 0.59 (q, J=5.6 Hz, 2H).

Synthesis of 1-(3-cyanophenyl)-5-cyclopropyl-1H-pyrazole-4-carboxylic Acid [INT 1-vvvvv]

To a solution of ethyl 1-(3-cyanophenyl)-5-cyclopropyl-1H-pyrazole-4-carboxylate [INT 1-uuuuu] (1.5 g, 5.33 mmol) in MeOH (6 mL) was added lithium hydroxide monohydrate (335 mg, 7.99 mmol) in $H_2O$ (2 mL). The reaction was stirred at 80° C. for 2 h. The reaction mixture was poured into 10 mL of water, acidified with aqueous 1 N HCl to pH=3-4 and extracted with EtOAc (20 mL×2). The combined organic layers were washed with brine (20 mL×2), dried over anhydrous $Na_2SO_4$ and concentrated under reduced pressure to give the crude product, which was purified by flash chromatography on silica gel (MeOH/DCM=0/1 to 1/10) to give 1-(3-cyanophenyl)-5-cyclopropyl-1H-pyrazole-4-carboxylic acid [INT 1-vvvvv] (740 mg, 2.92 mmol, 55.2% yield) as an off-white solid. $^{1}$H NMR (400 MHz, DMSO-d6) δ=12.38 (s, 1H), 8.18-8.15 (m, 1H), 7.99 (s, 1H), 7.98-7.92 (m, 2H), 7.79-7.73 (m, 1H), 2.22-2.12 (m, 1H), 0.86-0.81 (m, 2H), 0.47-0.41 (m, 2H).

Synthesis of tert-butyl N-[1-(3-cyanophenyl)-5-cyclopropyl-1H-pyrazol-4-yl]carbamate [INT 1-wwwww]

A solution of 1-(3-cyanophenyl)-5-cyclopropyl-1H-pyrazole-4-carboxylic acid [INT 1-vvvvv] (640 mg, 2.52 mmol), triethylamine (382 mg, 3.78 mmol) and diphenylphosphoryl azide (1.38 g, 5.04 mmol) in t-BuOH (8 mL) was stirred at 100° C. for 2 h under $N_2$. The reaction mixture was concentrated under reduced pressure to give the crude product, which was purified by flash chromatography on silica gel (EtOAc/PE=0/1 to 1/5) and by Prep HPLC (column: YMC Triart 30*150 mm*7 μm, table: 30-70% B (A=water(ammonia hydroxide v/v)-(ACN-THF 50/50), B=acetonitrile), flow rate: 50 mL/min, UV Detector 220 nm) to afford tert-butyl N-[1-(3-cyanophenyl)-5-cyclopropyl-1H-pyrazol-4-yl]carbamate [INT 1-wwwww] (110 mg, 339 μmol, 13.4% yield) as a white solid. m/z: [M+H]+ Calcd for C18H21N4O2, 325.2. Found 325.1. $^{1}$H NMR (400 MHz, $CDCl_3$) δ=8.00-7.91 (m, 2H), 7.91-7.86 (m, 1H), 7.66-7.60 (m, 1H), 7.60-7.54 (m, 1H), 6.19 (s, 1H), 1.88-1.76 (m, 1H), 1.54 (s, 9H), 1.00-0.93 (m, 2H), 0.52-0.46 (m, 2H).

Synthesis of 3-(4-amino-5-cyclopropyl-1H-pyrazol-1-yl)benzonitrile Hydrochloride [INT 1.30]

A solution of tert-butyl N-[1-(3-cyanophenyl)-5-cyclopropyl-1H-pyrazol-4-yl]carbamate [INT 1-wwwww] (110 mg, 339 μmol) in HCl/Dioxane (3 mL) was stirred at 20° C. for 12 h. The reaction mixture was concentrated under reduced pressure to give 3-(4-amino-5-cyclopropyl-1H-pyrazol-1-yl)benzonitrile hydrochloride [INT 1.30] (89.0 mg, 341 μmol) as an off-white solid. m/z: [M+H]+ Calcd for C13H13N4 225.1. Found 225.0. $^{1}$H NMR (400 MHz, DMSO-d6) δ=10.22 (br s, 2H), 8.18 (s, 1H), 8.02 (br d, J=8.0 Hz, 1H), 7.94 (br d, J=7.6 Hz, 1H), 7.79 (s, 1H), 7.78-7.72 (m, 1H), 2.15-2.03 (m, 1H), 0.91-0.80 (m, 2H), 0.61-0.47 (m, 2H).

Synthesis of 5-cyclopropyl-1-(pyridine-2-yl)-1H-pyrazol-4-amine Hydrochloride [Intermediate 1.31]

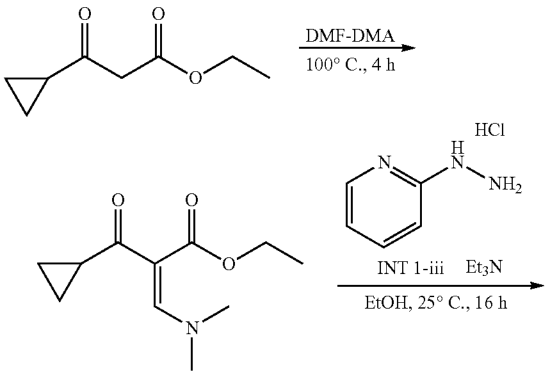

INT 1-xxxxx

-continued

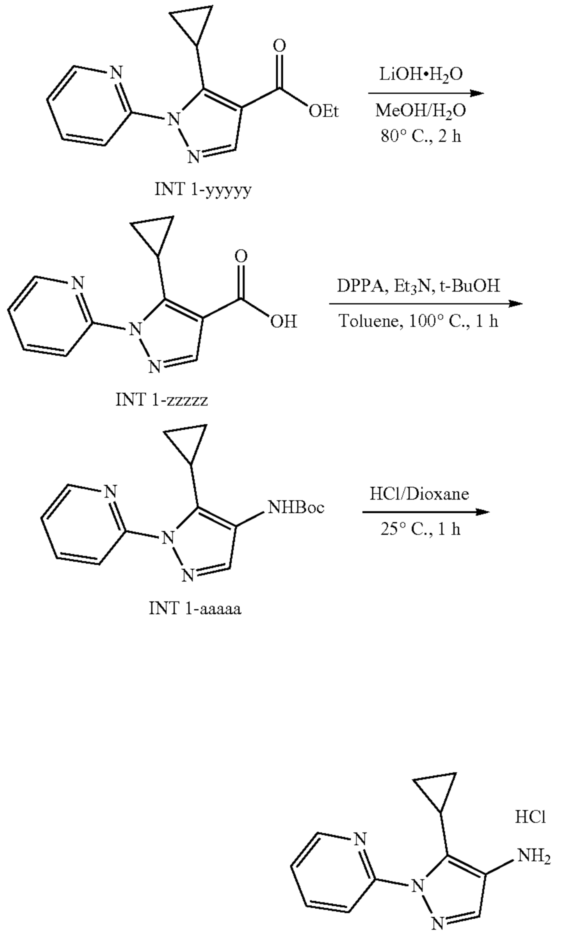

INT 1-yyyyy

INT 1-zzzzz

INT 1-aaaaa

INT 1.31

Synthesis of ethyl (2Z)-2-[(Z)-cyclopropanecarbonyl]-3-(dimethylamino)prop-2-enoate [INT 1-xxxxx]

A mixture of ethyl 3-cyclopropyl-3-oxopropanoate (20 g, 128 mmol) and N,N-dimethylformamide dimethyl acetal (30.5 g, 256 mmol) was stirred at 100° C. for 4 h. The mixture was concentrated under reduced pressure to give ethyl (2Z)-2-[(Z)-cyclopropanecarbonyl]-3-(dimethylamino)prop-2-enoate [INT 1-xxxxx] (27.0 g, 127 mmol). m/z: [M+H]+ Calcd for C11H18NO3 212.1. Found 212.1.

Synthesis of ethyl 5-cyclopropyl-1-(pyridin-2-yl)-1H-pyrazole-4-carboxylate [INT 1-yyyyy]

A solution of ethyl (2Z)-2-[(Z)-cyclopropanecarbonyl]-3-(dimethylamino)prop-2-enoate [INT 1-xxxxx] (5 g, 21.3 mmol), 2-hydrazinylpyridine hydrochloride [HCl salt of INT 1-iii] (3.71 g, 25.5 mmol), and $Et_3N$ (4.30 g, 42.6 mmol) in EtOH (50 mL) was stirred at 25° C. for 16 h. The reaction was concentrated under reduced pressure to give the crude product, which was purified by flash chromatography on silica gel (EtOAc/PE=0/1 to 1/3) to give ethyl 5-cyclopropyl-1-(pyridin-2-yl)-1H-pyrazole-4-carboxylate [INT 1-yyyyy] (2.80 g, 10.8 mmol, 51.0% yield) as a yellow oil. m/z: [M+H]+ Calcd for C14H16N3O2, 258.1. Found 258.0. $^{1}$H NMR (400 MHz, $CDCl_3$) δ=8.57 (dd, J=1.0, 4.8 Hz, 1H), 8.02 (s, 1H), 7.87 (dt, J=1.8, 7.8 Hz, 1H), 7.64 (d, J=8.1 Hz, 11H), 7.41-7.30 (m, 1H), 4.32 (q, J=7.1 Hz, 2H), 2.29 (tt, J=5.6, 8.6 Hz, 1H), 1.37 (t, J=7.1 Hz, 3H), 1.02-0.85 (m, 2H), 0.68-0.50 (m, 2H).

Synthesis of 5-cyclopropyl-1-(pyridin-2-yl)-1H-pyrazole-4-carboxylic Acid [INT 1-zzzzz]

A solution of ethyl 5-cyclopropyl-1-(pyridin-2-yl)-1H-pyrazole-4-carboxylate [INT 1-yyyyy] (2.5 g, 9.71 mmol) and lithium hydroxide monohydrate (1.01 g, 24.2 mmol) in THF (10 mL), $H_2O$ (10 mL) and $CH_3OH$ (10 mL) was stirred at 25° C. for 16 h. The reaction was concentrated under reduced pressure, and the resulting solution was acidified with aqueous 1 M HCl to pH=6. The resulting suspension was filtered and the filter cake was concentrated under reduced pressure to give 5-cyclopropyl-1-(pyridin-2-yl)-1H-pyrazole-4-carboxylic acid [INT 1-zzzzz] (1.90 g, 8.28 mmol, 85.5% yield) as a white solid. m/z: [M+H]+ Calcd for C12H12N3O2, 230.1. Found 230.0. $^{1}$H NMR (400 MHz, DMSO-d6) δ=12.41 (br s, 1H), 8.67-8.52 (m, 1H), 8.06 (dt, J=2.0, 7.8 Hz, 1H), 7.96 (s, 1H), 7.69 (d, J=8.1 Hz, 1H), 7.53 (ddd, J=1.0, 4.9, 7.5 Hz, 1H), 2.25 (tt, J=5.6, 8.7 Hz, 1H), 0.86-0.78 (m, 2H), 0.60-0.53 (m, 2H).

Synthesis of tert-butyl N-[5-cyclopropyl-1-(pyridin-2-yl)-1H-pyrazol-4-yl]carbamate [INT 1-aaaaaa]

A solution of 5-cyclopropyl-1-(pyridin-2-yl)-1H-pyrazole-4-carboxylic acid [INT 1-zzzzz] (1.8 g, 7.85 mmol), DPPA (3.21 g, 11.7 mmol), and $Et_3N$ (2.37 g, 23.5 mmol) in toluene (20 mL) was stirred at 25° C. for 15 min. 2-methylpropan-2-ol (581 mg, 7.84 mmol) was added and the reaction mixture was stirred at 100° C. for 1 h. The reaction was quenched by adding water (30 mL) and was extracted with EtOAc (2×50 mL). The combined organic layers were washed with brine (2×50 mL), dried over anhydrous $Na_2SO_4$ and concentrated under reduced pressure to give the crude product, which was purified by flash chromatography on silica gel (EtOAc/PE=0/1 to 1/3) to give tert-butyl N-[5-cyclopropyl-1-(pyridin-2-yl)-1H-pyrazol-4-yl]carbamate [INT 1-aaaaaa] (800 mg, 2.66 mmol, 34.0/6 yield) as a colorless oil. m/z: [M+H]+ Calcd for C16H21N4O2, 301.2. Found 301.2. $^{1}$H NMR (400 MHz, $CDCl_3$) δ=8.47 (dd, J=1.0, 4.8 Hz, 1H), 7.97 (br s, 1H), 7.84-7.76 (m, 1H), 7.75-7.66 (m, 1H), 7.21 (ddd, J=1.0, 4.9, 7.2 Hz, 1H), 6.28 (br s, 1H), 2.14 (ddd, J=2.7, 5.5, 8.2 Hz, 1H), 1.53 (s, 9H), 0.96-0.81 (m, 2H), 0.54-0.39 (m, 2H).

Synthesis of 5-cyclopropyl-1-(pyridine-2-yl)-1H-pyrazol-4-amine Hydrochloride [INT 1.31]

A solution of tert-butyl N-[5-cyclopropyl-1-(pyridin-2-yl)-1H-pyrazol-4-yl]carbamate [INT 1-aaaaaa] (700 mg, 2.33 mmol) in 4 M HCl in dioxane (10 mL) was stirred at 25° C. for 1 h. The reaction was concentrated under reduced pressure to give 5-cyclopropyl-1-(pyridine-2-yl)-1H-pyrazol-4-amine hydrochloride [INT 1.31] (550 mg, 2.32 mmol, 99.8% yield) as a yellow solid. m/z: [M+H]+ Calcd for C11H13N4 201.1. Found 201.1.

Synthesis of 5-cyclopropyl-1-(pyridin-3-yl)-1H-pyrazol-4-amine Hydrochloride [Intermediate 1.32]

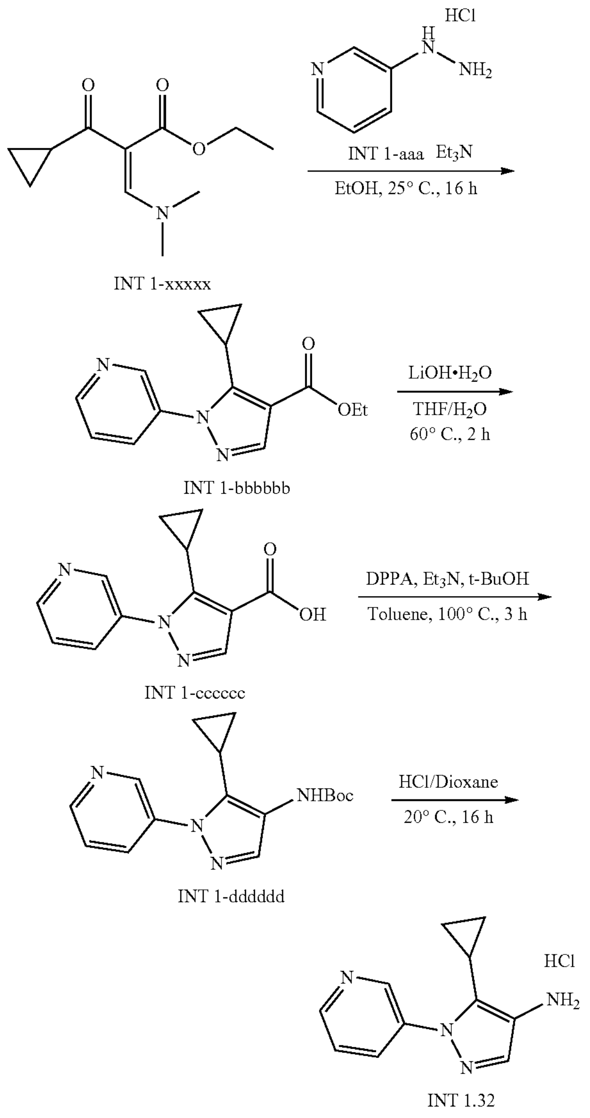

Synthesis of ethyl 5-cyclopropyl-1-(pyridin-3-yl)-H-pyrazole-4-carboxylate [INT 1-bbbbbb]

A solution of ethyl (2Z)-2-[(Z)-cyclopropanecarbonyl]-3-(dimethylamino)prop-2-enoate [INT 1-xxxxx] (5 g, 23.6 mmol), 3-hydrazinylpyridine hydrochloride [INT 1-aaa] (4.12 g, 28.3 mmol), and $Et_3N$ (4.76 g, 47.2 mmol) in EtOH (50 mL) was stirred at 25° C. for 16 h. The reaction was concentrated under reduced pressure to give the crude product, which was purified by flash chromatography on silica gel (EtOAc/PE=0/1 to 1/1) to give ethyl 5-cyclopropyl-1-(pyridin-3-yl)-1H-pyrazole-4-carboxylate [INT 1-bbbbbb] (1.70 g, 6.60 mmol, 28.0% yield) as a yellow oil. m/z: [M+H]+ Calcd for C14H16N3O2, 258.1. Found 258.1. $^{1}$H NMR (400 MHz, $CDCl_3$) δ=8.85 (d, J=2.2 Hz, 1H), 8.65 (dd, J=1.2, 4.7 Hz, 1H), 8.04 (s, 1H), 7.94-7.83 (m, 1H), 7.45

(dd, J=4.8, 8.2 Hz, 1H), 4.32 (q, J=7.2 Hz, 2H), 2.01-1.88 (m, 1H), 1.37 (t, J=7.2 Hz, 3H), 1.05-0.90 (m, 2H), 0.66-0.48 (m, 2H).

Synthesis of 5-cyclopropyl-1-(pyridin-3-yl)-1H-pyrazole-4-carboxylic acid [INT 1-cccccc]

To a mixture of ethyl 5-cyclopropyl-1-(pyridin-3-yl)-1H-pyrazole-4-carboxylate [INT 1-bbbbbb] (1.7 g, 6.60 mmol) in THF (6 mL) and $H_2O$ (2 mL) was added lithium hydroxide monohydrate (826 mg, 19.7 mmol). The reaction mixture was stirred at 60° C. for 2 hours. The reaction mixture was concentrated under reduced pressure. The resulting residue was acidified with aqueous 1 M HCl to pH=4. The reaction mixture was quenched by addition of $H_2O$ (20 mL) and extracted with EtOAc (20 mL×2). The combined organic layers were washed with brine (20 mL), dried over $Na_2SO_4$, filtered and concentrated under reduced pressure to afford 5-cyclopropyl-1-(pyridin-3-yl)-1H-pyrazole-4-carboxylic acid [INT 1-cccccc] (1 g, 4.36 mmol, 66.2% yield) as a yellow solid. m/z: [M+H]+ Calcd for C12H12N3O2, 230.1. Found 230.1.

Synthesis of tert-butyl (5-cyclopropyl-1-(pyridin-3-yl)-1H-pyrazol-4-yl)carbamate [INT 1-dddddd]

To a mixture of 5-cyclopropyl-1-(pyridin-3-yl)-1H-pyrazole-4-carboxylic acid [INT 1-cccccc] (500 mg, 2.18 mmol) in toluene (3 mL) and t-BuOH (2 mL) was added diphenylphosphoryl azide (899 mg, 3.27 mmol) and triethylamine (661 mg, 6.54 mmol). The reaction mixture was stirred at 100° C. under nitrogen for 3 hours. The reaction mixture was concentrated to give a residue which was purified by flash chromatography on silica gel (0-50% EtOAc in petroleum ether) to give tert-butyl (5-cyclopropyl-1-(pyridin-3-yl)-1H-pyrazol-4-yl)carbamate [INT 1-dddddd] (500 mg, 1.66 mmol, 76.4% yield) as a yellow oil. m/z: [M+H]+ Calcd for C16H21N4O2, 301.2. Found 301.2.

Synthesis of 5-cyclopropyl-1-(pyridin-3-yl)-1H-pyrazol-4-amine Hydrochloride [INT 1.32]

A solution of tert-butyl N-[5-cyclopropyl-1-(pyridin-3-yl)-1H-pyrazol-4-yl]carbamate [INT 1-dddddd] (500 mg, 1.66 mmol) in 4 M HCl/dioxane (5 mL) was stirred at 20° C. for 16 h. The reaction mixture was concentrated under reduced pressure to give 5-cyclopropyl-1-(pyridin-3-yl)-1H-pyrazol-4-amine hydrochloride [INT 1.32] (250 mg, 1.24 mmol, 75.3% yield) as a yellow solid. m/z: [M+H]+ Calcd for C11H13N4 201.1. Found 201.0.

Synthesis of (R)—N—((S)-1-(4-bromophenyl)-2,2,2-trifluoroethyl)-2-methylpropane-2-sulfinamide [Intermediate 2.1]

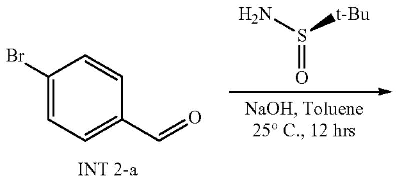

INT 2-a

-continued

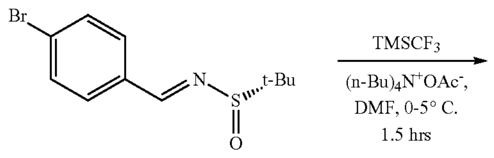

INT 2-b

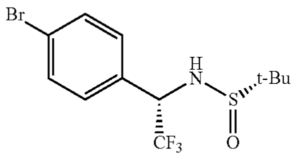

INT-2.1

Synthesis of (RE)-N-(4-bromobenzylidene)-2-methylpropane-2-sulfinamide [INT 2-b]

To a solution of 4-bromobenzaldehyde [INT 2-a] (100 g, 541 mmol, 1.0 eq) in toluene (500 mL) was added (R)-2-methylpropane-2-sulfinamide (72.1 g, 595 mmol, 1.1 eq) at 25° C. The mixture was stirred at 25° C. for 15 mins. Then to above reaction was added NaOH (21.6 g, 541 mmol, 1.0 eq) and the mixture was stirred at 25° C. for 12 hours. $Na_2SO_4$ (50 g) was added to the mixture and stirred for 20 mins. Four reaction mixtures were combined and filtered through celite to give the filtrate, which was concentrated in vacuum to give the crude product as an oil. The crude product was dissolved in petroleum ether (1.0 L) and stirred at −50° C. for 1.0 hour, filtered to give (R,E)-N-(4-bromobenzylidene)-2-methylpropane-2-sulfinamide [INT 2-b] (620 g, 2.15 mol, 99.5% yield) as a solid.

Synthesis of (R)—N—((S)-1-(4-bromophenyl)-2,2,2-trifluoroethyl)-2-methylpropane-2-sulfinamide [INT 2.1]

To a solution of (R,E)-N-(4-bromobenzylidene)-2-methylpropane-2-sulfinamide [INT 2-b] (206 g, 715 mmol, 1.0 eq) and tetrabutylammonium acetate (216 g, 715 mmol, 218 mL, 1.0 eq) in DMF (1.4 L) was added $TMSCF_3$ (259 g, 1.82 mol, 2.5 eq) at 0° C. The mixture was stirred at 5° C. for 1.5 hours. This process was repeated 2 times and the three reaction mixtures were combined for work-up. The mixture was poured into saturated $NH_4Cl$ solution (13.0 L) and stirred for 10 mins to give a suspension. The suspension was filtered and the filter cake was washed with water (5.0 L). The filter cake was triturated with MTBE/Petroleum ether (v/v=1:4, 2.0 L) and to give the product as a solid and the mother liquid was concentrated in vacuum to give the crude product as an oil which was purified by column chromatography on silica gel with petroleum ether/ethyl acetate (10/1-1/1) to give (R)—N—((S)-1-(4-bromophenyl)-2,2,2-trifluoroethyl)-2-methylpropane-2-sulfinamide [INT 2.1] (389 g, 1.09 mol, 50.6% yield) as a solid. $^1H$ NMR (400 MHz, $CDCl_3$) δ=1.25 (s, 9H), 3.64 (d, J=6.40 Hz, 1H), 4.79-4.83 (m, 1H), 7.32 (d, J=8.40 Hz, 2H), 7.56 (d, J=6.40 Hz, 2H).

Synthesis of(S)-1-(4-bromophenyl)-2,2,2-trifluoro-N-methylethan-1-amine [Intermediate 3.1]

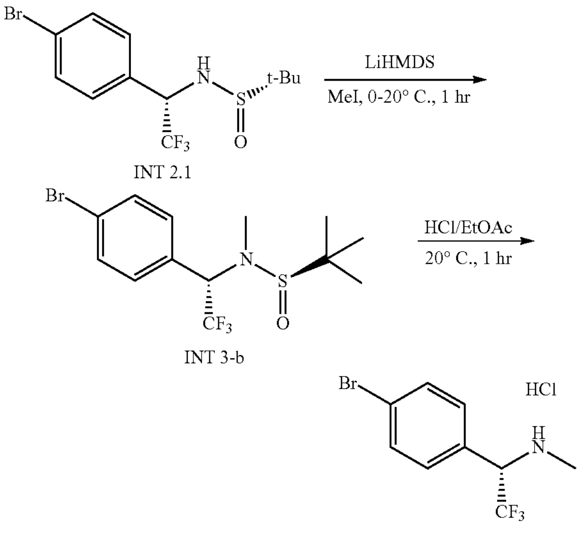

INT 2.1

INT 3-b

INT 3.1

Synthesis of (R)—N—((S)-1-(4-bromophenyl)-2,2,2-trifluoroethyl)-N,2-dimethylpropane-2-sulfinamide [INT 3-b]

To a solution of LiHMDS (1.0 M, 838 mL, 3.0 eq) was added (R)—N—((S)-1-(4-bromophenyl)-2,2,2-trifluoroethyl)-2-methylpropane-2-sulfinamide [INT 2.1] (100 g, 279 mmol, 1.0 eq) at 0-10° C. and the resulting mixture was stirred at 0-10° C. for 0.5 hour. To the above mixture was added MeI (119 g, 838 mmol, 52.1 mL, 3.0 eq) at 0-10° C. and the reaction was stirred at 25° C. for 1 hour. The process was repeated 2 times and the three combined reaction mixtures were poured into saturated aqueous $NH_4Cl$ (3.0 L) and diluted with EtOAc (1.0 L). The mixture was separated to give the organic layer and the aqueous layer was extracted with EtOAc (500 mL). The combined organic layer was washed with saturated NaCl (1.0 L) and dried with $Na_2SO_4$, filtered and concentrated in vacuum to give the crude product as an oil. The crude product was purified by column chromatography on silica gel with petroleum ether/ethyl acetate (15/1-1/1) to give (R)—N—((S)-1-(4-bromophenyl)-2,2,2-trifluoroethyl)-N,2-dimethylpropane-2-sulfinamide [INT 3-b] (161 g, 432.5 mmol, 51.6% yield) as an oil.

Synthesis of (S)-1-(4-bromophenyl)-2,2,2-trifluoro-N-methylethan-1-amine Hydrochloride [INT 3.1]

To the mixture of (R)—N—((S)-1-(4-bromophenyl)-2,2,2-trifluoroethyl)-N,2-dimethylpropane-2-sulfinamide [INT 3-b] (202 g, 543 mmol, 1.0 eq) in EtOAc (600 mL) was added HCl/EtOAc (4.0 M, 2.02 L, 14.9 eq) slowly. The above mixture was stirred at 20° C. for 1 hour. The reaction mixture was filtered to give a solid and eluted with EtOAc (200 mL) and the mother liquid was concentrated in vacuum to give a solid. The solid was purified by column chromatography on silica gel with petroleum ether/ethyl acetate (10/1-1/0) and combined with the filter cake and concentrated by oil pump at 45° C. for 1 hour to remove the solvent residue to give (S)-1-(4-bromophenyl)-2,2,2-trifluoro-N-methylethan-1-amine hydrochloride [INT 3.1](115 g, 378 mmol, 69.6% yield, 100% purity, HCl) as a solid. $^1H$ NMR (400 MHz, DMSO-$d_6$) δ=2.45 (s, 3H), 5.51 (s, 1H), 7.62 (d, J=8.4 Hz, 2H), 7.78 (d, J=8.40 Hz, 2H), 10.59 (s, 2H).

SFC: Rt=0.776 min, 99.98% ee; Column: Chiralpak AD-3, 100×4.6 mm, I.D., 3 μm; Mobile phase: A: $CO_2$, B: MeOH (0.05% IPAm); Gradient: A:B=97:3; Flow rate: 3 mL/min; Column temp.: 35° C.

LCMS: Rt=1.755 min, 100.0% purity, m/z=268.0, 270.0 (M+1)+. The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 μm particles). Detection methods are diode array (DAD) as well as positive electrospray ionization. MS range was 100-1000.

Synthesis of Tetrahydro-2H-thiopyran-4-carbonyl chloride 1,1-dioxide [Intermediate 4.1]

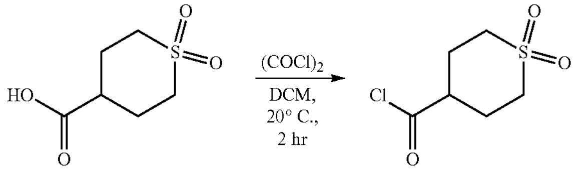

INT 4-a INT 4.1

To a solution of tetrahydro-2H-thiopyran-4-carboxylic acid 1,1-dioxide [INT 4-a] (41.0 g, 230 mmol, 1.0 eq) in DCM (410 mL) was added $(COCl)_2$ (58.4 g, 460 mmol, 40.3 mL, 2.0 eq) and DMF (168 mg, 2.30 mmol, 177 μL, 0.01 eq) at 0° C. under $N_2$. The mixture was warmed to 20° C. and stirred at 20° C. for 2 hours. The reaction mixture was concentrated in vacuo to give the crude product tetrahydro-2H-thiopyran-4-carbonyl chloride 1,1-dioxide [INT 4.1] (46.5 g, crude) as a solid.

Synthesis of 1-acetylpiperidine-4-carbonyl chloride [Intermediate 4.2]

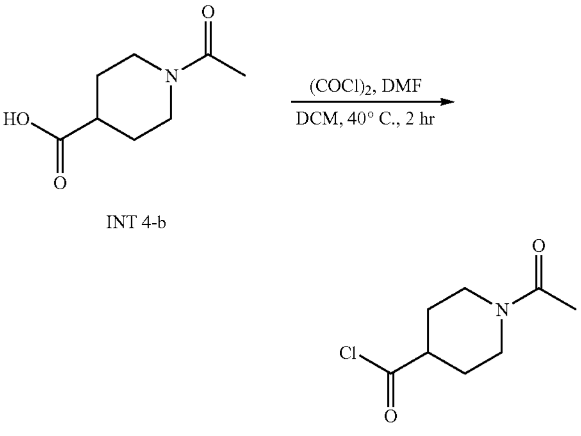

INT 4-b

INT 4.2

To a mixture of 1-acetylpiperidine-4-carboxylic acid [INT 4-b] (1 g, 5.84 mmol) in dichloromethane (10 mL) was added oxalyl dichloride (2.20 g, 17.5 mmol) and DMF (42.6 mg, 584 μmol) slowly and the mixture was stirred at 40° C. for 2 hr. The mixture was concentrated under reduced pressure to afford the crude 1-acetylpiperidine-4-carbonyl chloride [INT 4.2] (1.10 g, 5.80 mmol) as a green oil.

Synthesis of 1-acetylazetidine-3-carbonyl Chloride (Intermediate 4.3)

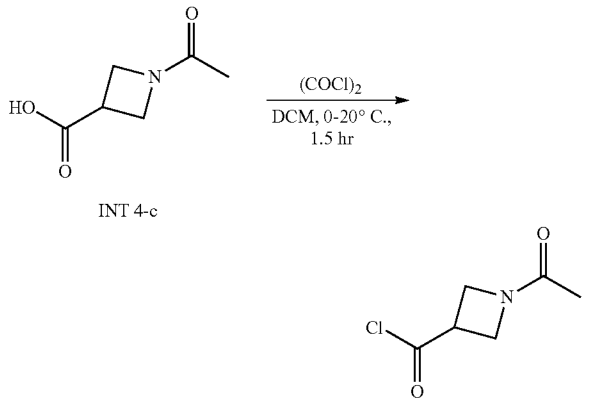

INT 4-c

INT 4.3

To a solution of 1-acetylazetidine-3-carboxylic acid [INT 4-c] (300 mg, 2.09 mmol) in DCM (4 mL) was added oxalyl chloride (397 mg, 3.13 mmol) at 0° C. The mixture was stirred at 20° C. for 1.5 hr. The reaction was concentrated under reduced pressure to give 1-acetylazetidine-3-carbonyl chloride [INT 4.3] (337 mg, 2.08 mmol).

Synthesis of Methyl (1r,4r)-4-(chlorocarbonyl)cyclohexane-1-carboxylate (Intermediate 4.4)

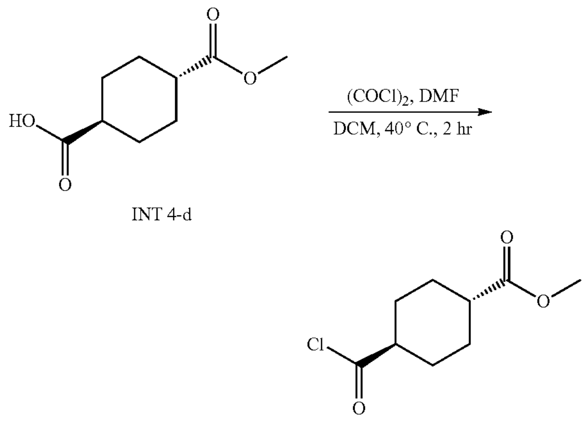

INT 4-d

INT 4.4

To a mixture of (1r,4r)-4-(methoxycarbonyl)cyclohexane-1-carboxylic acid [INT 4-d](1.45 g, 7.78 mmol) in dichloromethane (10 mL) was added oxalyl dichloride (2.93 g, 23.3 mmol) and DMF (56.8 mg, 778 μmol) slowly and the mixture was stirred at 40° C. for 2 hr. The mixture was concentrated under reduced pressure to afford the crude methyl (1r,4r)-4-(chlorocarbonyl)cyclohexane-1-carboxylate [INT 4.4] (1.59 g, 7.76 mmol) as a yellow gum.

Synthesis of methyl (1r,3r)-3-(carbonochloridoyl)cyclobutane-1-carboxylate (Intermediate 4.5)

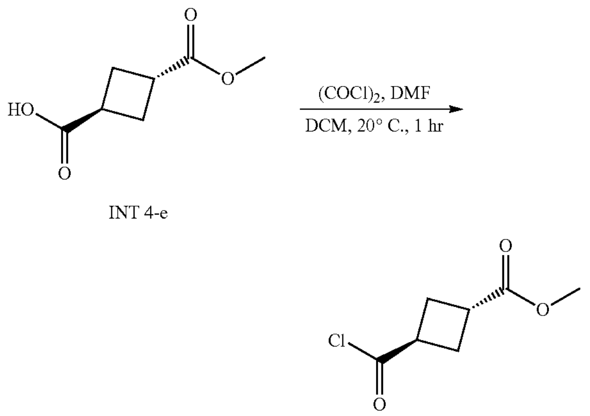

INT 4-e

INT 4.5

To a mixture of (1r,3r)-3-(methoxycarbonyl)cyclobutane-1-carboxylic acid [INT 4-e](100 mg, 632 μmol) in $CH_2Cl_2$ (2 mL) was added DMF (one drop) and oxalic dichloride (239 mg, 1.89 mmol) at 20° C. The mixture was stirred at 20° C. for 1 h. The reaction was concentrated under reduced pressure to give the crude methyl (1r,3r)-3-(carbonochloridoyl)cyclobutane-1-carboxylate [INT 4.5] (111 mg, 628 μmol) as a pale-yellow oil.

Synthesis of benzyl 3-(chlorocarbonyl)cyclobutane-1-carboxylate (Intermediate 4.6)

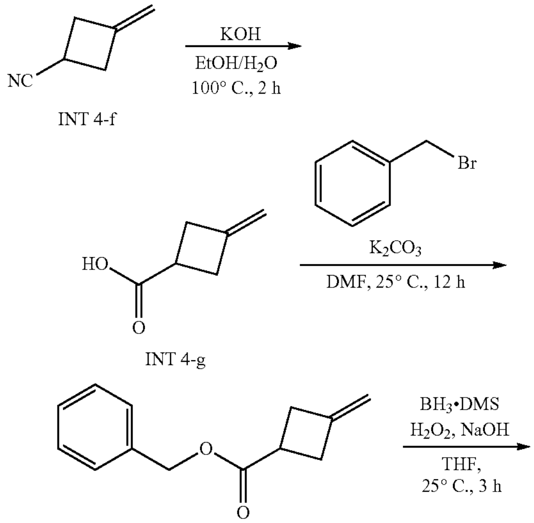

INT 4-f

INT 4-g

INT 4-h

-continued

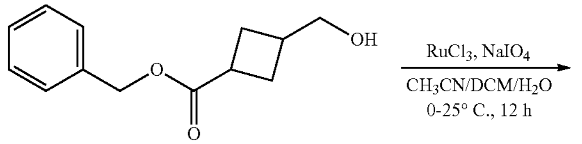

INT 4-i

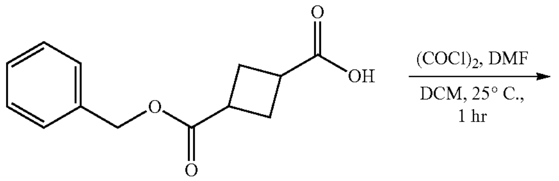

INT 4-j

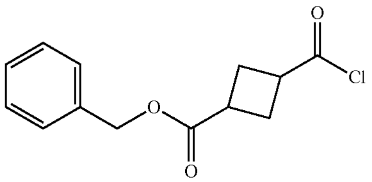

INT 4.6

Synthesis of 3-methylidenecyclobutane-1-carboxylic acid [INT 4-g]]

To a mixture of 3-methylidenecyclobutane-1-carbonitrile [INT 4-f] (20 g, 214 mmol) in EtOH (100 mL) and water (100 mL) was added potassium hydroxide (48.0 g, 856 mmol). The mixture was stirred at 100° C. for 2 h. The ethanol was removed under reduced pressure, after which the solution was cooled to below 10° C. and acidified with concentrated HCl to pH=1. The mixture was extracted with EtOAc (300 mL×2) and the combined organic extracts were dried over anhydrous sodium sulfate and concentrated under reduced pressure to give 3-methylidenecyclobutane-1-carboxylic acid [INT 4-g] (23.0 g, 205 mmol, 96.2% yield) as a yellow oil. $^1$H NMR (400 MHz, $CDCl_3$) δ=9.51 (br s, 1H), 4.82 (quin, J=2.4 Hz, 2H), 3.25-3.12 (m, 1H), 3.08-2.89 (m, 4H).

Synthesis of benzyl 3-methylidenecyclobutane-1-carboxylate [INT 4-h]]

To a mixture of 3-methylidenecyclobutane-1-carboxylic acid [INT 4-g] (13 g, 115 mmol) in DMF (120 mL) was added potassium carbonate (23.7 g, 172 mmol) and (bromomethyl)benzene (21.5 g, 126 mmol). The mixture was stirred at 25° C. for 12 h, after which it was combined with another of the same type. The mixture was diluted with water (200 mL) and extracted with ethyl acetate (250 mL×2). The combined organic phase was washed with saturated brine (100 mL×3), dried over anhydrous $Na_2SO_4$ and concentrated under reduced pressure to give the crude product, which was purified by flash chromatography on silica gel (EtOAc/PE=0/1 to 10/1) to give benzyl 3-methylidenecyclobutane-1-carboxylate [INT 4-h](33.0 g, 163 mmol) as a pale yellow oil. $^1$H NMR (400 MHz, $CDCl_3$) δ=7.43-7.31 (m, 5H), 5.16 (s, 2H), 4.83 (quin, J=2.4 Hz, 2H), 3.26-3.13 (m, 1H), 3.10-2.86 (m, 4H).

Synthesis of benzyl 3-(hydroxymethyl)cyclobutane-1-carboxylate [INT 4-i]]

To a mixture of benzyl 3-methylidenecyclobutane-1-carboxylate [INT 4-h] (20 g, 98.8 mmol) in THF (200 mL) was added borane dimethylsulfide (29.5 mL, 296 mmol) dropwise under an ice-salt bath. The mixture was stirred at 25° C. for 1 h. Then sodium hydroxide (20 mL, 60.0 mmol) and hydrogen peroxide (18 mL, 98.8 mmol) were added under an ice-salt bath. The mixture was stirred at 25° C. for another 2 h. The reaction was quenched with saturated sodium sulfite solution (100 mL), diluted with water (50 mL) and extracted with ethyl acetate (2×200 mL). The organic phases were washed with saturated brine (2×100 mL), dried over anhydrous $Na_2SO_4$ and concentrated under reduced pressure to give the crude product, which was purified by flash chromatography on silica gel (PE/EtOAc=1:0 to 1/3) to give benzyl 3-(hydroxymethyl)cyclobutane-1-carboxylate [INT 4-i] (6.50 g, 29.5 mmol, 29.9% yield) as a pale yellow oil. $^1$H NMR (400 MHz, $CDCl_3$) δ=7.41-7.30 (m, 5H), 5.14 (d, J=9.2 Hz, 2H), 3.67 (d, J=6.4 Hz, 1H), 3.60 (d, J=6.0 Hz, 1H), 3.22-3.05 (m, 1H), 2.64-2.28 (m, 3H), 2.14-2.01 (m, 2H).

Synthesis of 3-[(benzyloxy)carbonyl]cyclobutane-1-carboxylic Acid [INT 4-j]]

To a mixture of benzyl 3-(hydroxymethyl)cyclobutane-1-carboxylate [INT 4-i] (4.5 g, 20.4 mmol) in $CH_3CN$ (30 mL), water (30 mL) and $CH_2Cl_2$ (30 mL) was added sodium periodate (13.0 g, 61.1 mmol) and ruthenium(III) chloride (421 mg, 2.03 mmol) at 0° C. The mixture was raised to 25° C. and reacted for 12 hours. The reaction was poured into 1 N HCl (100 mL). The mixture was concentrated under reduced pressure to give a residue. The residue was diluted with water (50 mL) and extracted with EtOAc (100 mL×2). The combined organic phase was washed with brine (80 mL), dried over anhydrous $Na_2SO_4$ and concentrated under reduced pressure to give the crude product, which was purified by flash chromatography on silica gel (EtOAc/PE=0/1 to 1/3) to give 3-[(benzyloxy)carbonyl]cyclobutane-1-carboxylic acid [INT 4-j](3.36 g, 14.3 mmol, 70.4% yield) as a brown oil. m/z: [M+H]+ Calcd for C13H15O4 235.1. Found 235.1. $^1$H NMR (400 MHz, $CDCl_3$) δ=7.44-7.30 (m, 5H), 5.15 (d, J=8.0 Hz, 2H), 3.37-3.04 (m, 2H), 2.69-2.44 (m, 4H).

Synthesis of benzyl 3-(chlorocarbonyl)cyclobutane-1-carboxylate [INT 4.6]]

To a mixture of 3-[(benzyloxy)carbonyl]cyclobutane-1-carboxylic acid [INT 4-j] (3.36 g, 14.3 mmol) in $CH_2Cl_2$ (80 mL) was added DMF (one drop) and oxalyl chloride (3.62 g, 28.6 mmol) at 25° C. The mixture was stirred at 25° C. for 1 h. The reaction was concentrated under reduced pressure to give the crude benzyl 3-(chlorocarbonyl)cyclobutane-1-carboxylate [INT 4.6] (3.61 g, 14.2 mmol) as a black oil.

Synthesis of (S)—N-(1-(4-bromophenyl)-2,2,2-trifluoroethyl)-N-methyltetrahydro-2H-thiopyran-4-carboxamide 1,1-dioxide [Intermediate 5.1]

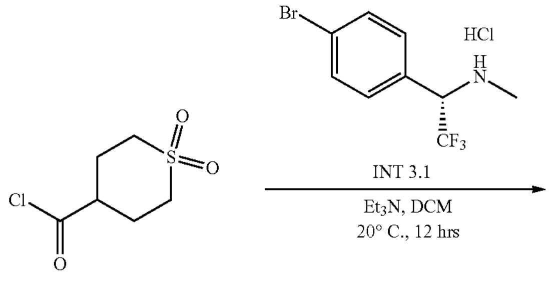

INT 4.1

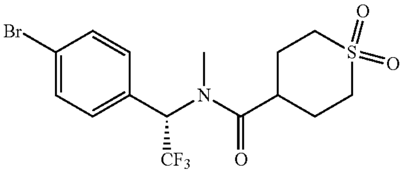

INT 5.1

To a solution of (S)-1-(4-bromophenyl)-2,2,2-trifluoro-N-methylethan-1-amine hydrochloride [INT 3.1] (39.0 g, 128 mmol, 1.0 eq, HCl) and TEA (45.7 g, 451 mmol, 62.8 mL, 3.5 eq) in DCM (200 mL) was added tetrahydro-2H-thiopyran-4-carbonyl chloride 1,1-dioxide [INT 4.1] (45.3 g, 231 mmol, 1.8 eq) at 0-10° C. The mixture was stirred at 20° C. for 12 hours. The mixture was separated to give the organic layer, and the aqueous layer was extracted with DCM (100 mL). The combined organic layer was concentrated in vacuum to give the crude product as an oil. The crude product was purified by column chromatography on silica gel with petroleum ether/ethyl acetate (15/1-3/1) to give (S)—N-(1-(4-bromophenyl)-2,2,2-trifluoroethyl)-N-methyltetrahydro-2H-thiopyran-4-carboxamide 1,1-dioxide [INT 5.1] (26.0 g, 60.7 mmol, 47.4% yield, 100% purity) as a solid. $^1$H NMR (400 MHz, CDCl3) δ=2.25-2.37 (m, 1H), 2.38-2.40 (m, 3H), 2.88-3.00 (m, 6H), 3.30-3.31 (m, 1H), 3.22-3.45 (m, 1H), 6.56-6.63 (m, 1H), 7.23 (d, J=8.00 Hz, 2H), 7.55 (d, J=8.40 Hz, 2H).

SFC: Rt=1.21 min, 100.0% ee; Column: Chiralpak AD-3, 50×4.6 mm I.D., 3 μm; Mobile phase: A: $CO_2$, B: MeOH (0.05% IPAm, v/v); Flow rate: 3.4 mL/min; Column temp.: 35° C.

LCMS: Rt=2.431 min, 100% purity, m/z=428.0, 430.0 (M+1)+. The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 μm particles). Detection methods are diode array (DAD) as well as positive electrospray ionization. MS range was 100-1000.

Synthesis of 1-acetyl-N-[(1S)-1-(4-bromophenyl)-2,2,2-trifluoroethyl]-N-methylpiperidine-4-carboxamide [Intermediate 5.2]

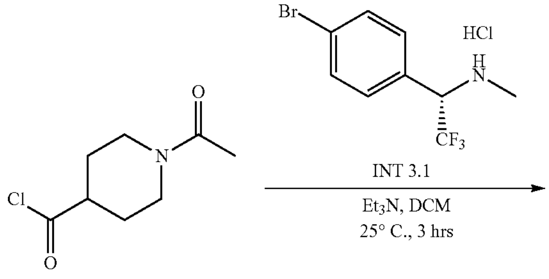

INT 4.2

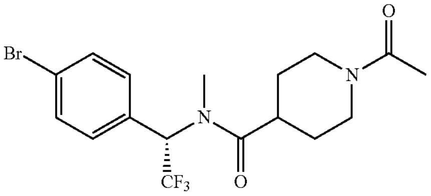

INT 5.2

To a mixture of [(1S)-1-(4-bromophenyl)-2,2,2-trifluoroethyl](methyl)amine hydrochloride [INT 3.1] (500 mg, 1.64 mmol) and $Et_3N$ (829 mg, 8.20 mmol) in dichloromethane (10 mL) was added 1-acetylpiperidine-4-carbonyl chloride [INT 4.2] (550 mg, 2.90 mmol) and the mixture was stirred at 25° C. for 3 hr. The mixture was concentrated under reduced pressure to give the crude product, which was purified by flash chromatography on silica gel (methanol/dichloromethane=0/1 to 1/20) to give 1-acetyl-N-[(1S)-1-(4-bromophenyl)-2,2,2-trifluoroethyl]-N-methylpiperidine-4-carboxamide [INT 5.2] (680 mg, 1.61 mmol, 98.5% yield) as a yellow solid. m/z: [M+H]+ Calcd for C17H21BrF3N2O2, 421.1, 423.1. Found 423.1. $^1$H NMR (400 MHz, $CDCl_3$) δ=7.55 (d, J=8.4 Hz, 2H), 7.24 (d, J=8.4 Hz, 2H), 6.62 (q, J=8.8 Hz, 1H), 4.05-3.82 (m, 1H), 3.23-3.04 (m, 1H), 2.90 (s, 3H), 2.87-2.71 (m, 2H), 2.70-2.43 (m, 1H), 2.13 (s, 3H), 1.92-1.63 (m, 4H).

Synthesis of 1-acetyl-N-[(1S)-1-(4-bromophenyl)-2,2,2-trifluoroethyl]-N-methylazetidine-3-carboxamide (Intermediate 5.3)

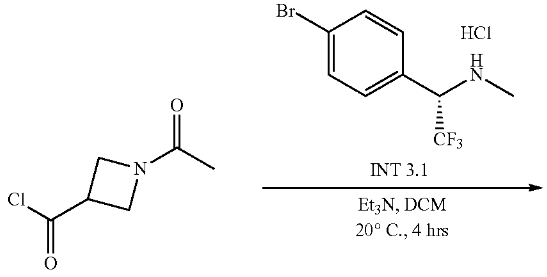

INT 4.3

-continued

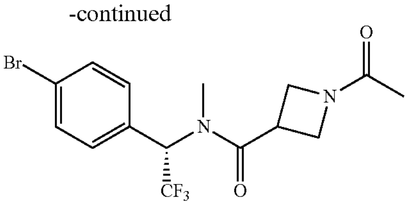

INT 5.3

To a solution of 1-acetylazetidine-3-carbonyl chloride [INT 4.3] (300 mg, 1.85 mmol) and [(1S)-1-(4-bromophenyl)-2,2,2-trifluoroethyl](methyl)amine hydrochloride [INT 3.1] (563 mg, 1.85 mmol) in $CH_2Cl_2$ (3 mL) was added triethylamine (561 mg, 5.55 mmol). The mixture was stirred at 20° C. for 4 h. The reaction was concentrated under reduced pressure to give the crude product, which was purified by flash chromatography on silica gel (EtOAc/PE=0/1 to 1/5) to give 1-acetyl-N-[(1S)-1-(4-bromophenyl)-2,2,2-trifluoroethyl]-N-methylazetidine-3-carboxamide [INT 5.3] (250 mg, 635 μmol, 34.3% yield) as a yellow oil. m/z: [M+H]+ Calcd for C15H17BrF3N2O2, 393.0, 395.0. Found 394.8.

Synthesis of Methyl (1S,4r)-4-(((S)-1-(4-bromophenyl)-2,2,2-trifluoroethyl)(methyl)carbamoyl)cyclohexane-1-carboxylate (Intermediate 5.4)

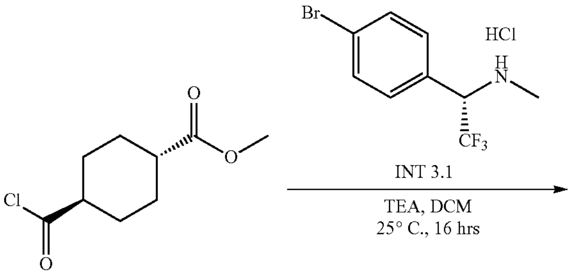

INT 4.4

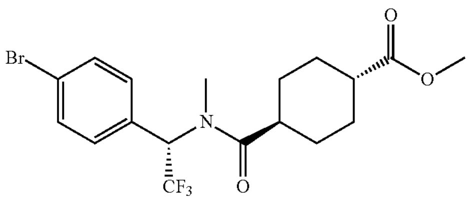

INT 5.4

To a mixture of methyl (1r,4r)-4-(carbonochloridoyl)cyclohexane-1-carboxylate [INT 4.4] (1.59 g, 7.76 mmol) and $Et_3N$ (2.65 g, 26.2 mmol) in dichloromethane (6 mL) was added a solution of [(1S)-1-(4-bromophenyl)-2,2,2-trifluoroethyl](methyl)amine hydrochloride [INT 3.1](1.6 g, 5.25 mmol) in dichloromethane (6 mL) and the mixture was stirred at 25° C. for 16 hr. Water (30 mL) was added and the mixture was extracted with dichloromethane (30 mL×2). The combined organic layers were washed with brine (30 mL), dried over anhydrous $Na_2SO_4$, filtered and concentrated under reduced pressure to give the crude product which was purified by flash chromatography on silica gel (EtOAc/Petroleum ether=1/10 to 1/5) to give methyl (1S,4r)-4-(((S)-1-(4-bromophenyl)-2,2,2-trifluoroethyl)(methyl)carbamoyl)cyclohexane-1-carboxylate [INT 5.4] (1.10 g, 2.52 mmol, 32.5% yield) as yellow oil. m/z: [M+H]+ Calcd for C18H22BrF3NO3 436.1, 438.1. Found 438.0.

Synthesis of methyl (1S,3r)-3-(((S)-1-(4-bromophenyl)-2,2,2-trifluoroethyl)(methyl)carbamoyl)cyclobutane-1-carboxylate (Intermediate 5.5)

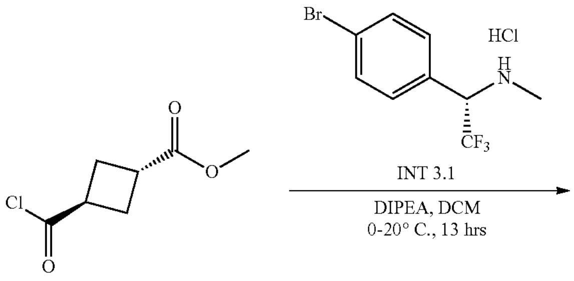

INT 4.5

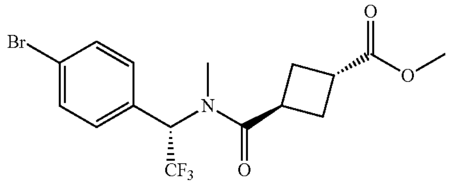

INT 5.5

To a mixture of methyl (1r,3r)-3-(carbonochloridoyl)cyclobutane-1-carboxylate [INT 4.5] (111 mg, 628 μmol) and [(1S)-1-(4-bromophenyl)-2,2,2-trifluoroethyl](methyl)amine hydrochloride [INT 3.1] (120 mg, 394 μmol) in $CH_2Cl_2$ (2 mL) was added N,N-diisopropylethylamine (254 mg, 1.97 mmol) at 0° C. The mixture was stirred at 0° C. for 1 hour and then was stirred at 20° C. for 12 h. The reaction was diluted with $CH_2Cl_2$ (50 mL) and 1 N HCl (20 mL). The organic phase was separated and washed with brine (20 mL), dried over anhydrous $Na_2SO_4$ and concentrated under reduced pressure to give the crude product, which was purified by flash chromatography on silica gel (EtOAc/PE=0/1 to 1/3) to give methyl (1S,3r)-3-(((S)-1-(4-bromophenyl)-2,2,2-trifluoroethyl)methyl)carbamoyl)cyclobutane-1-carboxylate [INT 5.5] (84.8 mg, 207 μmol, 53.0% yield (53% purity)) as a yellow oil. m/z: [M+H]+ Calcd for C16H18BrF3NO3 408.0. Found 408.0.

Synthesis of benzyl 3-{[(1S)-1-(4-bromophenyl)-2,2,2-trifluoroethyl](methyl)carbamoyl}cyclobutane-1-carboxylate (Intermediate 5.6)

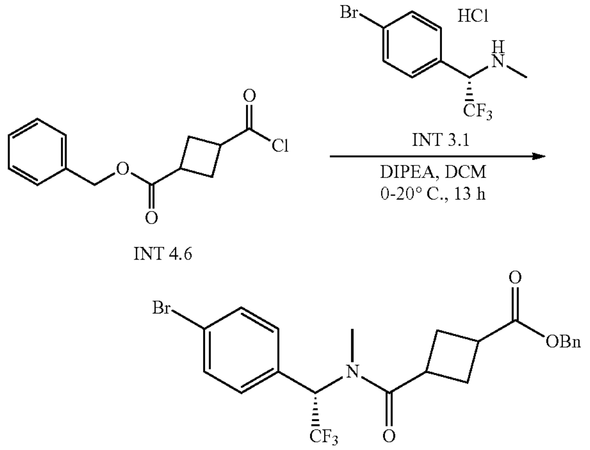

INT 4.6

INT 5.6

To a mixture of benzyl 3-(carbonochloridoyl)cyclobutane-1-carboxylate [INT 4.6](3.61 g, 14.2 mmol) and [(1S)-1-(4-bromophenyl)-2,2,2-trifluoroethyl](methyl)amine hydrochloride [INT 3.1] (2.5 g, 8.20 mmol) in $CH_2Cl_2$ (100 mL) was added N,N-diisopropylethylamine (5.28 g, 40.9 mmol) at 0° C. The mixture was stirred at 0° C. for 1 hour and stirred at 20° C. for 12 h. The reaction was diluted with $CH_2Cl_2$ (100 mL) and 1 N HCl (50 mL). The organic phase was separated and washed with brine (50 mL), dried over anhydrous $Na_2SO_4$ and concentrated under reduced pressure to give the crude product, which was purified by flash chromatography on silica gel (EtOAc/PE=0/1 to 1/3). The resulting product was further purified by Prep-HPLC (column: YMC-Triart Prep C18 150*40 mm*7 μm, table: 48-68% B (A=water (0.025% FA), B=acetonitrile), flow rate: 60 mL/min, UV Detector 220 nm) to give benzyl 3-{[(1S)-1-(4-bromophenyl)-2,2,2-trifluoroethyl](methyl)carbamoyl}cyclobutane-1-carboxylate [INT 5.6] (760 mg, 1.56 mmol, 19.1% yield) as a yellow oil. m/z: [M+H]+ Calcd for C22H22BrF3NO3 484.1. Found 484.0. $^1$H NMR (400 MHz, $CDCl_3$) δ=7.60-7.51 (m, 2H), 7.41-7.31 (m, 5H), 7.29-7.19 (m, 2H), 6.66-6.34 (m, 1H), 5.18-5.11 (m, 2H), 3.57-3.07 (m, 2H), 2.77-2.73 (m, 3H), 2.70-2.43 (m, 4H).

Synthesis of (1r,4r)-N-[(1S)-1-(4-bromophenyl)-2,2,2-trifluoroethyl]-4-cyano-N-methylcyclohexane-1-carboxamide (Intermediate 5.7)

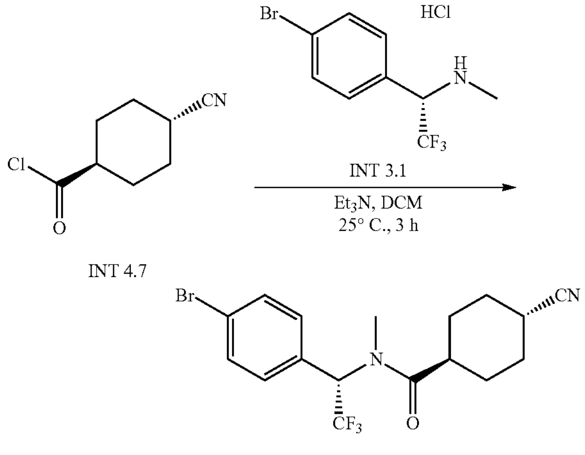

INT 4.7

INT 5.7

A mixture of [(1S)-1-(4-bromophenyl)-2,2,2-trifluoroethyl](methyl)amine hydrochloride [INT 3.1] (350 mg, 1.14 mmol) and triethylamine (576 mg, 5.70 mmol) in $CH_2Cl_2$ (5 mL) was stirred at 25° C. for 20 min. A solution of (1r,4r)-4-cyanocyclohexane-1-carbonyl chloride [INT 4.7] (391 mg, 2.28 mmol) in $CH_2Cl_2$ (5 mL) was added and the reaction was stirred at 25° C. for 3 hr. The mixture was concentrated under reduced pressure to give the crude product, which was purified by flash chromatography on silica gel (0-30% EtOAc in petroleum ether) to give (1r,4r)-N-[(1S)-1-(4-bromophenyl)-2,2,2-trifluoroethyl]-4-cyano-N-methylcyclohexane-1-carboxamide [INT 5.7] (300 mg, 743 μmol, 65.3% yield) as a white solid. $^1$H NMR (400 MHz, $CDCl_3$) δ=7.57-7.51 (m, 2H), 7.23 (d, J=8.4 Hz, 2H), 6.60 (q, J=8.8 Hz, 1H), 2.87 (s, 3H), 2.68-2.59 (m, 1H), 2.58-2.48 (m, 1H), 2.32-2.19 (m, 2H), 2.01-1.93 (m, 1H), 1.92-1.84 (m, 1H), 1.72-1.62 (m, 4H).

Synthesis of methyl (1r,4r)-4-{methyl[(1S)-2,2,2-trifluoro-1-(4-{[1-phenyl-5-(trifluoromethyl)-1H-pyrazol-4-yl]amino}phenyl)ethyl]carbamoyl}cyclohexane-1-carboxylate [Intermediate 6.1]

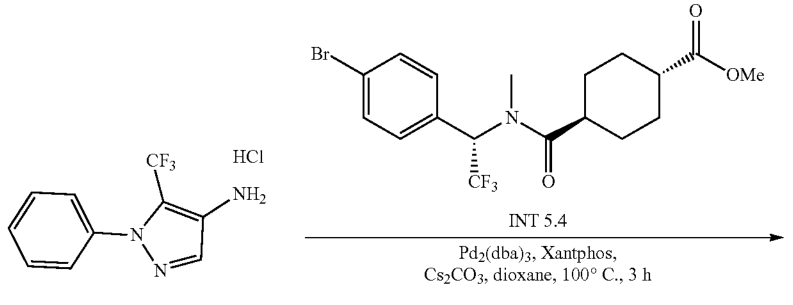

INT 1.6

-continued

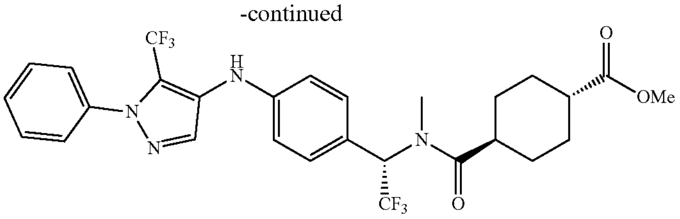

INT 6.1

A mixture of 1-phenyl-5-(trifluoromethyl)-1H-pyrazol-4-amine hydrochloride [INT 1.6] (140 mg, 531 μmol), methyl (1r,4r)-4-{[(1S)-1-(4-bromophenyl)-2,2,2-trifluoroethyl](methyl)carbamoyl}cyclohexane-1-carboxylate [INT 5.4] (231 mg, 531 μmol), xantphos (30.7 mg, 53.1 μmol), $Pd_2(dba)_3$ (48.6 mg, 53.1 μmol) and $Cs_2CO_3$ (518 mg, 1.59 mmol) in dioxane (3 mL) was stirred at 100° C. for 3 hr under $N_2$ atmosphere. Brine (50 mL) was added and the mixture was extracted with EtOAc (50 mL×2). The combined organic layers were washed with brine (50 mL×2), dried over anhydrous $Na_2SO_4$, filtered and concentrated under reduced pressure to give the crude product, which was purified by flash chromatography on silica gel (0-8% EtOAc in petroleum ether) to give methyl (1r,4r)-4-{methyl[(1S)-2,2,2-trifluoro-1-(4-{[1-phenyl-5-(trifluoromethyl)-1H-pyrazol-4-yl]amino}phenyl)ethyl]carbamoyl}cyclohexane-1-carboxylate [INT 6.1] (152 mg, 260 μmol, 49.1% yield) as a brown solid. m/z: [M+H]+ Calcd for C28H29F6N4O3, 583.2. Found 583.2.

Synthesis of methyl (1r,4r)-4-{methyl[(1S)-2,2,2-trifluoro-1-(4-{[1-(pyridin-4-yl)-5-(trifluoromethyl)-1H-pyrazol-4-yl]amino}phenyl)ethyl]carbamoyl}cyclohexane-1-carboxylate [Intermediate 6.2]

A mixture of 1-(pyridin-4-yl)-5-(trifluoromethyl)-1H-pyrazol-4-amine [INT 1.14] (80 mg, 350 μmol), methyl (1r,4r)-4-{[(1S)-1-(4-bromophenyl)-2,2,2-trifluoroethyl](methyl)carbamoyl}cyclohexane-1-carboxylate [INT 5.4] (152 mg, 350 μmol), $Pd_2(dba)_3$ (32.0 mg, 35.0 μmol), xantphos (40.5 mg, 70.0 μmol) and $Cs_2CO_3$ (228 mg, 700 μmol) in dioxane (3 mL) was stirred at 100° C. for 12 h under $N_2$. The mixture was worked up with another reaction of the same type. The reaction was quenched by adding water (20 mL) and was extracted with EtOAc (20 mL×2). The combined organic layers were washed with brine (20 mL×2), dried over anhydrous $Na_2SO_4$ and concentrated under reduced pressure to give the crude product, which was purified by flash chromatography on silica gel (PE/EtOAc=1/0 to 1/1) to give methyl (1r,4r)-4-{methyl[(1S)-2,2,2-trifluoro-1-(4-{[1-(pyridin-4-yl)-5-(trifluoromethyl)-1H-pyrazol-4-yl]amino}phenyl)ethyl]carbamoyl}cyclohexane-1-carboxylate [INT 6.2] (115 mg, 197 μmol) as a pale yellow oil. m/z: [M+H]+ Calcd for C27H28F6N5O3 584.2. Found 584.1.

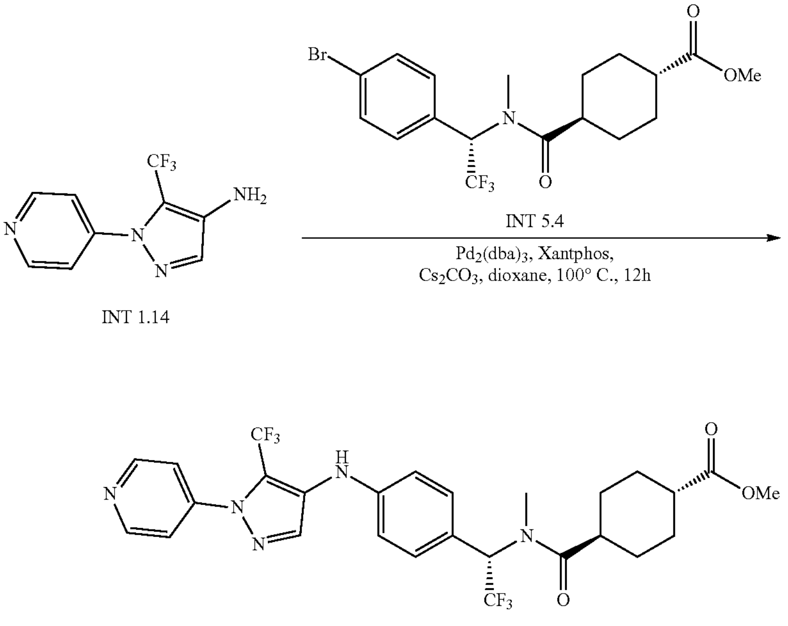

Synthesis of methyl (1r,4r)-4-{methyl[(1S)-2,2,2-trifluoro-1-(4-{[1-(pyridin-3-y)-5-(trifluoromethyl)-1H-pyrazol-4-yl]amino}phenyl)ethyl]carbamoyl}cyclohexane-1-carboxylate [Intermediate 6.3]

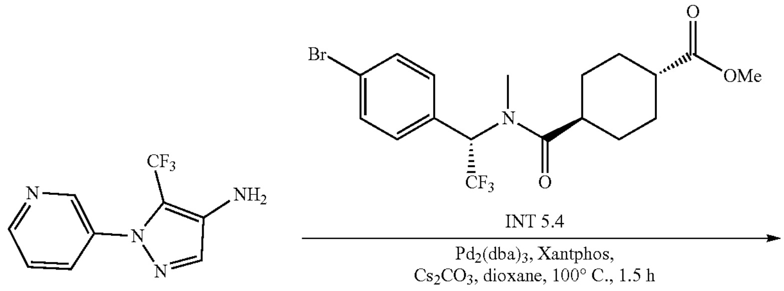

INT 1.13

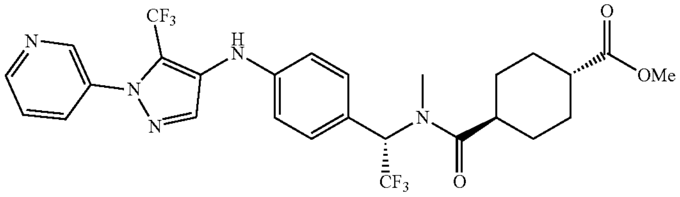

INT 6.3

A suspension of 1-(pyridin-3-yl)-5-(trifluoromethyl)-1H-pyrazol-4-amine hydrochloride [INT 1.13] (150 mg, 566 μmol), methyl (1r,4r)-4-{[(1S)-1-(4-bromophenyl)-2,2,2-trifluoroethyl](methyl)carbamoyl}cyclohexane-1-carboxylate [INT 5.4] (246 mg, 566 μmol), $Cs_2CO_3$ (550 mg, 1.69 mmol), $Pd_2(dba)_3$ (25.9 mg, 28.3 μmol) and xantphos (32.7 mg, 56.6 μmol) in dioxane (2 mL) was stirred at 100° C. for 1.5 h under $N_2$. The mixture was concentrated under reduced pressure to give the crude product, which was purified by flash chromatography on silica gel (MeOH/Dichloromethane=0/1 to 1/99) to give methyl (1r,4r)-4-{methyl[(1S)-2,2,2-trifluoro-1-(4-{[1-(pyridin-3-yl)-5-(trifluoromethyl)-1H-pyrazol-4-yl]amino}phenyl)ethyl]carbamoyl}cyclohexane-1-carboxylate [INT 6.3] (231 mg, 396 μmol, 70.0% yield) as a yellow oil. m/z: [M+H]+ Calcd for C27H28F6N5O3, 584.2. Found 584.1. $^1$H NMR (400 MHz, $CDCl_3$) δ=8.80 (d, J=2.8 Hz, 1H), 8.74 (dd, J=1.2, 4.8 Hz, 1H), 7.91-7.81 (m, 2H), 7.49 (dd, J=4.8, 8.0 Hz, 1H), 7.30 (s, 1H), 6.97 (d, J=8.8 Hz, 2H), 6.61 (q, J=8.8 Hz, 1H), 5.59 (s, 1H), 3.71 (s, 3H), 2.91 (s, 3H), 2.63-2.51 (m, 1H), 2.39 (tt, J=3.6, 12.0 Hz, 1H), 2.11 (br t, J=8.8 Hz, 2H), 1.96-1.83 (m, 2H), 1.70-1.61 (m, 2H), 1.56-1.45 (m, 2H).

Synthesis of methyl (1r,4r)-4-{methyl[(1S)-2,2,2-trifluoro-1-(4-{[1-(pyridin-2-y)-5-(trifluoromethyl)-1H-pyrazol-4-yl]amino}phenyl)ethyl]carbamoyl}cyclohexane-1-carboxylate [Intermediate 6.4]

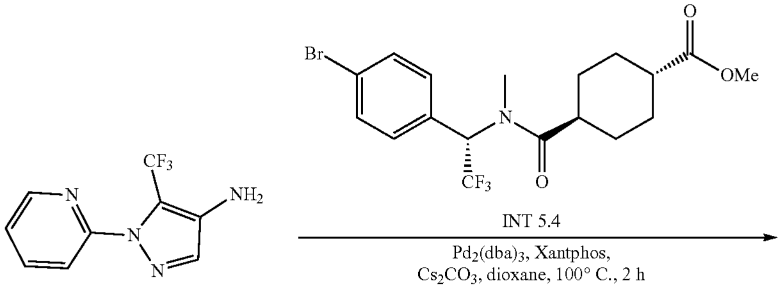

INT 1.15

-continued

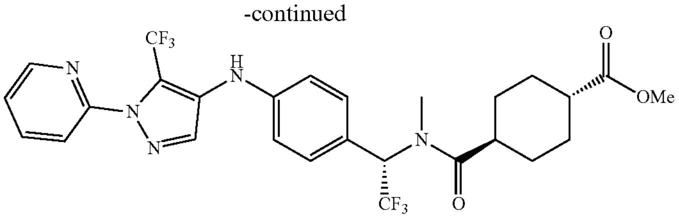

INT 6.4

To a solution of 1-(pyridin-2-yl)-5-(trifluoromethyl)-1H-pyrazol-4-amine [INT 1.15](100 mg, 438 μmol), methyl (1r,4r)-4-{[(1S)-1-(4-bromophenyl)-2,2,2-trifluoroethyl](methyl)carbamoyl}cyclohexane-1-carboxylate [INT 5.4] (191 mg, 438 μmol), $Cs_2CO_3$ (426 mg, 1.31 mmol) and xantphos (50.6 mg, 87.6 μmol) in dioxane (3 mL) was added $Pd_2(dba)_3$ (40.1 mg, 43.8 μmol) and the reaction mixture was stirred at 100° C. for 2 h under $N_2$. The reaction mixture was concentrated under reduced pressure to give the crude product, which was purified by flash chromatography on silica gel (EtOAc/PE=0/1 to 1/3) to give methyl (1r,4r)-4-{methyl[(1S)-2,2,2-trifluoro-1-(4-{[1-(pyridin-2-yl)-5-(trifluoromethyl)-1H-pyrazol-4-yl]amino}phenyl)ethyl]carbamoyl}cyclohexane-1-carboxylate [INT 6.4] (170 mg, 291 μmol, 66.6% yield) as a yellow oil. m/z: [M+H]+ Calcd for C27H28F6N5O3, 584.2. Found 584.1.

Synthesis of methyl (1r,4r)-4-{methyl[(1S)-2,2,2-trifluoro-1-[4-({5-[(1S)-1-methoxyethyl]-1-(pyridin-2-yl)-1H-pyrazol-4-yl}amino)phenyl]ethyl]carbamoyl}cyclohexane-1-carboxylate [Intermediate 6.5]

A mixture of 5-[(1S)-1-methoxyethyl]-1-(pyridin-2-yl)-1H-pyrazol-4-amine [free base of INT 1.27] (75 mg, 343 μmol), methyl (1r,4r)-4-{[(1S)-1-(4-bromophenyl)-2,2,2-trifluoroethyl](methyl)carbamoyl}cyclohexane-1-carboxylate [INT 5.4] (149 mg, 343 μmol), $Pd_2(dba)_3$ (31.3 mg, 34.3 μmol), xantphos (39.6 mg, 68.6 μmol) and $Cs_2CO_3$ (223 mg, 686 μmol) in dioxane (3 mL) was stirred at 100° C. for 3 h under $N_2$. The reaction was quenched by adding water (20 mL) and was extracted with EtOAc (20 mL×2). The combined organic layers were washed with brine (20 mL×2), dried over anhydrous $Na_2SO_4$ and concentrated under reduced pressure to give the crude product, which was purified by flash chromatography on silica gel (PE/EtOAc=1/0 to 511) to give methyl (1r,4r)-4-{methyl[(1S)-2,2,2-trifluoro-1-[4-({5-[(1S)-1-methoxyethyl]-1-(pyridin-2-yl)-1H-pyrazol-4-yl}amino)phenyl]ethyl]carbamoyl}cyclohexane-1-carboxylate [INT 6.5] (85.0 mg, 148 μmol, 43.3% yield) as a pale yellow oil. $^1H$ NMR (400 MHz, DMSO) δ=8.50 (d, J=4.0 Hz, 1H), 8.05-7.97 (m, 1H), 7.84-7.77 (m, 1H), 7.45-7.36 (m, 1H), 7.20 (s, 1H), 7.10 (d, J=8.0 Hz, 2H), 6.86 (d, J=8.0 Hz, 2H), 6.41 (q, J=8.0 Hz, 1H), 5.29 (q, J=8.0 Hz, 1H), 3.58 (s, 3H), 3.06 (s, 3H), 2.87 (s, 3H), 2.73-2.65 (m, 1H), 1.96-1.64 (m, 5H), 1.52 (d, J=6.0 Hz, 3H), 1.48-1.37 (m, 4H).

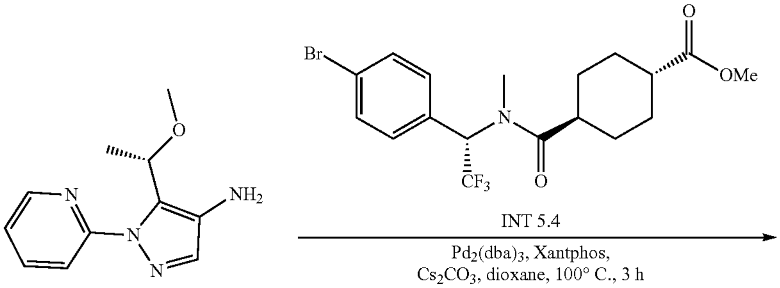

INT 1.27

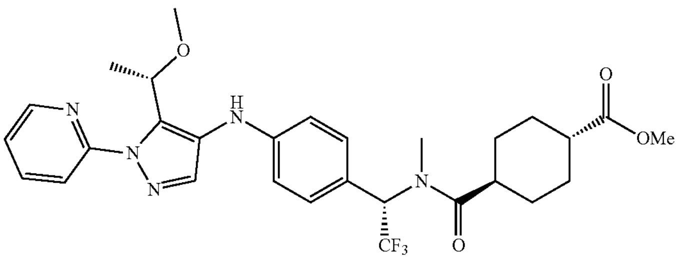

INT 6.5

Synthesis of methyl (1r,4r)-4-{methyl[(1S)-2,2,2-trifluoro-1-[4-({5-[(1S)-1-methoxyethyl]-1-phenyl-1H-pyrazol-4-yl}amino)phenyl]ethyl]carbamoyl}cyclohexane-1-carboxylate [Intermediate 6.6]

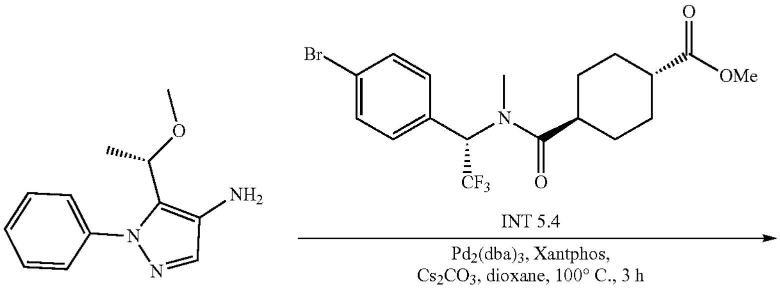

INT 1.26

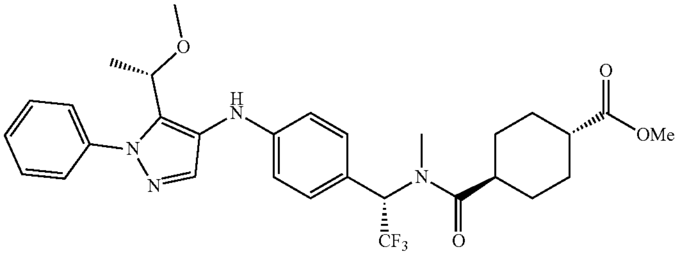

INT 6.6

A mixture of 5-[(1S)-1-methoxyethyl]-1-phenyl-1H-pyrazol-4-amine [free base of INT 1.26] (100 mg, 460 μmol), methyl (1r,4r)-4-{[(S)-1-(4-bromophenyl)-2,2,2-trifluoroethyl](methyl)carbamoyl}cyclohexane-1-carboxylate [INT 5.4] (200 mg, 460 μmol), xantphos (26.6 mg, 46.0 μmol), $Pd_2(dba)_3$ (42.1 mg, 46.0 μmol) and $Cs_2CO_3$ (449 mg, 1.38 mmol) in dioxane (1 mL) was stirred at 100° C. for 3 hr under $N_2$ atmosphere. Brine (20 mL) was added and the mixture was extracted with EtOAc (50 mL×2). The combined organic layers were washed with brine (20 mL×2), dried over anhydrous $Na_2SO_4$, filtered and concentrated under reduced pressure to give the crude product, which was purified by flash chromatography on silica gel (0-20% EtOAc in Petroleum ether) to give methyl (1r,4r)-4-{methyl[(1S)-2,2,2-trifluoro-1-[4-({5-[(1S)-1-methoxyethyl]-1-phenyl-1H-pyrazol-4-yl}amino)phenyl]ethyl]carbamoyl}cyclohexane-1-carboxylate [INT 6.6] (230 mg, 401 μmol, 87.4% yield) as a white solid. m/z: [M+H]+ Calcd for C30H36F3N4O4 573.3. Found 573.3.

Synthesis of methyl (1r,4r)-4-{methyl[(1S)-2,2,2-trifluoro-1-[4-({5-[(1S)-1-methoxyethyl]-1-(pyridin-4-yl)-1H-pyrazol-4-yl}amino)phenyl]ethyl]carbamoyl}cyclohexane-1-carboxylate [Intermediate 6.7]

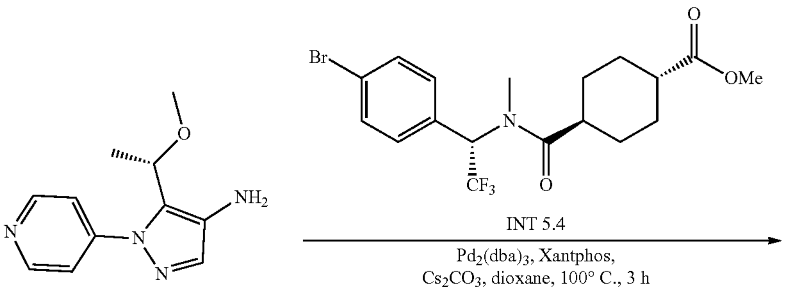

INT 1.28

-continued

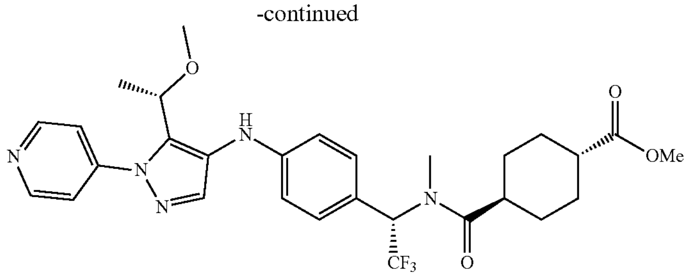

INT 6.7

A mixture of 5-[(1S)-1-methoxyethyl]-1-(pyridin-4-yl)-1H-pyrazol-4-amine [INT 1.28] (100 mg, 458 μmol), methyl (1r,4r)-4-{[(1S)-1-(4-bromophenyl)-2,2,2-trifluoroethyl](methyl)carbamoyl}cyclohexane-1-carboxylate [INT 5.4] (199 mg, 458 μmol), $Pd_2(dba)_3$ (41.9 mg, 45.8 μmol), xantphos (53.0 mg, 91.6 μmol) and $Cs_2CO_3$ (298 mg, 916 μmol) in dioxane (3 mL) was stirred at 100° C. for 3 h under N2. The reaction was quenched by adding water (20 mL) and was extracted with EtOAc (20 mL×2). The combined organic layers were washed with brine (20 mL×2), dried over anhydrous $Na_2SO_4$ and concentrated under reduced pressure to give the crude product, which was purified by flash chromatography on silica gel (PE/EtOAc=1/0 to 1/1) to give methyl (1r,4r)-4-{methyl[(1S)-2,2,2-trifluoro-1-[4-({5-[(1S)-1-methoxyethyl]-1-(pyridin-4-yl)-1H-pyrazol-4-yl}amino)phenyl]ethyl]carbamoyl}cyclohexane-1-carboxylate [INT 6.7] (230 mg, 400 μmol, 87.7% yield) as a pale yellow oil. m/z: [M+H]+ Calcd for C29H35F3N5O4 574.3. Found 574.3. $^1$H NMR (400 MHz, DMSO) δ=8.71 (d, J=8.0 Hz, 2H), 7.85 (s, 1H), 7.78-7.73 (m, 2H), 7.55 (s, 1H), 7.11 (d, J=8.0 Hz, 2H), 6.78 (d, J=8.0 Hz, 2H), 6.41 (q, J=8.0 Hz, 1H), 4.65 (q, J=8.0 Hz, 1H), 3.59 (s, 3H), 3.17 (s, 3H), 2.86 (s, 2.5H), 2.74-2.67 (m, 1H), 2.62 (s, 0.5H), 2.33-2.29 (m, 1H), 1.96-1.87 (m, 2H), 1.83-1.69 (m, 2H), 1.47-1.36 (m, 4H), 1.33 (d, J=4.0 Hz, 3H).

Synthesis of methyl (1S,4r)-4-(methyl((S)-2,2,2-trifluoro-1-(4-((5-((S)-1-methoxyethyl)-1-(pyridin-3-yl)-1H-pyrazol-4-yl)amino)phenyl)ethyl)carbamoyl)cyclohexane-1-carboxylate [Intermediate 6.8]

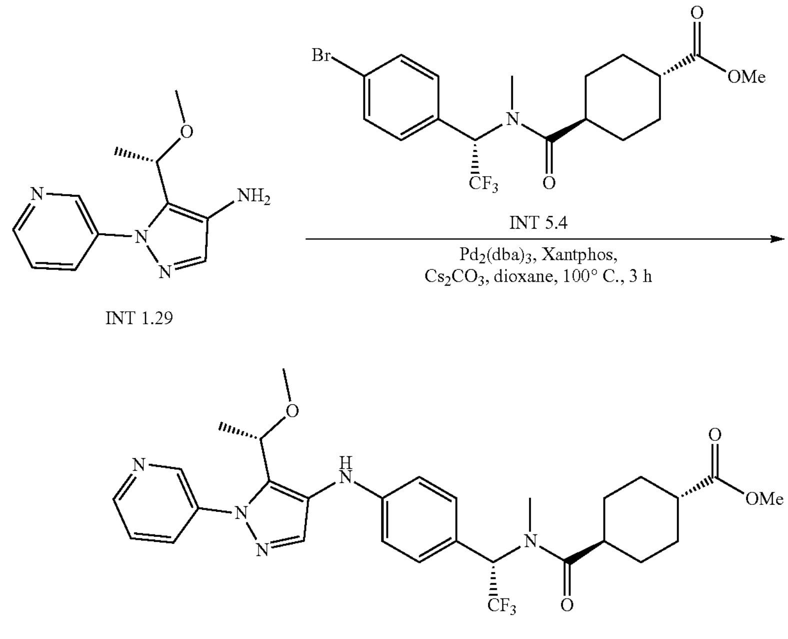

INT 6.8

A mixture of 5-[(1S)-1-methoxyethyl]-1-(pyridin-3-yl)-1H-pyrazol-4-amine [free base of INT 1.29] (20 mg, 91.6 μmol), methyl (1r,4r)-4-{[(1S)-1-(4-bromophenyl)-2,2,2-trifluoroethyl](methyl)carbamoyl}cyclohexane-1-carboxylate [INT 5.4] (39.9 mg, 91.6 μmol), xantphos (5.30 mg, 9.16 μmol), $Pd_2(dba)_3$ (8.38 mg, 9.16 μmol) and $Cs_2CO_3$ (89.2 mg, 274 μmol) in dioxane (1 mL) was stirred at 100° C. for 3 hr under $N_2$ atmosphere. The mixture was concentrated under reduced pressure to afford methyl (1S,4r)-4-(methyl((S)-2,2,2-trifluoro-1-(4-((5-((S)-1-methoxyethyl)-1-(pyridin-3-yl)-1H-pyrazol-4-yl)amino)phenyl)ethyl)carbamoyl)cyclohexane-1-carboxylate [INT 6.8] (50.0 mg, 87.1 μmol, 95.2% yield). m/z: [M+H]+ Calcd for C29H35F3N5O4 574.3. Found 574.2.

Synthesis of methyl (1S,4r)-4-(methyl((S)-2,2,2-trifluoro-1-(4-((1-(pyridazin-3-yl)-5-(trifluoromethyl)-1H-pyrazol-4-yl)amino)phenyl)ethyl)carbamoyl)cyclohexane-1-carboxylate [Intermediate 6.9]

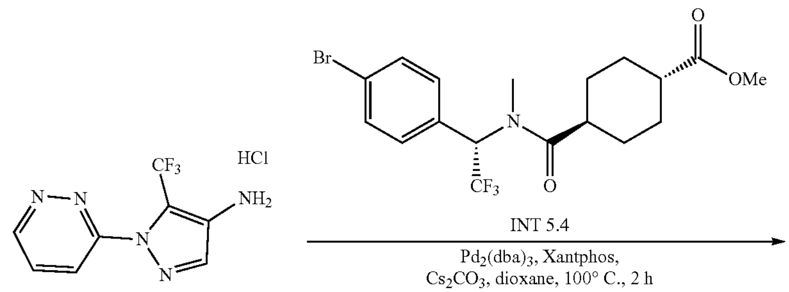

INT 5.4

INT 1.21

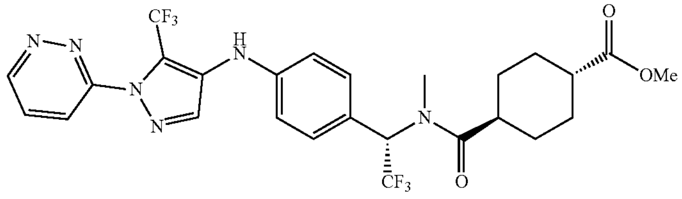

INT 6.9

A suspension of 1-(pyridazin-3-yl)-5-(trifluoromethyl)-1H-pyrazol-4-amine hydrochloride [INT 1.21] (500 mg, 1.88 mmol), methyl (1r,4r)-4-{[(1S)-1-(4-bromophenyl)-2,2,2-trifluoroethyl](methyl)carbamoyl}cyclohexane-1-carboxylate [INT 5.4] (820 mg, 1.88 mmol), $Cs_2CO_3$ (1.83 g, 5.64 mmol), $Pd_2(dba)_3$ (86.0 mg, 94.0 μmol) and xantphos (108 mg, 188 μmol) in dioxane (10 mL) was stirred at 100° C. for 2 h under $N_2$. The reaction mixture was concentrated to provide methyl (1S,4r)-4-(methyl((S)-2,2,2-trifluoro-1-(4-((1-(pyridazin-3-yl)-5-(trifluoromethyl)-1H-pyrazol-4-yl)amino)phenyl)ethyl)carbamoyl)cyclohexane-1-carboxylate [INT 6.9]. m/z: [M+H]+ Calcd for C26H27F6N6O3, 585.2. Found 585.1.

Synthesis of methyl (1r,4r)-4-{[(1S)-1-(4-{[1-(3-cyanophenyl)-5-[(1S)-1-methoxyethyl]-1H-pyrazol-4-yl]amino}phenyl)-2,2,2-trifluoroethyl](methyl)carbamoyl}cyclohexane-1-carboxylate [Intermediate 6.10]

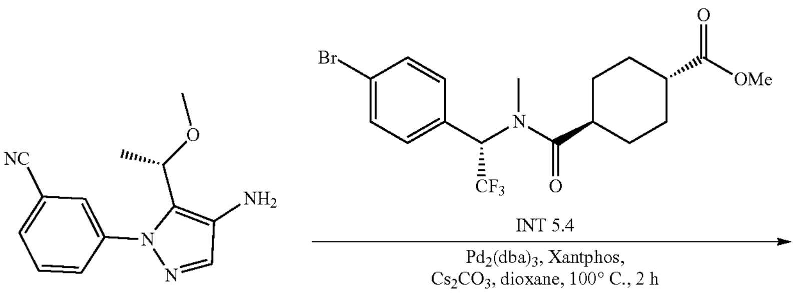

INT 5.4

INT 1.25

-continued

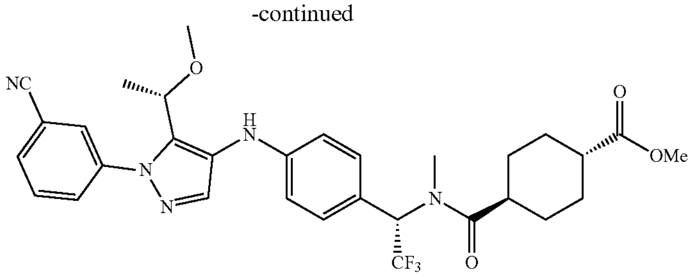

INT 6.10

To a mixture of 3-{4-amino-5-[(1S)-1-methoxyethyl]-1H-pyrazol-1-yl}benzonitrile [INT 1.25] (160 mg, 660 μmol) in dioxane (5 mL) was added methyl (1r,4r)-4-{[(1S)-1-(4-bromophenyl)-2,2,2-trifluoroethyl](methyl) carbamoyl}cyclohexane-1-carboxylate [INT 5.4](316 mg, 726 μmol), xantphos (114 mg, 198 μmol), $Cs_2CO_3$ (645 mg, 1.98 mmol) and $Pd_2(dba)_3$ (60.4 mg, 66.0 μmol). The reaction was stirred at 100° C. for 2 h under $N_2$. The mixture was concentrated under reduced pressure to give the crude product, which was purified by flash chromatography on silica gel (EtOAc/PE=0/1 to 1/1) to give methyl (1r,4r)-4-{[(1S)-1-(4-{[1-(3-cyanophenyl)-5-[(1S)-1-methoxyethyl]-1H-pyrazol-4-yl]amino}phenyl)-2,2,2-trifluoroethyl](methyl)carbamoyl}cyclohexane-1-carboxylate [INT 6.10] (250 mg, 418 μmol, 63.4% yield) as a yellow solid. m/z: [M+H]+ Calcd for C31H35F3N5O4 598.3. Found 598.1.

Synthesis of (1r,4r)-4-cyano-N-methyl-N-[(1S)-2,2,2-trifluoro-1-(4-{[1-phenyl-5-(trifluoromethyl)-1H-pyrazol-4-yl]amino}phenyl)ethyl]cyclohexane-1-carboxamide [Intermediate 6.11]

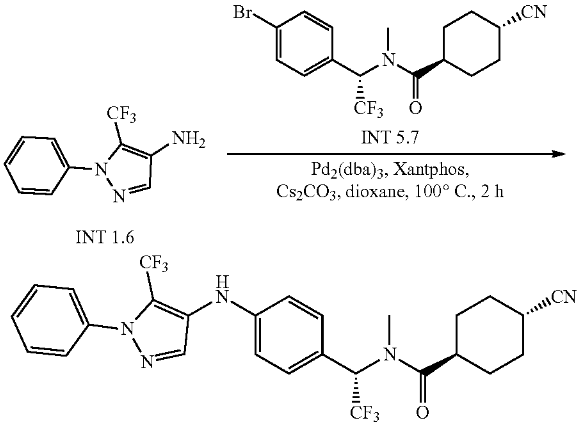

INT 6.11

To a mixture of 1-phenyl-5-(trifluoromethyl)-1H-pyrazol-4-amine [free base of INT 1.6] (100 mg, 440 μmol) in dioxane (5 mL) was added (1r,4r)-N-[(1S)-1-(4-bromophenyl)-2,2,2-trifluoroethyl]-4-cyano-N-methylcyclohexane-1-carboxamide [INT 5.6] (195 mg, 484 μmol), xantphos (76.3 mg, 132 μmol), $Cs_2CO_3$ (430 mg, 1.32 mmol) and $Pd_2(dba)_3$ (40.2 mg, 44.0 μmol). The reaction was stirred at 100° C. for 2 h under $N_2$. The reaction mixture was concentrated under reduced pressure to give the crude product, which was purified by flash chromatography on silica gel (EtOAc/PE=0/1 to 1/3) to give (1r,4r)-4-cyano-N-methyl-N-[(1S)-2,2,2-trifluoro-1-(4-{[1-phenyl-5-(trifluoromethyl)-1H-pyrazol-4-yl]amino}phenyl)ethyl]cyclohexane-1-carboxamide [INT 6.11] (100 mg, 181 μmol, 41.4% yield) as a yellow solid. m/z: [M+H]+ Calcd for C27H26F6N5O, 550.2. Found 550.4.

Synthesis of benzyl 3-{methyl[(1S)-2,2,2-trifluoro-1-(4-{[1-(pyridin-2-yl)-5-(trifluoromethyl)-1H-pyrazol-4-yl]amino}phenyl)ethyl] carbamoyl}cyclobutane-1-carboxylate [Intermediate 6.12]

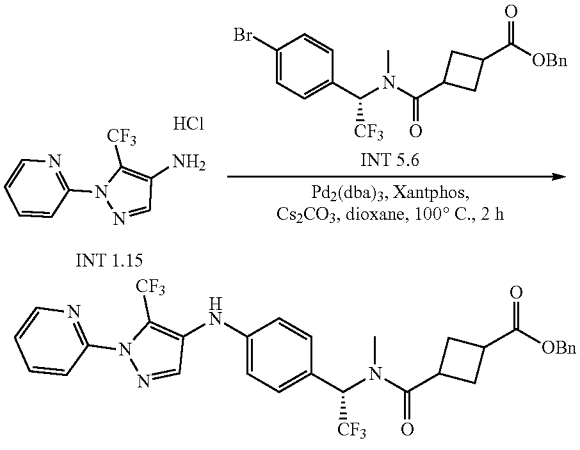

INT 6.12

A mixture of benzyl 3-{[(1S)-1-(4-bromophenyl)-2,2,2-trifluoroethyl](methyl)carbamoyl}cyclobutane-1-carboxylate [INT 5.6] (300 mg, 619 μmol), 1-(pyridin-2-yl)-5-(trifluoromethyl)-1H-pyrazol-4-amine hydrochloride [HCl salt of INT 1.15] (163 mg, 619 μmol), $Pd_2(dba)_3$ (56.6 mg, 61.9 μmol), xantphos (71.1 mg, 123 μmol) and $Cs_2CO_3$ (602 mg, 1.85 mmol) in dioxane (10 mL) was stirred at 100° C. for 2 hours under $N_2$ atmosphere. The reaction was quenched by adding water (40 mL) and was extracted with EtOAc (2×80 mL). The combined organic layers were washed with brine (2×50 mL), dried over anhydrous $Na_2SO_4$ and concentrated under reduced pressure to give benzyl 3-{methyl[(1S)-2,2,2-trifluoro-1-(4-{[1-(pyridin-2-yl)-5-(trifluoromethyl)-1H-pyrazol-4-yl]amino}phenyl)ethyl] carbamoyl}cyclobutane-1-carboxylate [INT 6.12] (390 mg, 617 μmol) as a black oil. m/z: [M+H]+ Calcd for C31H28F6N5O3, 632.2. Found 632.3.

Synthesis of benzyl 3-{methyl[(1S)-2,2,2-trifluoro-1-(4-{[1-phenyl-5-(trifluoromethyl)-1H-pyrazol-4-yl]amino}phenyl)ethyl]carbamoyl}cyclobutane-1-carboxylate [Intermediate 6.13]

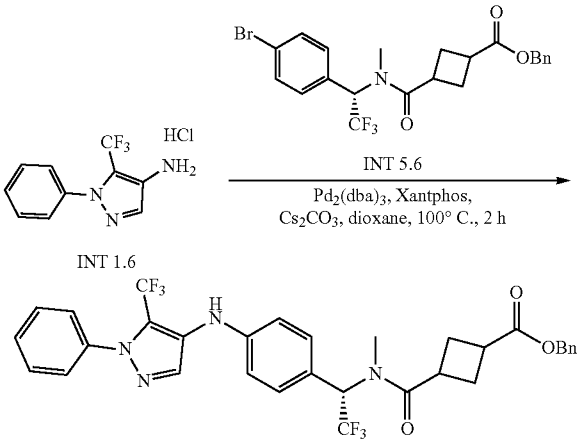

INT 6.13

A mixture of benzyl 3-{[(1S)-1-(4-bromophenyl)-2,2,2-trifluoroethyl](methyl)carbamoyl}cyclobutane-1-carboxylate [INT 5.6] (650 mg, 805 μmol), 1-phenyl-5-(trifluoromethyl)-1H-pyrazol-4-amine hydrochloride [INT 1.6] (150 mg, 568 μmol), $Pd_2(dba)_3$ (52.0 mg, 56.8 μmol), xantphos (65.3 mg, 113 μmol) and $Cs_2CO_3$ (553 mg, 1.70 mmol) in dioxane (10 mL) was stirred at 100° C. for 2 hours under $N_2$ atmosphere. The reaction was quenched by adding water (50 mL) and was extracted with EtOAc (2×80 mL). The combined organic layers were washed with brine (60 mL), dried over anhydrous $Na_2SO_4$ and concentrated under reduced pressure to give benzyl 3-{methyl[(1S)-2,2,2-trifluoro-1-(4-{[1-phenyl-5-(trifluoromethyl)-1H-pyrazol-4-yl]amino}phenyl)ethyl]carbamoyl}cyclobutane-1-carboxylate [INT 6.13] (330 mg, 523 μmol, 92.1% yield) as a brown oil. m/z: [M+H]+ Calcd for C32H29F6N4O3, 631.2. Found 631.2.

Exemplary Compounds of Formula (b)

The following compounds in Table 2 were synthesized according to Schemes 1-3 as described above with the identified intermediates.

TABLE 2

| Cmpd No. | Structure | Scheme | Intermed. | LCMS | $^1$H NMR |
|---|---|---|---|---|---|
| 1.1 | 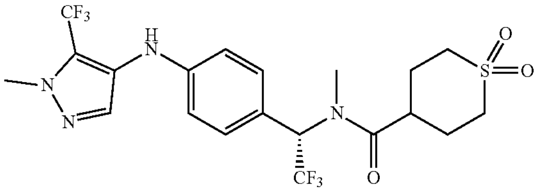 | 1 | INT 1.1 INT 2.1 INT 3.1 INT 4.1 INT 5.1 | [M + H]+ C20H23F6N4O3S 513.1 513.2 | (400 MHz, $CD_3OD$) δ = 7.55 (s, 1H), 7.19 (d, J = 8.4 Hz, 2H), 6.82 (d, J = 8.4 Hz, 2H), 6.57-5.95 (m, 1H), 4.00 (s, 3H), 3.30-3.09 (m, 5H), 2.98 (s, 3H), 2.39-2.10 (m, 4H) |
| 1.2 | 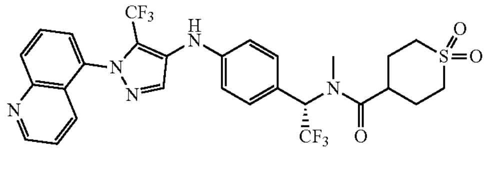 | 1 | INT 1.2 INT 2.1 INT 3.1 INT 4.1 INT 5.1 | [M + H]+ C28H26F6N5O3S 626.2 626.3 | (400 MHz, $CDCl_3$) δ = 9.01 (dd, J = 1.6, 4.0 Hz, 1H), 8.33 (d, J = 8.8 Hz, 1H), 7.95 (s, 1H), 7.83 (t, J = 8.0 Hz, 1H), 7.67 (br d, J = 6.8 Hz, 2H), 7.47 (dd, J = 4.0, 8.4 Hz, 1H), 7.31 (br d, J = 8.0 Hz, 2H), 7.02 (d, J = 8.8 Hz, 2H), 6.60 (q, J = 8.8 Hz, 1H), 5.64 (s, 1H), 3.47 (br d, J = 10.9 Hz, 1H), 3.35 (br dd, J = 2.9, 8.1 Hz, 1H), 3.06-2.98 (m, 2H), 2.95 (s, 4H), 2.51-2.32 (m, 3H), 2.31-2.21 (m, 1H) |

TABLE 2-continued

| Cmpd No. | Structure | Scheme | Inter-med. | LCMS | $^1$H NMR |
|---|---|---|---|---|---|
| 1.3 | 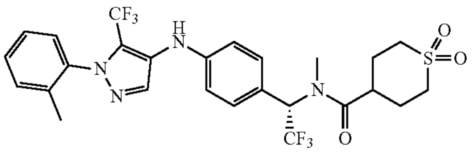 | 1 | INT 1.3<br>INT 2.1<br>INT 3.1<br>INT 4.1<br>INT 5.1 | [M + H]+<br>C26H27F6N4O3S<br>589.2<br>589.3 | (400 MHz, DMSO-d6) δ = 7.99-7.92 (m, 2H), 7.53-7.47 (m, 1H), 7.47-7.43 (m, 1H), 7.43-7.36 (m, 2H), 7.29-7.16 (m, 2H), 6.94-6.86 (m, 2H), 6.48-6.05 (m, 1H), 3.33-3.06 (m, 6H), 2.93-2.64 (m, 3H), 2.12-2.02 (m, 3H), 2.01 (s, 3H) |
| 1.4 | 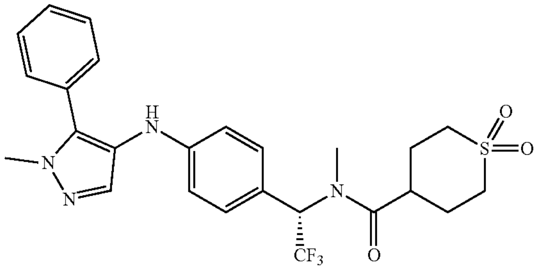 | 1 | INT 1.4<br>INT 2.1<br>INT 3.1<br>INT 4.1<br>INT 5.1 | [M + H]+<br>C25H28F3N4O3S<br>521.2<br>521.2 | (400 MHz, DMSO-d6) δ = 7.55-7.33 (m, 7H), 7.02 (d, J = 8.4 Hz, 2H), 6.61 (d, J = 8.8 Hz, 2H), 6.39-5.92 (m, 1H), 3.79 (s, 3H), 3.28-3.06 (m, 5H), 2.86-2.57 (m, 3H), 2.10-1.91 (m, 4H) |
| 1.5 | 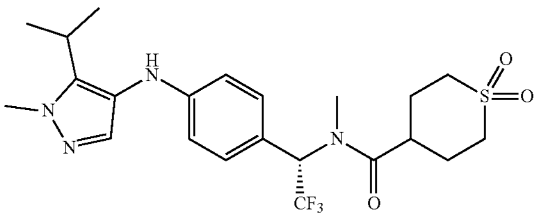 | 1 | INT 1.5<br>INT 2.1<br>INT 3.1<br>INT 4.1<br>INT 5.1 | [M + H]+<br>C22H30F3N4O3S<br>487.2<br>487.1 | (400 MHz, DMSO-d6) δ = 7.22-7.19 (m, 1H), 7.19-7.15 (m, 1H), 7.14-7.02 (m, 2H), 6.62-6.53 (m, 2H), 6.42-5.97 (m, 1H), 3.77 (s, 3H), 3.25-3.08 (m, 5H), 3.07-3.02 (m, 1H), 2.87 (s, 3H), 2.14-1.91 (m, 4H), 1.19 (d, J = 7.2 Hz, 6H) |
| 1.6 | 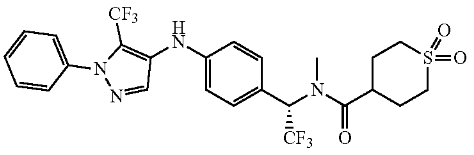 | 1 | INT 1.6<br>INT 2.1<br>INT 3.1<br>INT 4.1<br>INT 5.1 | [M + H]+<br>C25H25F6N4O3S<br>575.1<br>575.1 | (400 MHz, $CDCl_3$) δ = 7.80 (s, 1H), 7.56-7.46 (m, 5H), 7.28 (br s, 1H), 7.26 (br s, 1H), 6.95 (d, J = 8.8 Hz, 2H), 6.58 (q, J = 9.2 Hz, 1H), 5.53 (s, 1H), 3.47 (br d, J = 11.2 Hz, 1H), 3.40-3.32 (m, 1H), 3.07-2.94 (m, 3H), 2.93 (s, 3H), 2.51-2.32 (m, 3H), 2.32-2.21 (m, 1H) |

TABLE 2-continued

| Cmpd No. | Structure | Scheme | Inter-med. | LCMS | $^1$H NMR |
|---|---|---|---|---|---|
| 1.7 | 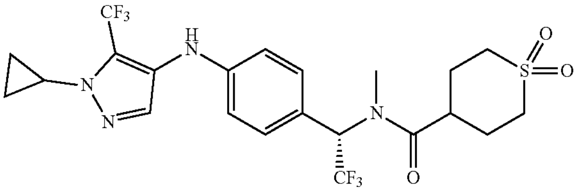 | 1 | INT 1.7<br>INT 2.1<br>INT 3.1<br>INT 4.1<br>INT 5.1 | [M + H]+<br>C22H25F6N4O3S<br>539.1<br>539.3 | (400 MHz, $CDCl_3$) δ = 7.50 (s, 1H), 7.22 (d, J = 8.4 Hz, 2H), 6.84 (d, J = 8.8 Hz, 2H), 6.55 (q, J = 8.8 Hz, 1H), 5.40 (s, 1H), 3.62 (tt, J = 3.6, 7.2 Hz, 1H), 3.46 (br d, J = 10.8 Hz, 1H), 3.40-3.30 (m, 1H), 3.04-2.92 (m, 3H), 2.91 (s, 3H), 2.48-2.33 (m, 3H), 2.30-2.19 (m, 1H), 1.36-1.27 (m, 2H), 1.14-1.06 (m, 2H) |
| 1.8 | 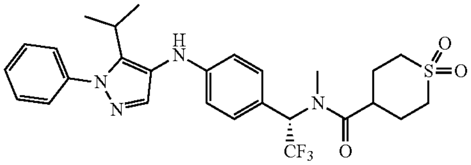 | 1 | INT 1.8<br>INT 2.1<br>INT 3.1<br>INT 4.1<br>INT 5.1 | [M + H]+<br>C27H32F3N4O3S<br>549.2<br>549.2 | (400 MHz, $CDCl_3$) δ = 7.56-7.40 (m, 6H), 7.17 (d, J = 8.4 Hz, 2H), 6.70 (d, J = 8.8 Hz, 2H), 6.54 (q, J = 9.2 Hz, 1H), 4.96 (s, 1H), 3.53-3.43 (m, 1H), 3.42-3.32 (m, 1H), 3.13-3.04 (m, 1H), 3.04-2.89 (m, 6H), 2.49-2.31 (m, 3H), 2.30-2.19 (m, 1H), 1.25 (d, J = 7.2 Hz, 6H) |
| 1.9 | 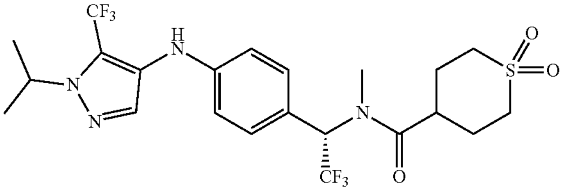 | 1 | INT 1.9<br>INT 2.1<br>INT 3.1<br>INT 4.1<br>INT 5.1 | [M + H]+<br>C22H27F6N4O3S<br>541.2<br>541.2 | (400 MHz, DMSO-d6) δ = 7.78-7.66 (m, 2H), 7.25-7.08 (m, 2H), 6.82-6.73 (m, 2H), 6.47-6.03 (m, 1H), 4.59 (td, J = 6.4, 12.8 Hz, 1H), 3.30-3.03 (m, 5H), 2.91-2.61 (m, 3H), 2.13-1.92 (m, 4H), 1.45 (d, J = 6.4 Hz, 6H) |

TABLE 2-continued

| Cmpd No. | Structure | Scheme | Inter-med. | LCMS | $^1$H NMR |
|---|---|---|---|---|---|
| 1.10 | 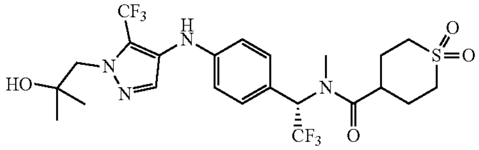 | 1 | INT 1.10<br>INT 2.1<br>INT 3.1<br>INT 4.1<br>INT 5.1 | [M + H]+<br>C23H29F6N4O4S<br>571.2<br>571.2 | (400 MHz, DMSO-d6) δ = 7.81-7.60 (m, 2H), 7.25-7.07 (m, 2H), 6.83-6.69 (m, 2H), 6.46-5.97 (m, 1H), 4.75 (s, 1H), 4.11 (s, 2H), 3.28-3.03 (m, 5H), 2.94-2.59 (m, 3H), 2.16-1.89 (m, 4H), 1.13 (s, 6H) |
| 1.11 | 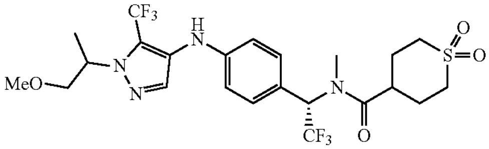 | 1 | INT 1.11<br>INT 2.1<br>INT 3.1<br>INT 4.1<br>INT 5.1 | [M + H]+<br>C23H29F6N4O4S<br>571.2<br>571.1 | (400 MHz, $CDCl_3$) δ = 7.63 (s, 1H), 7.21 (d, J = 8.4 Hz, 2H), 6.84 (d, J = 8.8 Hz, 2H), 6.55 (q, J = 9.2 Hz, 1H), 5.38 (br s, 1H), 4.75-4.60 (m, 1H), 3.90 (dd, J = 8.4, 9.6 Hz, 1H), 3.62 (dd, J = 5.2, 10.0 Hz, 1H), 3.53-3.43 (m, 1H), 3.39-3.32 (m, 4H), 3.04-2.88 (m, 6H), 2.48-2.30 (m, 3H), 2.30-2.19 (m, 1H), 1.50 (d, J = 6.8 Hz, 3H) |
| 1.12 | 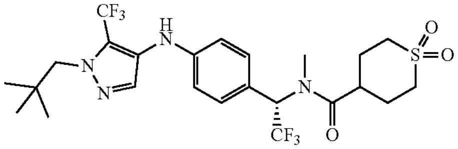 | 1 | INT 1.12<br>INT 2.1<br>INT 3.1<br>INT 4.1<br>INT 5.1 | [M + H]+<br>C24H31F6N4O3S<br>569.2<br>569.2 | 400 MHz, DMSO) δ = 7.78-7.69 (m, 2H), 7.24-7.10 (m, 2H), 6.80-6.71 (m, 2H), 6.38 (q, J = 8.0 Hz, 1H), 4.00 (s, 2H), 3.26-3.05 (m, 5H), 2.88 (s, 2.5H), 2.62 (s, 0.5H), 2.13-1.92 (m, 4H), 0.96 (s, 9H) |

TABLE 2-continued

| Cmpd No. | Structure | Scheme | Inter-med. | LCMS | $^1$H NMR |
|---|---|---|---|---|---|
| 1.13 | 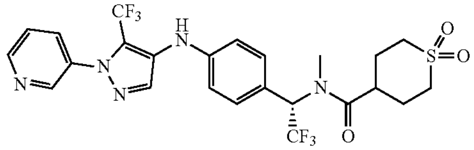 | 1 | INT 1.13<br>INT 2.1<br>INT 3.1<br>INT 4.1<br>INT 5.1 | [M + H]+<br>C24H24F6N5O3S<br>576.1<br>576.2 | (400 MHz, $CDCl_3$) δ = 8.79 (d, J = 2.0 Hz, 1H), 8.74 (d, J = 4.0 Hz, 1H), 7.86 (s, 1H), 7.83 (br d, J = 8.0 Hz, 1H), 7.48 (dd, J = 4.8, 8.0 Hz, 1H), 7.29 (s, 1H), 6.97 (d, J = 8.4 Hz, 2H), 6.66-6.19 (m, 1H), 5.62 (s, 1H), 3.53-3.43 (m, 1H), 3.40-3.31 (m, 1H), 3.06-2.97 (m, 2H), 2.96-2.91 (m, 4H), 2.50-2.31 (m, 3H), 2.30-2.20 (m, 1H) |
| 1.14 | 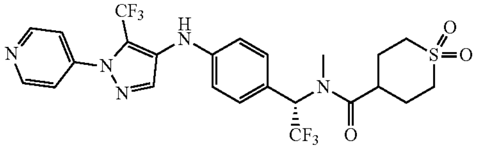 | 1 | INT 1.14<br>INT 2.1<br>INT 3.1<br>INT 4.1<br>INT 5.1 | [M + H]+<br>C24H24F6N5O3S<br>576.1<br>576.2 | (400 MHz, $CDCl_3$) δ = 8.82-8.74 (m, 2H), 8.21 (s, 1H), 8.11 (s, 1H), 7.61 (d, J = 8.0 Hz, 2H), 7.20 (d, J = 8.0 Hz, 2H), 6.97 (d, J = 8.0 Hz, 2H), 6.27 (q, J = 8.0 Hz, 1H), 3.28-3.06 (m, 5H), 2.90 (s, 2.5H), 2.64 (s, 0.5H), 2.14-1.93 (m, 4H) |
| 1.15 | 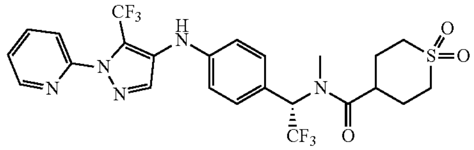 | 1 | INT 1.15<br>INT 2.1<br>INT 3.1<br>INT 4.1<br>INT 5.1 | [M + H]+<br>C24H24F6N5O3S<br>576.1<br>576.1 | (400 MHz, DMSO-d6) δ = 8.54 (td, J = 0.8, 4.8 Hz, 1H), 8.20-8.03 (m, 3H), 7.81 (d, J = 8.0 Hz, 1H), 7.54-7.48 (m, 1H), 7.30-7.19 (m, 2H), 7.04-6.90 (m, 2H), 6.43 (q, J = 9.2 Hz, 1H), 3.31-3.07 (m, 5H), 2.94-2.64 (m, 3H), 2.16-2.08 (m, 1H), 2.07-1.94 (m, 3H) |

TABLE 2-continued

| Cmpd No. | Structure | Scheme | Inter-med. | LCMS | $^1H$ NMR |
|---|---|---|---|---|---|
| 1.16 | 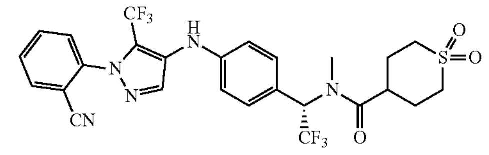 | 1 | INT 1.16<br>INT 2.1<br>INT 3.1<br>INT 4.1<br>INT 5.1 | [M + H]+<br>C26H24F6N5O3S<br>600.1<br>600.1 | (400 MHz, DMSO-d6) δ = 8.18-8.08 (m, 3H), 8.00-7.92 (m, 1H), 7.88-7.80 (m, 2H), 7.20 (br d, J = 8.4 Hz, 2H), 6.93 (d, J = 8.8 Hz, 2H), 6.50-6.00 (m, 1H), 3.27-3.10 (m, 5H), 2.90 (s, 3H), 2.11-1.97 (m, 4H) |
| 1.17 | 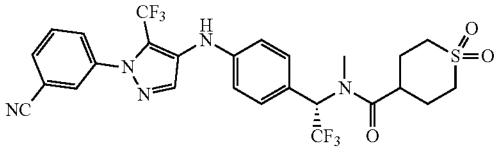 | 1 | INT 1.17<br>INT 2.1<br>INT 3.1<br>INT 4.1<br>INT 5.1 | [M + H]+<br>C26H24F6N5O3S<br>600.1<br>600.1 | (400 MHz, DMSO-d6) δ = 8.11 (d, J = 9.6 Hz, 2H), 8.07-8.00 (m, 2H), 7.92 (br d, J = 8.4 Hz, 1H), 7.84-7.76 (m, 1H), 7.30-7.14 (m, 2H), 7.02-6.89 (m, 2H), 6.49-6.05 (m, 1H), 3.31-3.06 (m, 5H), 2.95-2.60 (m, 3H), 2.16-1.92 (m, 4H) |
| 1.18 | 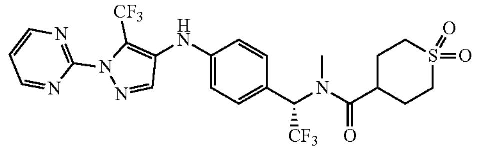 | 1 | INT 1.18<br>INT 2.1<br>INT 3.1<br>INT 4.1<br>INT 5.1 | [M + H]+<br>C23H23F6N6O3S<br>577.1<br>577.2 | (400 MHz, DMSO) δ = 8.94 (d, J = 4.0 Hz, 2H), 8.77 (s, 1H), 7.87 (s, 1H), 7.60 (t, J = 4.0 Hz, 1H), 7.18 (d, J = 8.0 Hz, 2H), 6.94 (d, J = 8.0 Hz, 2H), 6.26 (q, J = 8.0 Hz, 1H), 3.25-3.07 (m, 5H), 2.89 (s, 2.5H), 2.64 (s, 0.5H), 2.12-1.94 (m, 4H) |
| 1.19 | 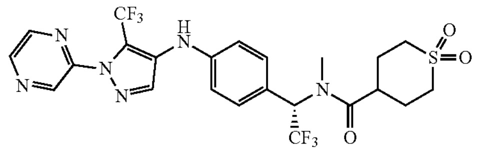 | 1 | INT 1.19<br>INT 2.1<br>INT 3.1<br>INT 4.1<br>INT 5.1 | [M + H]+<br>C23H23F6N6O3S<br>577.1<br>577.2 | (400 MHz, DMSO-d6) δ = 9.14 (d, J = 1.2 Hz, 1H), 8.75 (d, J = 2.8 Hz, 1H), 8.67-8.59 (m, 1H), 8.33-8.22 (m, 1H), 8.18 (s, 1H), 7.34-7.14 (m, 2H), 7.04-6.93 (m, 2H), 6.50-6.07 (m, 1H), 3.30-3.05 (m, 5H), 2.92-2.63 (m, 3H), 2.14-1.93 (m, 4H) |

TABLE 2-continued

| Cmpd No. | Structure | Scheme | Inter-med. | LCMS | $^1$H NMR |
|---|---|---|---|---|---|
| 1.20 | 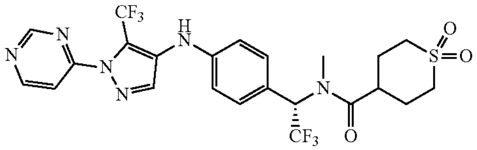 | 1 | INT 1.20<br>INT 2.1<br>INT 3.1<br>INT 4.1<br>INT 5.1 | [M + H]+<br>C23H23F6N6O3S<br>577.1<br>577.3 | (400 MHz, $CDCl_3$) δ = 9.09 (s, 1H), 8.82 (d, J = 5.6 Hz, 1H), 7.92 (s, 1H), 7.87 (dd, J = 1.2, 5.6 Hz, 1H), 7.30 (d, J = 8.4 Hz, 2H), 7.02 (d, J = 8.4 Hz, 2H), 6.59 (q, J = 8.8 Hz, 1H), 5.89 (s, 1H), 3.53-3.42 (m, 1H), 3.40-3.30 (m, 1H), 3.05-2.94 (m, 3H), 2.93 (s, 3H), 2.50-2.21 (m, 4H) |
| 1.21 | 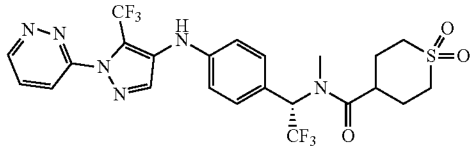 | 1 | INT 1.21<br>INT 2.1<br>INT 3.1<br>INT 4.1<br>INT 5.1 | [M + H]+<br>C23H23F6N6O3S<br>577.1<br>577.3 | (400 MHz, $CDCl_3$) δ = 9.23 (d, J = 4.8 Hz, 1H), 8.05 (d, J = 8.8 Hz, 1H), 7.96 (s, 1H), 7.70 (dd, J = 4.8, 8.8 Hz, 1H), 7.31 (br d, J = 8.4 Hz, 2H), 7.03 (d, J = 8.4 Hz, 2H), 6.60 (q, J = 8.8 Hz, 1H), 5.83 (br s, 1H), 3.58-3.30 (m, 2H), 3.08-2.91 (m, 6H), 2.51-2.24 (m, 4H) |
| 1.22 | 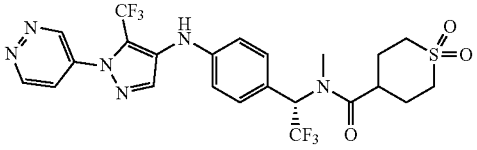 | 1 | INT 1.22<br>INT 2.1<br>INT 3.1<br>INT 4.1<br>INT 5.1 | [M + H]+<br>C23H23F6N6O3S<br>577.1<br>577.2 | (400 MHz, DMSO-d6) δ = 9.55 (d, J = 2.4 Hz, 1H), 9.47 (d, J = 5.6 Hz, 1H), 8.42-8.32 (m, 1H), 8.23 (s, 1H), 7.94-7.89 (m, 1H), 7.32-7.18 (m, 2H), 7.08-6.96 (m, 2H), 6.50-6.07 (m, 1H), 3.28-3.08 (m, 5H), 2.94-2.64 (m, 3H), 2.14-1.95 (m, 4H) |

TABLE 2-continued

| Cmpd No. | Structure | Scheme | Inter-med. | LCMS | $^1$H NMR |
|---|---|---|---|---|---|
| 1.23 | 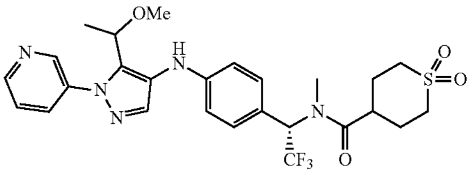 | 1 | INT 1.23<br>INT 2.1<br>INT 3.1<br>INT 4.1<br>INT 5.1 | [M + H]+<br>C26H31F3N5O4S<br>566.2<br>566.4 | (400 MHz, $CDCl_3$) δ = 8.79 (br s, 1H), 8.70 (br d, J = 4.0 Hz, 1H), 7.93 (br d, J = 7.6 Hz, 1H), 7.79 (s, 1H), 7.51 (dd, J = 4.8, 7.6 Hz, 1H), 7.22 (br d, J = 8.4 Hz, 2H), 6.86 (d, J = 8.4 Hz, 2H), 6.55 (q, J = 9.2 Hz, 1H), 5.67 (br s, 1H), 4.52 (q, J = 6.8 Hz, 1H), 3.54-3.43 (m, 1H), 3.40-3.30 (m, 1H), 3.26 (s, 3H), 3.06-2.88 (m, 6H), 2.50-2.30 (m, 3H), 2.25 (br s, 1H), 1.46 (d, J = 6.8 Hz, 3H) |
| 1.24 | 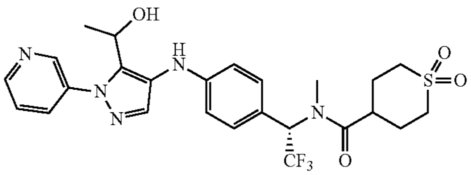 | 1 | INT 1.24<br>INT 2.1<br>INT 3.1<br>INT 4.1<br>INT 5.1 | [M + H]+<br>C25H29F3N5O4S<br>552.2<br>552.2 | (400 MHz, $CDCl_3$) δ = 8.79 (d, J = 2.4 Hz, 1H), 8.68 (dd, J = 1.2, 4.8 Hz, 1H), 7.96-7.89 (m, 1H), 7.72 (s, 1H), 7.48 (dd, J = 4.8, 8.0 Hz, 1H), 7.22 (br d, J = 8.4 Hz, 2H), 6.84 (d, J = 8.8 Hz, 2H), 6.55 (q, J = 9.2 Hz, 1H), 5.63 (d, J = 2.0 Hz, 1H), 5.03 (q, J = 6.4 Hz, 1H), 3.56-3.29 (m, 2H), 3.04-2.96 (m, 2H), 2.92 (s, 3H), 2.58-2.18 (m, 5H), 1.54 (dd, J = 1.2, 6.8 Hz, 3H) |

TABLE 2-continued

| Cmpd No. | Structure | Scheme | Inter-med. | LCMS | $^1$H NMR |
|---|---|---|---|---|---|
| 1.25 | 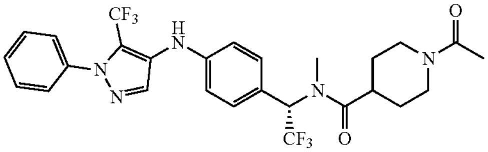 | 1 | INT 1.6<br>INT 2.1<br>INT 3.1<br>INT 4.2<br>INT 5.2 | [M + H]+<br>C27H28F6N5O2<br>568.2<br>568.2 | (400 MHz, $CD_3OD$) δ = 7.84 (s, 1H), 7.62-7.55 (m, 3H), 7.54-7.50 (m, 2H), 7.33-7.21 (m, 2H), 7.01-6.92 (m, 2H), 6.51 (q, J = 9.2 Hz, 1H), 4.61 (br s, 1H), 4.56 (br d, J = 12.8 Hz, 1H), 4.00 (br d, J = 10.8 Hz, 1H), 3.25-2.97 (m, 4H), 2.82-2.73 (m, 1H), 2.13 (d, J = 1.6 Hz, 3H), 1.94-1.60 (m, 4H) |
| 1.26 | 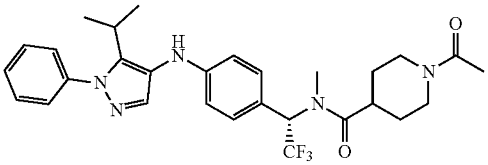 | 1 | INT 1.8<br>INT 2.1<br>INT 3.1<br>INT 4.2<br>INT 5.2 | [M + H]+<br>C29H35F3N5O2<br>542.3<br>542.2 | (400 MHz, $CDCl_3$) δ = 7.57-7.39 (m, 6H), 7.22-7.12 (m, 2H), 6.69 (d, J = 8.4 Hz, 2H), 6.55 (q, J = 9.2 Hz, 1H), 5.13-4.86 (m, 1H), 4.66-4.56 (m, 1H), 3.91 (br d, J = 13.6 Hz, 1H), 3.22-3.01 (m, 2H), 2.92 (d, J = 2.0 Hz, 3H), 2.85-2.63 (m, 2H), 2.12 (s, 3H), 1.91-1.69 (m, 4H), 1.25 (s, 3H), 1.24 (s, 3H) |
| 1.27 | 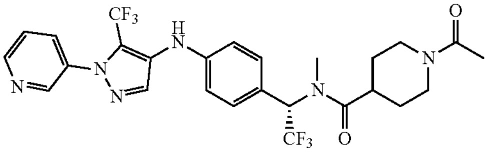 | 1 | INT 1.13<br>INT 2.1<br>INT 3.1<br>INT 4.2<br>INT 5.2 | [M + H]+<br>C26H27F6N6O2<br>569.2<br>569.1 | (400 MHz, DMSO-d6) δ = 8.86-8.72 (m, 2H), 8.15-8.00 (m, 3H), 7.65 (dd, J = 4.8, 8.0 Hz, 1H), 7.28-7.13 (m, 2H), 7.03-6.90 (m, 2H), 6.51-6.17 (m, 1H), 4.37 (br d, J = 12.8 Hz, 1H), 3.83 (br d, J = 10.4 Hz, 1H), 3.18-2.95 (m, 2H), 2.91 (s, 2H), 2.69-2.61 (m, 1H), 2.59 (br s, 1H), 2.00 (s, 3H), 1.81-1.62 (m, 2H), 1.60-1.29 (m, 2H) |

TABLE 2-continued
| Cmpd No. | Structure | Scheme | Inter-med. | LCMS | $^1$H NMR |
|---|---|---|---|---|---|
| 1.28 | 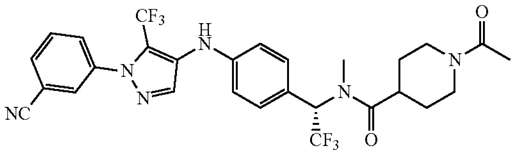 | 1 | INT 1.17 INT 2.1 INT 3.1 INT 4.2 INT 5.2 | [M + H]+ C28H27F6N6O2 593.2 593.1 | (400 MHz, DMSO-d6) δ = 8.11 (br d, J = 13.6 Hz, 2H), 8.07-8.00 (m, 2H), 7.92 (br d, J = 8.4 Hz, 1H), 7.85-7.75 (m, 1H), 7.30-7.13 (m, 2H), 7.03-6.88 (m, 2H), 6.53-6.14 (m, 1H), 4.37 (br d, J = 12.4 Hz, 1H), 3.83 (br d, J = 11.6 Hz, 1H), 3.17-2.94 (m, 2H), 2.94-2.60 (m, 4H), 2.00 (s, 3H), 1.83-1.60 (m, 2H), 1.59-1.29 (m, 2H) |
| 1.29 | 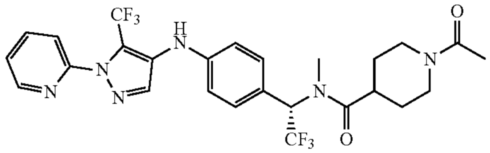 | 1 | INT 1.15 INT 2.1 INT 3.1 INT 4.2 INT 5.2 | [M + H]+ C26H27F6N6O2 569.2 569.2 | (400 MHz, DMSO-d6) δ = 8.56-8.51 (m, 1H), 8.17-8.12 (m, 1H), 8.11-8.05 (m, 2H), 7.81 (d, J = 8.0 Hz, 1H), 7.51 (ddd, J = 0.8, 4.8, 7.2 Hz, 1H), 7.33-7.17 (m, 2H), 7.02-6.92 (m, 2H), 6.52-6.16 (m, 1H), 4.38 (br d, J = 13.2 Hz, 1H), 3.84 (br d, J = 11.6 Hz, 1H), 3.20-3.07 (m, 1H), 3.06-2.96 (m, 1H), 2.93-2.59 (m, 4H), 2.00 (s, 3H), 1.81-1.63 (m, 2H), 1.60-1.47 (m, 1H), 1.38 (dquin, J = 4.0, 12.0 Hz, 1H) |

TABLE 2-continued
| Cmpd No. | Structure | Scheme | Inter-med. | LCMS | $^{1}H$ NMR |
|---|---|---|---|---|---|
| 1.30 | 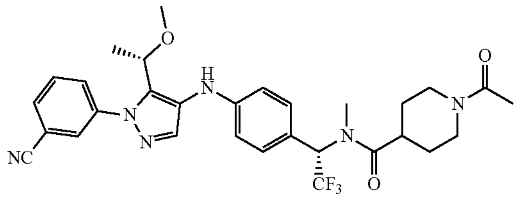 | 1 | INT 1.25 INT 2.1 INT 3.1 INT 4.2 INT 5.2 | [M − OCH3]+ C29H30F3N6O2 551.2 551.3 | (400 MHz, DMSO-d6) δ = 8.10-8.05 (m, 1H), 8.00-7.90 (m, 2H), 7.81-7.69 (m, 2H), 7.55-7.46 (m, 1H), 7.22-7.06 (m, 2H), 6.86-6.72 (m, 2H), 6.47-6.09 (m, 1H), 4.53 (q, J = 6.8 Hz, 1H), 4.47-4.31 (m, 1H), 3.82 (d, J = 10.8 Hz, 1H), 3.15-2.92 (m, 5H), 2.92-2.55 (m, 4H), 1.99 (s, 3H), 1.80-1.60 (m, 2H), 1.58-1.31 (m, 2H), 1.27 (d, J = 6.8 Hz, 3H) |
| 1.31 | 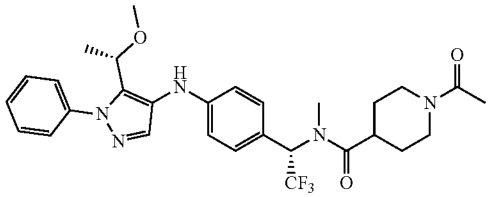 | 1 | INT 1.26 INT 2.1 INT 3.1 INT 4.2 INT 5.2 | [M + Na]+ C29H34F3N5NaO3 580.3 580.4 | (400 MHz, $CDCl_3$) δ = 7.75 (s, 1H), 7.55-7.41 (m, 5H), 7.22 (br t, J = 7.2 Hz, 2H), 6.88 (br d, J = 8.4 Hz, 2H), 6.65-6.47 (m, 1H), 5.91-5.41 (m, 1H), 4.60 (br s, 1H), 4.50 (q, J = 6.8 Hz, 1H), 3.92 (br d, J = 13.6 Hz, 1H), 3.23 (s, 3H), 3.20-3.11 (m, 1H), 2.93 (br s, 3H), 2.87-2.64 (m, 2H), 2.12 (s, 3H), 1.88 (br s, 2H), 1.76 (br d, J = 4.4 Hz, 2H), 1.47 (br d, J = 6.4 Hz, 3H) |

TABLE 2-continued
| Cmpd No. | Structure | Scheme | Inter-med. | LCMS | $^1$H NMR |
|---|---|---|---|---|---|
| 1.32 | 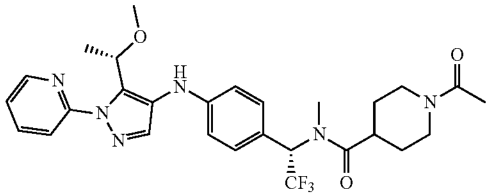 | 1 | INT 1.27<br>INT 2.1<br>INT 3.1<br>INT 4.2<br>INT 5.2 | [M + Na]+<br>C28H33F3N6NaO3<br>581.2<br>581.3 | (400 MHz, DMSO) δ = 8.51 (dd, J = 2.0, 4.0 Hz, 1H), 8.06-7.97 (m, 1H), 7.85-7.77 (m, 2H), 7.44-7.37 (m, 1H), 7.21 (s, 1H), 7.19-7.08 (m, 2H), 6.86 (d, J = 8.0 Hz, 2H), 6.29 (q, J = 8.0 Hz, 1H), 5.30 (q, J = 8.0 Hz, 1H), 4.42-4.32 (m, 1H), 3.88-3.77 (m, 1H), 3.16-3.07 (m, 1H), 3.06 (s, 3H), 3.04-2.94 (m, 1H), 2.91 (s, 2.5H), 2.63 (s, 1H), 2.59 (s, 0.5H), 1.99 (s, 3H), 1.79-1.54 (m, 3H), 1.52 (d, J = 8.0 Hz, 3H), 1.49-1.29 (m, 1H) |
| 1.33 | 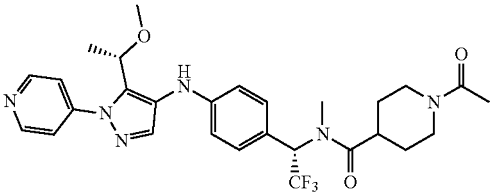 | 1 | INT 1.28<br>INT 2.1<br>INT 3.1<br>INT 4.2<br>INT 5.2 | [M + H]+<br>C28H34F3N6O3<br>559.3<br>559.3 | (400 MHz, DMSO) δ = 8.75-8.66 (m, 2H), 7.85 (s, 1H), 7.79-7.71 (m, 2H), 7.55 (s, 1H), 7.13 (d, J = 8.0 Hz, 2H), 6.79 (d, J = 8.0 Hz, 2H), 6.28 (q, J = 8.0 Hz, 1H), 4.66 (q, J = 8.0 Hz, 1H), 4.41-4.32 (m, 1H), 3.87-3.77 (m, 1H), 3.17 (s, 3H), 3.15-2.94 (m, 2H), 2.90 (s, 2.5H), 2.65-2.60 (m, 1H), 2.58 (s, 0.5H), 1.99 (s, 3H), 1.79-1.36 (m, 4H), 1.34 (d, J = 8.0 Hz, 3H) |

TABLE 2-continued
| Cmpd No. | Structure | Scheme | Inter-med. | LCMS | $^1H$ NMR |
|---|---|---|---|---|---|
| 1.34 | 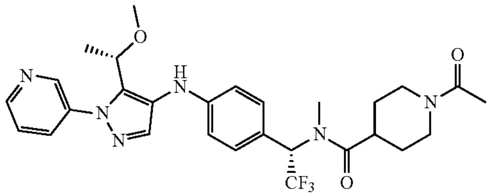 | 1 | INT 1.29 INT 2.1 INT 3.1 INT 4.2 INT 5.2 | [M + H]+ C28H34F3N6O3 559.3 559.2 | (400 MHz, $CDCl_3$) δ = 8.76 (d, J = 2.4 Hz, 1H), 8.69 (d, J = 4.4 Hz, 1H), 7.87 (br d, J = 8.4 Hz, 1H), 7.79 (s, 1H), 7.47 (dd, J = 4.8, 8.0 Hz, 1H), 7.26-7.18 (m, 2H), 6.86 (d, J = 8.8 Hz, 2H), 6.57 (q, J = 9.2 Hz, 1H), 5.67 (br s, 1H), 4.66-4.56 (m, 1H), 4.51 (q, J = 6.8 Hz, 1H), 3.91 (br d, J = 13.2 Hz, 1H), 3.25 (s, 3H), 3.19-3.05 (m, 1H), 2.93 (br s, 3H), 2.86-2.61 (m, 2H), 2.12 (s, 3H), 1.92-1.82 (m, 2H), 1.81-1.74 (m, 2H), 1.46 (d, J = 6.8 Hz, 3H) |
| 1.35 | 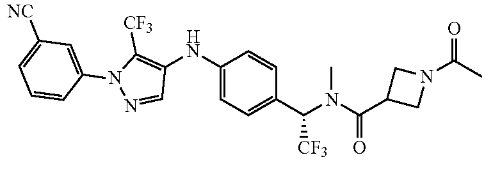 | 1 | INT 1.17 INT 2.1 INT 3.1 INT 4.3 INT 5.3 | [M + H]+ C26H23F6N6O2 565.2 565.1 | (400 MHz, DMSO-d6) δ = 8.11 (d, J = 10.0 Hz, 2H), 8.07-8.01 (m, 2H), 7.92 (br d, J = 8.4 Hz, 1H), 7.85-7.76 (m, 1H), 7.28-7.18 (m, 2H), 7.00-6.91 (m, 2H), 6.49-5.72 (m, 1H), 4.41-4.16 (m, 2H), 4.12-3.97 (m, 1H), 3.93-3.78 (m, 2H), 2.72 (s, 3H), 1.76 (d, J = 3.6 Hz, 3H) |

TABLE 2-continued

| Cmpd No. | Structure | Scheme | Inter-med. | LCMS | $^1$H NMR |
|---|---|---|---|---|---|
| 1.36 | 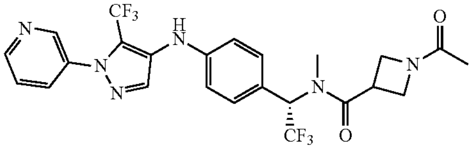 | 1 | INT 1.13 INT 2.1 INT 3.1 INT 4.3 INT 5.3 | [M + H]+ C24H23F6N6O2 541.2 541.2 | (400 MHz, $CDCl_3$) δ = 8.84-8.70 (m, 2H), 7.90-7.82 (m, 2H), 7.49 (dd, J = 4.8, 8.0 Hz, 1H), 7.34-7.18 (m, 2H), 7.05-6.93 (m, 2H), 6.55 (q, J = 8.8 Hz, 1H), 5.74 (br d, J = 5.6 Hz, 1H), 4.64-4.52 (m, 1H), 4.36-4.22 (m, 2H), 4.20-4.02 (m, 1H), 3.71-3.55 (m, 1H), 2.78 (d, J = 6.8 Hz, 3H), 1.91 (d, J = 3.6 Hz, 3H) |
| 1.37 | 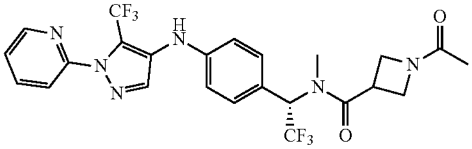 | 1 | INT 1.15 INT 2.1 INT 3.1 INT 4.3 INT 5.3 | [M + H]+ C24H23F6N6O2 541.2 541.3 | (400 MHz, DMSO-d6) δ = 8.54 (dd, J = 1.2, 4.8 Hz, 1H), 8.19-8.13 (m, 1H), 8.11-8.04 (m, 2H), 7.81 (d, J = 8.4 Hz, 1H), 7.51 (dd, J = 5.2, 7.2 Hz, 1H), 7.29-7.19 (m, 2H), 6.95 (d, J = 8.4 Hz, 2H), 6.41 (q, J = 9.2 Hz, 1H), 4.40-4.17 (m, 2H), 4.13-3.97 (m, 1H), 3.93-3.78 (m, 2H), 2.74-2.69 (m, 3H), 1.76 (d, J = 3.6 Hz, 3H) |
| 1.38 | 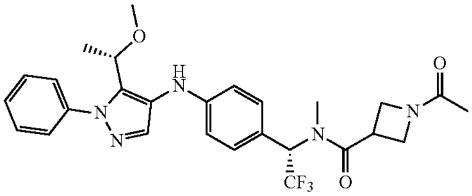 | 1 | INT 1.26 INT 2.1 INT 3.1 INT 4.3 INT 5.3 | [M + H]+ C27H31F3N5O3 530.2 530.3 | (400 MHz, $CDCl_3$) δ = 7.75 (d, J = 2.0 Hz, 1H), 7.55-7.42 (m, 5H), 7.23 (br t, J = 7.8 Hz, 2H), 6.89 (br d, J = 7.8 Hz, 2H), 6.56-6.45 (m, 1H), 5.73 (br s, 1H), 4.62-4.53 (m, 1H), 4.50 (q, J = 6.8 Hz, 1H), 4.32-4.04 (m, 3H), 3.67-3.54 (m, 1H), 3.23 (s, 3H), 2.76 (d, J = 6.8 Hz, 3H), 1.91 (d, J = 2.4 Hz, 3H), 1.47 (d, J = 6.8 Hz, 3H) |

TABLE 2-continued
| Cmpd No. | Structure | Scheme | Inter-med. | LCMS | $^1$H NMR |
|---|---|---|---|---|---|
| 1.39 | 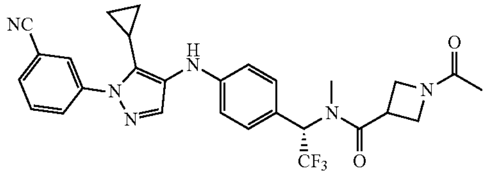 | 1 | INT 1.30<br>INT 2.1<br>INT 3.1<br>INT 4.3<br>INT 5.3 | [M + H]+<br>C28H28F3N6O2<br>537.2<br>537.3 | (400 MHz, DMSO-d6) δ = 8.21-8.17 (m, 1H), 8.08-8.03 (m, 1H), 7.87 (d, J = 7.6 Hz, 1H), 7.77-7.71 (m, 1H), 7.65 (s, 1H), 7.61-7.55 (m, 1H), 7.20-7.09 (m, 2H), 6.82-6.71 (m, 2H), 6.44-5.69 (m, 1H), 4.38-4.16 (m, 2H), 4.13-3.98 (m, 1H), 3.93-3.78 (m, 2H), 2.71 (s, 3H), 2.04-1.94 (m, 1H), 1.76 (d, J = 3.2 Hz, 3H), 0.77-0.69 (m, 2H), 0.48-0.42 (m, 2H) |
| 1.40 | 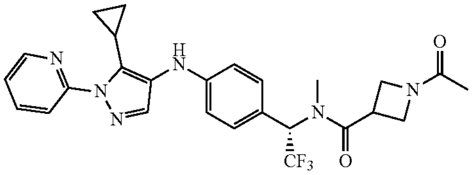 | 1 | INT 1.31<br>INT 2.1<br>INT 3.1<br>INT 4.3<br>INT 5.3 | [M + H]+<br>C26H28F3N6O2<br>513.2<br>513.3 | (400 MHz, DMSO-d6) δ = 8.52 (dd, J = 1.1, 4.8 Hz, 1H), 8.04-7.97 (m, 1H), 7.77 (d, J = 8.3 Hz, 1H), 7.61 (s, 1H), 7.52-7.46 (m, 1H), 7.41 (dd, J = 5.1, 7.0 Hz, 1H), 7.14 (br dd, J = 4.0, 8.3 Hz, 2H), 6.70 (d, J = 8.6 Hz, 2H), 6.44-5.67 (m, 1H), 4.37-4.15 (m, 2H), 4.11-3.96 (m, 1H), 3.93-3.77 (m, 2H), 2.72-2.68 (m, 3H), 2.38-2.28 (m, 1H), 1.75 (d, J = 2.9 Hz, 3H), 0.75-0.67 (m, 2H), 0.58 (br d, J = 4.8 Hz, 2H) |

TABLE 2-continued

| Cmpd No. | Structure | Scheme | Inter-med. | LCMS | $^1$H NMR |
|---|---|---|---|---|---|
| 1.41 | 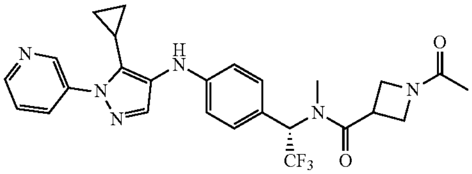 | 1 | INT 1.32 INT 2.1 INT 3.1 INT 4.3 INT 5.3 | [M + H]+ C26H28F3N6O2 513.2 513.3 | (400 MHz, DMSO-d6) δ = 8.94 (d, J = 2.4 Hz, 1H), 8.61 (dd, J = 1.2, 4.4 Hz, 1H), 8.17-8.11 (m, 1H), 7.65 (s, 1H), 7.61-7.52 (m, 2H), 7.19-7.09 (m, 2H), 6.81-6.72 (m, 2H), 6.38 (q, J = 9.6 Hz, 1H), 4.36-4.17 (m, 2H), 4.12-3.98 (m, 1H), 3.91-3.79 (m, 2H), 2.71 (s, 3H), 1.98-1.89 (m, 1H), 1.76 (s, 3H), 0.78-0.68 (m, 2H), 0.49 (br d, J = 5.2 Hz, 2H) |
| 2.1 | 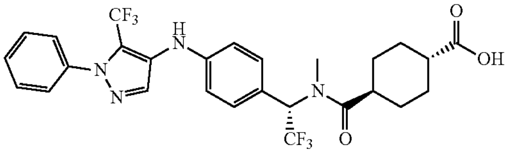 | 2 | INT 1.6 INT 2.1 INT 3.1 INT 4.4 INT 5.4 INT 6.1 | [M + H]+ C27H27F6N4O3 569.2 569.1 | (400 MHz, $CDCl_3$) δ = 7.80 (s, 1H), 7.54-7.44 (m, 5H), 7.26-7.24 (m, 2H), 6.94 (d, J = 8.8 Hz, 2H), 6.60 (q, J = 9.2 Hz, 1H), 5.51 (s, 1H), 2.90 (s, 3H), 2.62-2.53 (m, 1H), 2.42 (tt, J = 3.6, 12.0 Hz, 1H), 2.15 (br t, J = 8.8 Hz, 2H), 2.01-1.82 (m, 2H), 1.67 (q, J = 12.8 Hz, 2H), 1.56-1.42 (m, 2H) |
| 2.2 | 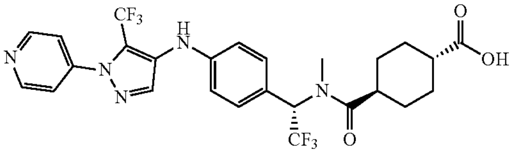 | 2 | INT 1.14 INT 2.1 INT 3.1 INT 4.4 INT 5.4 INT 6.2 | [M + H]+ C26H26F6N5O3 570.2 570.4 | (400 MHz, DMSO) δ = 8.78 (d, J = 4.0 Hz, 2H), 8.20 (s, 1H), 8.11 (s, 1H), 7.61 (d, J = 4.0 Hz, 2H), 7.18 (d, J = 8.0 Hz, 2H), 6.97 (d, J = 8.0 Hz, 2H), 6.30 (q, J = 8.0 Hz, 1H), 2.87 (s, 2.5H), 2.73-2.66 (m, 1H), 2.62 (s, 0.5H), 2.25-2.15 (m, 1H), 1.99-1.87 (m, 2H), 1.83-1.69 (m, 2H), 1.52-1.31 (m, 4H) |

TABLE 2-continued
| Cmpd No. | Structure | Scheme | Inter-med. | LCMS | $^1$H NMR |
|---|---|---|---|---|---|
| 2.3 | 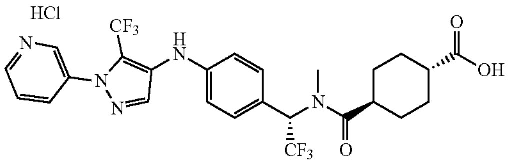 | 2 | INT 1.13 INT 2.1 INT 3.1 INT 4.4 INT 5.4 INT 6.3 | [M + H]+ C26H26F6N5O3 570.2 570.1 | (400 MHz, $CDCl_3$) δ = 8.87 (d, J = 2.0 Hz, 1H), 8.78 (dd, J = 1.2, 4.8 Hz, 1H), 8.01 (br d, J = 8.4 Hz, 1H), 7.90 (s, 1H), 7.63 (dd, J = 4.8, 8.0 Hz, 1H), 7.32-7.26 (m, 2H), 6.99 (d, J = 8.8 Hz, 2H), 6.62 (q, J = 9.2 Hz, 1H), 5.92-5.45 (m, 2H), 2.92 (s, 3H), 2.64-2.52 (m, 1H), 2.42 (tt, J = 3.2, 12.0 Hz, 1H), 2.17 (br t, J = 8.8 Hz, 2H), 1.98 (br d, J = 12.8 Hz, 1H), 1.88 (br d, J = 13.2 Hz, 1H), 1.75-1.61 (m, 2H), 1.60-1.44 (m, 2H) |
| 2.4 | 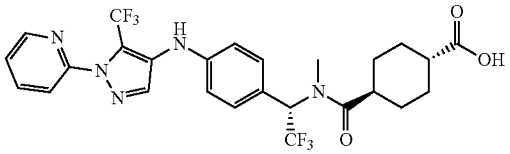 | 2 | INT 1.15 INT 2.1 INT 3.1 INT 4.4 INT 5.4 INT 6.4 | [M + H]+ C26H26F6N5O3 570.2 570.3 | (400 MHz, DMSO-d6) δ = 8.47 (dd, J = 1.2, 4.8 Hz, 1H), 8.10-8.06 (m, 1H), 8.04-7.99 (m, 2H), 7.75 (d, J = 8.0 Hz, 1H), 7.48-7.42 (m, 1H), 7.21-7.08 (m, 2H), 6.94-6.86 (m, 2H), 6.44-6.05 (m, 1H), 2.81 (s, 3H), 2.62 (br d, J = 3.6 Hz, 1H), 2.14 (br s, 1H), 1.94-1.80 (m, 2H), 1.79-1.57 (m, 2H), 1.44-1.25 (m, 4H) |

TABLE 2-continued
| Cmpd No. | Structure | Scheme | Inter-med. | LCMS | $^1$H NMR |
|---|---|---|---|---|---|
| 2.5 | 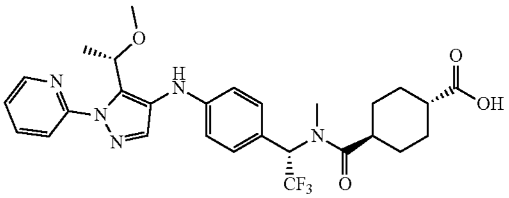 | 2 | INT 1.27<br>INT 2.1<br>INT 3.1<br>INT 4.4<br>INT 5.4<br>INT 6.5 | [M + H]+<br>C28H33F3N5O4<br>560.2<br>560.2 | (400 MHz, DMSO) δ = 8.50 (d, J = 4.0 Hz, 1H), 8.06-7.96 (m, 1H), 7.85-7.75 (m, 2H), 7.45-7.36 (m, 1H), 7.23-7.06 (m, 3H), 6.91-6.80 (m, 2H), 6.25 (q, J = 8.0 Hz, 1H), 5.29 (q, J = 8.0 Hz, 1H), 3.06 (s, 3H), 2.87 (s, 2.5H), 2.70-2.65 (m, 1H), 2.62 (s, 0.5H), 2.25-2.13 (m, 1H), 1.99-1.86 (m, 2H), 1.82-1.63 (m, 2H), 1.52 (d, J = 6.0 Hz, 3H), 1.49-1.30 (m, 4H) |
| 2.6 | 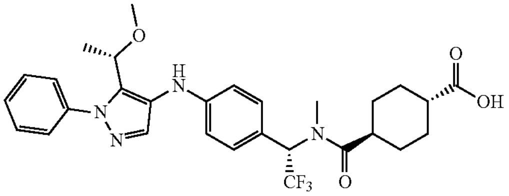 | 2 | INT 1.26<br>INT 2.1<br>INT 3.1<br>INT 4.4<br>INT 5.4<br>INT 6.6 | [M + H]+<br>C29H34F3N4O4<br>559.2<br>559.3 | (400 MHz, $CDCl_3$) δ = 7.76 (s, 1H), 7.55-7.48 (m, 2H), 7.48-7.42 (m, 3H), 7.22 (d, J = 8.4 Hz, 2H), 6.88 (d, J = 8.8 Hz, 2H), 6.58 (q, J = 9.2 Hz, 1H), 5.71 (br s, 1H), 4.50 (q, J = 6.8 Hz, 1H), 3.23 (s, 3H), 2.91 (s, 3H), 2.63-2.52 (m, 1H), 2.43 (tt, J = 3.6, 12.0 Hz, 1H), 2.21-2.10 (m, 2H), 2.03-1.82 (m, 2H), 1.75-1.60 (m, 2H), 1.55-1.44 (m, 5H) |

TABLE 2-continued

| Cmpd No. | Structure | Scheme | Inter-med. | LCMS | $^1$H NMR |
|---|---|---|---|---|---|
| 2.7 | 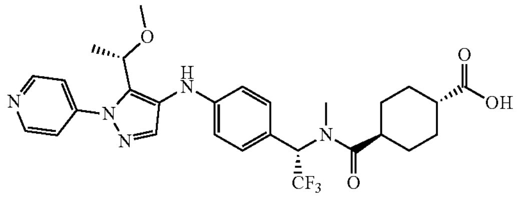 | 2 | INT 1.28<br>INT 2.1<br>INT 3.1<br>INT 4.4<br>INT 5.4<br>INT 6.7 | [M + H]+<br>C28H33F3N5O4<br>560.2<br>560.3 | (400 MHz, DMSO) δ = 8.71 (d, J = 8.0 Hz, 2H), 7.85 (s, 1H), 7.75 (d, J = 8.0 Hz, 2H), 7.54 (s, 1H), 7.11 (d, J = 8.0 Hz, 2H), 6.78 (d, J = 8.0 Hz, 2H), 6.09 (q, J = 8.0 Hz, 1H), 4.65 (q, J = 8.0 Hz, 1H), 3.17 (s, 3H), 2.86 (s, 2.5H), 2.72-2.65 (m, 1H), 2.61 (s, 0.5H), 2.25-2.13 (m, 1H), 1.97-1.68 (m, 4H), 1.49-1.36 (m, 4H), 1.33 (d, J = 8.0 Hz, 3H) |
| 2.8 | 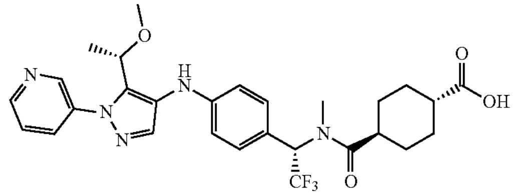 | 2 | INT 1.29<br>INT 2.1<br>INT 3.1<br>INT 4.4<br>INT 5.4<br>INT 6.8 | [M + H]+<br>C28H33F3N5O4<br>560.2<br>560.3 | (400 MHz, $CDCl_3$) δ = 8.78 (s, 1H), 8.69 (br d, J = 4.4 Hz, 1H), 7.89 (br d, J = 7.6 Hz, 1H), 7.80 (s, 1H), 7.48 (dd, J = 5.6, 7.6 Hz, 1H), 7.22 (br d, J = 7.6 Hz, 2H), 6.86 (br d, J = 8.4 Hz, 2H), 6.63-6.53 (m, 1H), 5.64 (br s, 1H), 4.51 (q, J = 6.8 Hz, 1H), 3.26 (s, 3H), 2.91 (s, 3H), 2.58 (br s, 1H), 2.48-2.37 (m, 1H), 2.16 (br s, 2H), 2.02-1.79 (m, 2H), 1.67 (br d, J = 12.4 Hz, 2H), 1.52 (br d, J = 12.0 Hz, 2H), 1.46 (br d, J = 6.8 Hz, 3H) |

TABLE 2-continued

| Cmpd No. | Structure | Scheme | Inter-med. | LCMS | $^{1}H$ NMR |
|---|---|---|---|---|---|
| 2.9 | 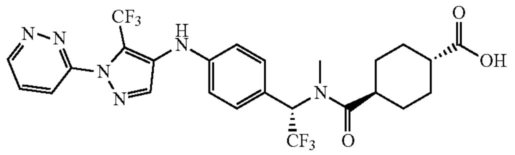 | 2 | INT 1.21<br>INT 2.1<br>INT 3.1<br>INT 4.4<br>INT 5.4<br>INT 6.9 | [M + H]+<br>C25H25F6N6O3<br>571.2<br>571.2 | (400 MHz, DMSO-d6) δ = 9.31 (dd, J = 1.2, 4.8 Hz, 1H), 8.29-8.23 (m, 1H), 8.20 (s, 1H), 8.16 (dd, J = 1.2, 8.8 Hz, 1H), 7.99 (dd, J = 4.8, 8.8 Hz, 1H), 7.28-7.14 (m, 2H), 7.04-6.93 (m, 2H), 6.44 (q, J = 9.6 Hz, 1H), 2.87 (s, 3H), 2.71-2.62 (m, 1H), 2.19 (br s, 1H), 1.99-1.85 (m, 2H), 1.82-1.64 (m, 2H), 1.53-1.29 (m, 4H) |
| 2.10 | 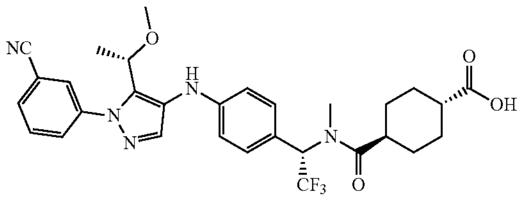 | 2 | INT 1.25<br>INT 2.1<br>INT 3.1<br>INT 4.4<br>INT 5.4<br>INT 6.10 | [M + H]+<br>C30H33F3N5O4<br>584.2<br>584.3 | (400 MHz, DMSO-d6) δ = 8.11-8.05 (m, 1H), 7.99-7.91 (m, 2H), 7.80-7.70 (m, 2H), 7.50 (s, 1H), 7.20-7.06 (m, 2H), 6.92-6.72 (m, 2H), 6.46-6.05 (m, 1H), 4.54 (q, J = 6.8 Hz, 1H), 3.12 (s, 3H), 2.86 (s, 4H), 2.19 (br s, 1H), 2.00-1.85 (m, 2H), 1.83-1.64 (m, 2H), 1.50-1.31 (m, 4H), 1.27 (d, J = 6.8 Hz, 3H) |
| 2.11 | 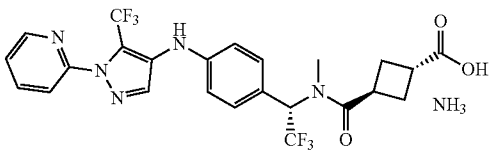 | 2 | INT 1.15<br>INT 2.1<br>INT 3.1<br>INT 4.6<br>INT 5.6<br>INT 6.12 | [M + H]+<br>C24H22F6N5O3<br>542.2<br>542.2 | (400 MHz, $CDCl_3$) δ = 8.58-8.48 (m, 1H), 7.89 (dt, J = 2.0, 8.0 Hz, 1H), 7.84 (s, 1H), 7.75 (d, J = 8.8 Hz, 1H), 7.34 (dd, J = 4.0, 6.8 Hz, 1H), 7.31-7.27 (m, 2H), 6.97 (d, J = 8.4 Hz, 2H), 6.57 (q, J = 8.4 Hz, 1H), 5.67 (s, 1H), 3.51 (br t, J = 8.3 Hz, 1H), 3.23 (td, J = 4.4, 9.5 Hz, 1H), 2.78 (s, 3H), 2.74-2.65 (m, 2H), 2.64-2.49 (m, 2H) |

TABLE 2-continued

| Cmpd No. | Structure | Scheme | Inter-med. | LCMS | $^1$H NMR |
|---|---|---|---|---|---|
| 2.12 | 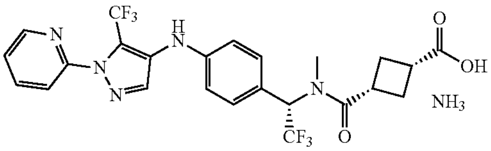 | 2 | INT 1.15<br>INT 2.1<br>INT 3.1<br>INT 4.6<br>INT 5.6<br>INT 6.12 | [M + H]+<br>C24H22F6N5O3<br>542.2<br>542.2 | (400 MHz, $CDCl_3$) δ = 8.58-8.49 (m, 1H), 7.88 (dt, J = 1.6, 8.0 Hz, 1H), 7.85 (s, 1H), 7.75 (d, J = 8.8 Hz, 1H), 7.34 (dd, J = 4.8, 7.2 Hz, 1H), 7.31-7.27 (m, 2H), 6.97 (d, J = 8.4 Hz, 2H), 6.55 (q, J = 8.8 Hz, 1H), 5.68 (s, 1H), 3.29 (quin, J = 8.8 Hz, 1H), 3.17 (quin, J = 8.8 Hz, 1H), 2.80 (s, 3H), 2.75-2.62 (m, 2H), 2.61-2.46 (m, 2H) |
| 2.13 | 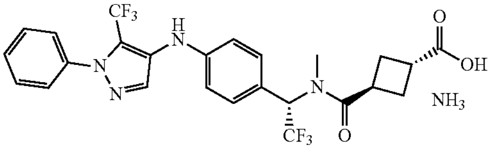 | 2 | INT 1.6<br>INT 2.1<br>INT 3.1<br>INT 4.6<br>INT 5.6<br>INT 6.13 | [M + H]+<br>C25H23F6N4O3<br>541.2<br>541.2 | (400 MHz, $CDCl_3$) δ = 7.81 (s, 1H), 7.54-7.45 (m, 5H), 7.29-7.27 (m, 2H), 6.99-6.93 (m, 2H), 6.61-6.51 (m, 1H), 5.54 (br s, 1H), 3.56-3.46 (m, 1H), 3.29-3.17 (m, 1H), 2.78 (s, 3H), 2.75-2.64 (m, 2H), 2.63-2.48 (m, 2H) |
| 2.14 | 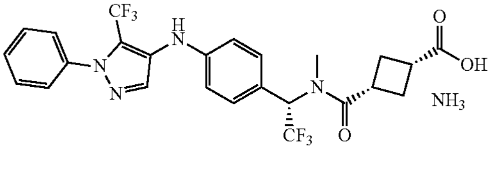 | 2 | INT 1.6<br>INT 2.1<br>INT 3.1<br>INT 4.6<br>INT 5.6<br>INT 6.13 | [M + H]+<br>C25H23F6N4O3<br>541.2<br>541.2 | (400 MHz, $CDCl_3$) δ = 7.81 (s, 1H), 7.49 (br s, 5H), 7.29-7.27 (m, 2H), 6.95 (d, J = 8.4 Hz, 2H), 6.54 (q, J = 8.4 Hz, 1H), 5.56 (br s, 1H), 3.35-3.23 (m, 1H), 3.21-3.08 (m, 1H), 2.80 (s, 3H), 2.75-2.60 (m, 2H), 2.59-2.46 (m, 2H) |

TABLE 2-continued

| Cmpd No. | Structure | Scheme | Inter-med. | LCMS | $^1$H NMR |
|---|---|---|---|---|---|
| 3.1 | 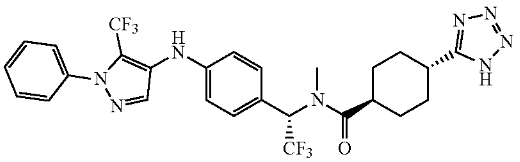 | 3 | INT 1.6 INT 2.1 INT 3.1 INT 4.7 INT 5.7 INT 6.11 | [M + H]+ C27H27F6N8O 593.2 593.2 | (400 MHz, $CDCl_3$) δ = 7.81 (s, 1H), 7.49 (br s, 5H), 7.27 (s, 2H), 6.96 (d, J = 8.8 Hz, 2H), 6.67-6.51 (m, 1H), 5.60 (s, 1H), 3.22-3.15 (m, 1H), 3.03-2.85 (m, 3H), 2.79 (br s, 1H), 2.28 (br s, 2H), 2.13-1.95 (m, 2H), 1.82 (br s, 4H) |

Example 2. MALT1 Biochemical Assay

Inhibitor potency was evaluated by measuring enzymatic activity of full length MALT1 at varying concentrations of compound. The enzymatic assay consists of a single substrate reaction that monitors the release of a fluorescent dye upon cleavage of the peptide substrate. The peptide substrate has the following sequence: Ac-Leu-Arg-Ser-Arg-Rh110-dPro (custom synthesis from WuXi AppTec, Shanghai, China). The assay buffer consists of 50 mM Hepes, pH 7.5, 0.8 M sodium citrate, 1 mM DTT, 0.004% tween-20, and 0.005% bovine serum albumin (BSA). Steady-state kinetic analysis of peptide substrate binding resulted in a Michaelis-Menten constant ($K_M$) of 150 μM. The assay was performed in a 384-well F-bottom polypropylene, black microplate (Greiner Bio_One, Catalog no. 781209) at 15 nM enzyme and 30 μM peptide substrate. The reaction was quenched after 60 minutes with the addition of iodoacetate at a final concentration of 10 mM. Total fluorescence was measured using an Envision (PerkinElmer) with fluorescence excitation at 485 nm and emission at 520 nm.

For potency determination, 1 μL of serially diluted compound (in 100% DMSO) was pre-incubated with 40 μL of enzyme for 30 minutes. The reaction was initiated with the addition of 10 μL of peptide substrate. The relative fluorescence units were transformed to percent inhibition by using 0% and 100% inhibition controls as reference. The 100% inhibition control consisted of 1 μM final concentration of (S)-1-(5-chloro-6-(2H-1,2,3-triazol-2-yl)pyridin-3-yl)-3-(2-chloro-7-(1-methoxyethyl)pyrazolo[1,5-a]pyrimidin-6-yl) urea ($IC_{50}$=15 nM), while the 0% inhibition control consisted of 2% DMSO. $IC_{50}$ values were calculated by fitting the concentration-response curves to a four-parameter logistic equation in GraphPad Prism.

Results from this assay are summarized in Table 3 below. In this table, "A" indicates $IC_{50}$ of less than 0.1 μM; "B" indicates $IC_{50}$ from 0.1 μM up to 1 μM; and "C" indicates $IC_{50}$ of greater than 1 μM. "N/A" indicates not tested. For a compound that was tested in more than one experiment, the result shown represents the mean value.

TABLE 3

| Compound | $IC_{50}$ (μM) |
|---|---|
| 1.1 | C |
| 1.2 | B |

TABLE 3-continued

| Compound | $IC_{50}$ (μM) |
|---|---|
| 1.3 | C |
| 1.4 | C |
| 1.5 | C |
| 1.6 | B |
| 1.7 | B |
| 1.8 | B |
| 1.9 | B |
| 1.10 | C |
| 1.11 | C |
| 1.12 | C |
| 1.13 | A |
| 1.14 | B |
| 1.15 | A |
| 1.16 | B |
| 1.17 | A |
| 1.18 | C |
| 1.19 | B |
| 1.20 | A |
| 1.21 | A |
| 1.22 | A |
| 1.23 | B |
| 1.24 | A |
| 1.25 | B |
| 1.26 | B |
| 1.27 | A |
| 1.28 | A |
| 1.29 | B |
| 1.30 | A |
| 1.31 | B |
| 1.32 | A |
| 1.33 | B |
| 1.34 | B |
| 1.35 | B |
| 1.36 | A |
| 1.37 | A |
| 1.38 | B |
| 1.39 | B |
| 1.40 | A |
| 1.41 | A |
| 2.1 | A |
| 2.2 | B |
| 2.3 | B |
| 2.4 | A |
| 2.5 | A |
| 2.6 | B |
| 2.7 | B |
| 2.8 | B |
| 2.9 | A |
| 2.10 | A |
| 2.11 | A |
| 2.12 | A |
| 2.13 | A |

TABLE 3-continued

| Compound | $IC_{50}$ (μM) |
|---|---|
| 2.14 | A |
| 3.1 | C |

Example 3. Jurkat IL-2 Assay

Inhibition was determined in a cell-based assay using Jurkat (ATCC, clone E6.1), an immortalized T-cell line, exposed to a dose response of compound and assessed for viability, and IL-2 inhibition by ELISA. Cells were cultured in RPMI/10% FBS (Invitrogen 11875093, Atlanta Biologicals S12450H), maintained below 3E6/mL and only used in assays while below passage 25. Compounds were stamped by ECHO onto 384w plates (PerkinElmer Culturplate, 6007680). The cells were plated in fresh media on top of compound and incubated for 30 minutes before stimulation with soluble anti-CD3/28/2 (Stemcell, 10970) for 24 hours. Supernatant was collected and assessed for IL-2 (MSD, 384w, L21SA-1). To assess viability of cells treated with compound, cells were lysed with CTG reagent (Promega, G7570), and measured by luminometer. IL-2 curves were calculated as percent of DMSO (100%) and signal-inhibiting (0%, (S)-1-(5-chloro-6-(2H-1,2,3-triazol-2-yl)pyridin-3-yl)-3-(2-chloro-7-(1-methoxyethyl)pyrazolo[1,5-a]pyrimidin-6-yl)urea) controls. $IC_{50}$s calculated using 4-parameter fit in GraphPad Prism.

Results from this assay are summarized in Table 4 below. In this table, "A" indicates $IC_{50}$ of less than 0.1 μM; "B" indicates $IC_{50}$ from 0.1 μM up to 1 μM; and "C" indicates $IC_{50}$ of greater than 1 μM. "N/A" indicates not tested. For a compound that was tested in more than one experiment, the result shown represents the mean value.

TABLE 4

| Compound | $IC_{50}$ (μM) |
|---|---|
| 1.1 | C |
| 1.2 | B |
| 1.3 | B |
| 1.4 | C |
| 1.5 | C |
| 1.6 | B |
| 1.7 | B |
| 1.8 | B |
| 1.9 | B |
| 1.10 | C |
| 1.11 | C |
| 1.12 | C |
| 1.13 | A |
| 1.14 | A |
| 1.15 | A |
| 1.16 | B |
| 1.17 | A |
| 1.18 | C |
| 1.19 | A |
| 1.20 | A |
| 1.21 | A |
| 1.22 | B |
| 1.23 | B |
| 1.24 | B |
| 1.25 | A |
| 1.26 | B |
| 1.27 | A |
| 1.28 | A |
| 1.29 | A |
| 1.30 | B |
| 1.31 | B |
| 1.32 | B |

TABLE 4-continued

| Compound | $IC_{50}$ (μM) |
|---|---|
| 1.33 | B |
| 1.34 | B |
| 1.35 | A |
| 1.36 | A |
| 1.37 | A |
| 1.38 | B |
| 1.39 | B |
| 1.40 | B |
| 1.41 | B |
| 2.1 | A |
| 2.2 | B |
| 2.3 | A |
| 2.4 | A |
| 2.5 | B |
| 2.6 | B |
| 2.7 | C |
| 2.8 | B |
| 2.9 | A |
| 2.10 | B |
| 2.11 | A |
| 2.12 | B |
| 2.13 | A |
| 2.14 | B |
| 3.1 | B |

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A compound represented by the Formula (I)

(I)

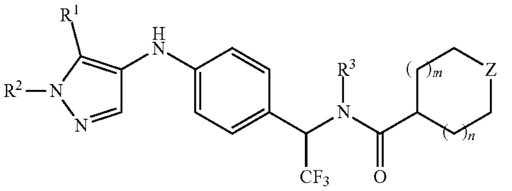

or a stereoisomer and/or a pharmaceutically acceptable salt thereof, wherein:

$R^1$ is selected from the group consisting of $C_{1-6}$alkyl, $C_{1-3}$haloalkyl, $C_{3-6}$cycloalkyl, and aryl, wherein $R^1$ may be optionally substituted on one or more available carbons by one, two, three, or more substituents each independently selected from $R^{1a}$;

$R^2$ is selected from the group consisting of $C_{1-6}$alkyl, $C_{3-6}$cycloalkyl, aryl, and 5-10 membered heteroaryl, wherein $R^2$ may be optionally substituted on one or more available carbons by one, two, three, or more substituents each independently selected from $R^{2a}$;

$R^3$ is hydrogen or $C_{1-3}$alkyl;

$R^{1a}$ is independently, for each occurrence, hydroxyl or —O—$C_{1-3}$alkyl;

$R^{2a}$ is independently, for each occurrence, selected from the group consisting of hydroxyl, cyano, $C_{1-6}$alkyl, and —O—$C_{1-3}$alkyl;

Z is —C(H)($R^A$)—, —$SO_2$—, or —$NR^A$—;

$R^A$ is —C(O)$C_{1-6}$alkyl, —C(O)OH, or 5-6 membered heteroaryl;

m is 0 or 1; and n is 0 or 1.

2. The compound of claim 1, wherein $R^1$ is selected from the group consisting of $C_{1-6}$alkyl, $C_{1-3}$haloalkyl, $C_{3-6}$cycloalkyl, and aryl, wherein the $C_{1-6}$alkyl may be optionally substituted with hydroxyl or —O—$C_{1-3}$alkyl.

3. The compound of claim 1, wherein $R^1$ is selected from the group consisting of —$CH(CH_3)_2$, $CF_3$, cyclopropyl, phenyl,

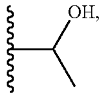 and 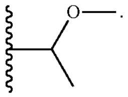.

4. The compound of claim 3, wherein $R^2$ is selected from the group consisting of $C_{1-6}$alkyl, $C_{3-6}$cycloalkyl, aryl, and 5-10 membered heteroaryl, wherein the $C_{1-6}$alkyl and aryl may be optionally substituted with hydroxyl, cyano, $C_{1-6}$alkyl, or —O—$C_{1-3}$alkyl.

5. The compound of claim 3, wherein $R^2$ is selected from the group consisting of $CH_3$, cyclopropyl, —$C(H)(CH_3)_2$, —$CH_2C(CH_3)_3$, phenyl,

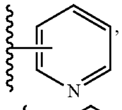, 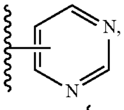, 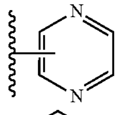, 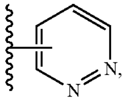, and 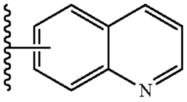.

6. The compound of claim 5, wherein $R^3$ is $CH_3$.

7. The compound of claim 6, wherein m is 1 and n is 1.

8. The compound of claim 7, wherein Z is —C(H)($R^A$)—.

9. The compound of claim 8, wherein $R^A$ is —C(O)OH.

10. A compound represented by Formula (Ic):

(Ic)

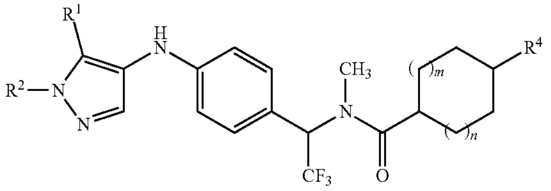

or a stereoisomer and/or a pharmaceutically acceptable salt thereof, wherein:

$R^1$ is $C_{1-6}$alkyl or $C_{1-3}$haloalkyl, wherein the $C_{1-6}$alkyl may be optionally substituted with —O—$C_{1-3}$alkyl;

$R^2$ is aryl or 5-6 membered heteroaryl, wherein the aryl may be optionally substituted with cyano;

$R^4$ is —C(O)OH or 5-6 membered heteroaryl;

m is 0 or 1; and n is 0 or 1.

11. The compound of claim 10, wherein $R^1$ is $C_{1-6}$alkyl or $C_{1-3}$haloalkyl, wherein the $C_{1-6}$alkyl may be optionally substituted with —O—$CH_3$.

12. The compound of claim 10, wherein $R^1$ is $CF_3$ or

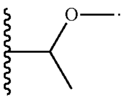 [SMILES: *C(C)OC]

13. The compound of claim 12, wherein $R^2$ is phenyl,
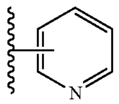
or
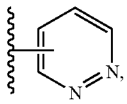
wherein the phenyl is optionally substituted with cyano.
14. The compound of claim 13, wherein $R^4$ is —C(O)OH.
15. The compound of claim 14, wherein m is 1 and n is 1.
* * * * *